US007819298B2

(12) United States Patent
Hall et al.

(10) Patent No.: US 7,819,298 B2
(45) Date of Patent: Oct. 26, 2010

(54) SURGICAL STAPLING APPARATUS WITH CONTROL FEATURES OPERABLE WITH ONE HAND

(75) Inventors: Steven G. Hall, Cincinnati, OH (US); Randall J. Tanguay, Lebanon, OH (US); Jeffrey D. Messerly, Cincinnati, OH (US); Galen C. Robertson, Cincinnati, OH (US); Andrew M. Zwolinski, Cincinnati, OH (US); Frederick E. Shelton, IV, Hillsboro, OH (US); Geoffrey C. Hueil, Mason, OH (US); Mark S. Ortiz, Milford, OH (US); Douglas B. Hoffman, Harrison, OH (US); Patrick A. Weizman, Liberty Township, OH (US); Dean B. Bruewer, Fairfield, OH (US); Gregory B. Blair, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 281 days.

(21) Appl. No.: 12/031,030

(22) Filed: Feb. 14, 2008

(65) Prior Publication Data
US 2009/0206124 A1 Aug. 20, 2009

(51) Int. Cl.
 *A61B 17/68* (2006.01)
(52) U.S. Cl. .................. 227/176.1; 227/19; 227/175.2; 227/180.1
(58) Field of Classification Search ........... 227/19, 227/176.1, 175.1, 175.2, 180.1; 606/139, 606/219
See application file for complete search history.

(56) References Cited

U.S. PATENT DOCUMENTS

| 2,804,848 | A | 9/1957 | O'Farrell et al. |
| 2,853,074 | A | 9/1958 | Olson |
| 3,490,675 | A | 1/1970 | Green et al. |
| 3,551,987 | A | 1/1971 | Wilkinson |
| 3,643,851 | A | 2/1972 | Green et al. |
| 3,662,939 | A | 5/1972 | Bryan |
| 3,717,294 | A | 2/1973 | Green |
| 3,819,100 | A | 6/1974 | Noiles et al. |
| 4,331,277 | A | 5/1982 | Green |
| 4,383,634 | A | 5/1983 | Green |
| 4,396,139 | A | 8/1983 | Hall et al. |
| 4,402,445 | A | 9/1983 | Green |

(Continued)

FOREIGN PATENT DOCUMENTS

CA  2458946 A1  3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner*—Scott A. Smith

(57) ABSTRACT

A surgical stapling apparatus. Various embodiments include a rotatable elongated body that extends from a rotatable shroud on handle assembly and has a distal end configured for attachment to a disposable loading unit. The apparatus further includes a lockable rotation system for selectively locking the rotatable shroud to prevent rotation thereof about a longitudinal axis.

13 Claims, 114 Drawing Sheets

U.S. PATENT DOCUMENTS

| | | |
|---|---|---|
| 4,415,112 A | 11/1983 | Green |
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,576,167 A | 3/1986 | Noiles et al. |
| 4,580,712 A | 4/1986 | Green |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,655,222 A | 4/1987 | Florez et al. |
| 4,664,305 A | 5/1987 | Blake, III et al. |
| 4,667,674 A | 5/1987 | Korthoff et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,869,414 A | 9/1989 | Green et al. |
| 4,869,415 A | 9/1989 | Fox |
| 4,880,015 A | 11/1989 | Nierman |
| 4,941,623 A | 7/1990 | Pruitt |
| 4,944,443 A | 7/1990 | Oddsen et al. |
| 5,014,899 A | 5/1991 | Presty et al. |
| 5,042,707 A | 8/1991 | Taheri |
| 5,065,929 A | 11/1991 | Schulze et al. |
| 5,071,430 A | 12/1991 | de Salis et al. |
| 5,084,057 A | 1/1992 | Green et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,171,247 A | 12/1992 | Hughett et al. |
| 5,171,249 A | 12/1992 | Stefanchik et al. |
| 5,209,747 A | 5/1993 | Knoepfler |
| 5,211,649 A | 5/1993 | Kohler et al. |
| 5,221,036 A | 6/1993 | Takase |
| 5,222,975 A | 6/1993 | Crainich |
| 5,246,443 A | 9/1993 | Mai |
| 5,258,009 A | 11/1993 | Conners |
| 5,282,806 A | 2/1994 | Haber et al. |
| 5,282,829 A | 2/1994 | Hermes |
| 5,304,204 A | 4/1994 | Bregen |
| 5,314,424 A | 5/1994 | Nicholas |
| 5,333,422 A | 8/1994 | Warren et al. |
| 5,341,724 A | 8/1994 | Vatel |
| 5,342,395 A | 8/1994 | Jarrett et al. |
| 5,342,396 A | 8/1994 | Cook |
| 5,350,400 A | 9/1994 | Esposito et al. |
| 5,352,235 A | 10/1994 | Koros et al. |
| 5,352,238 A | 10/1994 | Green et al. |
| 5,358,510 A | 10/1994 | Luscombe et al. |
| 5,366,479 A | 11/1994 | McGarry et al. |
| 5,379,933 A | 1/1995 | Green et al. |
| 5,383,880 A | 1/1995 | Hooven |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,397,324 A | 3/1995 | Carroll et al. |
| 5,405,344 A | 4/1995 | Williamson et al. |
| 5,415,334 A | 5/1995 | Williamson, IV et al. |
| 5,417,361 A | 5/1995 | Williamson, IV |
| 5,425,745 A | 6/1995 | Green et al. |
| 5,449,365 A | 9/1995 | Green et al. |
| 5,456,401 A | 10/1995 | Green et al. |
| 5,474,566 A | 12/1995 | Alesi et al. |
| 5,478,354 A | 12/1995 | Tovey et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,503,638 A | 4/1996 | Cooper et al. |
| 5,509,596 A | 4/1996 | Green et al. |
| 5,529,235 A | 6/1996 | Boiarski et al. |
| 5,533,521 A | 7/1996 | Granger |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,547,117 A | 8/1996 | Hamblin et al. |
| 5,549,628 A | 8/1996 | Cooper et al. |
| 5,553,765 A | 9/1996 | Knodel et al. |
| 5,554,169 A | 9/1996 | Green et al. |
| 5,558,665 A | 9/1996 | Kieturakis |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,624,452 A | 4/1997 | Yates |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |

| | | | | | | |
|---|---|---|---|---|---|---|
| 5,647,526 A | 7/1997 | Green et al. | | 5,878,938 A | 3/1999 | Bittner et al. |
| 5,649,937 A | 7/1997 | Bito et al. | | 5,893,506 A | 4/1999 | Powell |
| 5,651,491 A | 7/1997 | Heaton et al. | | 5,894,979 A | 4/1999 | Powell |
| 5,653,373 A | 8/1997 | Green et al. | | 5,897,562 A | 4/1999 | Bolanos et al. |
| 5,653,374 A | 8/1997 | Young et al. | | 5,901,895 A | 5/1999 | Heaton et al. |
| 5,655,698 A | 8/1997 | Yoon | | 5,906,625 A | 5/1999 | Bito et al. |
| 5,657,921 A | 8/1997 | Young et al. | | 5,908,427 A | 6/1999 | McKean et al. |
| 5,662,258 A | 9/1997 | Knodel et al. | | 5,911,353 A | 6/1999 | Bolanos et al. |
| 5,662,260 A | 9/1997 | Yoon | | 5,915,616 A | 6/1999 | Viola et al. |
| 5,667,527 A | 9/1997 | Cook | | 5,918,791 A | 7/1999 | Sorrentino et al. |
| 5,669,544 A | 9/1997 | Schulze et al. | | 5,919,198 A | 7/1999 | Graves, Jr. et al. |
| 5,673,840 A | 10/1997 | Schulze et al. | | 5,938,667 A | 8/1999 | Peyser et al. |
| 5,673,841 A | 10/1997 | Schulze et al. | | 5,941,442 A | 8/1999 | Geiste et al. |
| 5,673,842 A | 10/1997 | Bittner et al. | | 5,951,552 A | 9/1999 | Long et al. |
| 5,678,748 A | 10/1997 | Plyley et al. | | 5,951,574 A | 9/1999 | Stefanchik et al. |
| 5,680,981 A | 10/1997 | Mililli et al. | | 5,954,259 A | 9/1999 | Viola et al. |
| 5,680,982 A | 10/1997 | Schulze et al. | | 5,988,479 A | 11/1999 | Palmer |
| 5,680,983 A | 10/1997 | Plyley et al. | | 6,010,054 A | 1/2000 | Johnson et al. |
| 5,685,474 A | 11/1997 | Seeber | | 6,032,849 A | 3/2000 | Mastri et al. |
| 5,688,270 A | 11/1997 | Yates et al. | | 6,033,427 A | 3/2000 | Lee |
| 5,690,269 A | 11/1997 | Bolanos et al. | | 6,045,560 A | 4/2000 | McKean et al. |
| 5,692,668 A | 12/1997 | Schulze et al. | | 6,050,472 A | 4/2000 | Shibata |
| 5,697,543 A | 12/1997 | Burdorff | | 6,079,606 A | 6/2000 | Milliman et al. |
| 5,700,270 A | 12/1997 | Peyser et al. | | 6,083,242 A | 7/2000 | Cook |
| 5,702,408 A | 12/1997 | Wales et al. | | 6,086,600 A | 7/2000 | Kortenbach |
| 5,704,534 A | 1/1998 | Huitema et al. | | 6,099,551 A | 8/2000 | Gabbay |
| 5,706,997 A | 1/1998 | Green et al. | | 6,102,271 A | 8/2000 | Longo et al. |
| 5,706,998 A | 1/1998 | Plyley et al. | | 6,109,500 A | 8/2000 | Alli et al. |
| 5,709,334 A | 1/1998 | Sorrentino et al. | | 6,117,158 A | 9/2000 | Measamer et al. |
| 5,711,472 A | 1/1998 | Bryan | | 6,119,913 A | 9/2000 | Adams et al. |
| 5,713,505 A | 2/1998 | Huitema | | 6,126,058 A | 10/2000 | Adams et al. |
| 5,715,987 A | 2/1998 | Kelley et al. | | 6,131,789 A | 10/2000 | Schulze et al. |
| 5,715,988 A | 2/1998 | Palmer | | 6,155,473 A | 12/2000 | Tompkins et al. |
| 5,716,366 A | 2/1998 | Yates | | 6,156,056 A | 12/2000 | Kearns et al. |
| 5,718,359 A | 2/1998 | Palmer et al. | | 6,162,208 A | 12/2000 | Hipps |
| 5,725,536 A | 3/1998 | Oberlin et al. | | 6,168,605 B1 | 1/2001 | Measamer et al. |
| 5,725,554 A | 3/1998 | Simon et al. | | 6,171,330 B1 | 1/2001 | Benchetrit |
| 5,728,121 A | 3/1998 | Bimbo et al. | | 6,202,914 B1 | 3/2001 | Geiste et al. |
| 5,730,758 A | 3/1998 | Allgeyer | | 6,228,084 B1 | 5/2001 | Kirwan, Jr. |
| 5,732,871 A | 3/1998 | Clark et al. | | 6,241,139 B1 | 6/2001 | Milliman et al. |
| 5,732,872 A | 3/1998 | Bolduc et al. | | 6,241,723 B1 | 6/2001 | Heim et al. |
| 5,735,445 A | 4/1998 | Vidal et al. | | 6,250,532 B1 | 6/2001 | Green et al. |
| 5,735,874 A | 4/1998 | Measamer et al. | | 6,264,086 B1 | 7/2001 | McGuckin, Jr. |
| 5,743,456 A | 4/1998 | Jones et al. | | 6,264,087 B1 | 7/2001 | Whitman |
| 5,752,644 A | 5/1998 | Bolanos et al. | | 6,273,897 B1 | 8/2001 | Dalessandro et al. |
| 5,758,814 A | 6/1998 | Gallagher et al. | | 6,302,311 B1 | 10/2001 | Adams et al. |
| 5,762,255 A | 6/1998 | Chrisman et al. | | 6,315,184 B1 | 11/2001 | Whitman |
| 5,762,256 A | 6/1998 | Mastri et al. | | 6,325,810 B1 | 12/2001 | Hamilton et al. |
| 5,779,130 A | 7/1998 | Alesi et al. | | 6,330,965 B1 | 12/2001 | Milliman et al. |
| 5,779,131 A | 7/1998 | Knodel et al. | | 6,387,113 B1 | 5/2002 | Hawkins et al. |
| 5,779,132 A | 7/1998 | Knodel et al. | | 6,387,114 B2 | 5/2002 | Adams |
| 5,782,396 A | 7/1998 | Mastri et al. | | 6,406,440 B1 | 6/2002 | Stefanchik |
| 5,782,397 A | 7/1998 | Koukline | | RE37,814 E | 8/2002 | Allgeyer |
| 5,785,232 A | 7/1998 | Vidal et al. | | 6,436,107 B1 | 8/2002 | Wang et al. |
| 5,794,834 A | 8/1998 | Hamblin et al. | | 6,443,973 B1 | 9/2002 | Whitman |
| 5,797,536 A | 8/1998 | Smith et al. | | 6,482,200 B2 | 11/2002 | Shippert |
| 5,797,537 A | 8/1998 | Oberlin et al. | | 6,488,197 B1 | 12/2002 | Whitman |
| 5,797,538 A | 8/1998 | Heaton et al. | | 6,491,201 B1 | 12/2002 | Whitman |
| 5,799,857 A | 9/1998 | Robertson et al. | | 6,494,896 B1 | 12/2002 | D'Alessio et al. |
| 5,807,393 A | 9/1998 | Williamson, IV et al. | | 6,503,257 B2 | 1/2003 | Grant et al. |
| 5,820,009 A | 10/1998 | Melling et al. | | 6,505,768 B2 | 1/2003 | Whitman |
| 5,826,776 A | 10/1998 | Schulze et al. | | 6,517,565 B1 | 2/2003 | Whitman et al. |
| 5,829,662 A | 11/1998 | Allen et al. | | 6,569,171 B2 | 5/2003 | DeGuillebon et al. |
| 5,833,690 A | 11/1998 | Yates et al. | | 6,578,751 B2 | 6/2003 | Hartwick |
| 5,833,695 A | 11/1998 | Yoon | | 6,588,643 B2 | 7/2003 | Bolduc et al. |
| 5,836,503 A | 11/1998 | Ehrenfels et al. | | 6,592,597 B2 | 7/2003 | Grant et al. |
| 5,839,639 A | 11/1998 | Sauer et al. | | 6,601,749 B2 | 8/2003 | Sullivan et al. |
| 5,855,311 A | 1/1999 | Hamblin et al. | | 6,602,252 B2 | 8/2003 | Mollenauer |
| 5,865,361 A | 2/1999 | Milliman et al. | | 6,616,686 B2 | 9/2003 | Coleman et al. |
| 5,868,760 A | 2/1999 | McGuckin, Jr. | | 6,619,529 B2 | 9/2003 | Green et al. |
| 5,871,135 A | 2/1999 | Williamson, IV et al. | | 6,620,166 B1 | 9/2003 | Wenstrom, Jr. et al. |
| 5,876,401 A | 3/1999 | Schulze et al. | | 6,629,988 B2 | 10/2003 | Weadock |
| 5,878,937 A | 3/1999 | Green et al. | | 6,644,532 B2 | 11/2003 | Green et al. |

| | | |
|---|---|---|
| 6,656,193 B2 | 12/2003 | Grant et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,682,528 B2 | 1/2004 | Frazier et al. |
| 6,695,199 B2 | 2/2004 | Whitman |
| 6,698,643 B2 | 3/2004 | Whitman |
| 6,716,233 B1 | 4/2004 | Whitman |
| 6,723,087 B2 | 4/2004 | O'Neill et al. |
| 6,752,768 B2 | 6/2004 | Burdorff et al. |
| 6,755,338 B2 | 6/2004 | Hahnen et al. |
| 6,767,356 B2 | 7/2004 | Kanner et al. |
| 6,773,438 B1 | 8/2004 | Knodel et al. |
| 6,786,382 B1 | 9/2004 | Hoffman |
| 6,786,896 B1 | 9/2004 | Madhani et al. |
| 6,793,652 B1 | 9/2004 | Whitman et al. |
| 6,805,273 B2 | 10/2004 | Bilotti et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,821,273 B2 | 11/2004 | Mollenauer |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,874,669 B2 | 4/2005 | Adams et al. |
| 6,877,647 B2 | 4/2005 | Ratcliff et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,055,730 B2 | 6/2006 | Ehrenfels et al. |
| 7,055,731 B2 | 6/2006 | Shelton, IV et al. |
| 7,056,330 B2 | 6/2006 | Gayton |
| 7,059,508 B2 | 6/2006 | Shelton, IV et al. |
| 7,070,083 B2 | 7/2006 | Jankowski |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,090,673 B2 | 8/2006 | Dycus et al. |
| 7,090,684 B2 | 8/2006 | McGuckin, Jr. et al. |
| 7,097,089 B2 | 8/2006 | Marczyk |
| 7,108,695 B2 | 9/2006 | Witt et al. |
| 7,108,709 B2 | 9/2006 | Cummins |
| 7,111,769 B2 | 9/2006 | Wales et al. |
| 7,112,214 B2 | 9/2006 | Peterson et al. |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,160,299 B2 | 1/2007 | Baily |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,964 B2 | 6/2007 | Mastri et al. |
| 7,235,089 B1 | 6/2007 | McGuckin, Jr. |
| 7,238,195 B2 | 7/2007 | Viola |
| 7,241,288 B2 | 7/2007 | Braun |
| 7,246,734 B2 | 7/2007 | Shelton, IV |
| 7,258,262 B2 | 8/2007 | Mastri et al. |
| 7,278,563 B1 | 10/2007 | Green |
| 7,296,724 B2 | 11/2007 | Green et al. |
| 7,297,149 B2 | 11/2007 | Vitali et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,556 B2 | 12/2007 | Metzger |
| 7,328,828 B2 | 2/2008 | Ortiz et al. |
| 7,328,829 B2 | 2/2008 | Arad et al. |
| 7,343,920 B2 | 3/2008 | Toby et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,510,107 B2 | 3/2009 | Timm et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,588,175 B2 | 9/2009 | Timm et al. |

| Patent/Publication | Date | Inventors |
|---|---|---|
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,631,793 B2 | 12/2009 | Rethy et al. |
| 7,641,093 B2 | 1/2010 | Doll et al. |
| 7,658,311 B2 | 2/2010 | Boudreaux |
| 7,665,646 B2 | 2/2010 | Prommersberger |
| 7,669,747 B2 | 3/2010 | Weisenburgh, II et al. |
| 7,673,782 B2 | 3/2010 | Hess et al. |
| 2002/0117534 A1 | 8/2002 | Green et al. |
| 2002/0165541 A1 | 11/2002 | Whitman |
| 2004/0006372 A1 | 1/2004 | Racenet et al. |
| 2004/0034369 A1 | 2/2004 | Sauer et al. |
| 2004/0044364 A1 | 3/2004 | DeVries et al. |
| 2004/0094597 A1 | 5/2004 | Whitman et al. |
| 2004/0108357 A1 | 6/2004 | Milliman et al. |
| 2004/0111081 A1 | 6/2004 | Whitman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0243176 A1 | 12/2004 | Hahnen et al. |
| 2004/0254608 A1 | 12/2004 | Huitema et al. |
| 2005/0054946 A1 | 3/2005 | Krzyzanowski |
| 2005/0059997 A1 | 3/2005 | Bauman et al. |
| 2005/0080454 A1 | 4/2005 | Drews et al. |
| 2005/0103819 A1 | 5/2005 | Racenet et al. |
| 2005/0107824 A1 | 5/2005 | Hillstead et al. |
| 2005/0119669 A1 | 6/2005 | Demmy |
| 2005/0125009 A1 | 6/2005 | Perry et al. |
| 2005/0131390 A1 | 6/2005 | Heinrich et al. |
| 2005/0131457 A1 | 6/2005 | Douglas et al. |
| 2005/0143759 A1 | 6/2005 | Kelly |
| 2005/0171522 A1 | 8/2005 | Christopherson |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0256522 A1 | 11/2005 | Francischelli et al. |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085031 A1 | 4/2006 | Bettuchi |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0122636 A1 | 6/2006 | Bailly et al. |
| 2006/0149163 A1 | 7/2006 | Hibner et al. |
| 2006/0151567 A1 | 7/2006 | Roy |
| 2006/0180634 A1 | 8/2006 | Shelton, IV et al. |
| 2006/0217729 A1 | 9/2006 | Eskridge et al. |
| 2006/0226196 A1 | 10/2006 | Hueil et al. |
| 2006/0241655 A1 | 10/2006 | Viola |
| 2006/0241692 A1 | 10/2006 | McGuckin, Jr. et al. |
| 2006/0273135 A1 | 12/2006 | Beetel |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0034668 A1 | 2/2007 | Holsten, IV |
| 2007/0045379 A1 | 3/2007 | Shelton, IV |
| 2007/0055219 A1 | 3/2007 | Whitman et al. |
| 2007/0073340 A1 | 3/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0246505 A1 | 10/2007 | Pace-Floridia et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |

| | | |
|---|---|---|
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314955 A1 | 12/2008 | Boudreaux et al. |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0090763 A1 | 4/2009 | Zemlok et al. |
| 2009/0200355 A1 | 8/2009 | Baxter, III et al. |
| 2009/0206123 A1 | 8/2009 | Doll et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206136 A1 | 8/2009 | Moore et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2009/0292283 A1 | 11/2009 | Odom |
| 2010/0032470 A1 | 2/2010 | Hess et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096435 A1 | 4/2010 | Fuchs et al. |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 1775926 A | 1/1972 |
| DE | 9412228 U | 9/1994 |
| DE | 19924311 A1 | 11/2000 |
| DE | 69328576 T2 | 1/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0070230 B1 | 10/1985 |
| EP | 0033548 B1 | 5/1986 |
| EP | 0276104 A2 | 7/1988 |
| EP | 0639349 A2 | 2/1994 |
| EP | 0324636 B1 | 3/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0667119 B1 | 7/1996 |
| EP | 0770355 A1 | 5/1997 |
| EP | 0503662 B1 | 6/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0676173 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0760230 B1 | 2/1999 |
| EP | 0537572 B1 | 6/1999 |
| EP | 0552050 B1 | 5/2000 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0741996 B1 | 2/2004 |
| EP | 0705570 B1 | 4/2004 |
| EP | 1086713 B1 | 5/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |

| | | | | | | |
|---|---|---|---|---|---|---|
| EP | 1479348 | A1 | 11/2004 | WO | WO 97/39688 A2 | 10/1997 |
| EP | 1520521 | A1 | 4/2005 | WO | WO 98/17180 A1 | 4/1998 |
| EP | 1520523 | A1 | 4/2005 | WO | WO 98/30153 A1 | 7/1998 |
| EP | 1520525 | A1 | 4/2005 | WO | WO 99/12483 A1 | 3/1999 |
| EP | 1522264 | A1 | 4/2005 | WO | WO 99/15086 A1 | 4/1999 |
| EP | 1550408 | A1 | 7/2005 | WO | WO 99/34744 A1 | 7/1999 |
| EP | 1557129 | A1 | 7/2005 | WO | WO 99/45849 A1 | 9/1999 |
| EP | 1064883 | B1 | 8/2005 | WO | WO 00/24322 A1 | 5/2000 |
| EP | 1157666 | B1 | 9/2005 | WO | WO 00/57796 A1 | 10/2000 |
| EP | 1621138 | A2 | 2/2006 | WO | WO 00/64365 A1 | 11/2000 |
| EP | 1621139 | A2 | 2/2006 | WO | WO 00/72762 A1 | 12/2000 |
| EP | 1621141 | A2 | 2/2006 | WO | WO 00/72765 A1 | 12/2000 |
| EP | 1621145 | A2 | 2/2006 | WO | WO 01/05702 A1 | 1/2001 |
| EP | 1652481 | A2 | 5/2006 | WO | WO 01/10482 A1 | 2/2001 |
| EP | 1382303 | B1 | 6/2006 | WO | WO 01/54594 A1 | 8/2001 |
| EP | 1045672 | B1 | 8/2006 | WO | WO 01/62158 A1 | 8/2001 |
| EP | 1617768 | B1 | 8/2006 | WO | WO 01/62162 A1 | 8/2001 |
| EP | 1702567 | A2 | 9/2006 | WO | WO 01/62164 A2 | 8/2001 |
| EP | 1129665 | B1 | 11/2006 | WO | WO 01/91646 A1 | 12/2001 |
| EP | 1256317 | B1 | 12/2006 | WO | WO 02/07608 A2 | 1/2002 |
| EP | 1728473 | A1 | 12/2006 | WO | WO 02/07618 A1 | 1/2002 |
| EP | 1728475 | A2 | 12/2006 | WO | WO 02/17799 A1 | 3/2002 |
| EP | 1479346 | B1 | 1/2007 | WO | WO 02/19920 A1 | 3/2002 |
| EP | 1484024 | B1 | 1/2007 | WO | WO 02/30297 A2 | 4/2002 |
| EP | 1754445 | A2 | 2/2007 | WO | WO 02/32322 A2 | 4/2002 |
| EP | 1759812 | A1 | 3/2007 | WO | WO 02/43571 A2 | 6/2002 |
| EP | 1769756 | A1 | 4/2007 | WO | WO 02/058568 A1 | 8/2002 |
| EP | 1769758 | A1 | 4/2007 | WO | WO 02/060328 A1 | 8/2002 |
| EP | 1785097 | A2 | 5/2007 | WO | WO 02/067785 A2 | 9/2002 |
| EP | 1790293 | A2 | 5/2007 | WO | WO 02/098302 A1 | 12/2002 |
| EP | 1300117 | B1 | 8/2007 | WO | WO 03/000138 A2 | 1/2003 |
| EP | 1813199 | A1 | 8/2007 | WO | WO 03/001329 A2 | 1/2003 |
| EP | 1813201 | A1 | 8/2007 | WO | WO 03/013363 A1 | 2/2003 |
| EP | 1813203 | A2 | 8/2007 | WO | WO 03/020106 A2 | 3/2003 |
| EP | 1813207 | A1 | 8/2007 | WO | WO 03/020139 A2 | 3/2003 |
| EP | 1813209 | A1 | 8/2007 | WO | WO 03/079909 A3 | 3/2003 |
| EP | 1839596 | A1 | 10/2007 | WO | WO 03/030743 A2 | 4/2003 |
| EP | 1872727 | A1 | 1/2008 | WO | WO 03/037193 A1 | 5/2003 |
| EP | 1897502 | A1 | 3/2008 | WO | WO 03/047436 A3 | 6/2003 |
| EP | 1702568 | B1 | 7/2008 | WO | WO 03/057048 A1 | 7/2003 |
| EP | 1980213 | A2 | 10/2008 | WO | WO 03/057058 A1 | 7/2003 |
| EP | 1759645 | B1 | 11/2008 | WO | WO 03/063694 A1 | 8/2003 |
| EP | 1693008 | B1 | 12/2008 | WO | WO 03/077769 A1 | 9/2003 |
| EP | 1749486 | B1 | 3/2009 | WO | WO 03/082126 A1 | 10/2003 |
| EP | 2090256 | A2 | 8/2009 | WO | WO 03/088845 A2 | 10/2003 |
| EP | 1813206 | B1 | 4/2010 | WO | WO 03/090630 A2 | 11/2003 |
| FR | 999646 | A | 2/1952 | WO | WO 03/094743 A1 | 11/2003 |
| FR | 1112936 | A | 3/1956 | WO | WO 03/094745 A1 | 11/2003 |
| FR | 2765794 | A | 1/1999 | WO | WO 03/094746 A1 | 11/2003 |
| GB | 939929 | A | 10/1963 | WO | WO 03/094747 A1 | 11/2003 |
| GB | 1210522 | A | 10/1970 | WO | WO 03/101313 A1 | 12/2003 |
| GB | 2336214 | A | 10/1999 | WO | WO 03/105698 A2 | 12/2003 |
| JP | 6007357 | A | 1/1994 | WO | WO 03/105702 A2 | 12/2003 |
| JP | 7051273 | A | 2/1995 | WO | WO 2004/006980 A2 | 1/2004 |
| JP | 8033641 | A | 2/1996 | WO | WO 2004/028585 A2 | 4/2004 |
| JP | 8229050 | A | 9/1996 | WO | WO 2004/032754 A2 | 4/2004 |
| JP | 2000287987 | A | 10/2000 | WO | WO 2004/032760 A2 | 4/2004 |
| JP | 2001286477 | A | 10/2001 | WO | WO 2004/032762 A2 | 4/2004 |
| JP | 2002369820 | A | 12/2002 | WO | WO 2004/032763 A2 | 4/2004 |
| JP | 2005505322 | T | 2/2005 | WO | WO 2004/047653 A2 | 6/2004 |
| JP | 2005103293 | A | 4/2005 | WO | WO 2004/049956 A2 | 6/2004 |
| RU | 2187249 | C2 | 8/2002 | WO | WO 2004/086987 A1 | 10/2004 |
| RU | 2225170 | C2 | 3/2004 | WO | WO 2004/096057 A2 | 11/2004 |
| SU | 1377053 | A1 | 2/1988 | WO | WO 2004/105621 A1 | 12/2004 |
| SU | 1561964 | A1 | 5/1990 | WO | WO 2004/112618 A2 | 12/2004 |
| SU | 1722476 | A1 | 3/1992 | WO | WO 2004/112652 A2 | 12/2004 |
| WO | WO 93/08755 | A1 | 5/1993 | WO | WO 2005/027983 A2 | 3/2005 |
| WO | WO 95/18572 | A1 | 7/1995 | WO | WO 2005/037329 A2 | 4/2005 |
| WO | WO 95/23557 | A1 | 9/1995 | WO | WO 2005/078892 A1 | 8/2005 |
| WO | WO 95/29639 | A1 | 11/1995 | WO | WO 2005/096954 A2 | 10/2005 |
| WO | WO 96/22055 | A1 | 7/1996 | WO | WO 2005/112808 A1 | 12/2005 |
| WO | WO 96/35464 | A1 | 11/1996 | WO | WO 2005/115251 A2 | 12/2005 |
| WO | WO 97/34533 | A1 | 9/1997 | WO | WO 2006/044490 A2 | 4/2006 |

| | | |
|---|---|---|
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.
7539?cookieSet=1&journalCode=vsu which redirects to http://www3.interscience.wiley.com/journal/119040681/
abstract?CRETRY=1&SRETRY=0; [online] accessed: Sep. 22, 2008 (2 pages).

U.S. Appl. No. 12/031,628, filed Feb. 14, 2008.
U.S. Appl. No. 12/031,611, filed Feb. 14, 2008.
U.S. Appl. No. 11/729,008, filed Mar. 28, 2007.
U.S. Appl. No. 12/031,001, filed Feb. 14, 2008.
U.S. Appl. No. 11/821,277, filed Jun. 22, 2007.
U.S. Appl. No. 12/031,368, filed Feb. 14, 2008.
U.S. Appl. No. 12/031,326, filed Feb. 14, 2008.
U.S. Appl. No. 12/030,980, filed Feb. 14, 2008.
U.S. Appl. No. 12/031,066, filed Feb. 14, 2008.
U.S. Appl. No. 12/030,974, filed Feb. 14, 2008.
The Sodem Aseptic Battery Transfer Kit, Sodem Systems, 2000, 3 pages.

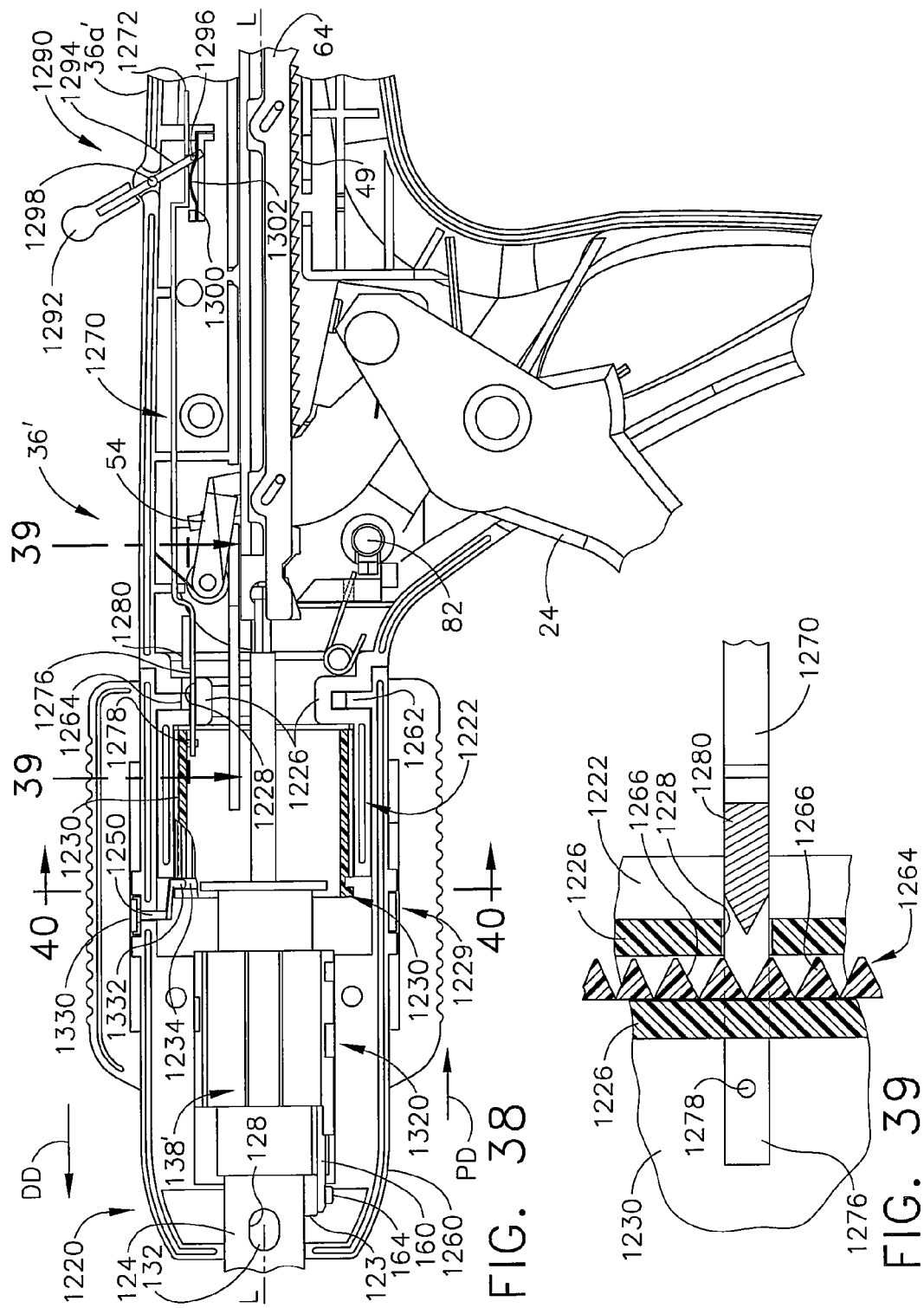

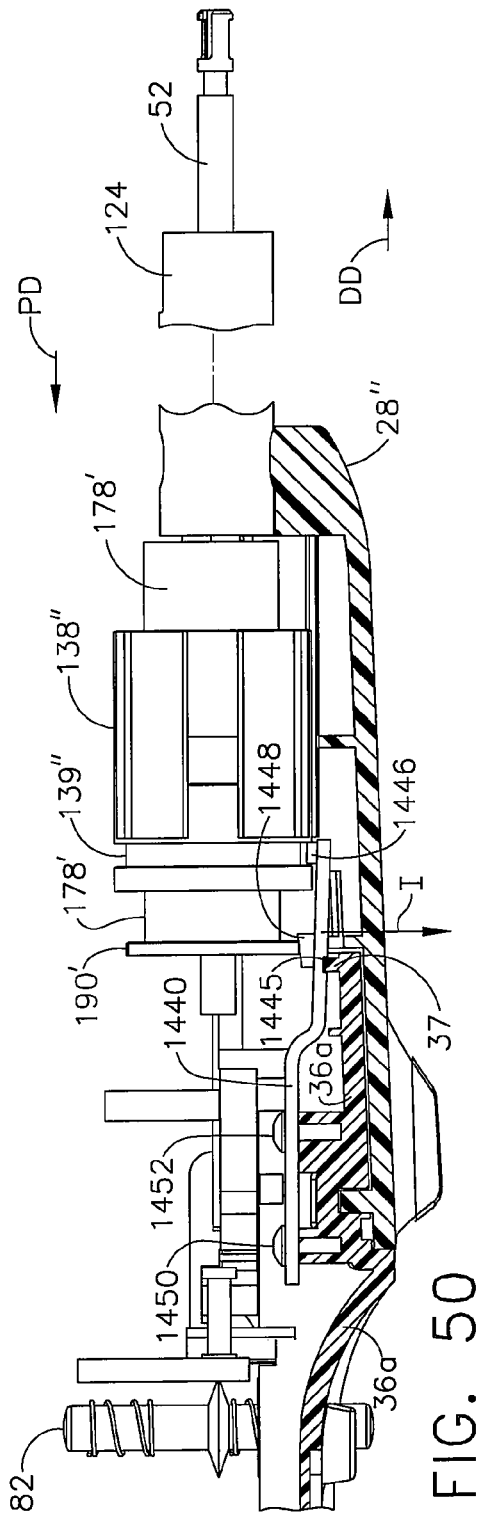
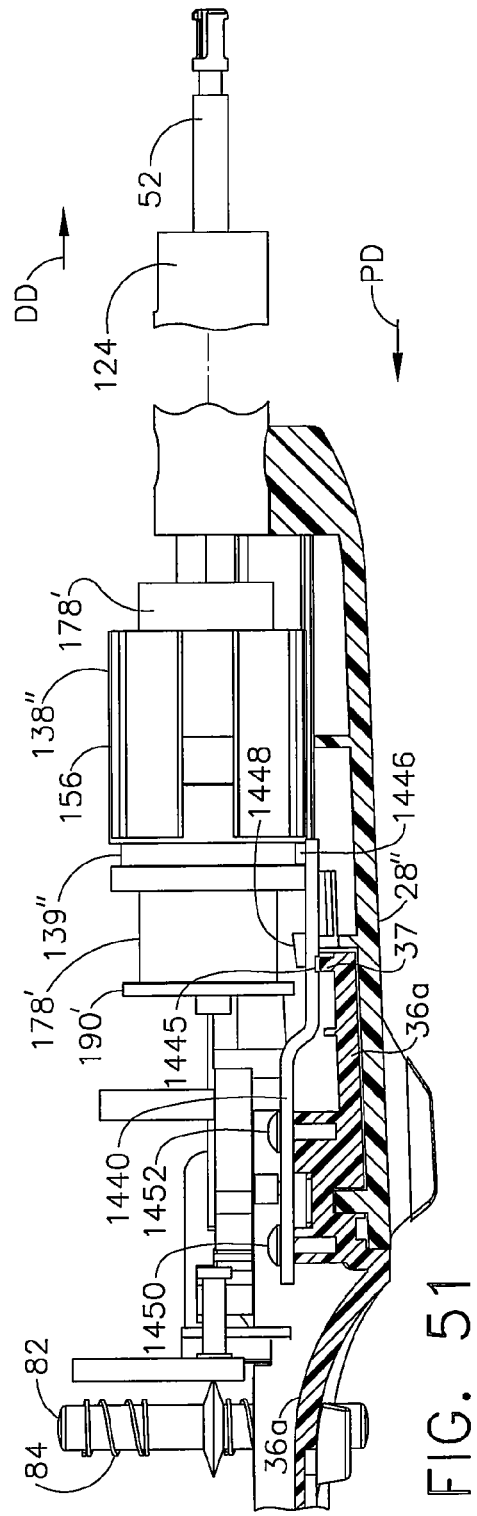

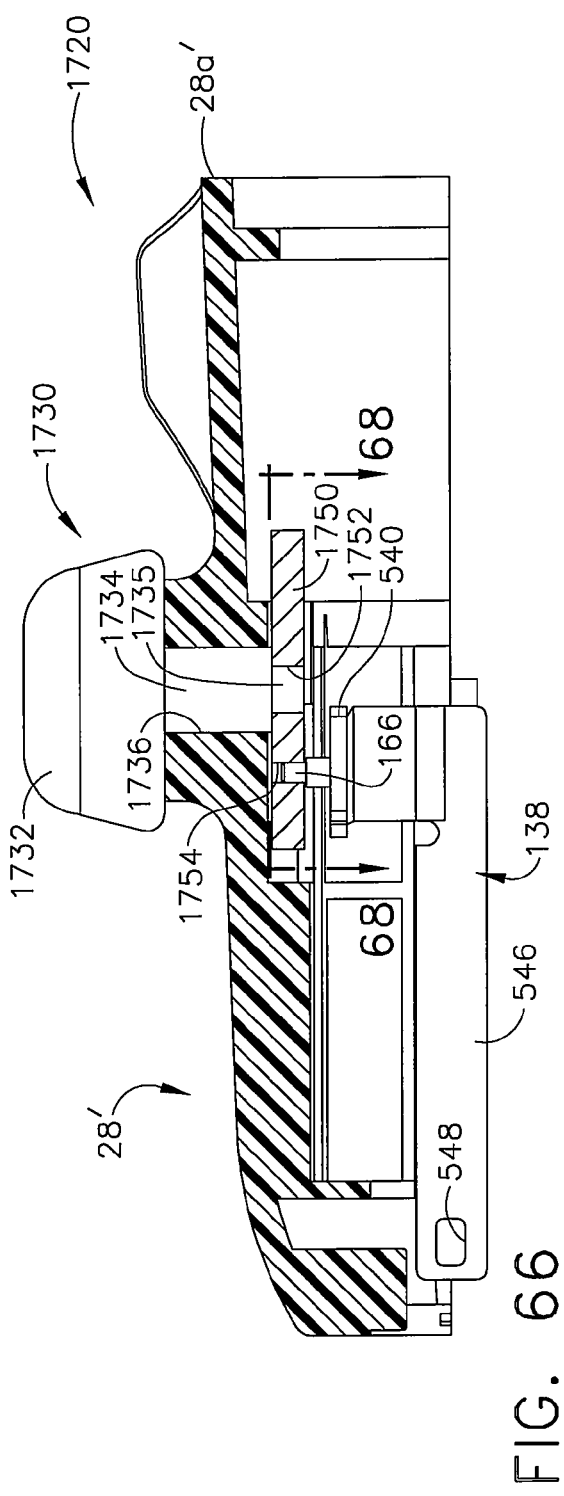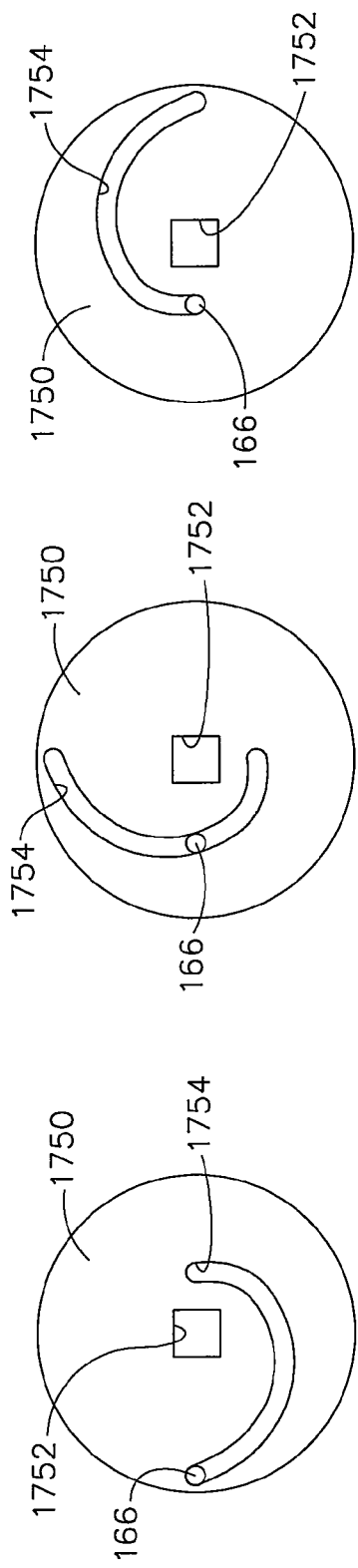

SURGICAL STAPLING APPARATUS WITH CONTROL FEATURES OPERABLE WITH ONE HAND

FIELD OF THE INVENTION

The present invention relates in general to endoscopic surgical instruments including, but not limited to, surgical stapler instruments that have disposable loading units that are capable of applying lines of staples to tissue while cutting the tissue between those staple lines and, more particularly, to improvements relating to such instruments and disposable loading units.

BACKGROUND

The following U.S. Patent applications which are herein incorporated by reference are commonly owned by the Assignee of the present application:
(1) U.S. patent application Ser. No. 12/031,368 entitled Surgical Stapling Apparatus With Load-Sensitive Firing Mechanism to Geoffrey C. Hueil et al.;
(2) U.S. patent application Ser. No. 12/031,326, now U.S. Patent Publication No. 2009/0206130, entitled Surgical Stapling Apparatus With Interlockable Firing System to Steven G. Hall et al.;
(3) U.S. patent application Ser. No. 12/031,001, now U.S. Patent Publication No. 2009/0206133, entitled Articulatable Loading Units For Surgical Stapling and Cutting Instruments to Jerome R. Morgan et al.;
(4) U.S. patent application Ser. No. 12/030,980, now U.S. Patent Publication No. 2009/0206123, entitled Surgical Stapling Apparatus With Reprocessible Handle Assembly to Kevin R. Doll et al.;
(5) U.S. patent application Ser. No. 12/031,066, now U.S. Patent Publication No. 2009/0206129, entitled Surgical Stapling Apparatus With Articulatable Components to Kevin R. Doll et al.;
(6) U.S. patent application Ser. No. 12/030,974, now U.S. Patent Publication No. 2009/0206128, entitled Surgical Stapling Apparatus With Retractable Firing Systems to Geoffrey C. Hueil et al.

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument commonly includes a plurality of reciprocating wedges which, when driven distally, pass through openings in the staple cartridge and engage drivers supporting the staples to effect the firing of the staples toward the anvil.

Different types of surgical staplers suitable for endoscopic applications are known. For example, one type of surgical stapler employs a staple cartridge. The staple cartridge typically supports a plurality of staples oriented on both sides of a longitudinally extending slot in the cartridge body that is adapted to receive a cutting member that is driven longitudinally therethrough. As the cutting member is driven through the cartridge slot, the staples are driven upward into the anvil portion of the instrument. The cutting member may be supported on a driven member that comprises a portion of the instrument apart from the cartridge. Examples of those types of devices are described in U.S. Pat. No. 6,905,057 to Jeffrey S. Swayze and Frederick E. Shelton, IV, entitled Surgical Stapling Instrument Incorporating a Firing Mechanism Having a Linked Rack Transmission and U.S. Pat. No. 7,083,075 to Jeffery S. Swayze, Frederick E. Shelton, IV, Kevin Ross Doll, and Douglas B. Hoffman entitled Multi-Stroke Mechanism With Automatic End of Stroke Retractions, the disclosures of which are herein incorporated by reference in their entireties.

Other types of surgical stapling instruments are configured to operate with disposable loading units (DLU's) that are constructed to support a cartridge and knife assembly therein. Such devices that are designed to accommodate DLU's purport to offer the advantage of a "fresh" knife blade for each firing of the instrument. An example of such surgical stapling instrument and DLU arrangement is disclosed in U.S. Pat. No. 5,865,361 to Milliman et al., the disclosure of which is herein incorporated by reference in its entirety.

Depending upon the nature of the operation, it may be desirable to adjust the positioning of the DLU or end effector of an endoscopic surgical instrument. In particular, it is often desirable to orient the DLU or end effector at an angle relative to the longitudinal axis of the shaft of the instrument. The transverse or non-axial movement of the DLU or end effector relative to the instrument shaft is often conventionally referred to as "articulation". This articulated positioning permits the clinician to more easily engage tissue in some instances, such as behind an organ. In addition, articulated positioning advantageously allows a DLU or an endoscope to be positioned behind the end effector without being blocked by the instrument shaft.

Approaches to articulating a surgical stapling apparatus tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 to Schulze et al., the disclosure of which is herein incorporated by reference, discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation. Still other examples of articulatable surgical stapling devices are disclosed in U.S. Pat. Nos. 6,250,532 and 6,644,532.

Due to the types firing systems commonly employed in connection with DLU's, the actuator arrangements for articulating the DLU must often generate high amounts of torque to bend the firing structure. This problem is exacerbated by the lack of available space for accommodating actuating devices that are large enough to generate those required forces. In addition, prior articulation arrangements required the clinician to use two hands to articulate the device.

Thus, there is a need for a surgical cutting and stapling instrument that is configured to accommodate DLU's and has improved articulation capabilities including the ability to articulate the instrument using one hand.

SUMMARY

In one aspect of the invention, there is provided a surgical stapling apparatus that may have a handle assembly that includes a handle housing and a movable handle that is movable relative to the handle housing through an actuation stroke. An actuation shaft may be supported at least in part within the handle housing and may be mounted to generate actuation motions in response to manipulation of the movable handle. A rotatable shroud may be movably coupled to the handle housing and have an elongated body coupled thereto for rotational travel therewith about a longitudinal axis defined by the elongated body. The elongated body may have a distal end that is configured to be operably attached to a disposable loading unit and a proximal end that is configured to interface with the actuation shaft to transfer the actuation motions from the actuation shaft to the disposable loading unit. The surgical stapling apparatus may further have a lockable rotation system for selectively locking the rotatable shroud to prevent rotation thereof about the longitudinal axis.

In another general aspect of various embodiments of the present invention, there is provided a surgical stapling apparatus that may have a handle assembly that includes a movable handle and a stationary handle housing. The movable handle may be movable through actuation strokes relative to the stationary handle housing. An actuation shaft may be supported at least in part within the handle housing and may be mounted to generate actuation motions in response to manipulation of the movable handle. The surgical stapling apparatus may further include an elongated body that has a distal end that is configured to be operably attached to a disposable loading unit and a proximal end that interfaces with the actuation shaft to transfer the actuation motions from the actuation shaft to the disposable loading unit. An articulation system may be operably supported by the handle assembly and configured to interface with the elongated body to selectively apply articulation motions thereto in response to manipulation of an articulation trigger operably supported adjacent the movable handle such that the articulation trigger may be operated by a same hand used to manipulate the movable handle.

In still another general aspect of various embodiments of the present invention there is provided a surgical stapling apparatus that may have a handle assembly that includes a movable handle and a handle housing. The movable handle may be movable through actuation strokes relative to the handle housing. An actuation shaft may be supported at least in part within the handle housing and may be mounted for longitudinal movement therein in response to manipulation of the movable handle through the actuation strokes. The surgical stapling apparatus may further have an elongated body that protrudes from the handle housing. The elongated body may have a distal end that is configured to be operably attached to a disposable loading unit and a proximal end that is configured to interface with the actuation shaft to transfer the actuation motions from the actuation shaft to the disposable loading unit. An articulation system may be operably supported by the handle assembly and be configured to interface with the elongated body to selectively apply articulation motions thereto. A selector arrangement may be configured to interface with the movable handle, the actuation shaft and the articulation system such that when the selector arrangement is in a firing orientation, manipulation of the movable handle through the actuation strokes actuates the actuation shaft and when the selector arrangement is in an articulation orientation, manipulation of the movable handle through the actuation strokes actuates the articulation system.

In another general aspect of various embodiments of the present invention, there is provided an articulation mechanism for a surgical stapling apparatus that may have a handle housing and an elongated body that protrudes from the handle housing and is configured to be operably coupled to an articulatable disposable loading unit that is responsive to axial motions transmitting by the elongated body. Various embodiments of the articulation mechanism may include a translation member that is movably supported within a portion of the handle housing for selective longitudinal movement therein. The translation member may interface with the elongated body. A rotatable cam disc may be rotatably supported by the handle assembly and configured to interface with the translation member such that rotation of the cam disc in a first direction moves the translation member in a first axial direction and rotation of the rotatable cam disc in a second direction moves the translation member in a second axial direction.

In another general aspect of various embodiments of the present invention, there is provided an articulation mechanism for a surgical stapling apparatus that has a handle housing and an elongated body that protrudes from the handle housing and is configured to be operably coupled to an articulatable disposable loading unit that is responsive to axial motions transmitted by the elongated body. Various embodiments of the articulation mechanism may comprise a translation member that is movably supported within a portion of the handle housing for selective longitudinal movement therein. The translation member may interface with the elongated body. An articulation ring may be rotatably supported within a portion of the handle assembly and be configured to operably interface with the translation member such that rotation of the articulation ring within the handle housing in a first direction moves the translation member in a first axial direction and rotation of the articulation ring in a second direction moves the translation member in a second axial direction. An articulation knob may be movably supported by the handle housing and may also be configured to interface with the articulation ring to impart rotary motions thereto.

BRIEF DESCRIPTION OF THE FIGURES

The accompanying drawings, which are incorporated in and constitute a part of this specification, illustrate embodiments of the invention, and, together with the general description of various embodiments of the invention given above, and the detailed description of the embodiments given below, serve to explain various principles of the present invention.

FIG. 38 is a side view of the portion of the surgical stapling apparatus embodiment depicted in FIG. 36 with the selector switch thereof in a distal unlocked position.

FIG. 39 is an enlarged view of the bolt disengaged from the rotation lock ring when the apparatus is in the rotation mode.

FIG. 50 is a partial top view of the handle assembly depicted in FIG. 49 with some components shown in cross-section and with the articulation system thereof in a locked position.

FIG. 51 is a partial top view of the handle assembly depicted in FIGS. 49 and 50 with some components shown in cross-section and with the articulation system thereof in an unlocked position.

FIG. 66 is a partial top cross-sectional view of the articulation mechanism of FIG. 65.

FIG. 67 illustrates a position of the cam disc and articulation pin of the articulation mechanism embodiment of FIGS. 65 and 66 in a left articulated position.

FIG. 68 illustrates a position of the cam disc and articulation pin of the articulation mechanism embodiment of FIGS. 65 and 66 in a straight (non-articulated) position.

FIG. 69 illustrates a position of the cam disc and articulation pin of the articulation mechanism embodiment of FIGS. 65 and 66 in a right articulated position.

FIG. 10 is a perspective view of the disposable loading unit of FIGS. 98-100 illustrating passive articulation travel and active articulation travel thereof.

FIG. 117 is a perspective view of another articulation system embodiment of the present invention.

FIG. 118 is an exploded assembly view of the articulation system of FIG. 117.

FIG. 119 is a side assembly view of a portion of the articulation system of FIGS. 117 and 118 with some components thereof shown in cross-section for clarity.

FIG. 120 is a partial perspective assembly view of various articulation bar and pin embodiments of the present invention.

FIG. 121 is a cross-sectional view of the articulation bar and pin embodiments depicted in FIG. 120.

FIG. 122 is a perspective view of another surgical stapling apparatus embodiment of the present invention employed in connection with a conventional trocar to perform an endoscopic surgical procedure.

FIG. 123 is an exploded partial assembly view of an articulation system embodiment of the surgical stapling apparatus of FIG. 122.

DETAILED DESCRIPTION

Figure 1:
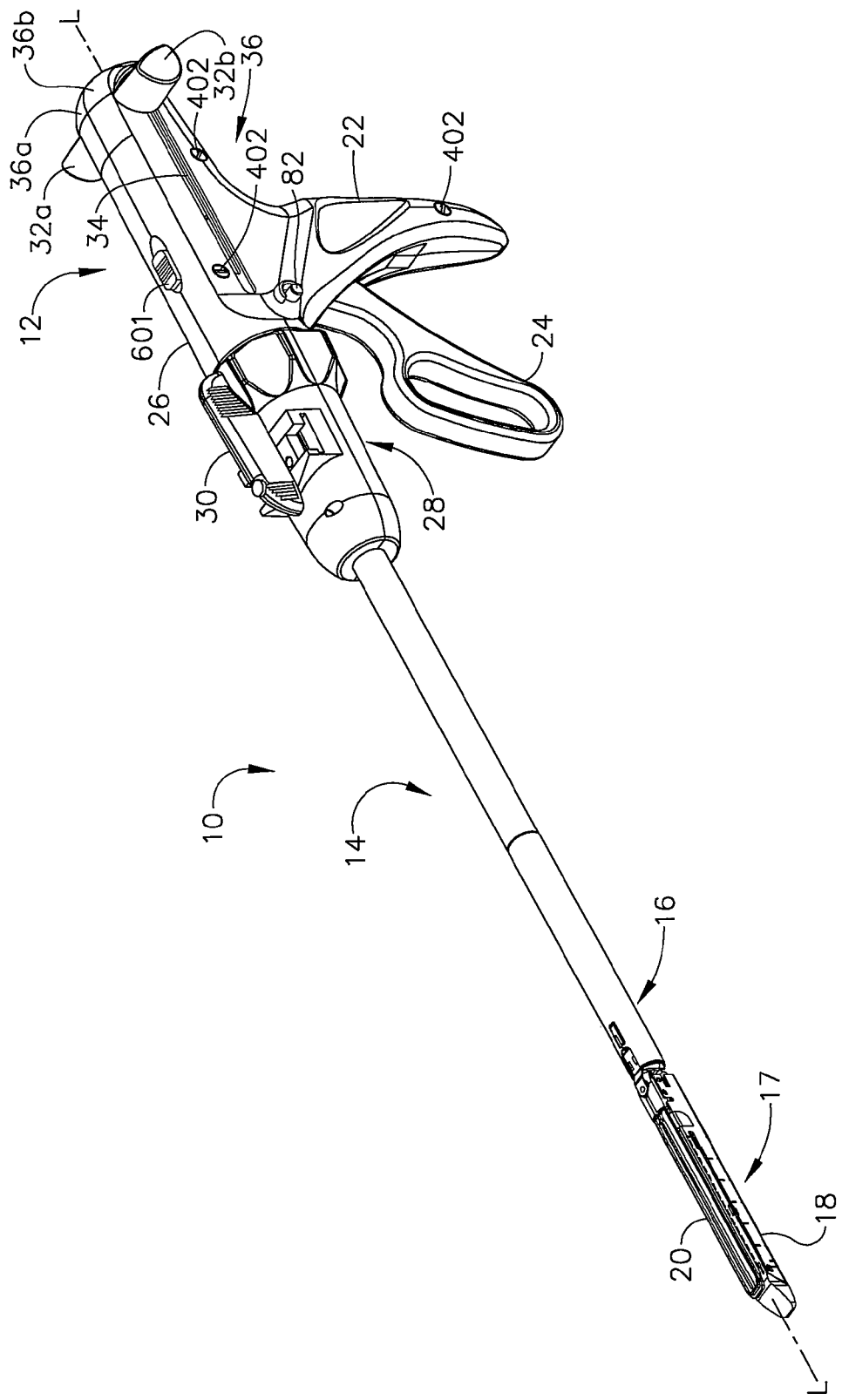
FIG. 1 is a perspective view of a reusable surgical stapling apparatus of various embodiments of the present invention with an articulatable disposable loading unit coupled thereto.
Figure 2:
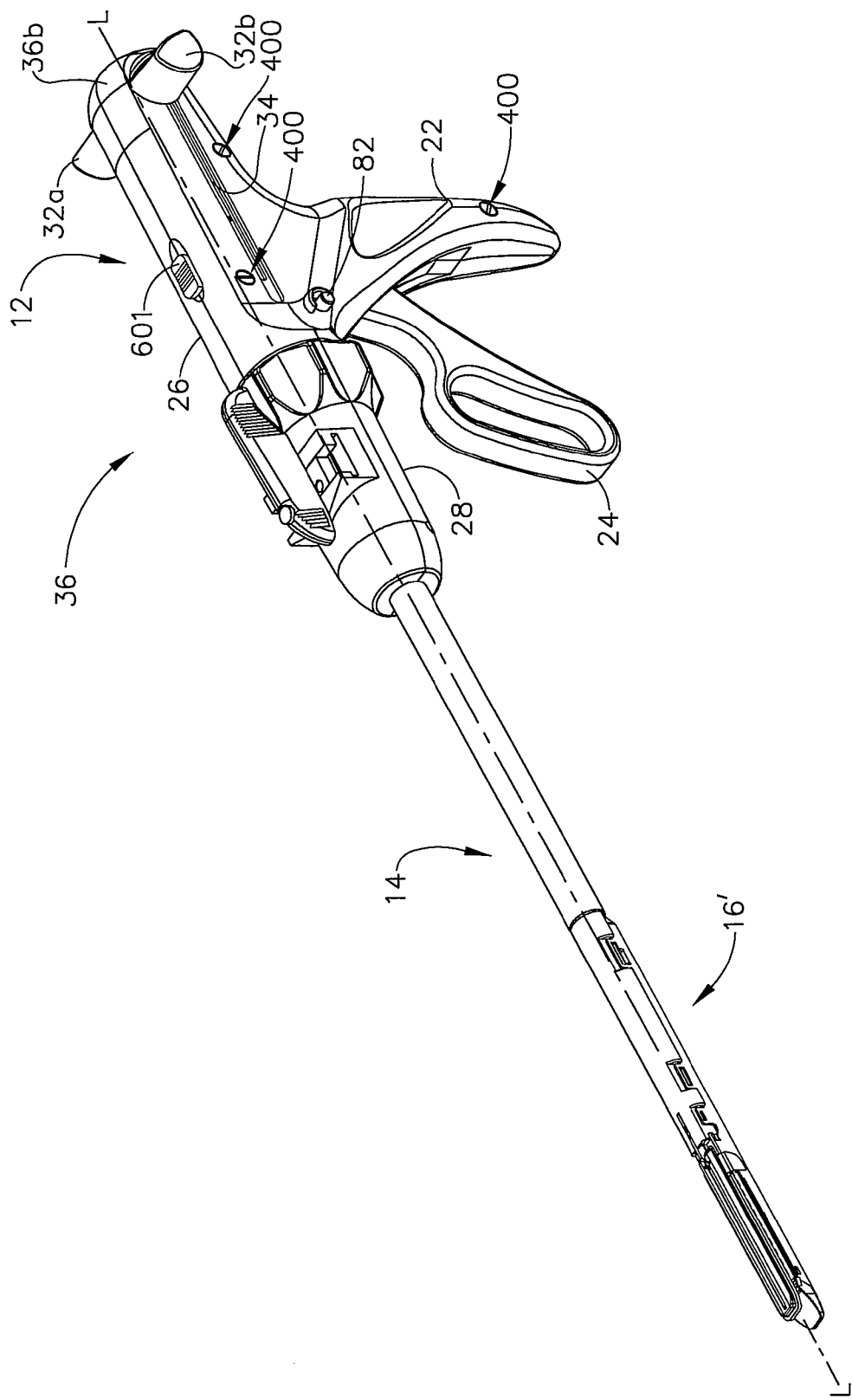
FIG. 2 is a perspective view of a reusable surgical stapling apparatus of various embodiments of the present invention with a non-articulatable disposable loading unit coupled thereto.

Turning to the Drawings, wherein like numerals denote like components throughout the several views, FIG. 1 depicts a reusable surgical instrument, which in the illustrative versions is more particularly a surgical stapling apparatus 10, capable of practicing the unique benefits of various embodiments of the present invention. The surgical stapling apparatus 10 may include a handle assembly 12 and an elongated body 14. FIG. 1 illustrates surgical stapling apparatus 10 with an articulatable disposable loading unit 16 coupled thereto. FIG. 2 illustrates surgical stapling apparatus 10 with a non-articulating disposable loading unit 16' coupled thereto. The disposable loading units 16, 16' may include a tool assembly 17 that includes a cartridge assembly 18 that houses a plurality of surgical staples therein. The tool assembly 17 may further include a staple-forming anvil 20. Such disposable loading units 16, 16' may perform surgical procedures such as cutting tissue and applying staples on each side of the cut. Various embodiments of the present invention may be used in connection with the disposable loading units disclosed in U.S. Pat. No. 5,865,361 to Milliman et al., the disclosure of which is herein incorporated by reference.

It will be appreciated that the terms "proximal" and "distal" are used herein with reference to a clinician gripping the handle assembly of an instrument. Thus, the tool assembly 17 is distal with respect to the more proximal handle assembly 12. It will be further appreciated that, for convenience and clarity, spatial terms such as "vertical", "horizontal", "up", "down", "right", and "left" are used herein with respect to the drawings. However, surgical instruments are used in many orientations and positions, and these terms are not intended to be limiting and absolute.

As was discussed above, prior surgical stapling apparatuses such as those disclosed in U.S. Pat. No. 5,865,361 are ill-suited for reprocessing (i.e., re-sterilization) to enable the instruments to be reused because they are not easily disassembled. The surgical stapling apparatus 10 depicted in FIGS. 1-20 is adapted to be conveniently reprocessed and can be used in connection with articulatable disposable loading units 16 (FIG. 1) and non-articulating disposable loading units 16' (FIG. 2) as will be discussed in further detail below. The various embodiments of the surgical stapling apparatus 10 may employ a handle assembly 12 that is constructed to facilitate cleaning and sterilization of the various components housed therein. For example, handle assembly 12 may include a stationary handle portion 22, a movable handle 24, and a barrel portion 26. A rotatable knob 28 may be mounted on the forward end of barrel portion 26 to facilitate rotation of elongated body 14 with respect to handle assembly 12 about longitudinal axis "L-L" of the stapling apparatus 10. As will be discussed in further detail below, some handle assembly embodiments may also include an articulation lever 30 that is mounted on the forward end of barrel portion 26 adjacent rotatable knob 28. Other embodiments may be designed to be used in connection with non-articulatable disposable loading units and thus the handle assembly 12 may not include such articulation components. Handle assembly 12 may further include handle housing 36, which may be formed from a first housing segment 36a and a second housing segment 36b, which, when coupled together, form handle housing 36. To facilitate easy disassembly of handle assembly 12, the housing segments 36a, 36b may be coupled together with, at east one and, preferably three quick release fasteners 400.

Figure 3:
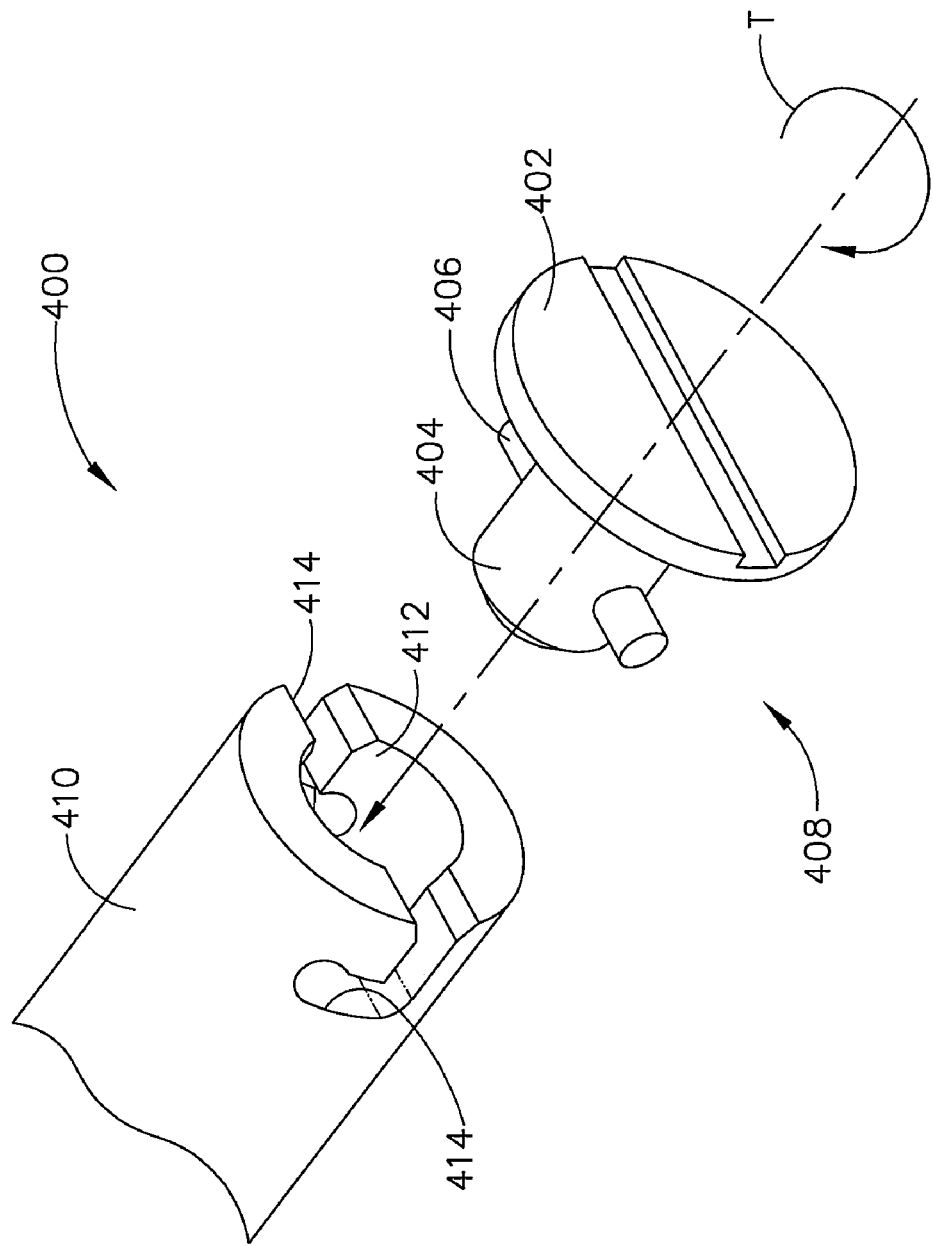
FIG. 3 is a partial exploded perspective view of a quick disconnect fastener embodiment of the present invention.

As shown in FIG. 3, a quick release fastener 400 may comprise a bayonet-type fastener that includes a screw head portion 402 that has a barrel or body portion 404 protruding therefrom that is sized to be received in a hole 412 in a corresponding stand off member 410 formed in the housing segment 36a. A rod or cross member 406 is mounted in the body portion 404 to form a substantially T-shaped connector portion 408 sized to be received in slot segments 414 on each side of the hole 412. The slot segments 414 are configured such that when the T-shaped connector portion 408 is inserted into the hole 412 and slot segments 414 and turned as illustrated by the arrow "T" in FIG. 3, the rod 406 releasably retains the connector portion 408 in position. In various embodiments, the body portion 404 of the quick release fastener 400 may extend through a corresponding hole in the housing segment 36b and then have the rod or cross member 406 attached thereto such that the quick release fastener 400 is non-removably coupled to the second housing segment 36b so that when the housing segment 36b is detached from the first housing segment 36a, the quick release fasteners 400 do not become lost and remain with the second housing segment 36b for cleaning/sterilization purposes.

Referring to FIGS. 4-8, a movable handle 24 may be pivotably coupled to a firing assembly 500 that may be removed from the handle housing 36 for cleaning/sterilization purposes. In various embodiments, the firing assembly 500 may comprise an internal frame assembly 510 that operably supports the movable handle 24. As can be seen in those Figures, the movable handle 24 may be pivotally attached to the internal frame assembly 510 by pivot pin 38. A biasing member 40, which may comprise a torsion spring, biases movable handle 24 away from stationary handle portion 22. See FIGS. 6-8. An actuation shaft 46 may be supported within the internal frame assembly 510 and may include a toothed rack 48. A driving pawl 42 having a rack engagement tooth 43 thereon is pivotably mounted to one end of movable handle 24 about a pivot pin 44. See FIG. 8. A biasing member 50, which may comprise a torsion spring, is positioned to urge driving pawl 42 towards toothed rack 48 of actuation shaft 46. See FIG. 7. Movable handle 24 is pivotable to move rack engagement tooth 43 of driving pawl 42 into contact with toothed rack 48 of actuation shaft 46 to advance the actuation shaft 46 linearly in the distal direction "DD". The distal end of actuation shaft 46 may have a cavity 47 formed therein to receive the proximal end 49 of a control rod 52 (FIG. 4) such that linear advancement of actuation shaft 46 causes corresponding linear advancement of control rod 52.

The internal frame assembly 510 may further include a locking pawl 54 that has a locking protrusion 55 thereon and is pivotably coupled to the frame assembly 510 about pivot pin 57 and is biased into a cavity 512 in the actuation shaft 46 by a biasing member 56, which may comprise a torsion spring. Locking protrusion 55 of locking pawl 54 is movable into engagement with the cavity 512 to retain actuation shaft 46 in a longitudinally fixed position when no disposable loading unit has been coupled to the elongated body 14 as will be discussed in further detail below.

Figure 6:
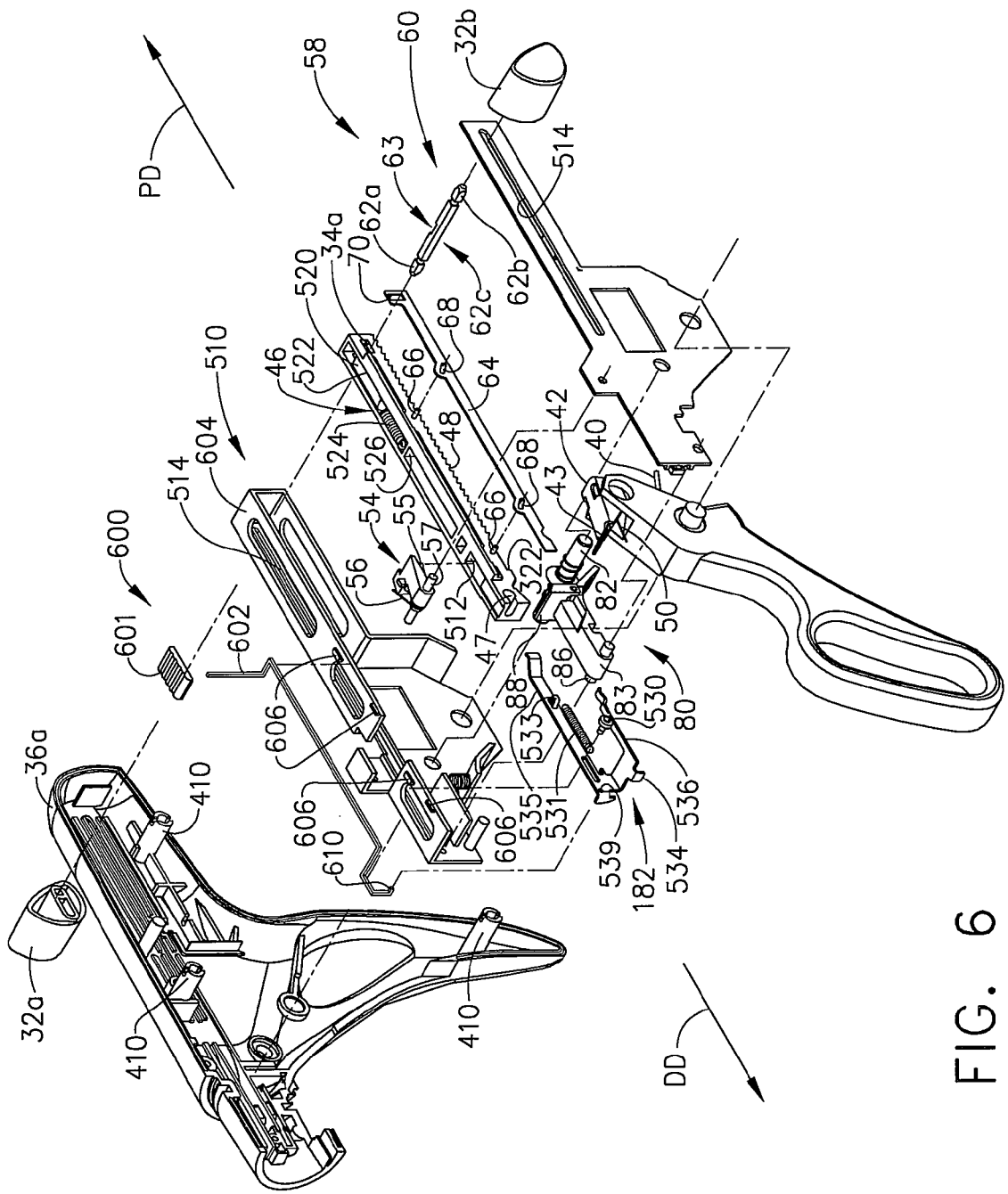
FIG. 6 is an exploded assembly view of a portion of a handle assembly of the reusable surgical stapling apparatus embodiment of FIGS. 4 and 5.
Figure 7:
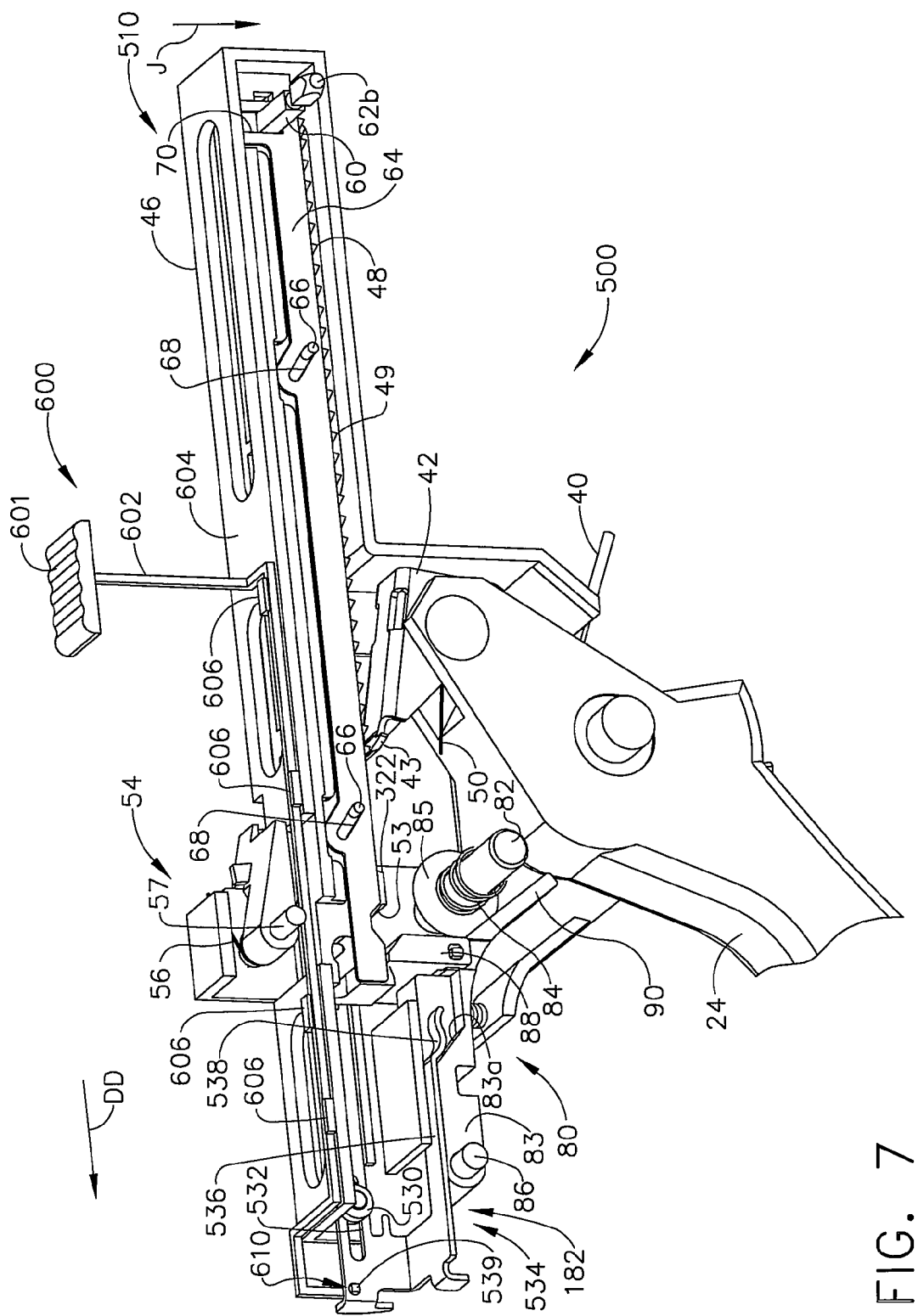
FIG. 7 is a partial right side perspective view of a firing assembly embodiment of the present invention.
Figure 8:
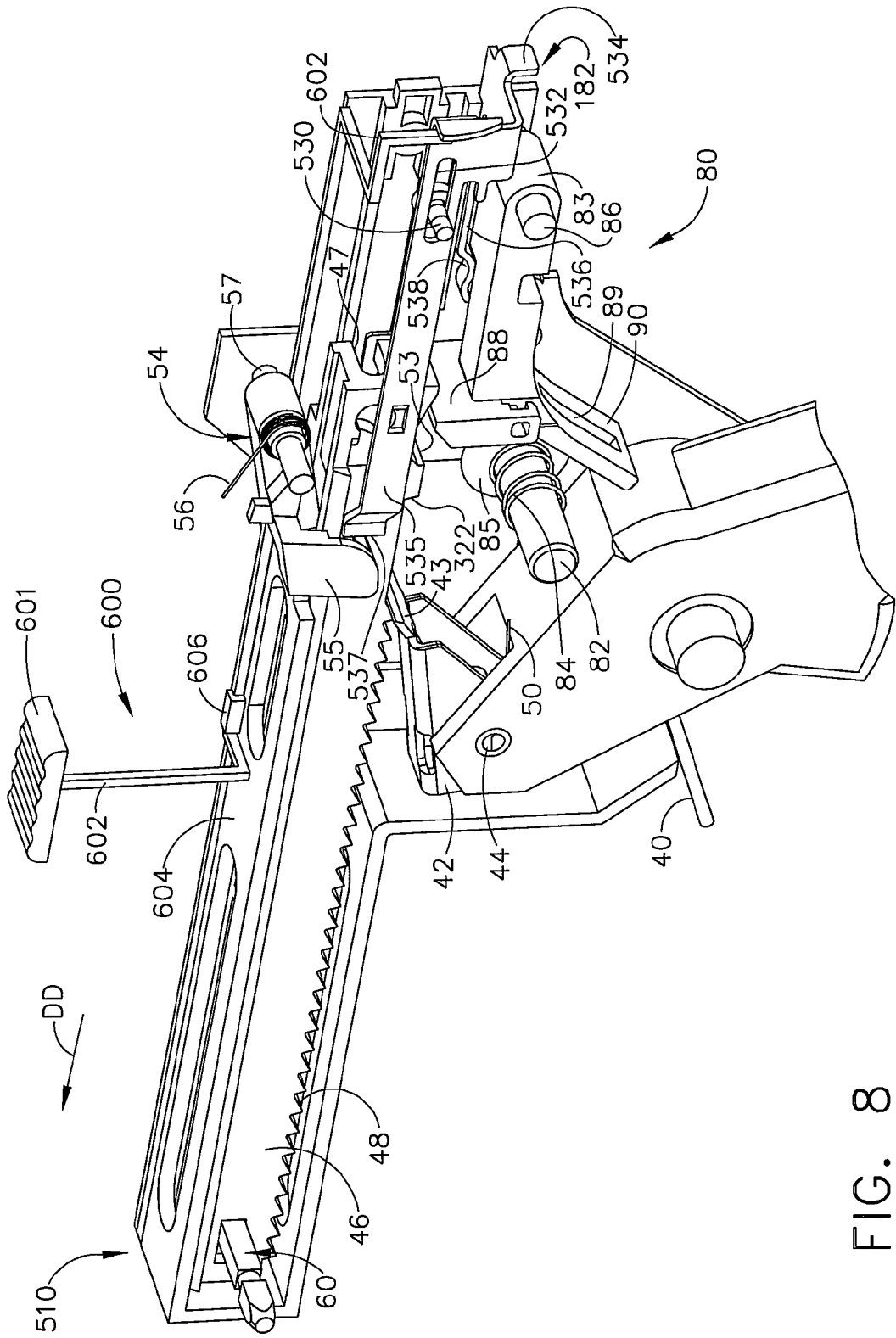
FIG. 8 is a partial left side perspective view of the firing assembly embodiment of FIG. 7.
Figure 9:
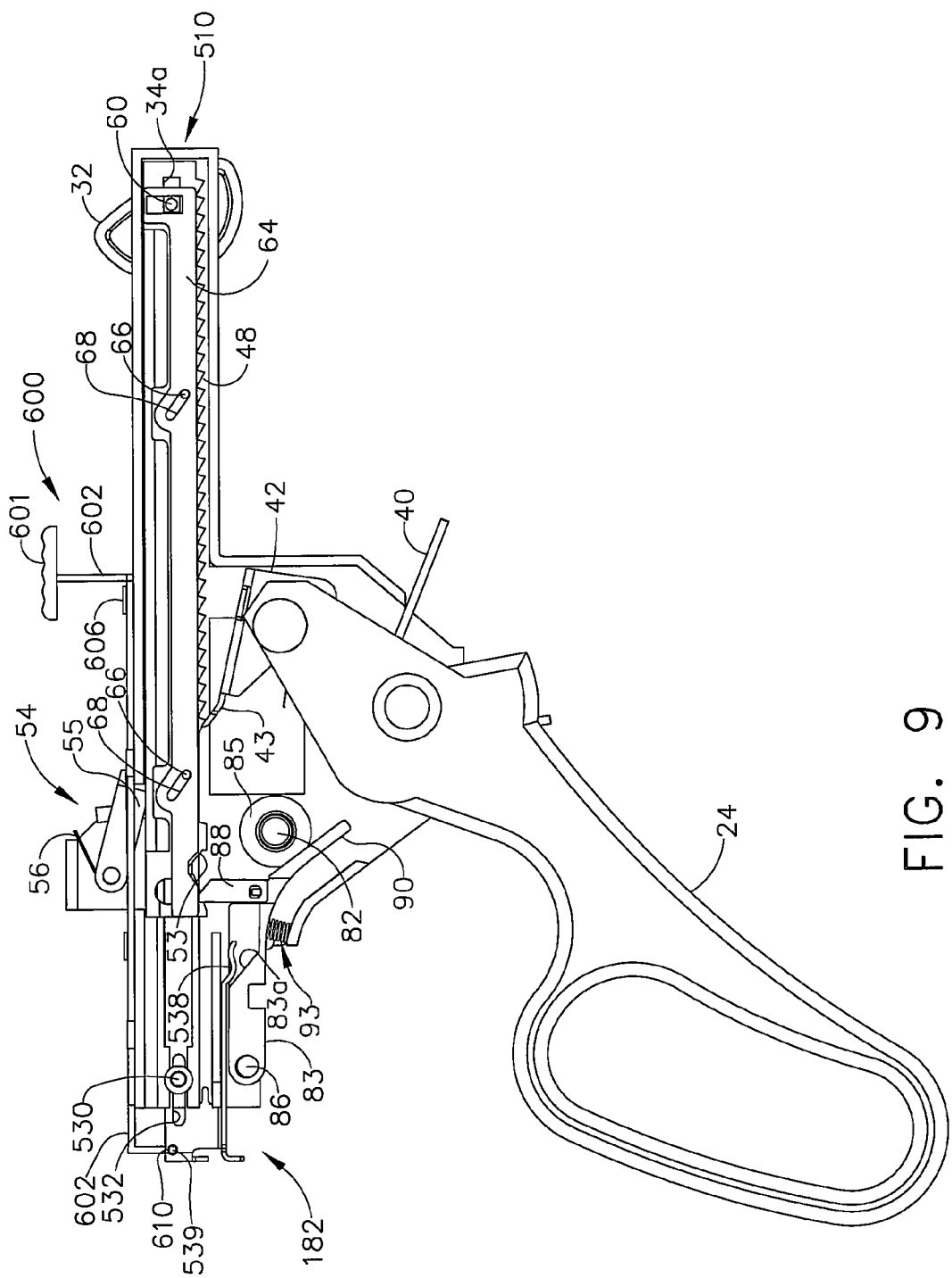
FIG. 9 is a left side view of the firing assembly embodiment of FIGS. 7 and 8.
Figure 10:
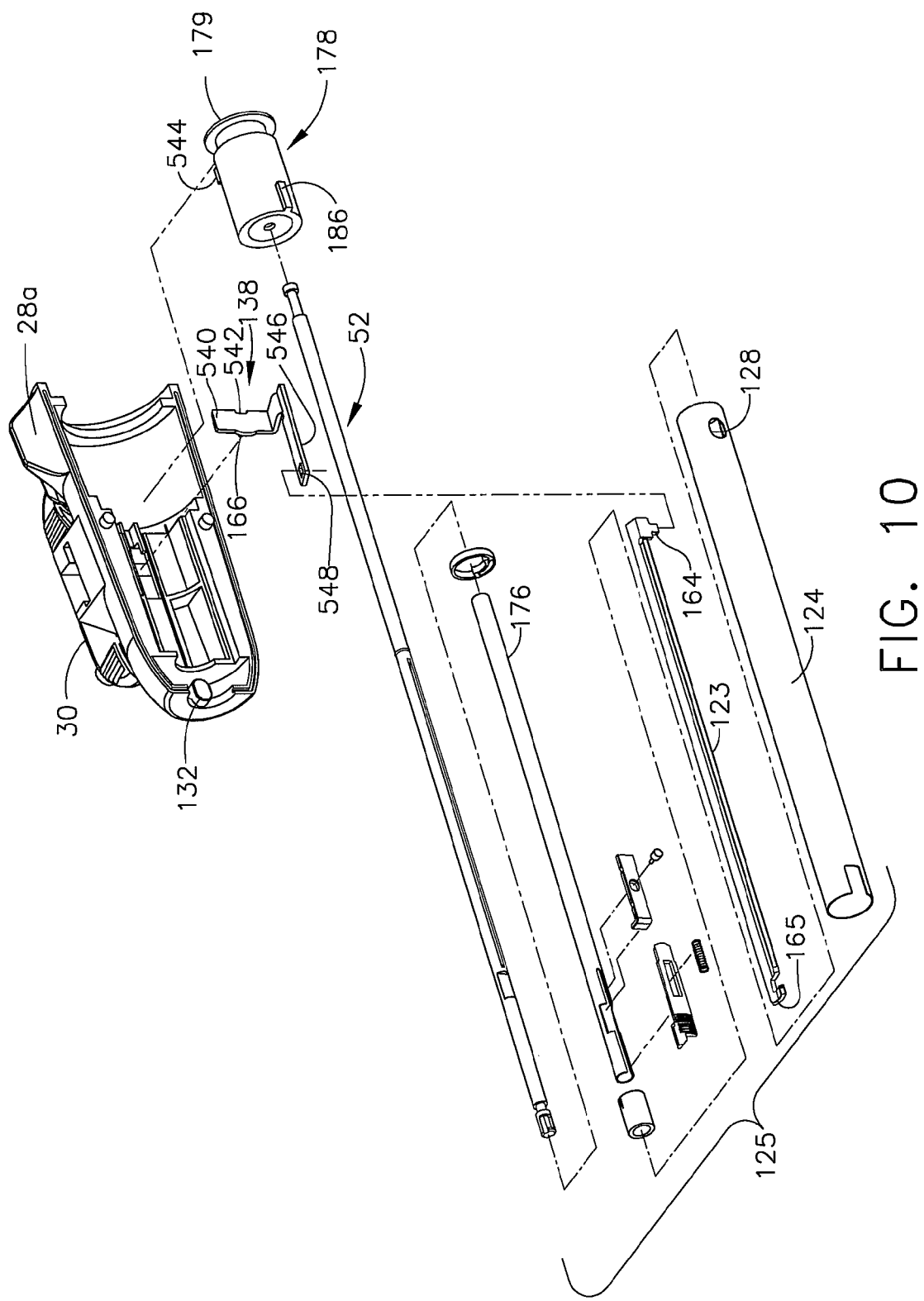
FIG. 10 is an exploded assembly view of a control rod assembly embodiment of various embodiments of the present invention.
Figure 11:
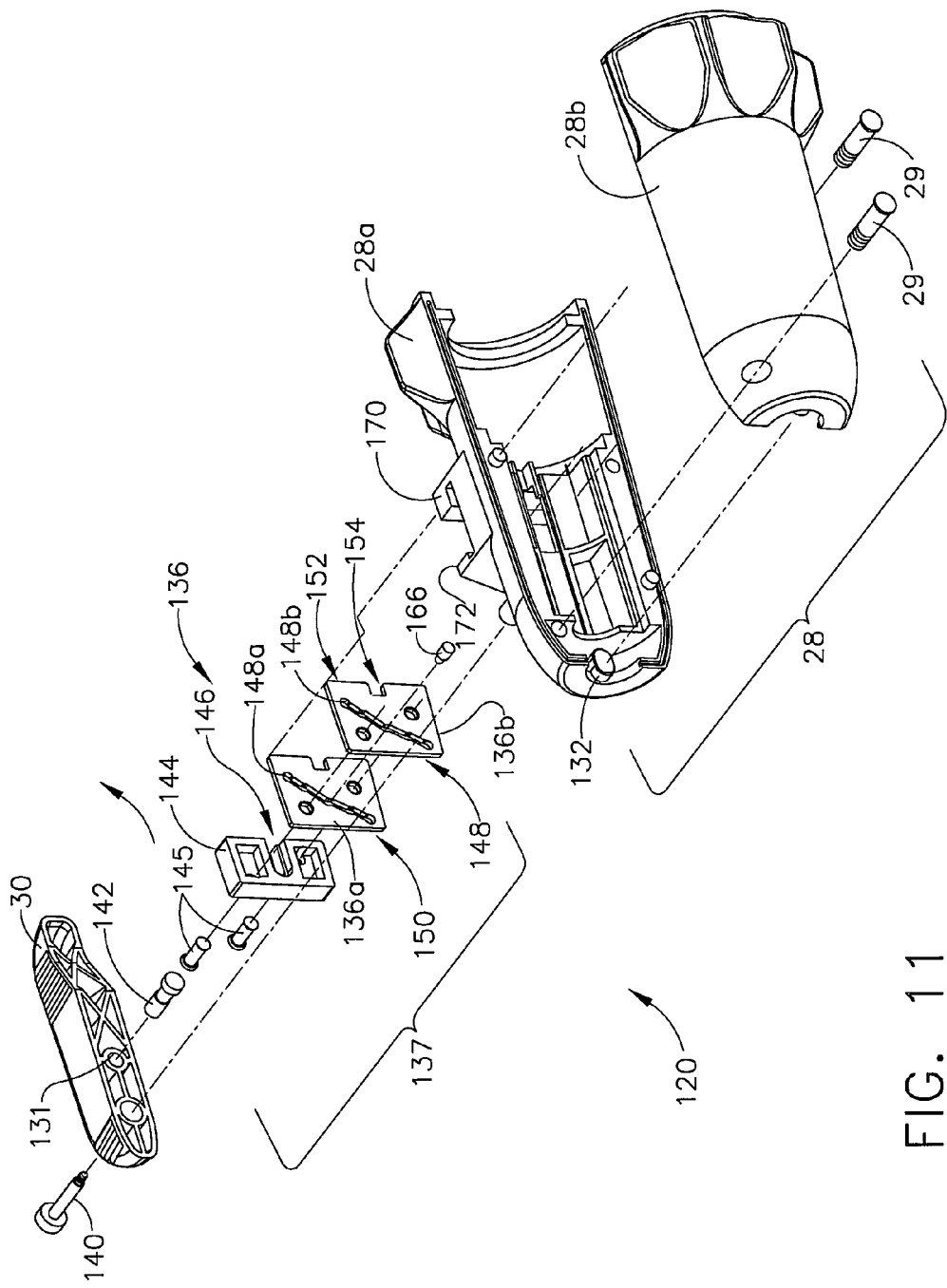
FIG. 11 is an exploded assembly view of a rotation knob assembly and articulation mechanism embodiment of the present invention.

The internal frame assembly 510 may also operably house a retraction mechanism 58 that may comprise a right hand retractor knob 32a and a left hand retractor knob 32b that are connected to the proximal end of actuation shaft 46 by a coupling rod 60. See FIG. 6. Coupling rod 60 may include right and left engagement portions 62a and 62b for receiving retractor knobs 32a and 32b, respectively and a central portion 62C which is dimensioned and configured to translate within a pair of longitudinal slots 514 in the internal frame assembly 510 and slots 34a formed in actuation shaft 46 adjacent the proximal end thereof. The retractor knobs 32a, 32b, may each have a cavity therein to enable them to be pressed onto the corresponding engagement portions 62a, 62b, respectively. In various embodiments of the present invention, the coupling rod 60 may be configured so that when the retractor knobs 32a, 32b are removed therefrom for disassembly purposes, the coupling rod 60 remains mounted in position with the internal frame assembly 510. See FIGS. 7, 8 and 17. As shown in FIG. 6, the central portion 62C may be provided with a notch 63 that is adapted to be retainingly engaged by a retaining tab (not shown) formed on a proximal end of a retainer 520 that is slidably received in a cavity 522 in the actuation shaft 46. A retract spring 524 is attached between a cross post 526 in the actuation shaft 46 and the retainer 520 to pull the retainer 520 distally such that the retaining tab formed on the proximal end thereof retainingly engages the notch 63 in the coupling rod 60. Those of ordinary skill in the art will understand that when the retractor knobs 32a, 32b are detached from the coupling rod 60, the coupling rod 60 remains coupled to the internal frame assembly 510 by the tab on the retainer 520.

A release plate 64 may be operatively associated with actuation shaft 46 and is mounted for movement with respect thereto in response to manipulation of retractor knobs 32a, 32b. A pair of spaced apart pins 66 may extend outwardly from a lateral face of actuation shaft 46 to engage a pair of corresponding angled cam slots 68 formed in release plate 64. Upon movement of retractor knobs 32a, 32b in the proximal direction "PD", pins 66 can release the release plate 64 downwardly with respect to actuation shaft 46 and with respect to toothed rack 48 such that the bottom portion of release plate 64 extends below toothed rack 48 to disengage rack engagement tooth 43 of driving pawl 42 from toothed rack 48. A transverse slot 70 is formed at the proximal end of release plate 64 to accommodate the central portion 62c of coupling rod 60, and elongated slots 34 (FIG. 1) are defined in the barrel section 26 of handle assembly 12 to accommodate the longitudinal translation of coupling rod 60 as retraction knobs 32a, 32b are pulled in the proximal direction "PD" to retract actuation shaft 46 and thus retract control rod 52 in the proximal direction "PD".

In various embodiments, the internal frame assembly 510 may also operably support a firing lockout assembly 80 which may include a plunger 82 and a pivotable locking member 83. See FIGS. 7 and 8. Plunger 82 is biased to a central position by biasing springs 84 and includes annular tapered camming surfaces 85. Each end of plunger 82 extends through handle housing 36 adjacent an upper end of stationary handle portion 22. Pivotable locking member 83 may be pivotably attached at its distal end about pivot pin 86 and may include a locking gate 88 and proximal extension 90 having a slot 89 formed therein. See FIGS. 7 and 8. Pivotable locking member 83 may be biased by a spring 93 (FIG. 9) to cause the locking gate 88 attached thereto to enter into a locking detent 53 in the bottom of the actuation shaft 46 to prevent advancement of actuation shaft 46 and subsequent firing of stapling apparatus 10. Annular tapered camming surface 85 on plunger 82 is positioned to extend into tapered slot 89 in proximal extension 90. Lateral movement of plunger 82 in either direction against the bias of either spring 84 moves tapered camming surface 85 into engagement with the sidewalls of the tapered slot 89 in the proximal extension 90 to pivot pivotable locking member 83 about pivot pin 86 to move locking gate 88 out of the locking detent 53 to permit advancement of actuation shaft 46.

As can be further seen in FIGS. 6-9, a sensor link 182 may also be operably supported by the internal frame assembly 510. As can be seen in those Figures, the sensor link 182 may be slidably attached to the internal frame assembly 510 by a pin or screw 530 that extends through a slot 532 in the sensor link 182 such that the sensor link 182 may slide longitudinally relative to the internal frame assembly 510. A distal end of a spring 531 may be attached to the screw 530 and the proximal end of the spring 531 may be hooked over a hook 533 on the sensor link 182. See FIG. 6. Spring 531 serves to bias the sensor link 182 in the distal direction "DD". The sensor link 182 may further include a proximal locking arm 535 that has an inwardly protruding proximal end 537 configured to interact with the locking pawl 54. In particular, when no disposable loading unit 16, 16' is attached to the stapling apparatus 10, the sensor link 182 is biased distally by spring 531. When in that "unloaded" position, the proximal end 537 of the proximal locking arm 535 disengages the locking pawl 54 to retain the locking pawl 54 in the locked position wherein the locking protrusion 55 is received in cavity 512 to retain actuation shaft 46 in a longitudinally fixed position. Thus, when no disposable loading unit 16, 16' is coupled to the surgical stapling apparatus 10, the stapling apparatus 10 cannot normally be fired.

The sensor link 182 may further have a downwardly extending distal tab 534 formed thereon for contact with a flange 179 formed on a sensor cylinder 178. See FIGS. 4 and 5. As will be discussed in further detail below, a sensor tube 176 is oriented to interface with the sensor cylinder 178. See FIG. 10. Sensor link 182 may further have a spring arm 536 with a downwardly extending end 538 which engages a camming surface 83a on pivotable locking member 83. See FIG. 7. When a disposable loading unit 16, 16' is coupled to the distal end of elongated body 14, the disposable loading unit 16, 16' engages the distal end of the sensor tube 176 to drive sensor tube 176 proximally, and thereby drive sensor cylinder 178 and sensor link 182 proximally. Movement of sensor link 182 proximally causes end 538 of spring arm 536 to move proximally of camming surface 83a to allow locking member 83 to pivot under the bias of a spring 92 from a position permitting firing of stapling apparatus 10 (i.e., permit the actuation of actuation shaft 46) to a blocking position, wherein the locking gate 88 is received in the locking detent 53 in actuation shaft 46 and prevent firing of stapling apparatus 10. Sensor link 182 prevents firing when a disposable loading unit 16 is absent. Locking member 83 prevents firing when closing and opening the anvil assembly 20. Also, as the sensor link 182 is moved proximally, the proximal end 537 of the proximal locking arm 535 serves to pivot the locking pawl 54 such that the locking protrusion 55 moves out of cavity 512 to permit actuation shaft 46 to be actuated. See FIG. 8.

Figure 4:
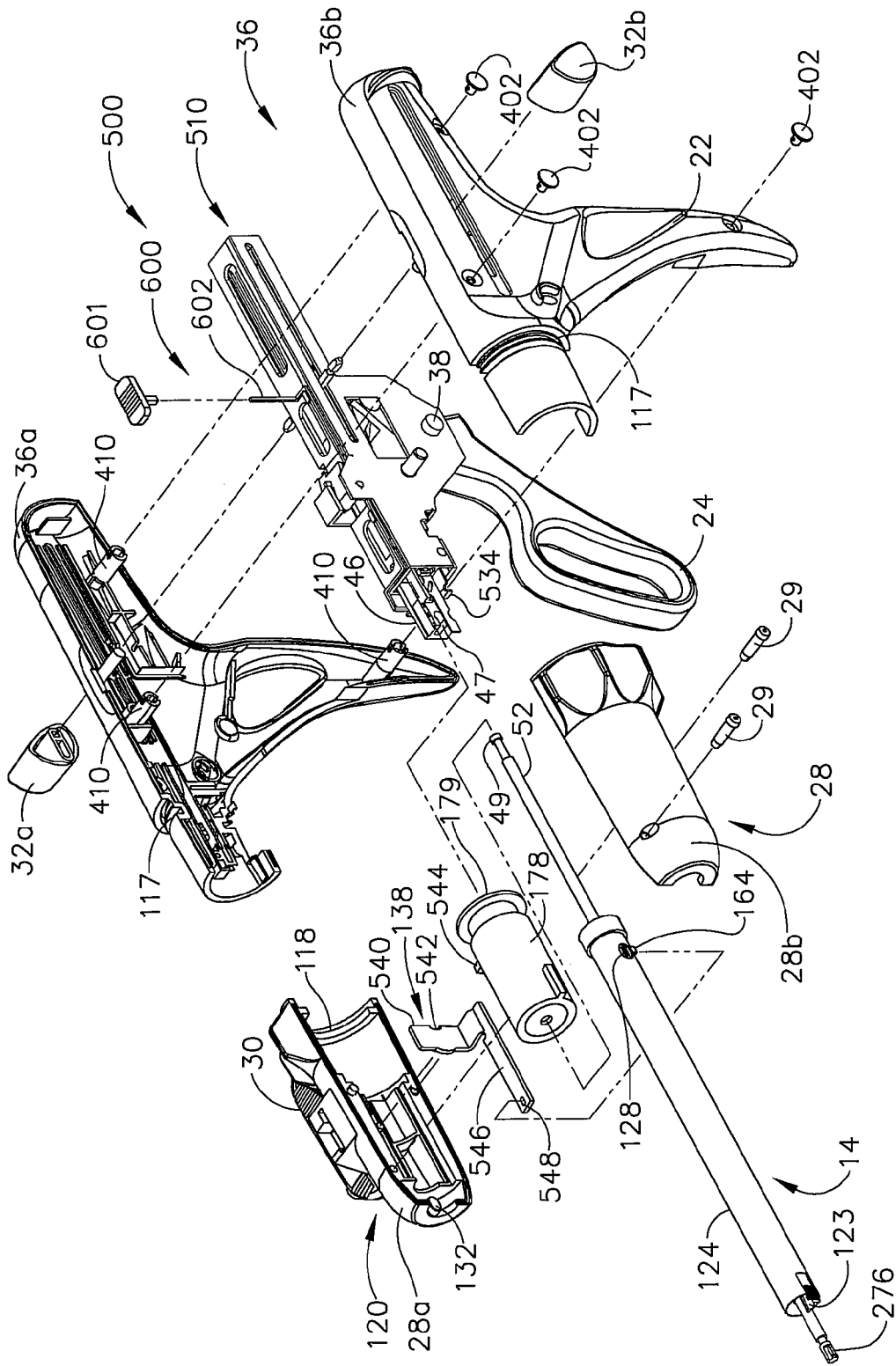
FIG. 4 is an exploded assembly view of a reusable surgical stapling apparatus of various embodiments of the present invention.
Figure 5:
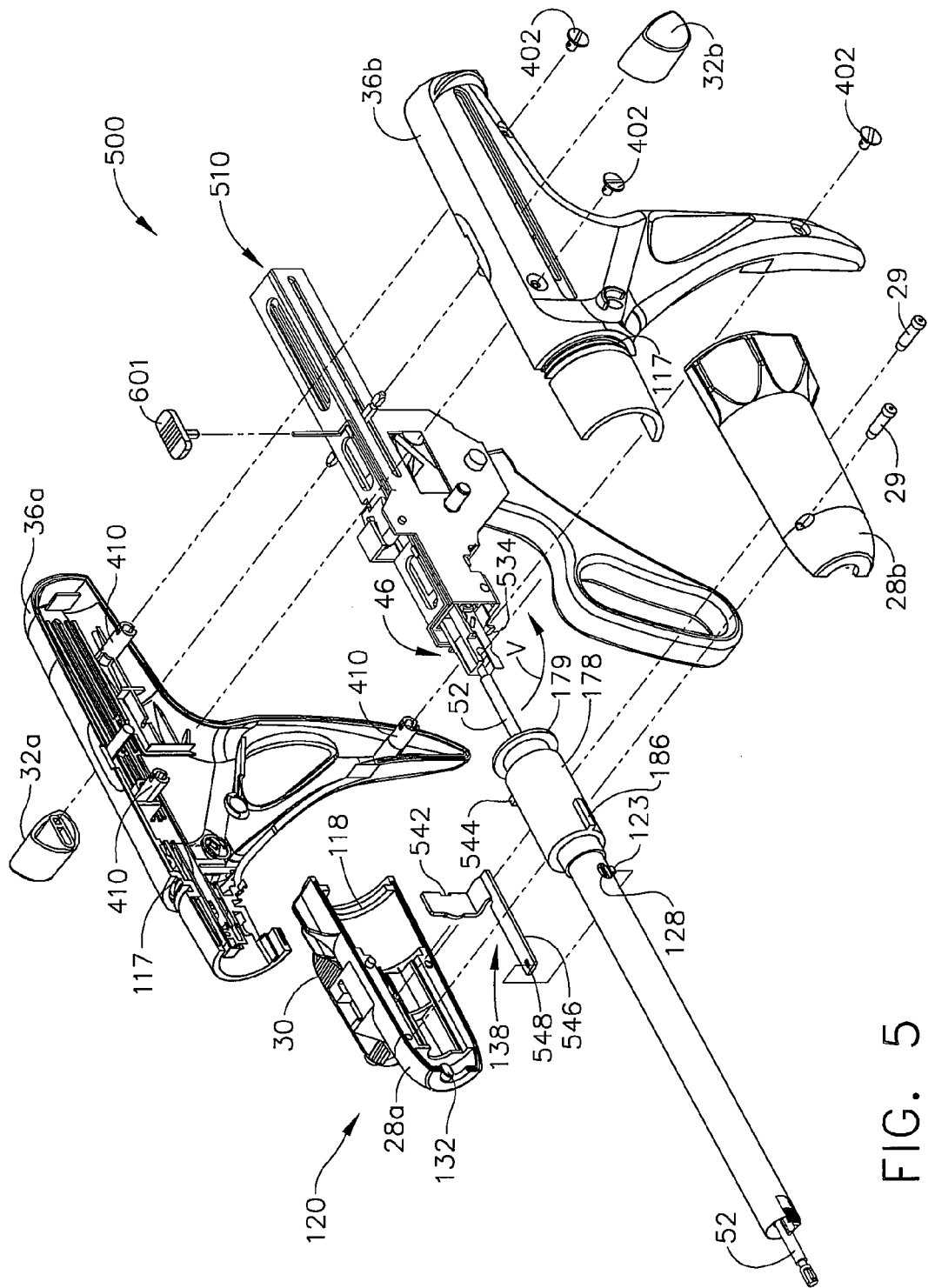
FIG. 5 is another exploded assembly view of the reusable surgical stapling apparatus of FIG. 4.

As shown in FIG. 4, the handle housing 36 may include an annular channel 117 configured to receive an annular rib 118 formed on the proximal end of rotation knob 28, which is preferably formed from molded half-sections 28a and 28b that may be interconnected by screws 29. Annular channel 117 and rib 118 permit relative rotation between rotation knob 28 and handle housing 36. As illustrated in FIG. 4, elongated body 14 may include an outer casing 124 that is sized to support a sensor tube 176 (shown in FIG. 10) and articulation link 123. Such assembly of components 123, 124, 176, and 52 is, at times referred to herein as a "control rod assembly 125", and may include other components journaled on the control rod 52. The proximal end of casing 124 includes diametrically opposed openings 128, which are dimensioned to receive radial projections 132 formed on the distal end of rotation knob 28. See FIGS. 4 and 5. Projections 132 and openings 128 fixedly secure rotation knob 28 and elongated body 14 in relation to each other, both longitudinally and rotatably. Rotation of rotation knob 28 with respect to handle assembly 12 thus results in corresponding rotation of elongated body 14 about longitudinal axis L-L with respect to handle assembly 12. It will also be appreciated that because the disposable loading unit 16, 16' is coupled to the distal end of the elongated body 14, rotation of the elongated body 14 also results in the rotation of the disposable loading unit 16, 16'.

In various embodiments, an articulation mechanism 120 may be supported on rotatable knob 28 and include an articulation lever 30 and a cam member 136. See FIG. 11. Articulation lever 30 may be pivotably mounted about pivot pin 140 which may be threadedly attached to rotation knob 28. A shifting pin 142 may be received in a socket 131 in the bottom of articulation lever 30 and extend downwardly therefrom for engagement with cam member 136. Cam member 136 may include a housing 144 that has an elongated slot 146 extending through one side thereof. A pair of camming plates 136a, 136b may be coupled to housing 144 by a pair of rivets 145 or other suitable fasteners to form a camming plate assembly 137. In other embodiments, the camming plate assembly 137 may be integrally formed with the housing 144. The camming plates 136a and 136b may have a stepped camming surface 148a, 148b, respectively that form a stepped camming surface 148. Each step of camming surface 148 corresponds to a particular degree of articulation of stapling apparatus 10. Elongated slot 146 is configured to receive shifting pin 142 protruding from articulation lever 30. Camming plate assembly 137 is attached to housing 144 in such a manner so as to form a distal stepped portion 150 and a proximal stepped portion 152. Proximal stepped portion 152 includes a recess 154.

As can be seen in FIG. 4, the articulation mechanism 120 may further include a translation member 138 that has an upstanding arm portion 540 that has a notch 542 therein that is sized to receive a tab 544 formed on the sensor cylinder 178. The distal end of translation member 138 may include an arm 546 which includes an opening 548 configured to receive a finger 164 extending from the proximal end of articulation link 123. See FIGS. 4 and 10. A pin 166 that may be constructed from a non-abrasive material, e.g., Teflon®, is secured to translation member 138 and dimensioned to be received within stepped camming surface 148. In an assembled condition, distal and proximal stepped portions 150 and 152 of cam member 136 are positioned beneath flanges 170 and 172 formed on rotation knob 28 to restrict cam member 136 to transverse movement with respect to the longitudinal axis "L-L" of stapling apparatus 10. When articulation lever 30 is pivoted about pivot pin 140, cam member 136 is moved transversely on rotation knob 28 to move stepped camming surface 148 transversely relative to pin 166, forcing pin 166 to move proximally or distally along stepped camming surface 148. Since pin 166 is fixedly attached to translation member 138, translation member 138 is moved proximally or distally to effect corresponding proximal or distal movement of the articulation link 123.

The sensor cylinder 178 may have a nub portion 544 configured to be received within recess 154 in the camming plate assembly 137. When an articulating disposable loading unit 16 is operably coupled to the distal end of elongated body 14 of stapling apparatus 10, the nub 544 moves proximally of recess 154 in cam member 136. With nub 544 positioned proximally of recess 154, cam member 136 is free to move transversely to effect articulation of stapling apparatus 10. As explained in U.S. Pat. No. 5,865,361, a non-articulating disposable loading unit 16' does not have an extended insertion tip. As such, when a non-articulating disposable loading unit 16' is inserted in elongated body 14, sensor cylinder 178 is not moved proximally a sufficient distance to move nub 544 from recess 154. Thus, cam member 136 is prevented from moving transversely by nub 544 which is positioned in recess 154 and articulation lever 30 is locked in its central position.

As can be seen in FIGS. 4-9, this embodiment may also include a firing lockout override assembly 600 that has an override button 601 that has an override wire 602 attached thereto. The override wire 602 may be slidably supported within wire form retention tabs 606 formed on the top surface 604 of the internal frame assembly 510. A distal end 610 of the override wire 602 is mounted in a hole 539 in the distal end of the sensor link 182. When the override button 601 is moved in the proximal direction "PD", the override wire 602 pulls the sensor link 182 proximally which biases the locking pawl 54 out of locking engagement with the actuation shaft 46 and also causes end 538 of spring arm 536 to move proximally of camming surface 83a to allow locking member 83 to pivot under the bias of spring 92 from a position permitting firing of stapling apparatus 10 (i.e., permit the actuation of actuation shaft 46) to a blocking position, wherein the locking gate 88 is received in the locking detent 53 in actuation shaft 46 and prevents firing of stapling apparatus 10 unless the plunger 82 is depressed.

Referring to FIGS. 1, 2, 9 and 10, to use stapling apparatus 10, a disposable loading unit 16, 16' is first secured to the distal end of elongated body 14. The stapling apparatus 10 can be used with articulatable disposable loading units 16 and non-articulatable disposable loading units 16' that each have, for example, linear rows of staples between about 30 mm and about 60 mm. A method of coupling a disposable loading unit 16, 16' to elongated body 14 is disclosed in U.S. Pat. No. 5,865,361. When the insertion tip of the disposable loading unit 16, 16' engages the distal end of sensor tube 176, the disposable loading unit sensing mechanism is actuated. As the insertion tip engages and moves sensor tube 176 proximally, the sensor tube 176 effects proximal movement of sensor cylinder 178 and sensor link 182 in the proximal "PD" direction to pivot locking member 83 counter-clockwise, from a non-blocking position to a position wherein gate 88 blocks movement of actuation shaft 46.

When a disposable loading unit 16, 16' is coupled to stapling apparatus 10, tool assembly 17 can be positioned about a target tissue. To clamp the target tissue between the staple forming anvil 20 and cartridge assembly 18, movable handle 24 is pivoted toward the stationary handle portion 22 against the bias of torsion spring 40 to move driving pawl 42 into engagement with a shoulder 322 on actuation shaft 46. Engagement between shoulder 322 and driving pawl 42 advances actuation shaft 46 distally and thus advances control rod 52 distally. Control rod 52 is connected at its distal end to the axial drive assembly in the disposable loading unit 16, 16', including the drive beam therein, such that distal movement of control rod 52 effects distal movement of the drive beam in the distal direction to thereby cause the staple forming anvil 20 to pivot closed in the manner described in U.S. Pat. No. 5,865,361. In various embodiments, one complete stroke of movable handle 24 may advance actuation shaft 46 approximately 15 mm which may be sufficient to clamp tissue during the first stroke but not to fire staples. The actuation shaft 46 is maintained in its longitudinal position after the movable handle 24 is released by the locking gate 88 which is biased into the detent 53 in the bottom of the actuation shaft 46. Upon release of movable handle 24, drive pawl 42 moves over rack 48 as torsion spring 40 returns handle 24 to a position spaced from stationary handle 22. In this position, driving pawl 42 is urged into engagement with toothed rack 48 to further retain actuation shaft 46 in its longitudinal fixed position.

To "fire" the staples supported within the cartridge assembly 18 (i.e., drive the staples into the staple forming anvil 20), movable handle 24 is actuated again. In various embodiments, the stapling apparatus 10 may be capable of receiving disposable loading units 16, 16' having linear rows of staples of between about 30 mm and about 60 mm. In such arrangements, the stapling apparatus 10 may be configured such that each stroke of the movable handle 24 advances actuation shaft 46 15 mm. Because one stroke is required to clamp tissue, the movable handle 24 must be actuated (n+1) strokes to fire staples, where n is the length of the linear rows of staples in the disposable loading unit attached to the stapling apparatus 10 divided by 15 mm.

Before the staples may be fired, firing lockout assembly 80 must be actuated to move locking gate 88 from its blocking position to a non-blocking position. This may be accomplished by activating plunger 82 to cause camming surface 85 to engage the sidewalls of slot 89 of locking member 83 and thereby pivot locking member 83 in the counterclockwise direction in FIG. 9. Thereafter, movable handle 24 may be actuated an appropriate number of strokes to advance actuation shaft 46, and thus control rod 52 and drive beam in the distal direction "DD" to fire the disposable loading unit 16, 16' in a known manner. To retract actuation shaft 46 and thus control rod 52 and the drive member of the disposable loading unit 16, 16' after firing staples, retraction knobs 32a, 32b may be pulled proximally causing pins 66 to move release plate 64 in the direction indicated by arrow "J" in FIG. 7 over teeth 49 to disengage drive pawl 42 from engagement with teeth 49 of the toothed rack 48.

Those of ordinary skill in the art will understand that the disposable loading units 16, 16' are sterilized and packaged in sterile packaging materials prior to use. Likewise, the stapling apparatus 10 is also sterilized prior to use. After the disposable loading unit 16, 16' is used, it is discarded. While the stapling apparatus 10 could also conceivably be re-sterilized for additional uses, those prior instruments such as those described in the aforementioned U.S. Pat. No. 5,865,361 and other known instruments adapted for use with disposable loading units are not well-suited for easy disassembly to facilitate sterilization of their various internal components. Consequently, such units are often disposed of after a single use. As will be further explained below, the stapling apparatus 10 is constructed to facilitate easy disassembly to permit the stapling apparatus 10 to be reprocessed (i.e., re-sterilized).

Figure 12:
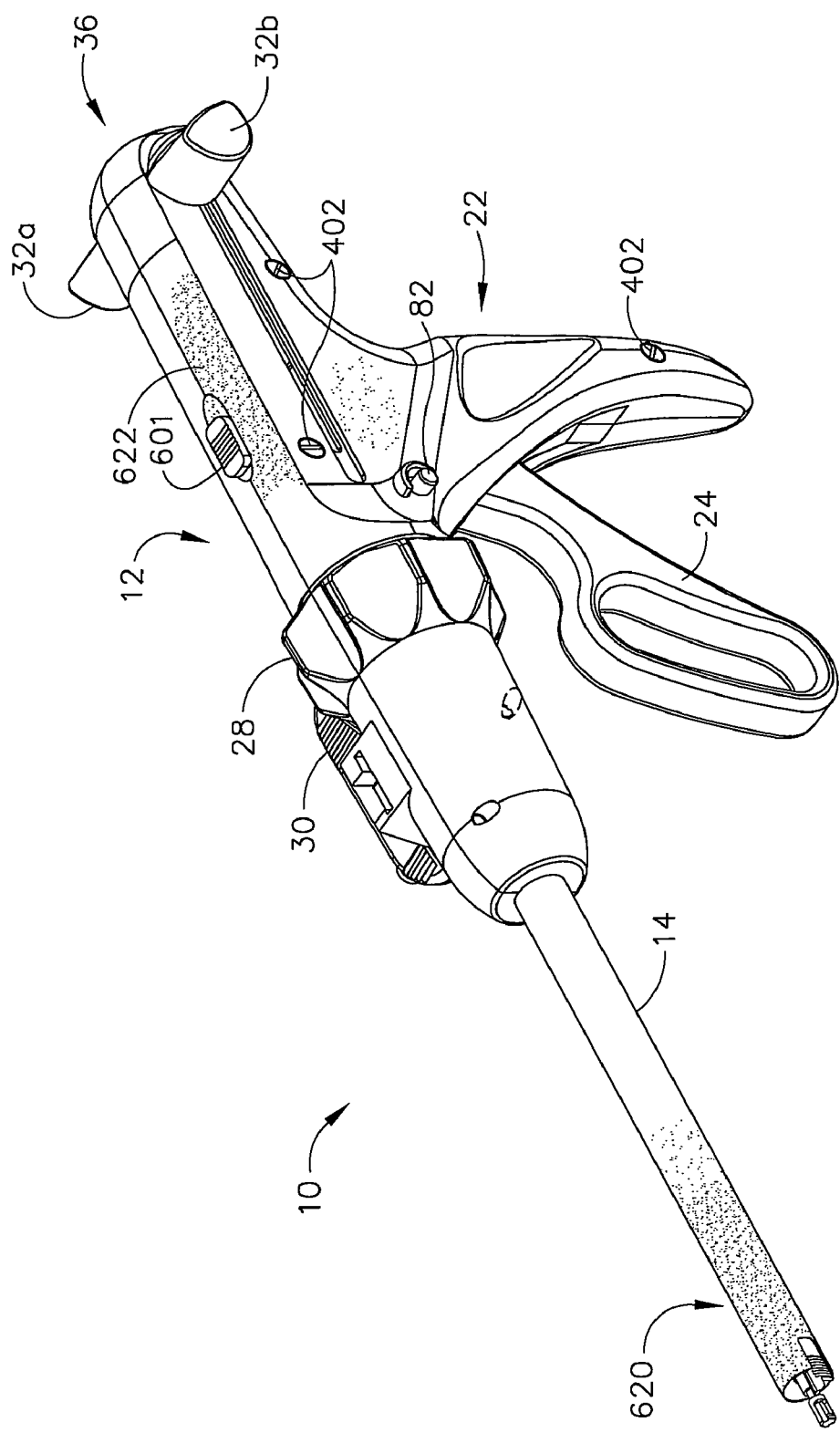
FIG. 12 is a perspective view of a contaminated reusable surgical stapling apparatus of FIGS. 1 and 2 with the disposable loading unit detached therefrom.
Figure 13:
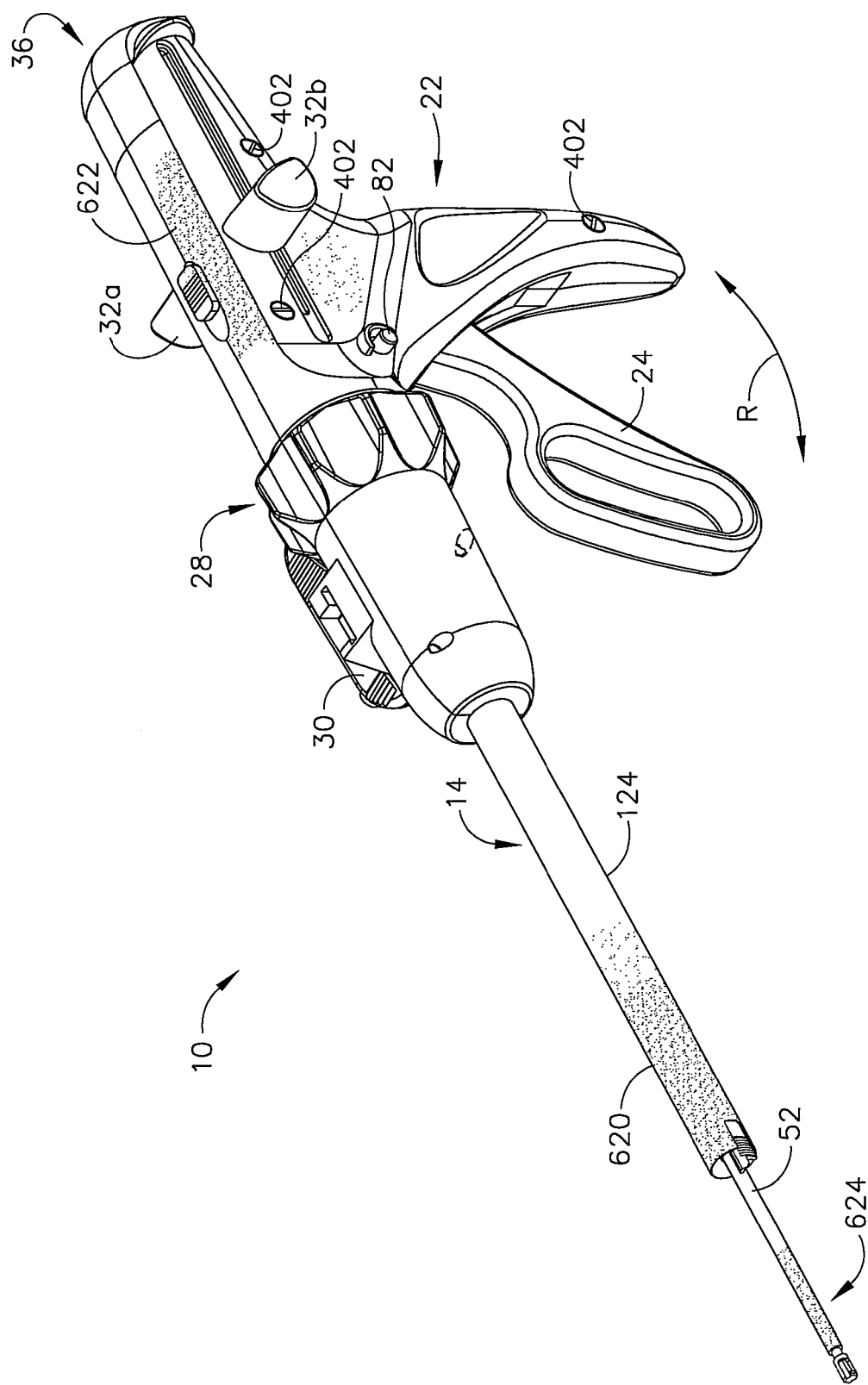
FIG. 13 is a perspective view of the contaminated reusable surgical stapling apparatus of FIG. 12 with the control rod extended out of the distal end of the elongated body.
Figure 14:
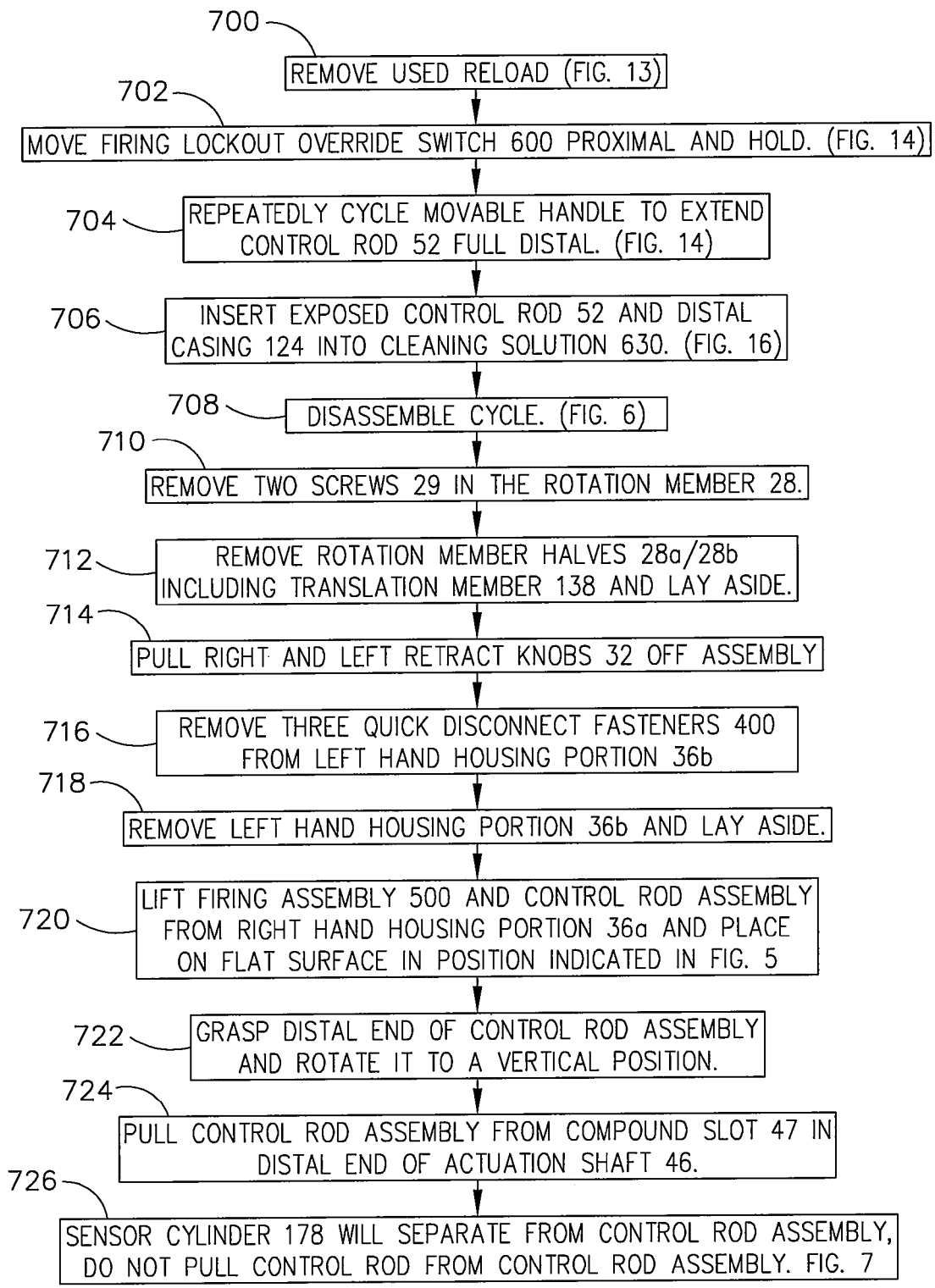
FIG. 14 is a diagrammatic representation of a collection of actions of a cleaning method embodiment of the present invention.
Figure 15:
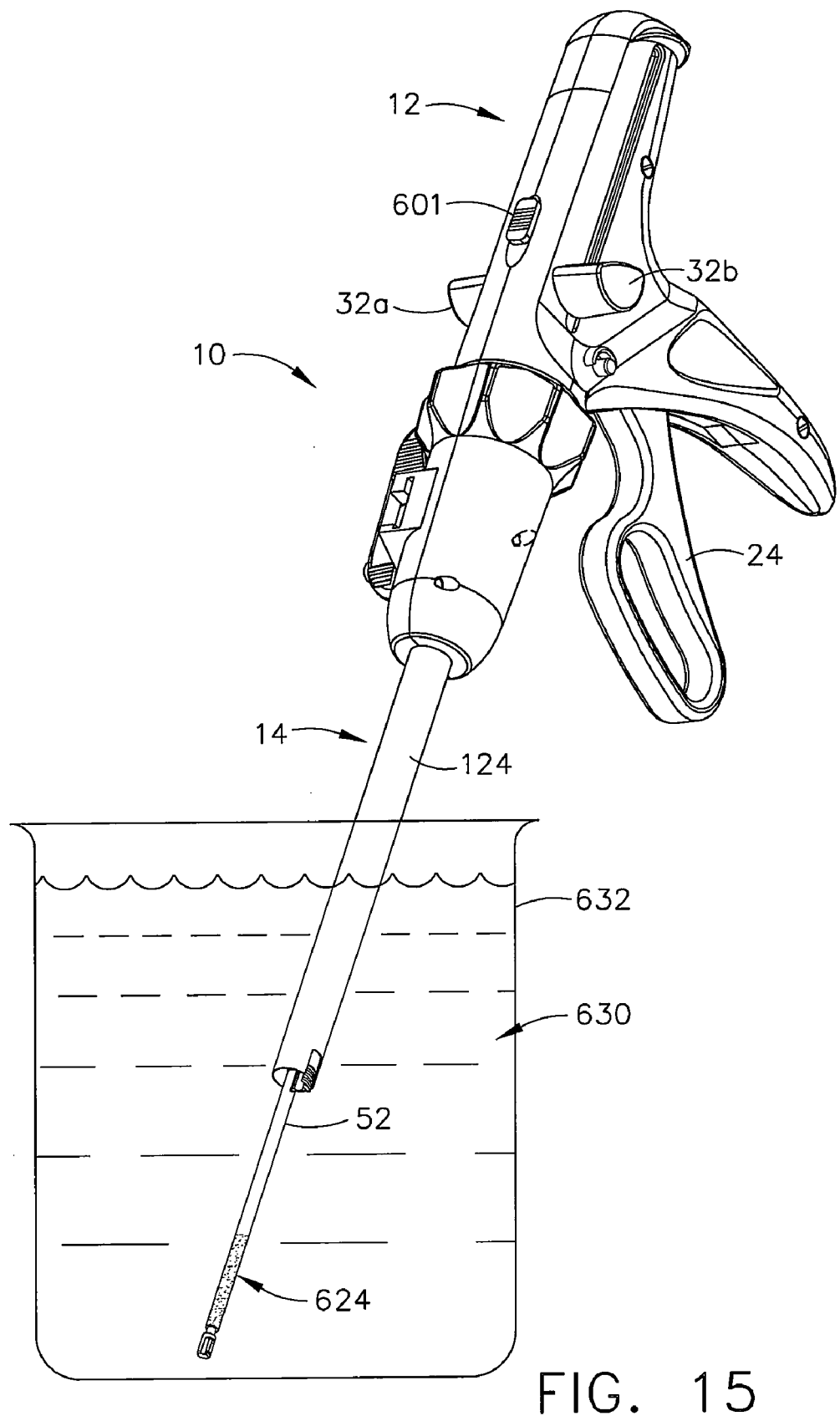
FIG. 15 is a perspective view depicting the submersion of the extended control rod into a cleaning solution.
Figure 16:
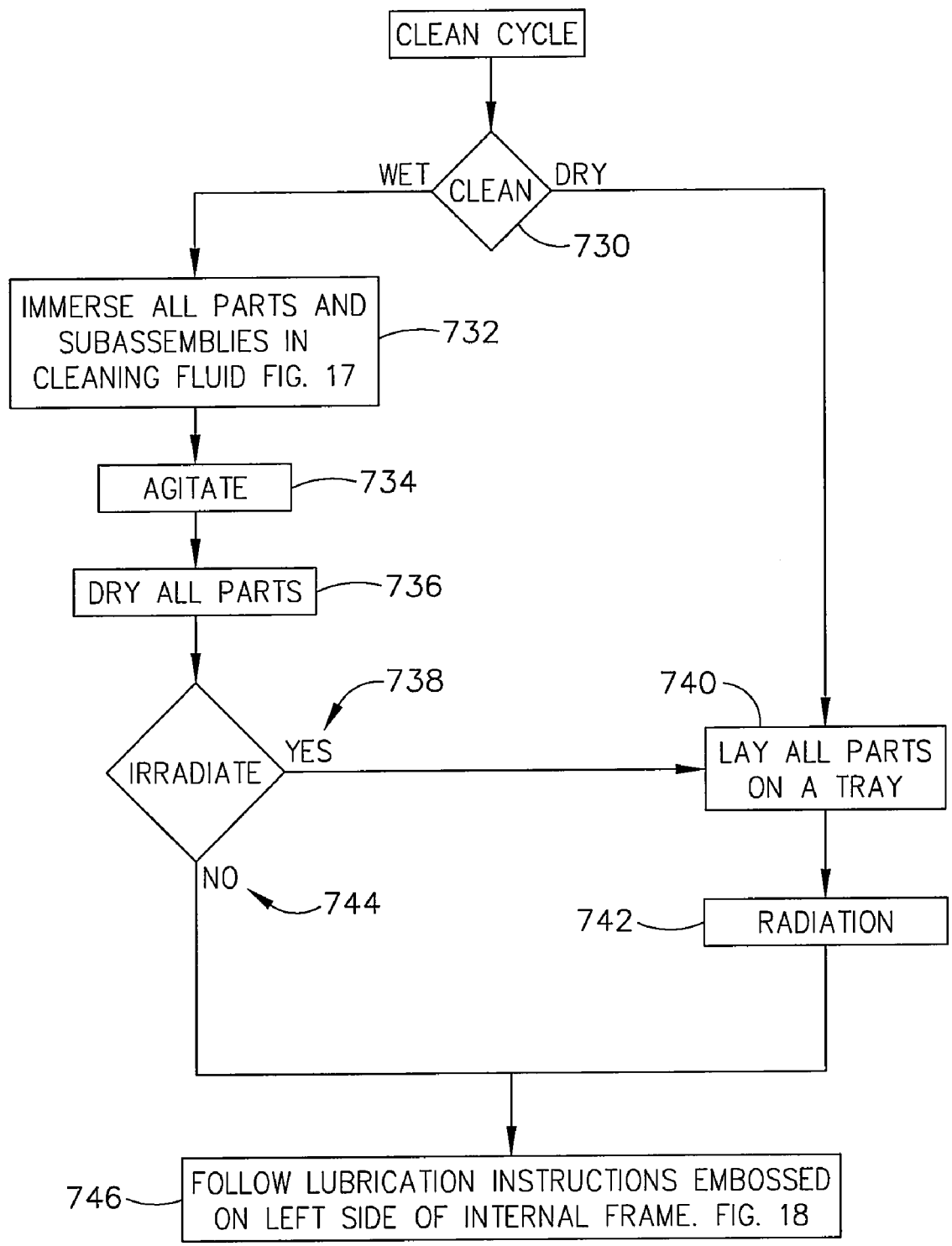
FIG. 16 is another diagrammatic representation of a collection of other actions of a cleaning method embodiment of the present invention.
Figure 17:
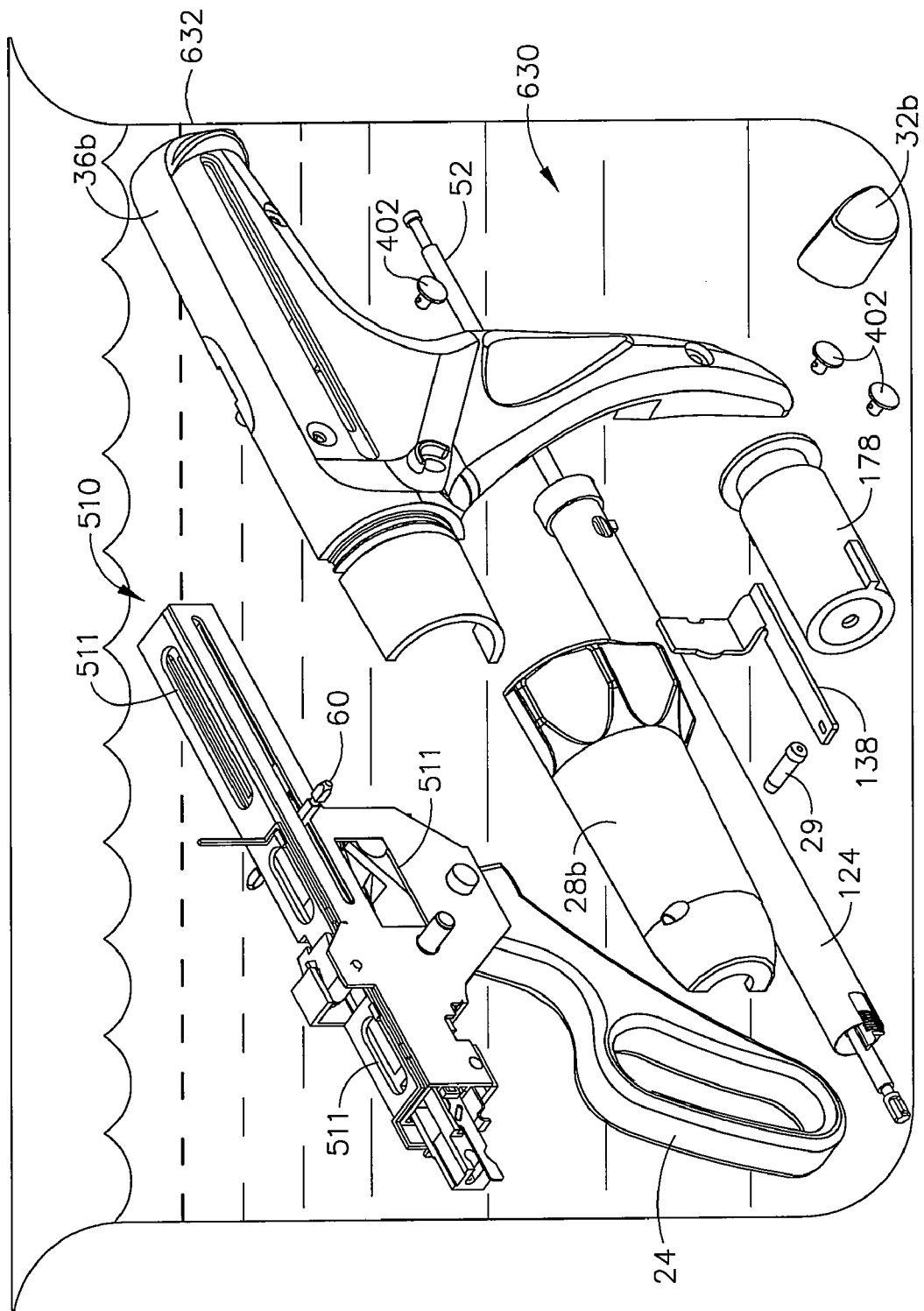
FIG. 17 is a perspective view depicting the submersion of various components of an embodiment of the present invention in a cleaning solution.

FIG. 12 depicts the stapling apparatus 10 after it has been used and the disposable loading unit (not shown) has been decoupled therefrom (action 700 in FIG. 14). The stippling 620, 622 represents exemplary areas of contamination on the elongated body 14 and the handle assembly 12, respectively. To begin the reprocessing of the stapling apparatus 10, the user moves the firing override button 601 proximally and holds the override button 601 in that proximal position (action 702). Such action moves the sensor link 182 proximally in the above-described manner and permits the user to actuate the actuation shaft 46. The user also moves the plunger 82 to enable the movable handle 24 to be cycled to actuate the actuation shaft 46. The user may then repeatedly cycle the movable handle 24 (represented by arrow "R" in FIG. 13) to extend the control rod 52 such that the contaminated portion 624 of the control rod 52 extends out of the casing 124 (action 704). See FIG. 13. The user may then insert the exposed contaminated portion 624 of the control rod 52 and the distal end of the casing 124 into an appropriate cleaning or sterilization medium 630 such as, for example, Ethylene Oxide, Peroxide, etc. (action 706). See FIG. 15.

To sterilize the handle assembly 12, the handle assembly 12 may be easily disassembled (action 708). Referring again to FIG. 5, the user may separate the rotation knob segments 28a and 28b by removing the screws or fasteners 29 (action 710). The rotation knob segments 28a and 28b, as well as the translation member 138, are removed and laid aside (action 712). The right and left retract knobs 32a, 32b are then pulled off of the coupling rod 60 (action 714). The three quick release fasteners 400 may then be removed from the left hand housing portion 36b—unless the fasteners 400 are loosely coupled thereto (action 716). The handle housing segment 36b may then be laid aside (action 718). The user may then lift the firing assembly 500 from the housing segment 36a and place it on a flat surface (action 720). The user may then grasp the distal end of the control rod 52 and rotate it vertically (represented by arrow "V" in FIG. 5—action 722). The control rod 52 may then be pulled from the cavity 47 in the actuation shaft 46 as shown in FIG. 4 (action 724). The user may then detach the sensor cylinder 178 from the proximal end of the sensor tube 176 (action 726). Thus, the stapling apparatus 10 may be separated into the parts shown in FIG. 4. The user may then select a desired cleaning/sterilization cycle (action 730). See FIG. 16. In particular, the user may choose between a "wet" cleaning cycle wherein the components are submerged in an appropriate cleaning solution 630 (FIG. 17) or a "dry" cleaning cycle wherein radiation is employed or a combination of both cycles may be employed. Those of ordinary skill in the art will recognize that FIG. 17 only illustrates some of the handle assembly components being submerged in the cleaning medium 630. It will be appreciated that it is intended that all of the handle assembly components be submerged either simultaneously (if the container is large enough) or one at a time or in small groups until all of the components have been cleaned (action 732). It will be appreciated, however, those components that have been worn or damaged may be replaced with new sterilized components to complete the assembly. The reservoir 632 containing the cleaning medium 630 may be agitated or the cleaning medium may be stirred or otherwise agitated using conventional methods to drive the cleaning medium 630 through the openings 511 in the internal frame assembly 510 into contact with all of the components retained therein (action 734). After the components have all been exposed to the cleaning medium 630 for a desired amount of time, the components may be removed from the cleaning medium 630 and then air dried or dried utilizing other conventional methods (action 736).

After the components have been cleaned by the cleaning medium (actions 732-736), the user may also choose to irradiate the components (actions 740, 742) or the user may elect not to irradiate the components (action 744) at which point the user then may lubricate certain components (action 746) as will be discussed in further detail below. If the user elects to irradiate the disassembled components either after wet cleaning the components or in lieu of wet cleaning, the user may lay all of the component parts on an appropriate tray or other object (not shown). Radiation may then be applied to the components using convention irradiation techniques. For example, electron beam radiation may be employed. Other forms of vapor sterilization mediums, such as for example, Ethylene Oxide vapor mediums, Peroxide vapor mediums may also be employed.

Figure 18:
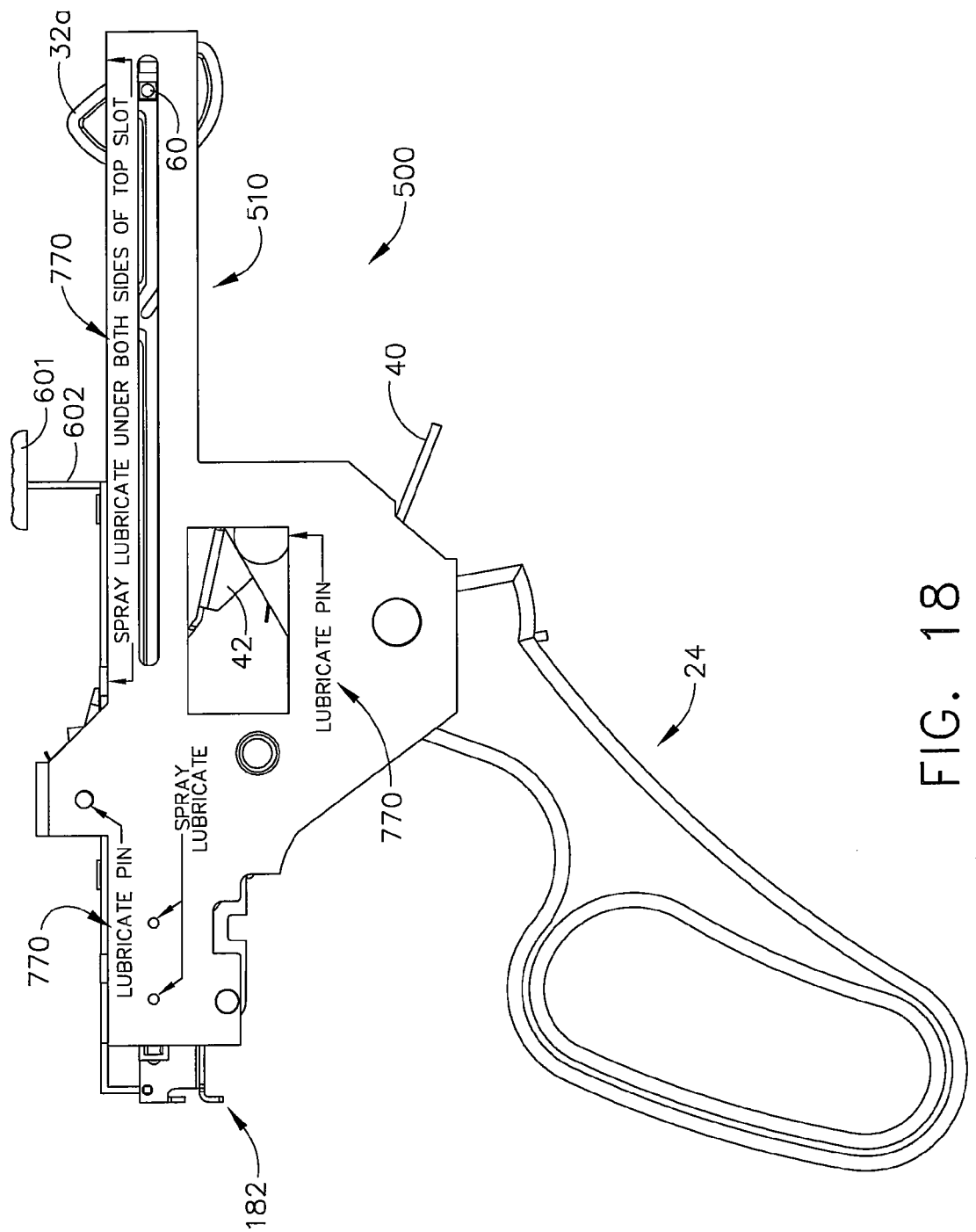
FIG. 18 is a side view of a firing assembly embodiment of various embodiments of the present invention.

After the components have been sterilized, certain components may be lubricated (action 746). As can be seen in FIG. 18, in various components, lubrication instructions 770 may be embossed or otherwise provided on the internal frame assembly 510. A sterile lubrication medium such as, for example, Sodium Sterate may be applied to the various components as shown in FIG. 18.

Figure 19:
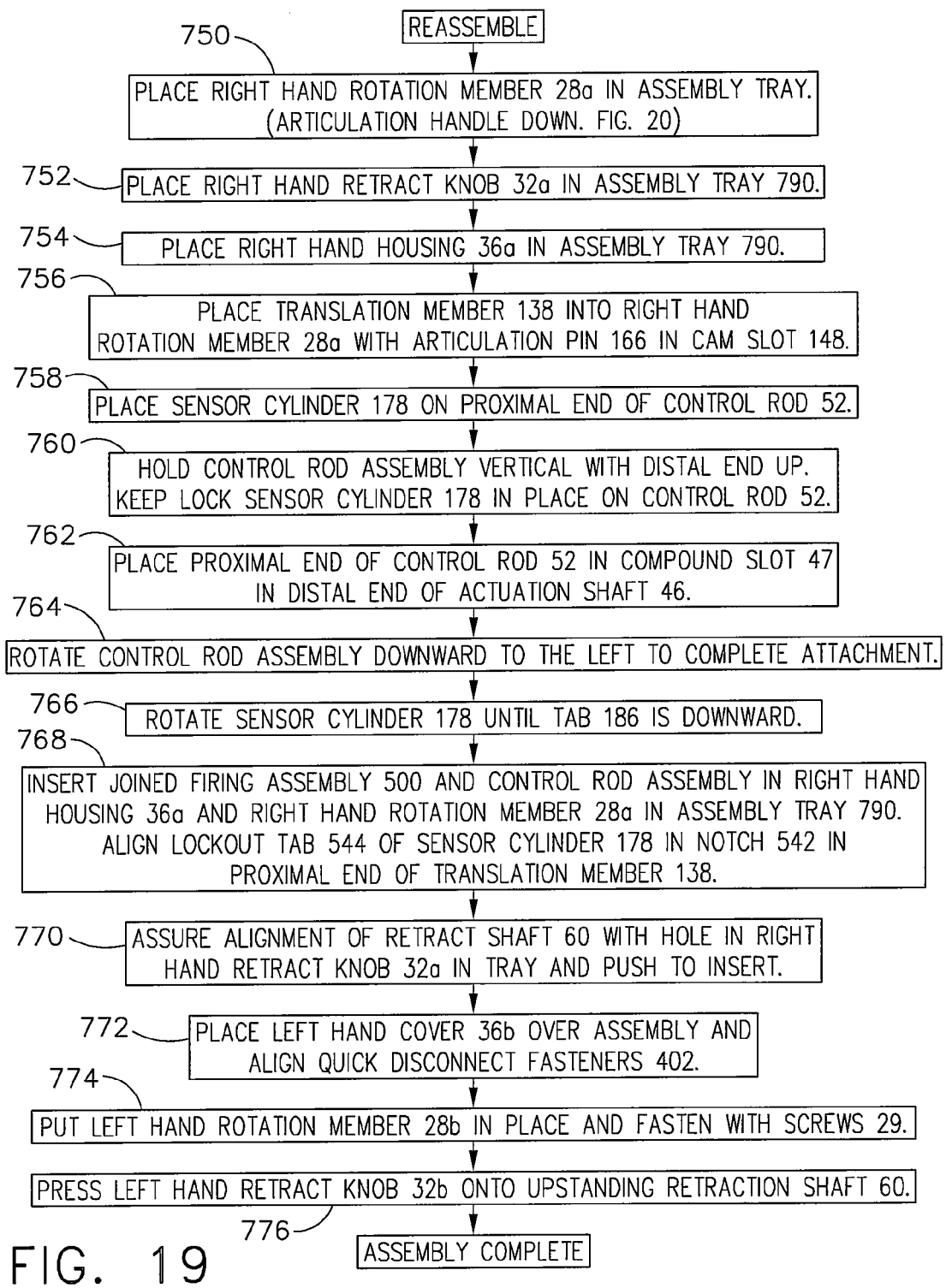
FIG. 19 is a diagrammatic representation of a collection of actions of a reassembly method embodiment of the present invention.
Figure 20:
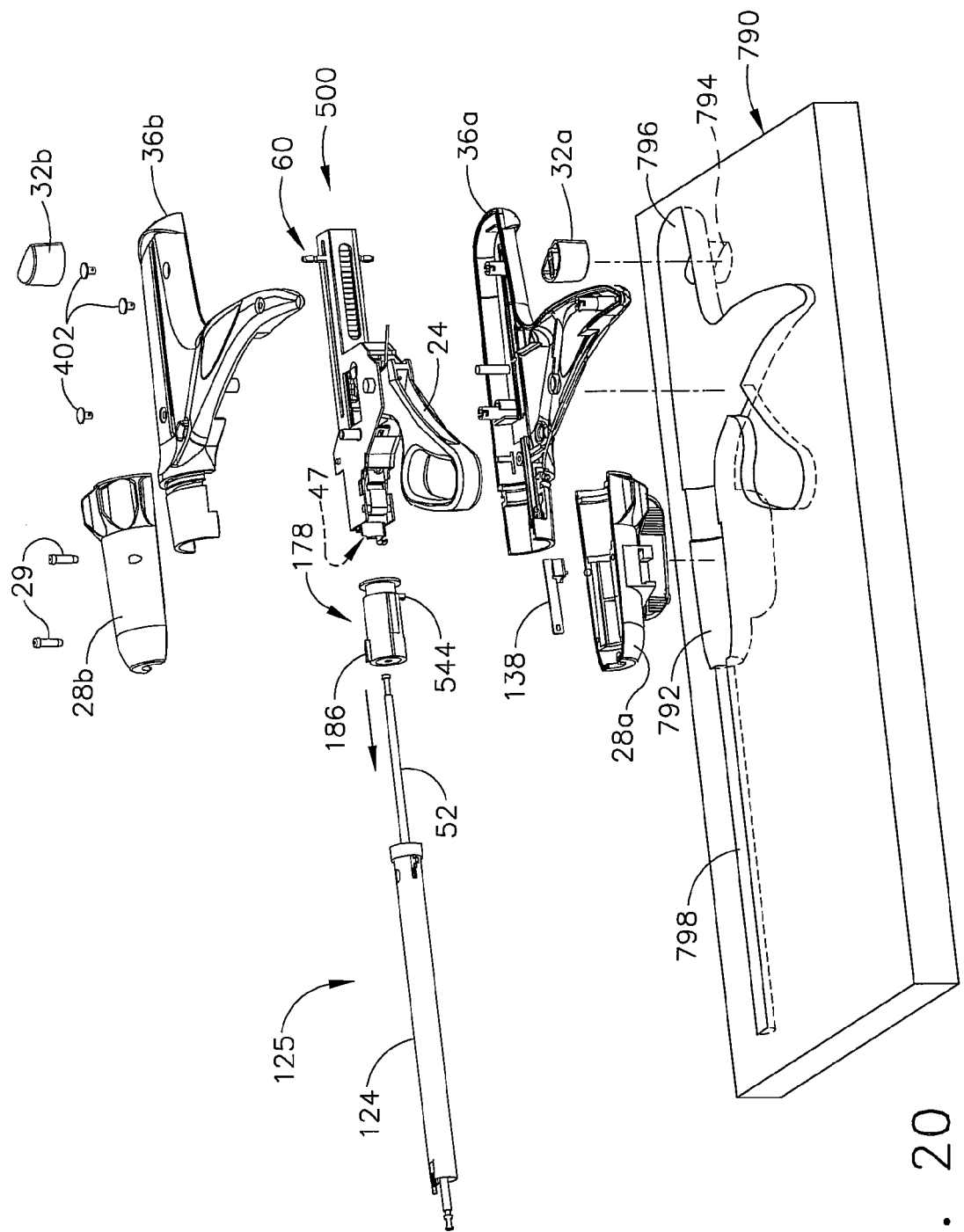
FIG. 20 is an exploded view depicting use of an assembly tray of an embodiment of the present invention.

The components may then be reassembled as outlined in FIG. 19. To assist with the assembly of the components, a sterile assembly member or tray 790 that has a series of complementary cavities 792, 794 therein may be employed. See FIG. 20. One method of reassembly includes the action 750 which comprises placing the rotation knob segment 28a in the complementary shaped cavity 792 in the assembly tray 790. The retract knob 32a may be placed in the complementary cavity 794 (action 752). The first housing segment 36a may be placed in the complementary cavity 796 (action 754). The translation member 138 may be placed into the right hand rotation member 28a with the pin 166 attached thereto inserted into the stepped cam slot 148 in the cam member 136 that is mounted under the flanges 170, 172 in the right hand rotation knob segment 28a (action 756). The sensor cylinder 178 may be placed onto the proximal end of the control rod 52 (action 758). The control rod assembly 125 is oriented vertically with the distal end up. The sensor cylinder 178 is retained on the control rod 52 (action 760). The proximal end of the control rod 52 is inserted into the cavity 47 in the actuation shaft 46 (action 762). The control rod assembly 125 is then rotated downward to the left to complete the attachment to the actuation shaft 46 (action 764). The sensor cylinder 178 is rotated until tab 544 is downward (action 766). The joined firing assembly 500 and control rod assembly 125 is inserted into the first handle housing segment 36a and the right hand rotation knob segment 28a in the corresponding cavities 798, 792, 796 in the assembly tray 790. The lockout tab 544 on the sensor cylinder 178 is inserted into the notch 542 in the translation member 138 (action 768). The coupling rod 60 may be aligned for insertion into a hole (not shown) in the right hand retract knob 32a (action 770). The second handle housing segment 36b is then placed over the assembly and aligned to enable the quick release fasteners 400 to couple the handle housing segments 36a, 36b together (action 772). The rotation knob segment 28b may be oriented to mate with the rotation knob segment 28a and coupled thereto with screws 29 (action 774). The left hand retract knob 32b may then be pressed onto the retraction shaft 60 to complete the assembly (action 776).

The firing lockout assembly 80 described above, as well as the firing lockout assembly disclosed in the aforementioned U.S. Pat. No. 5,865,361, can be difficult to use because the clinician must depress the plunger 82 to enable actuation shaft 46 to be actuated by cycling the movable handle 24. Such arrangement generally requires the clinician to use both hands (one to hold onto the handle assembly and actuate the movable handle and the other hand to depress the plunger 82). It would be more desirable to have a surgical stapling apparatus that has a more ergonomically efficient firing lockout trigger arrangement that does not require the clinician to use both hands to fire the instrument. FIGS. 21-33 illustrate a stapling apparatus 810 that is substantially similar to the stapling apparatus 10 described above or maybe substantially similar to the stapling apparatus described in U.S. Pat. No. 5,865,361 or other prior surgical instruments that employ the plunger-type lockout assembly, except that stapling apparatus 810 employs a firing lockout system 880 that is much easier to use and does not require both hands to fire the instrument.

Figure 21:
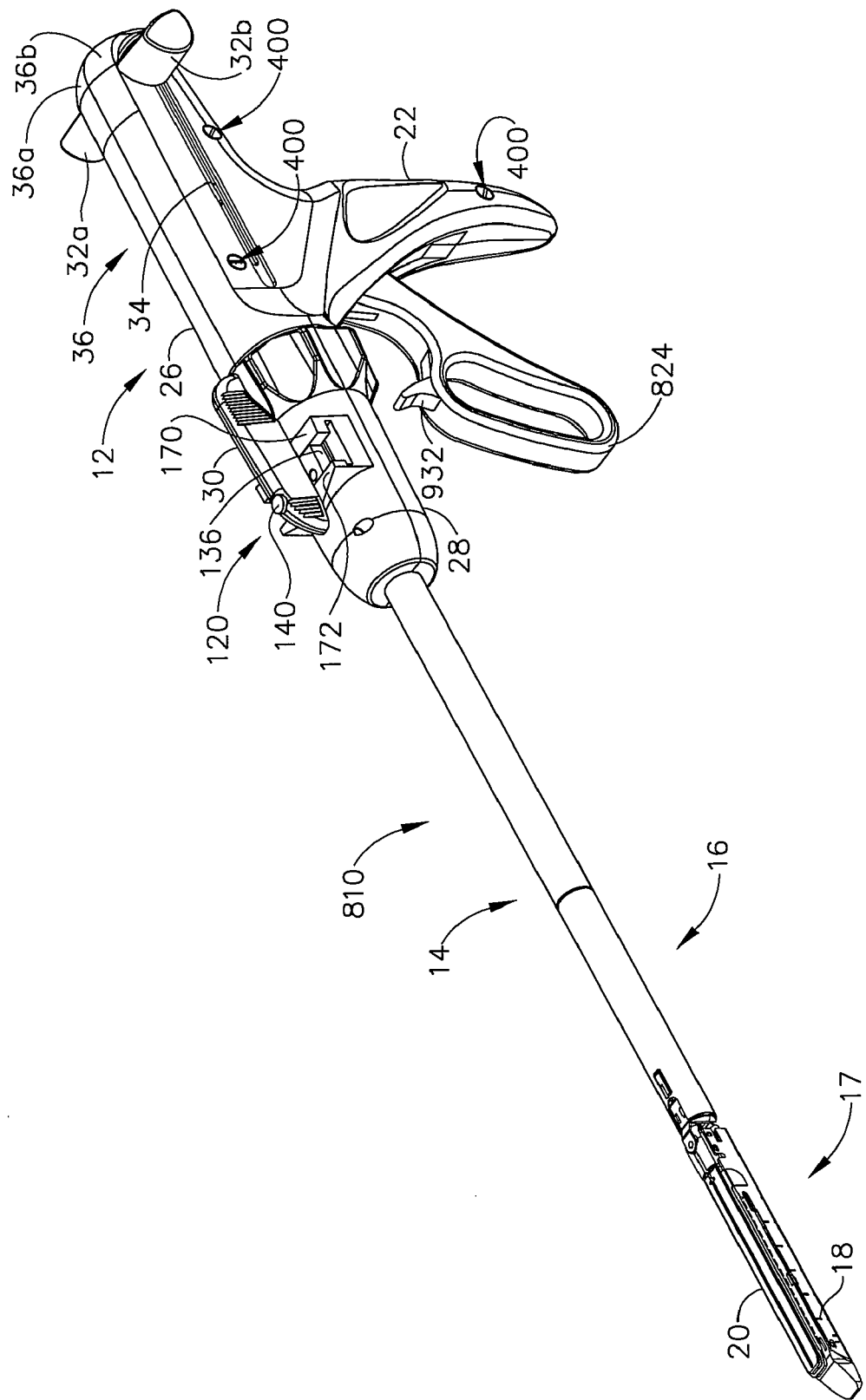
FIG. 21 is a perspective view of another surgical stapling apparatus of an embodiment of the present invention attached to a non-articulatable disposable loading unit.
Figure 22:
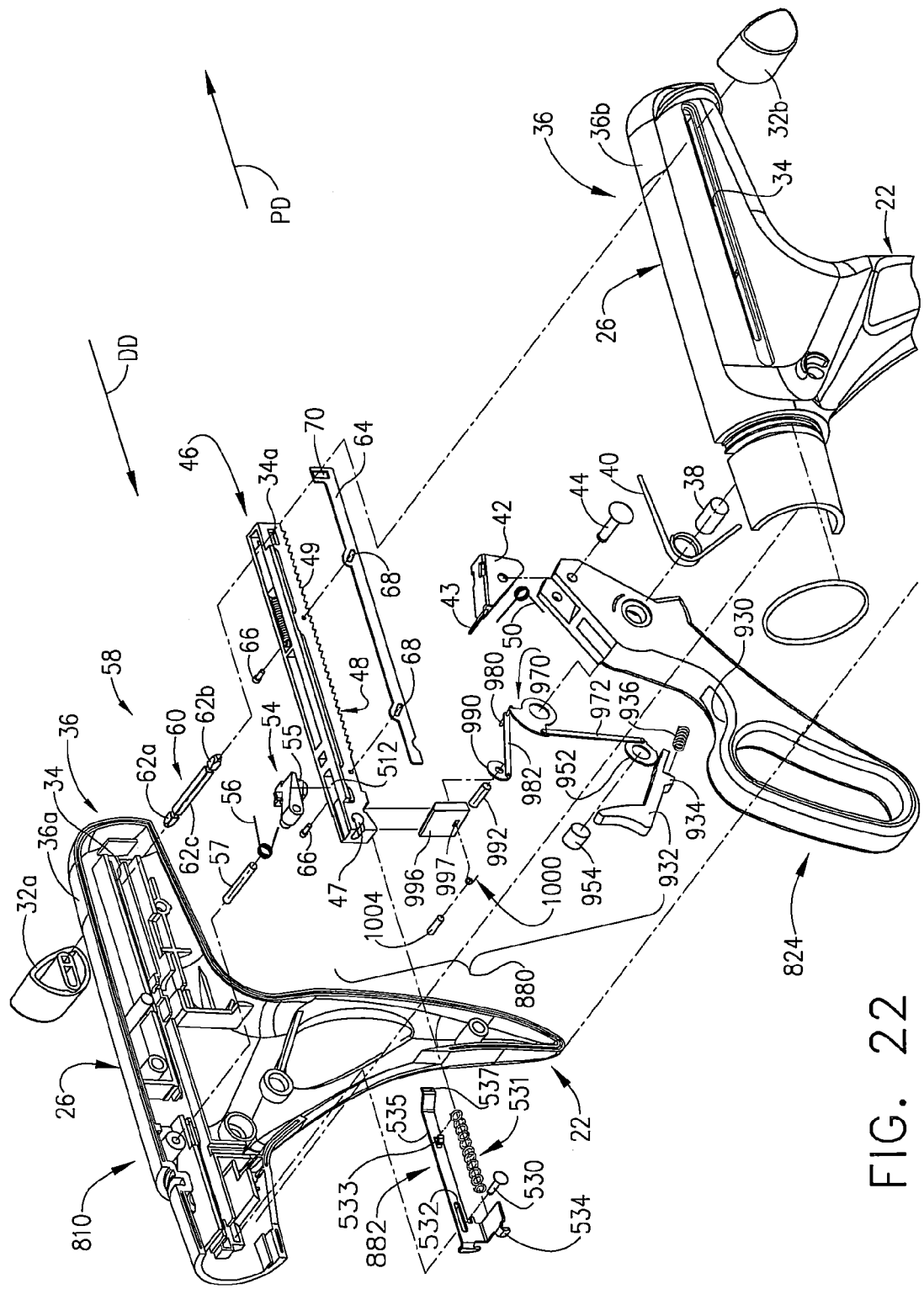
FIG. 22 is an exploded assembly view of a handle assembly of the surgical stapling apparatus depicted in FIG. 21.

Referring to FIGS. 21 and 22, handle assembly 12 includes a handle housing 36, which is preferably formed from molded handle housing segments 36a and 36b, which collectively form stationary handle member 22 and barrel portion 26 of handle assembly 12. A movable handle 824 may be pivotably supported between handle housing segments 36a and 36b about pivot pin 38. See FIG. 22. A biasing member 40, that may comprise a torsion spring, biases movable handle 824 away from stationary handle 22. An actuation shaft 46 may be supported within barrel portion 26 of handle housing 36 and includes a rack 48 of teeth 49. A driving pawl 42 that has a rack engagement tooth 43 thereon may be pivotably mounted to one end of movable handle 824 about a pivot pin 44. A biasing member 50, which may comprise a torsion spring, may be employed to urge driving pawl 42 towards rack 48 on actuation shaft 46. As movable handle 824 is actuated (e.g., pivoted), it moves driving pawl 42 such that rack engagement tooth 43 drivingly engages toothed rack 48 of actuation shaft 46 to advance the actuation shaft 46 linearly in the distal direction "DD". The forward end of actuation shaft 46 has a cavity 47 formed therein to receive the proximal end 53 of a control rod 52 (FIG. 23) such that linear advancement of actuation shaft 46 causes corresponding linear advancement of control rod 52.

The stapling apparatus 810 may further have a locking pawl 54 that has a rack locking member 55 that may be pivotably mounted within the handle housing 36 about pivot pin 57 and is biased towards toothed rack 48 by biasing member 56, which is also preferably a torsion spring. Rack locking protrusion 55 of locking pawl 54 is oriented for movement into a cavity 512 in actuation shaft 46, such that when rack locking protrusion 55 is in the cavity 512, actuation shaft 46 is retained in a longitudinally fixed position when no disposable loading unit has been coupled to the stapling apparatus 810.

Various embodiments may also include a retraction mechanism 58 that may comprise a right retractor knob 32a and a left retractor knob 32b that are connected to the proximal end of actuation shaft 46 by a coupling rod 60. See FIG. 22. Coupling rod 60 may include right and left engagement portions 62a and 62b for receiving retractor knobs 32a, 32b and a central portion 62c which is dimensioned and configured to translate within a pair of longitudinal slots 34a respectively formed in actuation shaft 46 adjacent the proximal end thereof. A release plate 64 may be operatively associated with actuation shaft 46 and is mounted for movement with respect thereto in response to manipulation of retractor knobs 32a, 32b. A pair of spaced apart pins 66 may extend outwardly from a lateral face of actuation shaft 46 to engage a pair of corresponding angled cam slots 68 formed in release plate 64. Upon movement of retractor knobs 32a, 32b in the proximal direction "PD", pins 66 can release plate 64 downwardly with respect to actuation shaft 46 and with respect to toothed rack 48 such that the bottom portion of release plate 64 extends below toothed rack 48 to disengage engagement tooth 43 of driving pawl 42 from toothed rack 48. A slot 70 may be formed at the proximal end of release plate 64 to accommodate the central portion 62c of coupling rod 60, and elongated slots 34 are provided in the barrel section 26 of handle assembly 12 to accommodate the longitudinal translation of coupling rod 60 as retraction knobs 32a, 32b are pulled in the proximal direction "PD" to retract actuation shaft 46 and thus retract control rod 52 rearwardly.

The stapling apparatus 810 may further include a sensor link 882 that may be slidably attached to the handle housing segment 36a by a pin or screw 530 that extends through a slot 532 in the sensor link 882 such that the sensor link 882 may slide longitudinally relative to the handle housing 36. A distal end of a spring 531 may be attached to the screw 530 and the proximal end of the spring 531 may be hooked over a hook 533 on the sensor link 882. See FIG. 22. Spring 531 serves to bias the sensor link 882 in the distal direction "DD". The sensor link 882 further includes a proximal locking arm 535 that has an inwardly protruding proximal end 537 configured to interact with the locking pawl 54. In particular, when no disposable loading unit 16, 16' is attached to the instrument 810, the sensor link 882 is biased distally by spring 531. When in that "unloaded" position, the proximal end 537 of the proximal locking arm 535 disengages the locking pawl 54 to retain the locking pawl 54 in the locked position wherein the locking protrusion 55 is received in cavity 512 to retain actuation shaft 46 in a longitudinally fixed position. Thus, when no disposable reload unit 16, 16' is coupled to the instrument 810, the instrument 810 cannot be fired.

Figure 23:
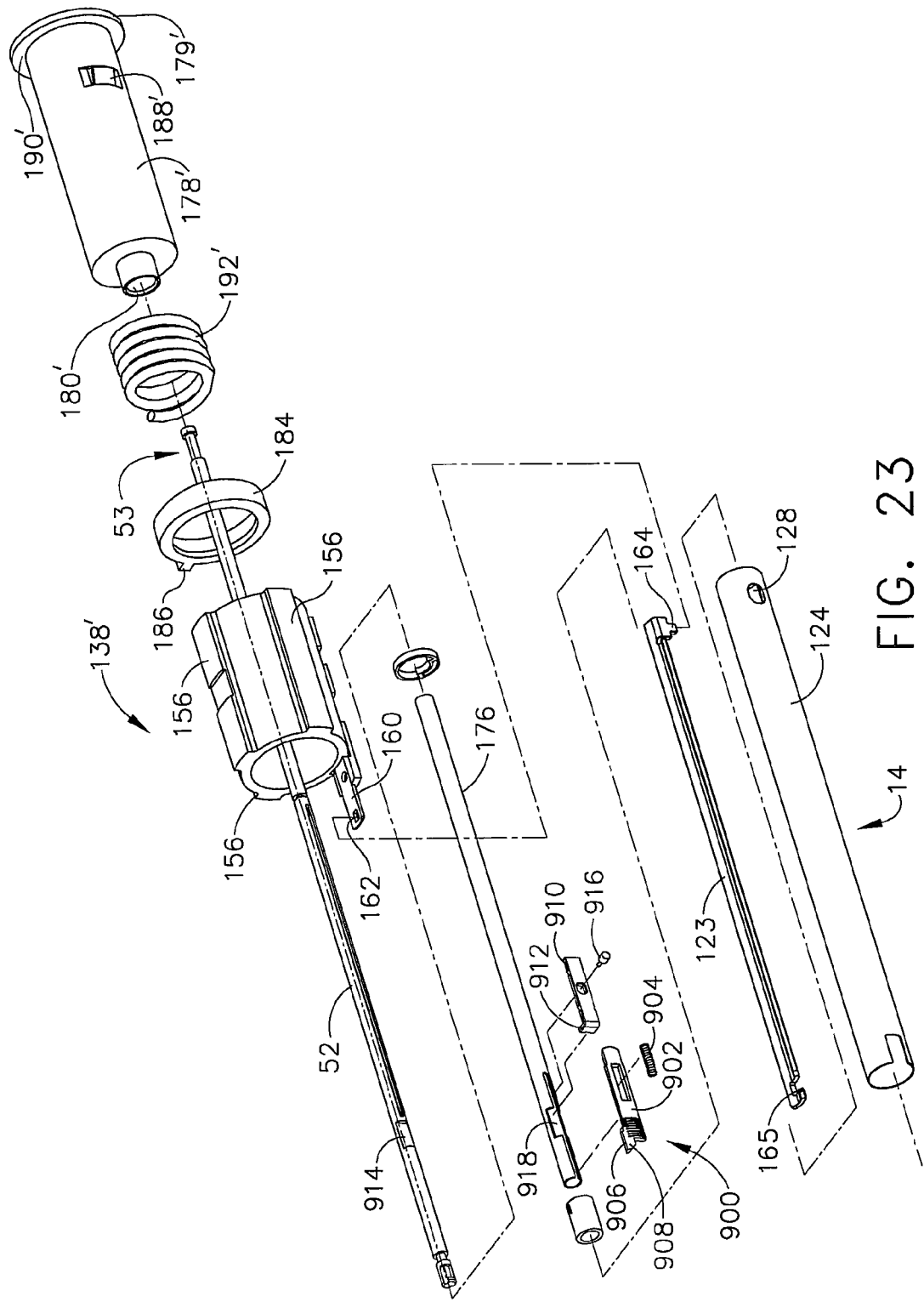
FIG. 23 is an exploded assembly view of another disposable loading unit sensing mechanism embodiment of various embodiments of the present invention.
Figure 24:
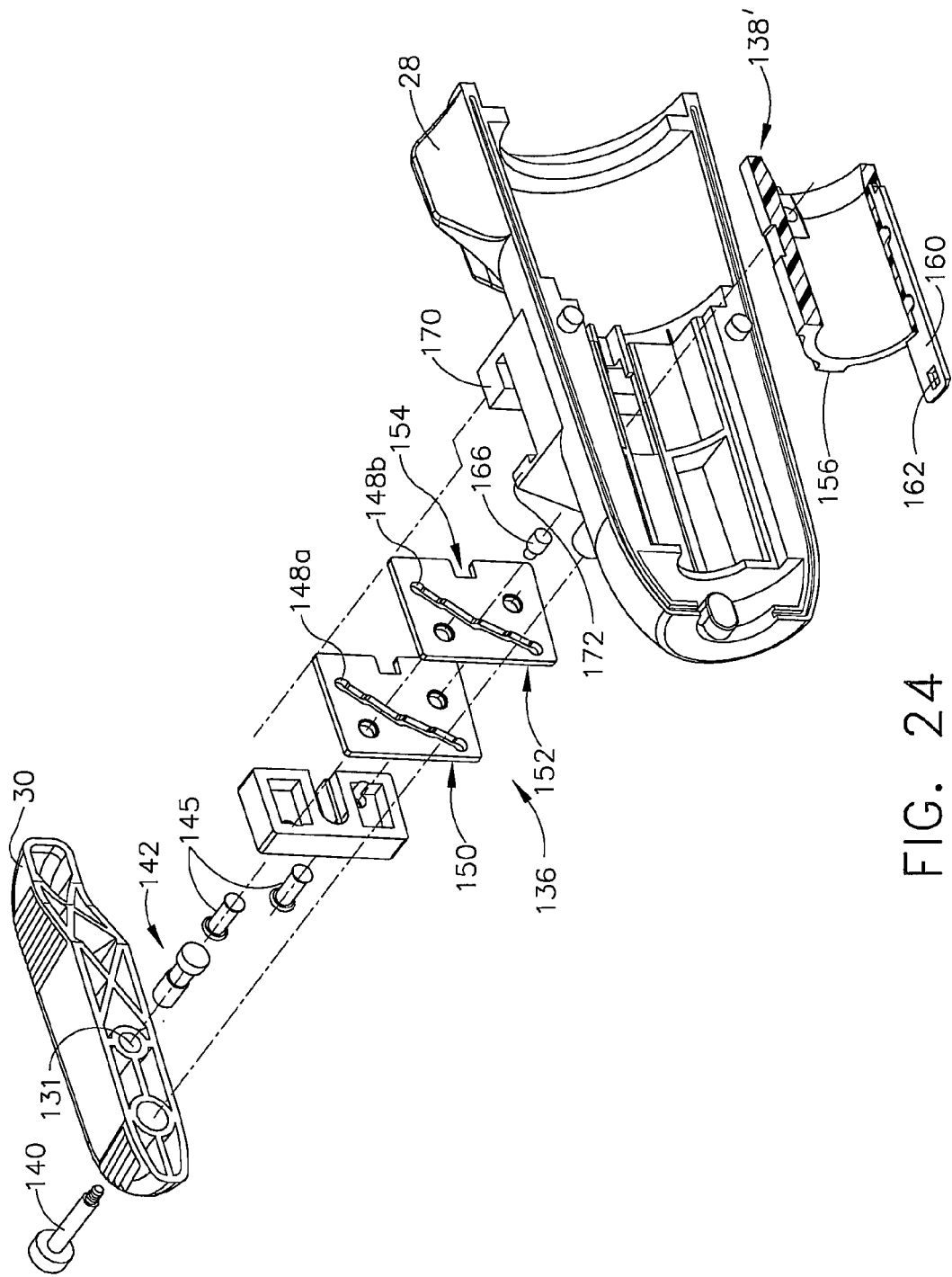
FIG. 24 is an exploded assembly view of another rotation knob assembly and articulation mechanism embodiment of the present invention.

Referring to FIG. 23, a disposable loading unit sensing mechanism may extend within stapling apparatus 810 from elongated body 14 into handle assembly 12. The sensing mechanism may include a sensor tube 176 which is slidably supported within the outer casing 124. The distal end of sensor tube 176 is positioned towards the distal end of elongated body 14 and the proximal end of sensor tube 176 is secured within the distal end of a sensor cylinder 178' via a pair of nubs 180'. The distal end of a sensor link 882 is oriented in abutting relationship with the flanged proximal end 190' of sensor cylinder 178'.

The sensor link 882 may further have a downwardly extending distal tab 534 formed thereon for contact with a flange 179 formed on a sensor cylinder 178'. See FIGS. 22 and 23. As will be discussed in further detail below, a sensor tube 176 is oriented to interface with the sensor cylinder 178'. See FIG. 23. When a disposable loading unit 16, 16' is coupled to the distal end of elongated body 14, the disposable loading unit 16, 16' engages the distal end of the sensor tube 176 to drive sensor tube 176 proximally, and thereby drive sensor cylinder 178' and sensor link 882 proximally. As the sensor link 882 is moved proximally, the proximal end 537 of the proximal locking arm 535 to pivot the locking pawl 54 such that the locking protrusion 55 moves out of cavity 512 to permit actuation shaft 46 to be actuated.

The stapling apparatus 810 may also employ an articulation mechanism 120 of the type and construction described in detail above, with the following noted differences. In various embodiments, an articulation mechanism 120 may be supported on rotatable knob 28 and include an articulation lever 30, a cam member 136 and a translation member 138'. In various embodiments, translation member 138' may include a plurality of ridges 156 which are configured to be slidably received within grooves (not shown) formed along the inner walls of rotation knob 28. Engagement between ridges 156 and those grooves prevent relative rotation of rotation knob 28 and translation member 138' while permitting relative linear movement. The distal end of translation member 138' may include an arm 160 which includes an opening 162 configured to receive a finger 164 extending from the proximal end of articulation link 123. See FIG. 23.

In an assembled condition, proximal and distal stepped portions 150 and 152 of cam member 136 are positioned beneath flanges 170 and 172 formed on rotation knob 28 to restrict cam member 136 to transverse movement with respect to the longitudinal axis "L-L" of stapling apparatus 810. When articulation lever 30 is pivoted about pivot pin 140, cam member 136 is moved transversely on rotation knob 28 to move stepped camming surface 148 (refer to FIG. 11) transversely relative to pin 166, forcing pin 166 to move proximally or distally along stepped cam slot 148. Since pin 166 is fixedly attached to translation member 138', translation member 138' is moved proximally or distally to effect corresponding proximal or distal movement of first actuation link 123. See FIGS. 23 and 24.

Referring again to FIG. 24, cam member 136 may include a recess 154. A locking ring 184 having a nub portion 186 configured to be received within recess 154 is positioned about sensor cylinder 178' between a control tab portion 188' and a proximal flange portion 190'. See FIG. 23. A spring 192' positioned between flange portion 190' and locking ring 184 urges locking ring 184 distally about sensor cylinder 178'. When an articulating disposable loading unit 16 having an extended tip portion is inserted into the distal end of elongated body 14 of stapling apparatus 810, insertion tip causes control tab portion 188' to move proximally into engagement with locking ring 184 to urge locking ring 184 and nub portion 186 proximally of recess 154 in cam member 136. With nub portion 186 positioned proximally of recess 154, cam member 136 is free to move transversely to effect articulation of stapling apparatus 810. Other non-articulating disposable loading units may not have an extended insertion tip. As such, when a non-articulating disposable loading unit 16 is coupled to elongated body 14, sensor cylinder 178' is not retracted proximally a sufficient distance to move nub portion 186 from recess 154. Thus, cam member 136 is prevented from moving transversely by nub portion 186 of locking ring 184 which is positioned in recess 154 and articulation lever 30 is locked in its central position.

Referring to FIG. 23, the distal end of elongated body 14 may include a control rod locking mechanism 900 which may be activated during coupling of a disposable loading unit 16, 16' with the distal end of elongated body 14. Control rod locking mechanism 900 may include a blocking plate 902 which is biased distally by a spring 904 and includes a proximal finger 906 having angled cam surface 908. In various embodiments, a firing shaft lock 910 that has a lock tab 912 protruding therefrom may be employed. The lock tab 912 may be configured to selectively engage a notch 914 in the control rod 52. The firing shaft lock 910 may be provided with a biasing member in the form of a leaf spring (not shown) or the like and have a lock pin 916 extending therethrough. The leaf spring serves to bias the firing shaft lock 910 outwardly when the proximal end of the blocking plate 902 is forward in a distal position. Blocking plate 902 may be movable from a distal position spaced from lock tab 912 to a proximal position located behind lock tab 912. In the proximal position, the blocking plate 902 causes the lock tab 912 to extend through a slot 918 in the sensor tube 176 into engagement with notch 914 in the control rod 52.

During insertion of a disposable loading unit 16, 16' into the distal end of elongated body 14, as will be described in further detail below, cam surface 908 of blocking plate 902 is engaged by a nub on the disposable loading unit 16, 16' as the disposable loading unit 16, 16' is rotated into engagement with elongated body 14 to urge plate 902 to the proximal position. Locking tab 912, which is positioned within notch 914, is retained therein by blocking plate 902 while the nub engages cam surface 908 to prevent longitudinal movement of control rod 52 during assembly. When the disposable loading unit 16, 16' is properly positioned with respect to the elongated body 14, the nub on the proximal end of the disposable loading unit 16, 16' passes off cam surface 908 allowing spring 904 to return blocking plate 902 to its distal position to permit subsequent longitudinal movement of control rod 52. It is noted that when the disposable loading unit nub passes off cam surface 908, an audible clicking sound may be produced indicating that the disposable loading unit 16, 16' is properly fastened to the elongated body 14.

Figure 25:
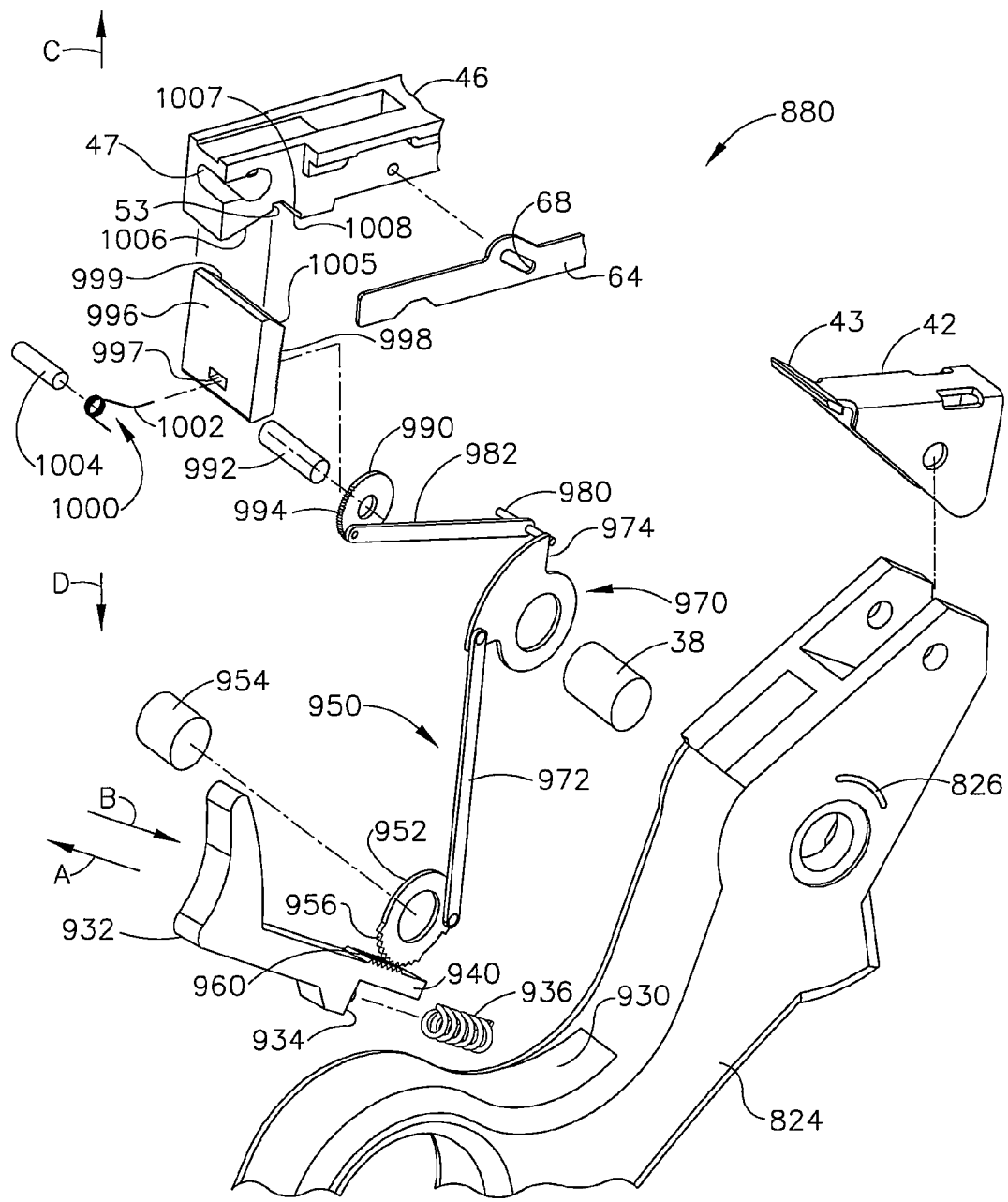
FIG. 25 is an exploded assembly view of a firing release trigger assembly of an embodiment of the present invention.
Figure 26:
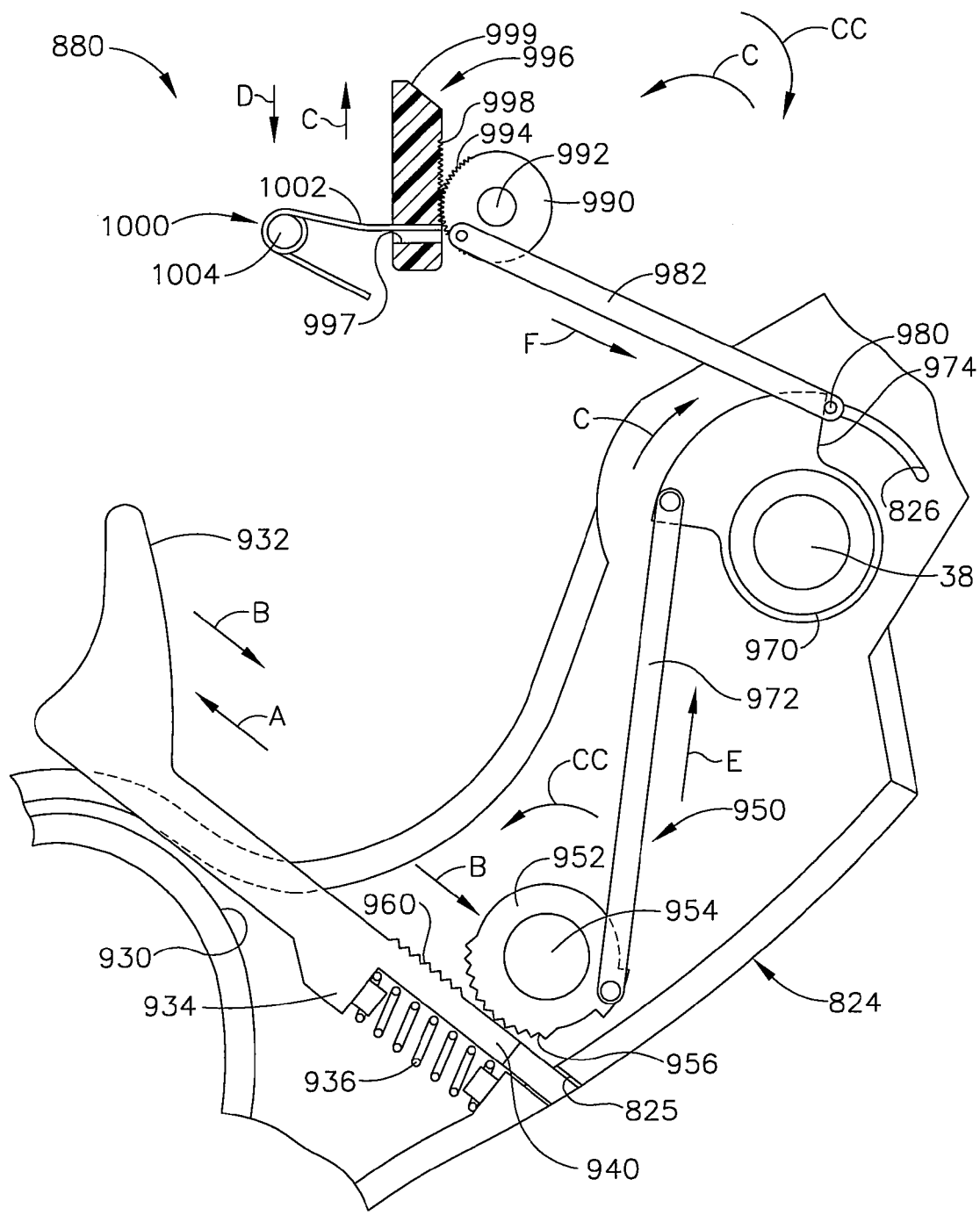
FIG. 26 is a partial assembly view of the firing release trigger assembly depicted in FIG. 25.

Referring now to FIGS. 22, 25 and 26, the stapling apparatus 810 may employ an improved firing lockout assembly 880. In this embodiment, the movable handle 824 may be provided with a cavity 930 sized to receive a proximal portion of a firing release trigger 932. As can be seen in those Figures, the firing release trigger 932 may have a nub 934 formed thereon and a release spring 936 may extend between the bottom of the cavity 930 and the nub 934 to apply a biasing force to the firing release trigger 932 in the "A" direction. As can be most particularly seen in FIG. 26, the firing release trigger 932 may have a proximal tail portion 940 that is sized to slidably extend into a slot 825 formed in the movable handle 824 as the firing release trigger is depressed in the "B" direction. The improved firing lock out assembly 880 may further include a gear linkage assembly 950. In various embodiments, the gear linkage assembly 950 may include a first gear 952 that is rotatably received on a first gear pin 954 that is attached to the movable handle 824. First gear 952 may have a first gear segment 956 that is arranged for meshing engagement with a release trigger gear rack 960 formed on the tail portion 940 of the firing release trigger 932. First gear 952 may be linked to a release pawl 970 by a first connector link 972 that is pivotally pinned or otherwise attached to the first gear 952 and the release pawl 970. As can be seen in FIGS. 22 and 25, the release pawl 970 may be pivotally supported on pin 38.

In various embodiments, release pawl 970 may have an engagement portion 974 that is configured to engage a release pin 980 that is attached to a second connector link 982 and is constrained to ride in an arcuate slot 826 formed in the movable handle 824. As the present Detailed Description proceeds, it will become apparent that the slot 826 prevents actuation of the movable handle 824 from moving the second connector link 982. The second connector link 982 may also be pivotally pinned or attached to a gate gear 990 that is rotatably journaled on a gear pin 992 that is supported by handle housing segments 36a, 36b. Gate gear 990 has a segment of gear teeth 994 thereon oriented for meshing engagement with a gate rack 998 formed on a locking gate 996. The locking gate 996 may have a slot 997 therein that is adapted to receive a portion 1002 of a gate spring 1000 that is supported on a gate pin 1004 that extends between the handle housing segments 36a, 36b. Gate spring 1000 serves to bias the locking gate 996 in the "C" direction. See FIG. 26.

Figure 27:
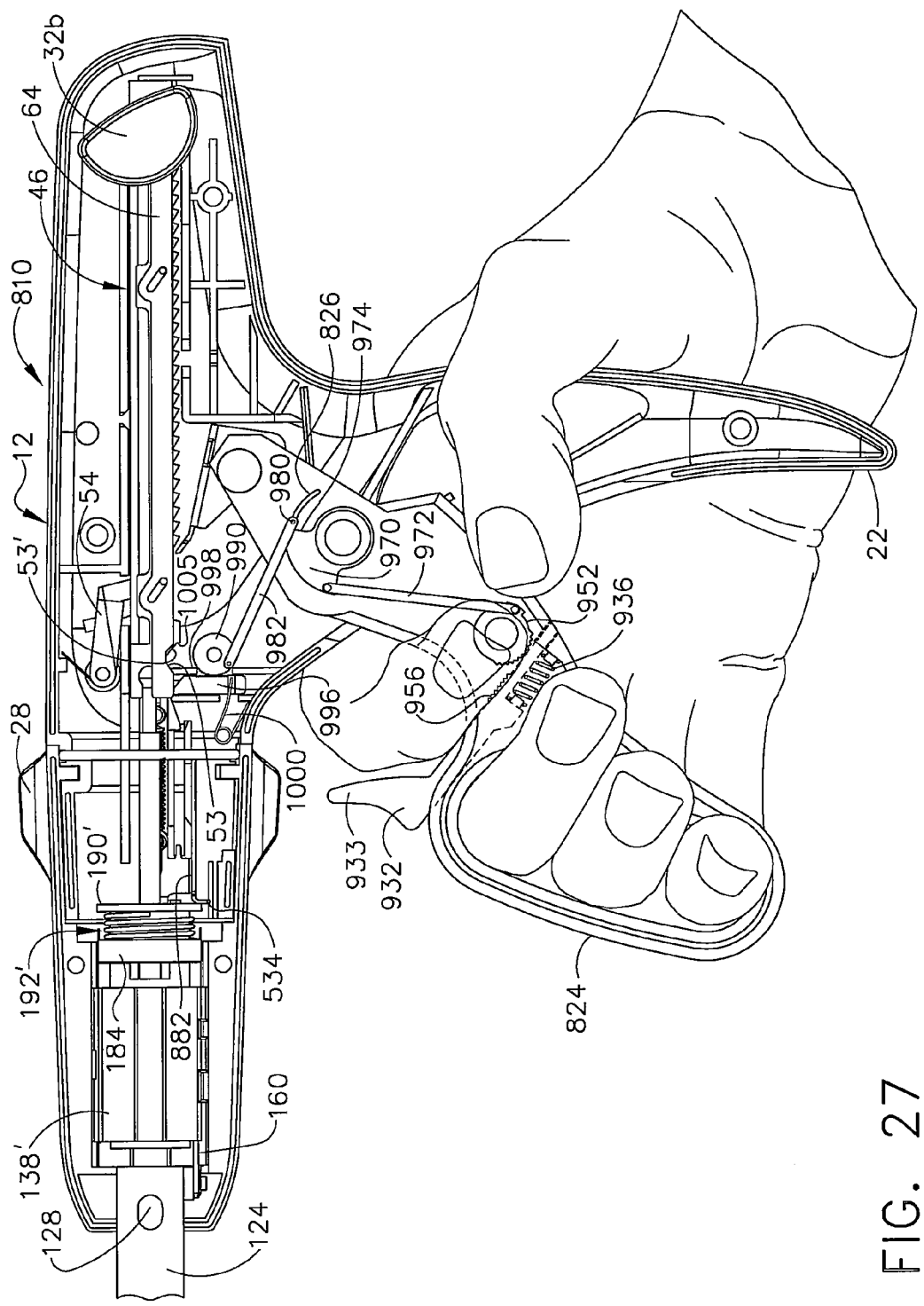
FIG. 27 is an assembly view of a handle assembly embodiment of the present invention.
Figure 28:
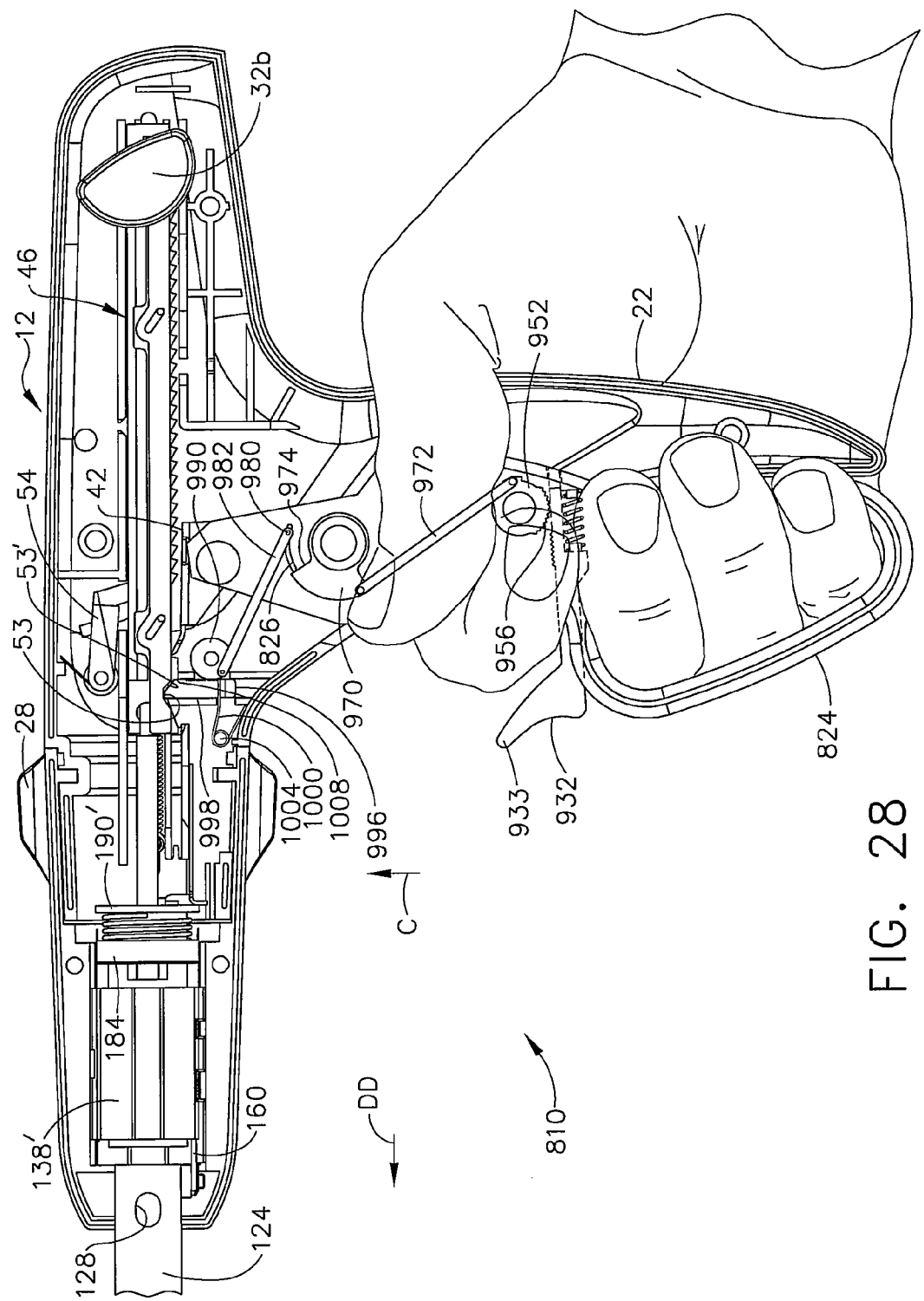
FIG. 28 is another assembly view of a handle assembly embodiment of the present invention with the movable handle thereof pulled against the stationary handle portion to close the anvil on the disposable loading unit.
Figure 29:
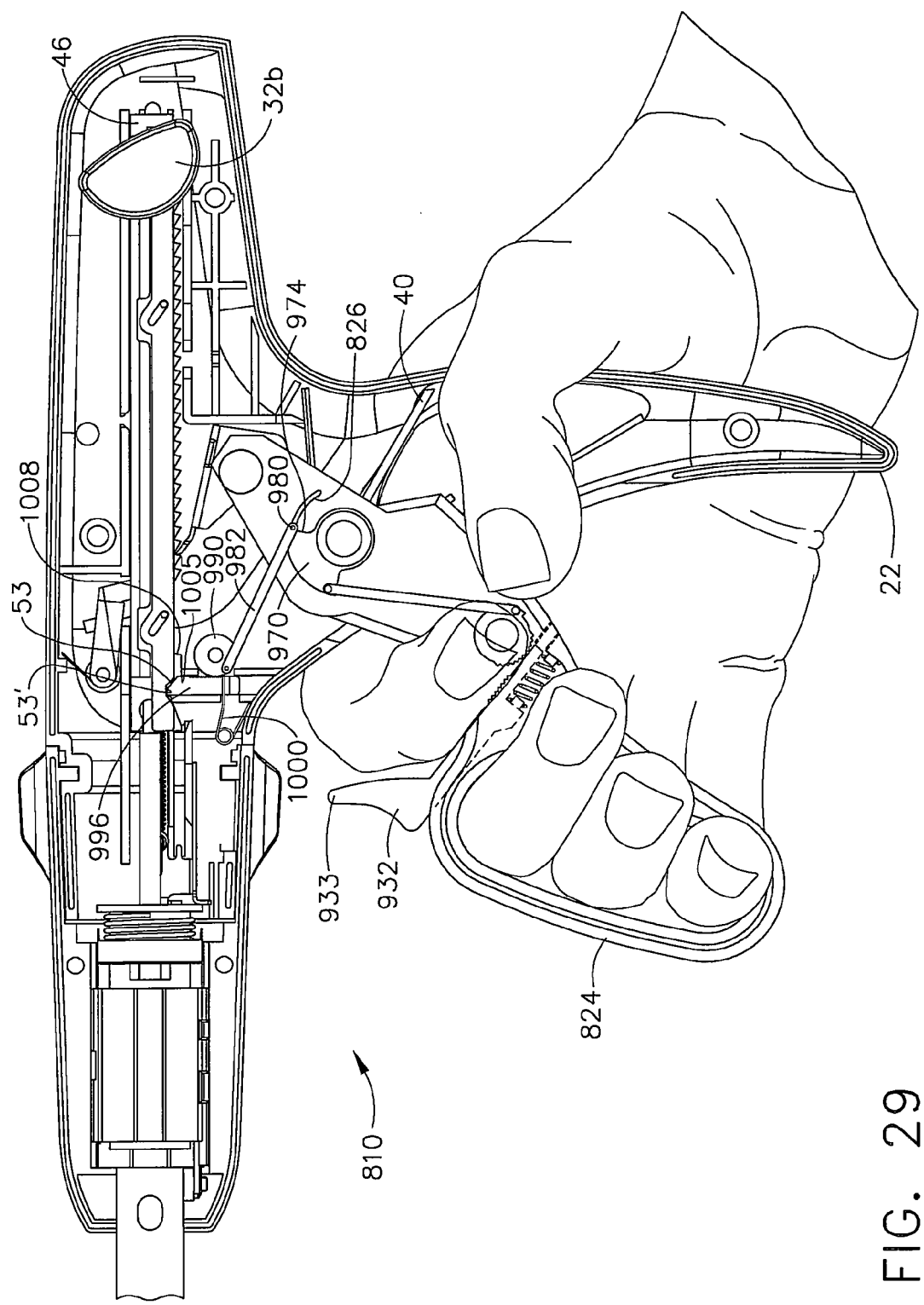
FIG. 29 is another assembly view of a handle assembly embodiment of the present invention with the movable handle returned to a starting position after the anvil has been closed.

Operation of the firing lockout assembly 880 will now be described with reference to FIGS. 27-30. FIG. 27 illustrates the stapling apparatus 810 prior to clamping tissue in the disposable loading unit (not shown). As can be seen in that Figure, the engagement portion 974 of the release pawl 970 is not in contact with the release pin 980 at this stage of operation. As can also be seen, the upper end of the locking gate 996 is at the distal end of the actuation shaft 46. FIG. 28 illustrates a first actuation of movable handle 824 to cause the staple forming anvil of the disposable loading unit to close in the manner described above. The clinician has not yet depressed the firing release trigger 932 and has conveniently placed his or her index finger behind the actuation portion 933 of the firing release trigger 932. By actuating the movable handle 824, the actuation shaft 46 is driven in the distal direction "DD" by the driving pawl 42 in the manner described above. As can be seen in FIG. 28, the actuation shaft 46 has moved to a position wherein the end of the locking gate 996 has entered into the locking detent 53 in the actuation shaft 46 and corresponding locking detent 53' in the release plate 64. As more easily seen in FIG. 25, the upper end of the locking gate 996 has a chamfered or tapered portion 999 formed thereon that meets with the vertical extending proximal side 1005 of the locking gate 996. As can also be seen in FIG. 25, the locking detent 53 in the actuation shaft 46 has angled surfaces 1006, 1007 and also a vertical ledge portion 1008. When the upper end of the locking gate 996 is completely biased into the locking detent 53 by the gate spring 1000, the proximal side 1005 of the locking gate 996 is in confronting relationship with the vertical ledge 1008 in the actuation shaft 46 to thereby prevent movement of the actuation shaft 46. However, when the locking gate 996 is pulled in the direction "D", the angled surfaces 1006, 1007, as well as the chamfered surface 999 on the locking gate 996, enable the actuation shaft 46 to move longitudinally past the locking gate 996 without the locking gate 996 having to be completely biased out of contact with the actuation shaft 46.

Figure 30:
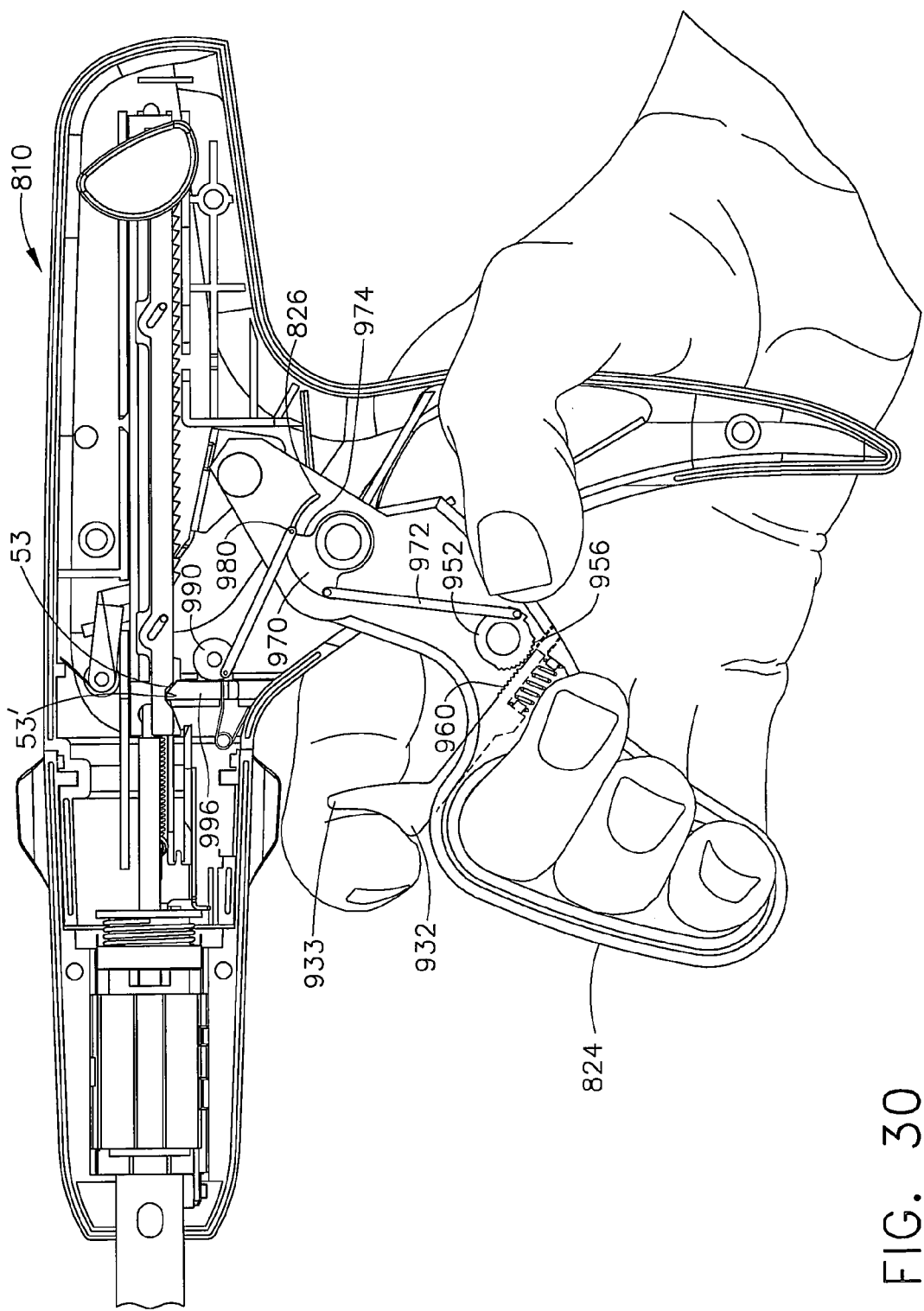
FIG. 30 is another assembly view of a handle assembly embodiment of the present invention prior to activating the firing release trigger.

Returning to FIG. 28, when in that position, the slot 826 in the movable handle 824 permitted the movable handle to be pulled toward the stationary handle portion 22 without causing the pin 980 to move the second connection link 982 which in turn would actuate the locking gate 996. As can be seen in FIG. 28, the spring 1000 has biased the locking gate 996 into the blocking position wherein the locking gate 996 is received in locking detents 53, 53' and the proximal surface 998 thereof is in confronting relationship with the vertical ledge 1008 in the actuation shaft 46. After the movable handle 824 has been pulled to the first position shown in FIG. 28 to close the staple forming anvil, the clinician then permits the movable handle 824 to move to the position illustrated in FIG. 29 under the biasing force of the handle closure spring 40. At this stage, the retractor knobs 32a, 32b could be pulled proximally to cause the staple forming anvil to unclamp the tissue in the event that the clinician wishes to re-manipulate the tool 17 or, the clinician may wish to commence the firing cycle by placing his or her index finger on the actuation portion 933 of the firing release trigger 932 as illustrated in FIG. 30.

Figure 31:
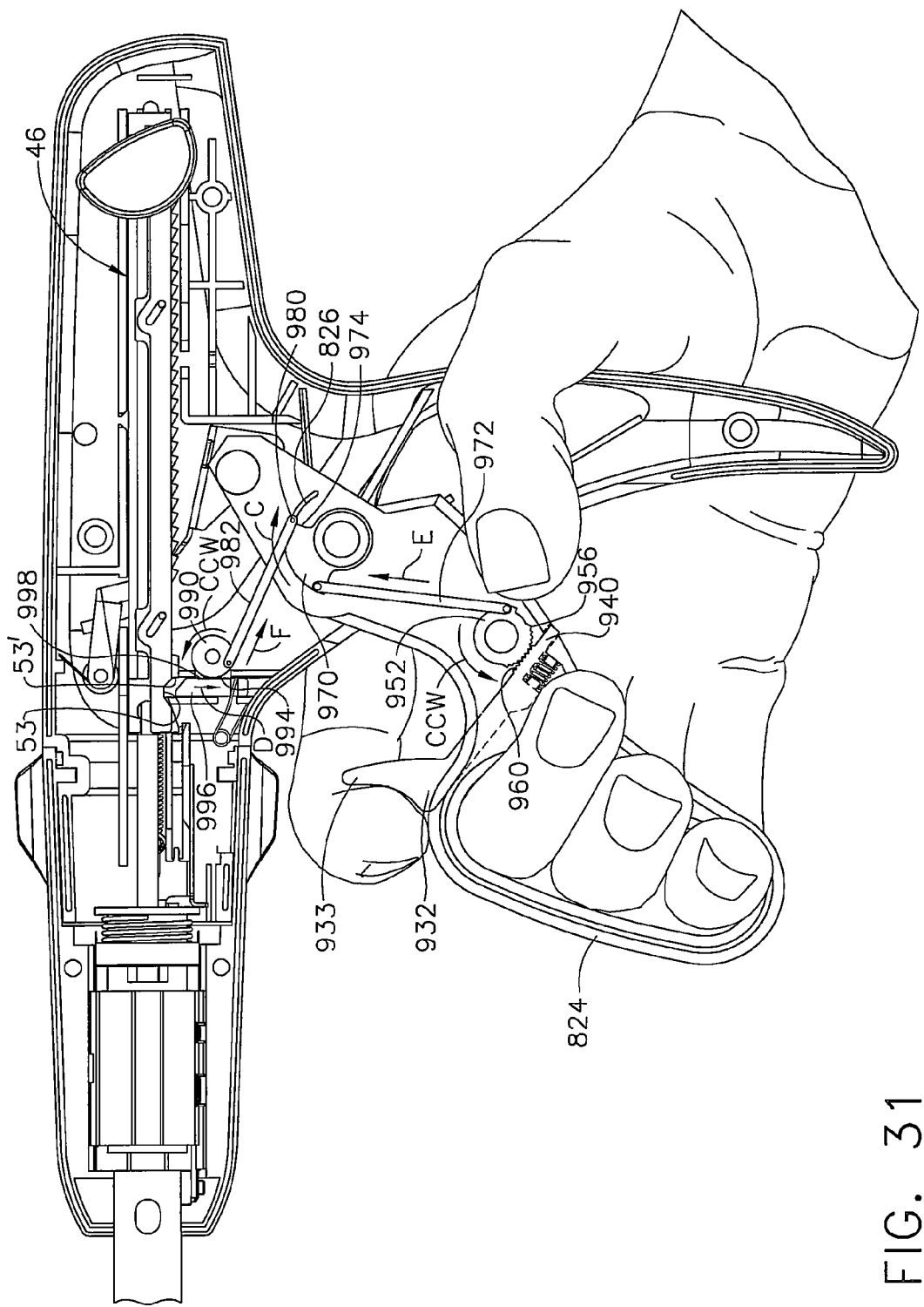
FIG. 31 is another assembly view of a handle assembly embodiment of the present invention with the firing release trigger activated.

In FIG. 31, the clinician has depressed the firing release trigger 932. Such action causes the release trigger gear rack 960 in the release trigger tail portion 940 to mesh with the first gear segment 956 on the first gear 952 to cause the first gear 952 to rotate in the counterclockwise direction "CCW". As the first gear 952 rotates in the counterclockwise direction, it pushes the first connector link 972 in the "E" direction, causes the release pawl 970 to rotate in the clockwise "C" direction. As the release pawl 970 rotates in the "C" direction, the engagement surface 974 contacts release pin 980 and draws the second connection link 982 in the "F" direction. As the second connector link 982 moves in the "F" direction, it causes the gate gear 990 to rotate in the counterclockwise direction "CCW". The gear teeth 994 on the gate gear 990 mesh with the gate rack 998 and drive the locking gate 996 in the "D" direction out of blocking engagement with the locking detents 53, 53'.

Figure 32:
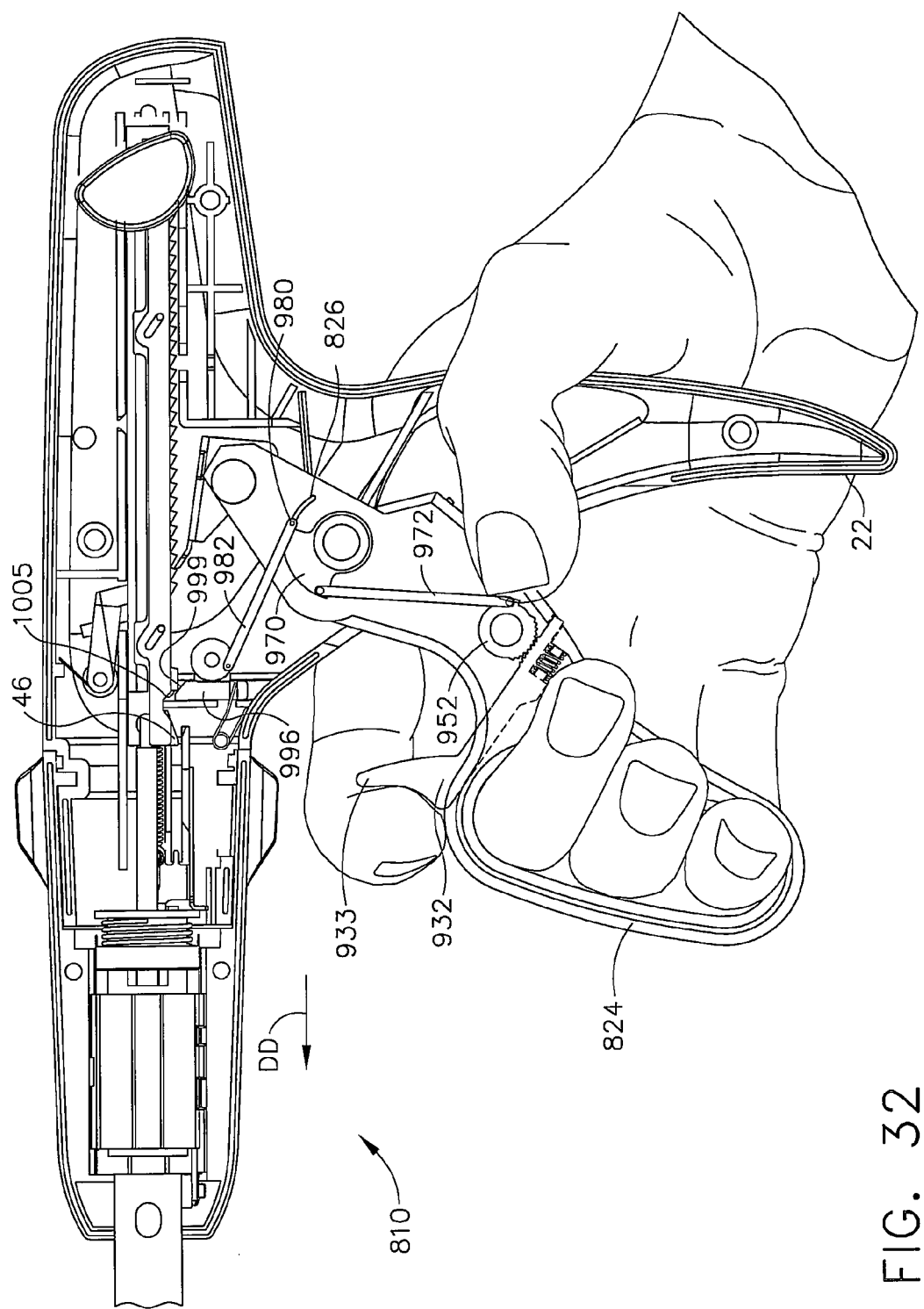
FIG. 32 is another assembly view of a handle assembly embodiment of the present invention with the firing release trigger activated and the movable handle starting to be actuated.
Figure 33:
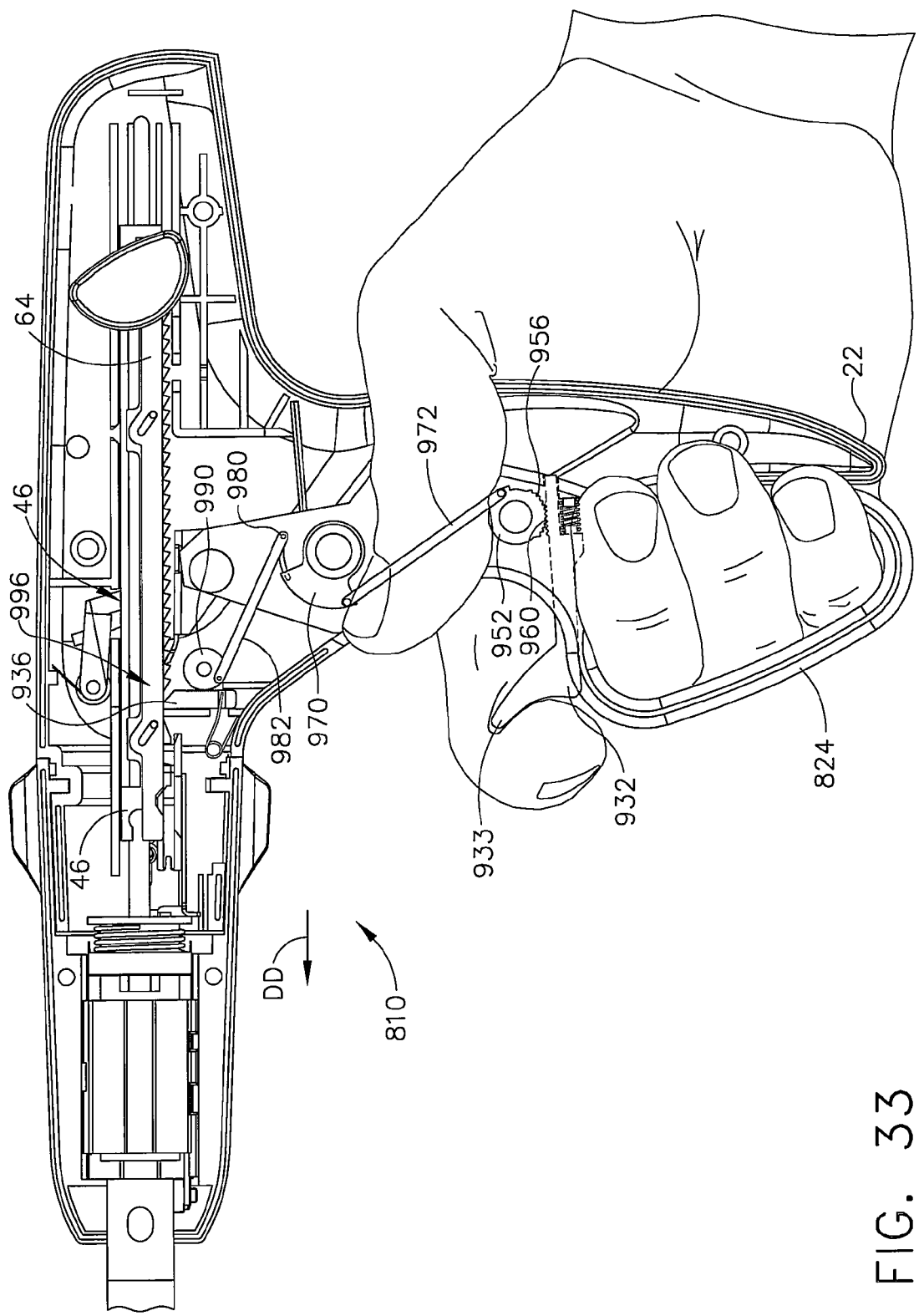
FIG. 33 another assembly view of a handle assembly embodiment of the present invention with the firing release trigger activated with the movable handle thereof pulled against the stationary handle portion.

FIG. 32 illustrates the position of the locking gate 996 relative to the actuation shaft 46 as the actuation shaft 46 begins to move in the distal direction "DD" by actuating the movable handle 824. As can be seen in that Figure, the upper chamfered portion 999 of the locking gate 996 is now in contact with the vertical edge 1005 in the actuation shaft 46 and permits the actuation shaft 46 to move distally. FIG. 33 illustrates the completion of a first firing stroke of the movable handle 824. As can be seen in that Figure, the upper end of the locking gate 996 rides on the bottom of the actuation shaft 46 and the plate 64 as the actuation shaft 46 is advanced in the distal direction "DD". Link 982, proximal end has moved to the proximal end of slot 826 during that stroke.

Figure 34:
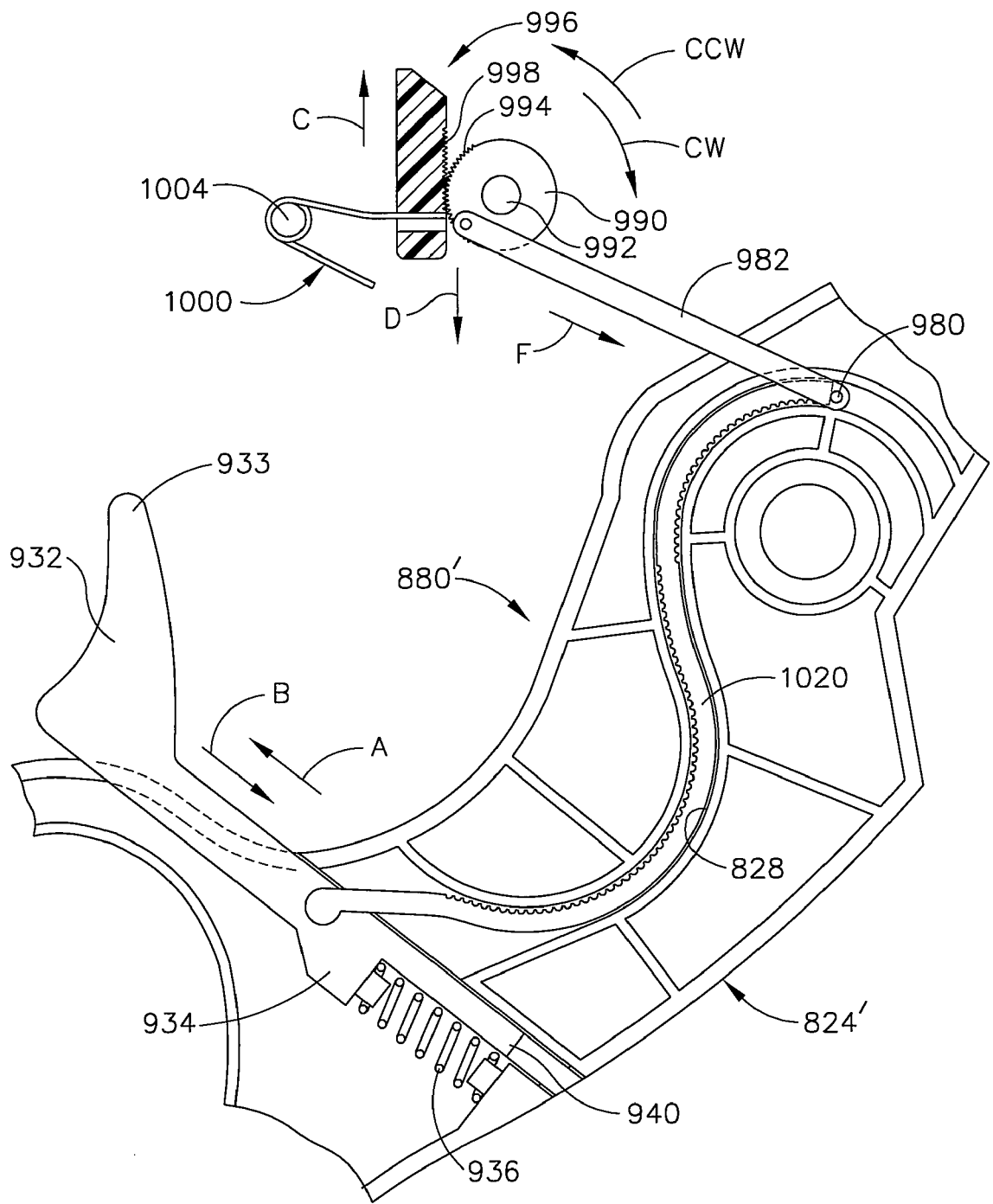
FIG. 34 is a partial assembly view of another firing release trigger embodiment of the present invention.
Figure 35:
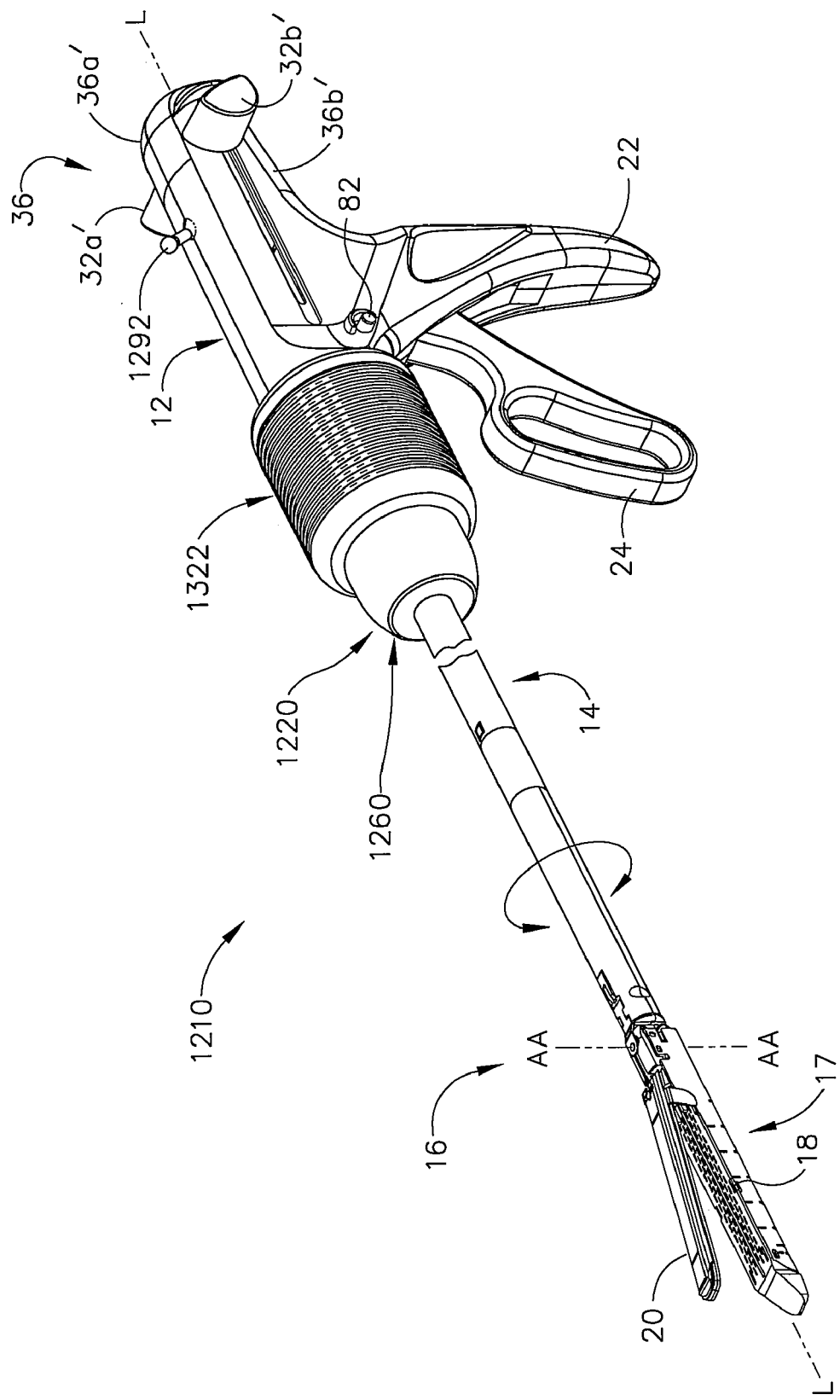
FIG. 35 is a perspective view of another surgical stapling apparatus embodiment of the present invention.

FIG. 34 illustrates an alternative stapling apparatus embodiment 810' that employs an alternative firing lockout assembly 880' that may be substantially the same as the firing lockout assembly 880 described above, except for the differences noted below. In particular, the firing lock out assembly 880' employs a flexible bar 1020 that is constrained to move in a serpentine passage 828 formed in the movable handle 824'. The flexible bar 1020 replaces the first gear 952, the first connector link 972, and the release pawl 970. One end of the flexible bar 1020 is coupled to the firing release trigger 932 and the other end of the flexible bar 1020 is constrained to contact the release pin 980 which is also constrained to move in the slot 828. Thus, as the firing release trigger 932 is depressed, the flexible bar 1020 pushes the release pin 980 which causes the second connector link 982 to move in the "F" direction. As the second connector link 982 moves in the "F" direction, the gate gear 990 moves in the counter clockwise direction "CC" and drives the locking gate 996 in the "D" direction. When the clinician releases the firing release trigger 932, the release spring 936 drives the firing release trigger 932 in the "A" direction pulling the flexible bar 1020 away from the release pin 980, thereby permitting the release pin 980 to move unconstrained in the slot 828. As the release pin 980 is unconstrained, the gate spring 1000 is permitted to bias the locking gate 996 in the "C" direction. As the locking gate 996 is biased in the "C" direction, the gate gear 990 is driven unconstrained in a clockwise "C" direction. Those of ordinary skill in the art will appreciate that the firing lockout arrangements 880, 880' described above enable the clinician to operate the instruments with one hand. This represents a vast improvement over those firing lockout systems disclosed in U.S. Pat. No. 5,865,361 and other prior stapling apparatuses configured for use with disposable loading units.

FIGS. 35-46 depict a surgical stapling apparatus 1210 that addresses at least some of the aforementioned problems associated with prior surgical stapling apparatuses that are designed to accommodate articulatable disposable loading units. More particularly and with reference to FIG. 35, the surgical stapling apparatus 1210 may be substantially similar in construction as the various instruments described above, except for the selectively lockable rotation system 1220 and the articulation system 1320 (FIG. 36) as will be described in detail below. Those components that are the same as the components employed in the above-mentioned embodiments will be labeled with the same element numbers and those of ordinary skill in the art can refer to the disclosure set forth hereinabove that explains their construction and operation.

Figure 36:
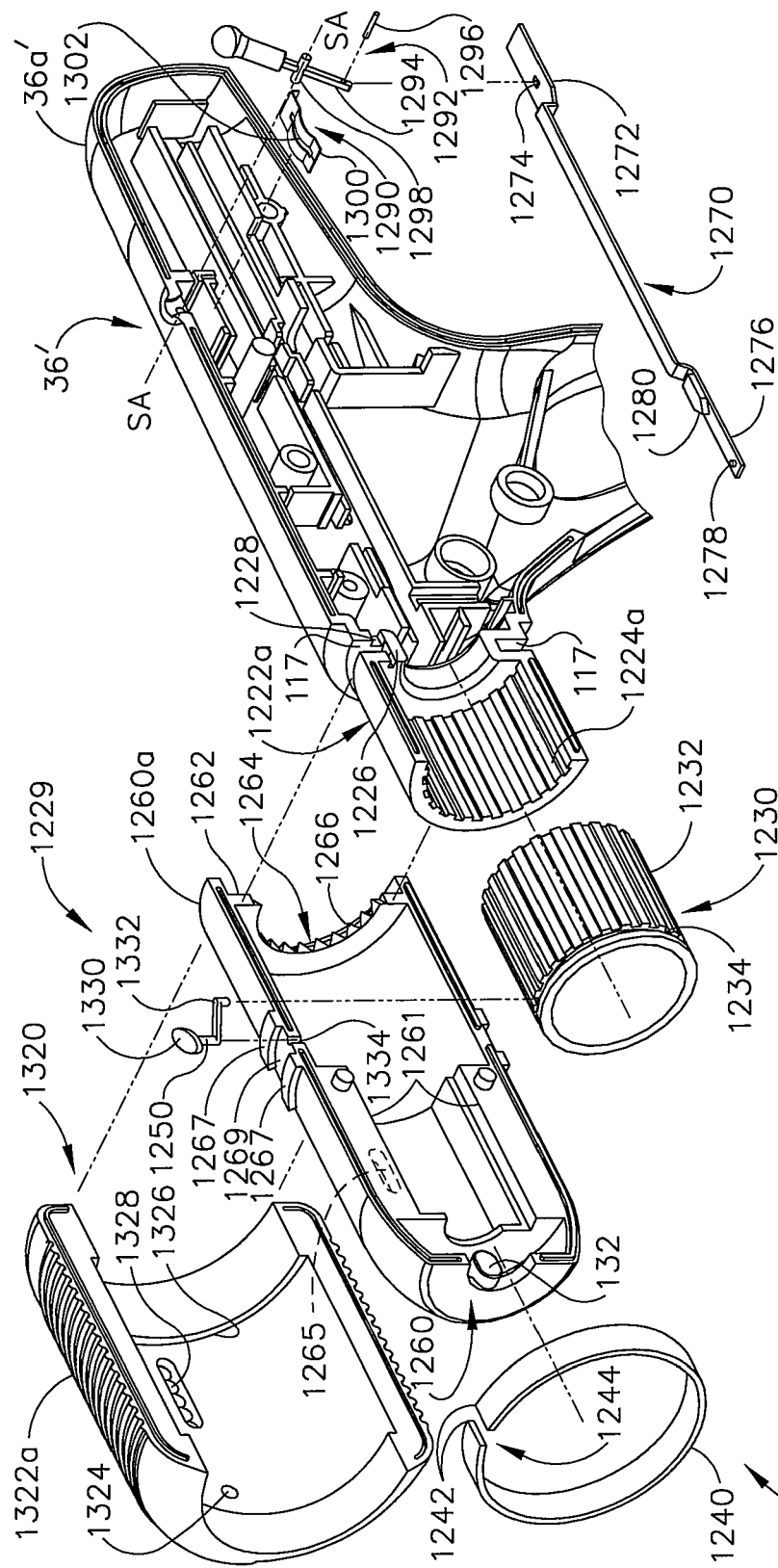
FIG. 36 is a partial exploded assembly view of a portion of the handle assembly and rotatable shroud of the surgical stapling apparatus of FIG. 35.
Figure 44:
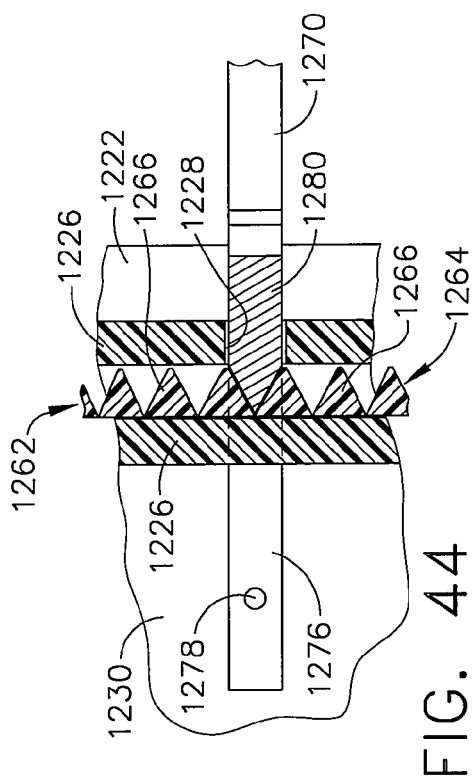
FIG. 44 is an enlarged view of the bolt engaging the rotation lock ring to lock the apparatus in the articulation mode.
Figure 45:
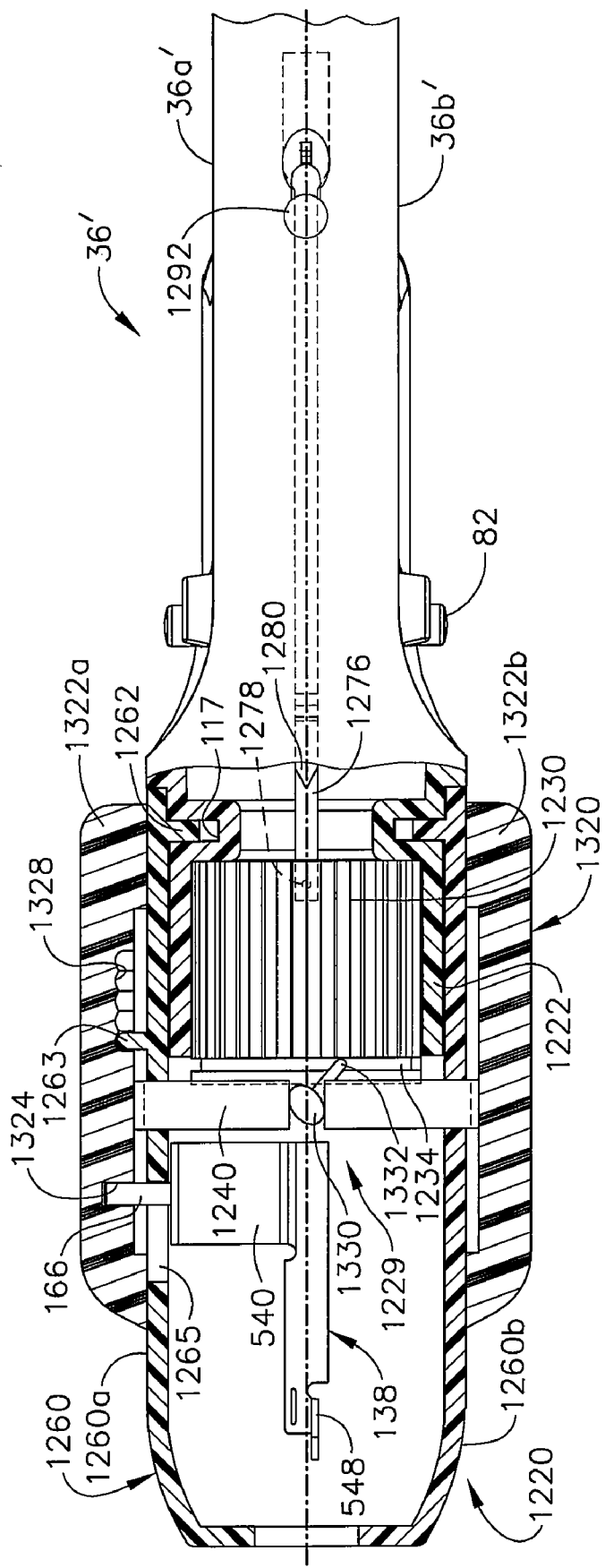
FIG. 45 is a partial cross-sectional view of the surgical stapling apparatus of FIG. 43 taken along line 45-45 in FIG. 43.

In one embodiment, the surgical stapling apparatus 1210 may include a handle assembly 12 that has an elongated body 14 that is operably coupled thereto and which protrudes distally therefrom. A distal end of the elongated body 14 may be coupled to an articulatable disposable loading unit 16. The disposable loading unit 16 may include a tool assembly 17 that is selectively articulatable about an articulation axis "A1-"A1" by articulation motions transferred thereto by the elongated body 14 as is known. See FIG. 35. In various embodiments of the present invention, the proximal end of the elongated body 14 may be coupled to a rotatable shroud 1260 that is coupled to handle housing 36'. As can be seen in FIGS. 36, 44 and 45, handle housing 36' may include an annular channel 117 configured to receive an annular rib 1262 formed on the proximal end of rotatable shroud 1260, which is preferably formed from molded shroud segments 1260a and 1260b. Annular channel 117 and rib 1262 permit relative rotation between shroud 1260 and handle housing 36'. Rotation of rotatable shroud 1260 causes the elongated body 14 and the disposable loading unit attached thereto to rotate about the longitudinal axis "L-L" defined by the elongated body 14. Various embodiments of surgical stapling apparatus 1210 may include a selectively lockable rotation system 1220 for selectively locking the rotatable shroud 1260 to prevent rotation thereof (as well as rotation of elongated body 14 and disposable loading unit 16) relative to the handle assembly 12 about the longitudinal axis "L-L".

In various embodiments, the lockable rotation system 1220 may include a cylindrical distal cover 1222 formed or otherwise provided on the distal end of the handle housing 36'. FIG. 36 illustrates housing segment 36a' of handle housing 36' that has one cover segment 1222a formed thereon. Those of ordinary skill in the art will understand that the housing segment 36b' of handle housing 36' has a mating cover segment 1222b formed thereon that cooperates with cover segment 1222a to form distal cover 1222. See FIG. 40.

The lockable rotation system 1220 may further include a brake system 1229. In particular, cover segment 1222a may have an internal spline section 1224a and cover segment 1222b may have an internal spline 1224b. Internal spline sections 1224a, 1224b cooperate to form an internal spline 1224 which is configured to support a brake tube 1230 of the brake system 1229. In various embodiments, the brake tube 1230 has an external spline 1232 formed thereon that is sized to be received in internal spline 1224 in the distal cover 1222 such that the brake tube 1230 can move axially relative to the distal cover 1222, but is constrained to rotate therewith. The brake system 1229 may further include a brake band 1240 that interacts with a brake arm pin 1250 that is operably supported in a rotatable shroud 1260. The operation of the brake arm pin 1250 and brake band 1240 will be discussed in further detail below.

The brake tube 1230 may be moved axially relative to the cylindrical distal cover 1222 by a switch bar 1270 that is operably connected to a selector switch assembly 1290. As can be seen in FIG. 36, the switch bar 1270 has a proximal end 1272 and a distal end 1276. The proximal end 1272 may have a hole 1274 for receipt of a shaft portion 1294 of a selector switch 1292. The shaft portion 1294 extends through the hole 1274 in the switch bar 1270 and is pinned thereto by a cross pin 1296. In addition, the selector switch 1292 may have a fastener pin 1298 that pivotally couples the shaft portion 1294 to the housing 36'. A detent spring 1300 may be employed to lock the selector switch 1292 in position. The detent spring 1300 may have a bulbous portion 1302 that is adapted to be engaged by the cross pin 1296 as the selector switch 1292 is pivoted distally and proximally about a axis "SA-SA" defined by fastener pin 1298. See FIG. 36. Thus, as the selector switch 1292 is pivoted to the proximal position (FIGS. 42, 43 and 46) and as the selector switch 1292 is pivoted to the distal position (FIGS. 37, 38, 41 and 45) the bulbous portion 1302 of spring 1300 retains the selector switch 1292 and the switch bar 1270 in position.

Referring again to FIG. 36, the distal end 1276 of the switch bar 1270 may have a connector pin 1278 protruding therefrom that is adapted to couple the switch bar 1270 to the brake tube 1230. See FIG. 38. Thus, linear movement of the switch bar in the proximal direction "PD" and distal direction "DD" causes the brake tube 1230 to also move in those directions within the cylindrical distal cover portion 1222. As can also be seen in FIGS. 36-39 and 41-46, the distal end 1276 of the switch bar 1270 may further have a bolt 1280 formed thereon or attached thereto. The bolt 1280 is adapted to selectively meshingly engage a rotation lock ring 1264 that comprises a series of teeth 1266 formed on or otherwise provided on the annular rib 1262. As can be seen in FIG. 36, the annular channel 117 in the cylindrical distal cover 1222 is formed by a inwardly extending flange 1226 that has a groove 1228 therethrough to receive the distal end 1276 of the switch bar 1270 therethrough. Thus, as will be discussed in further detail below, when the switch bar 1270 is moved in the distal direction "DD", the bolt 1280 can be brought into meshing engagement with the teeth 1266 of the rotation lock ring 1264 of the shroud 1260 and thereby prevent the shroud 1260 from rotating with respect to the cover 1222 and shroud 36. See FIG. 44.

Various embodiments of the surgical stapling apparatus 1210 may further include a unique and novel articulation system 1320 which, as will be described below, interfaces with the components forming the elongated body 14 to selectively apply articulation motions thereto for transfer to the disposable loading unit 16. The articulation system 1320 may include a translation member 138'. For example, the translation member 138' may include a plurality of ridges 156 which are configured to be slidably received within grooves 1261 formed along the inner walls of the shroud 1260. Engagement between ridges 156 and those grooves 1261 (FIGS. 36 and 37) prevents relative rotation of the translation member 138' and the shroud 1260 while permitting relative linear movement between those components. The distal end of translation member 138' may include an arm 160 which includes an opening 162 configured to receive a finger 164 extending from the proximal end of articulation link 123. See FIG. 37. Also in this embodiment, the translation member 138' has an articulation pin 166 protruding therefrom that extends through an articulation slot 1265 in the articulation shroud 1260. The articulation pin 166 is received in a hole 1324 (FIG. 36) formed in a linear articulation and rotation grip 1320 that is received on the shroud 1260. The articulation system may further include a linear articulation and rotation grip 1322 that may be fabricated from two grip segments 1322a, 1322b that are coupled together about the shroud 1260. The hole 1324 may be provided in the grip segment 1322a as shown in FIG. 36. Thus, when the clinician moves the grip 1322 axially in the proximal direction "PD" and distal direction "DD", the translation member 138', as well as the articulation link 123, moves in those directions to effectuate articulation of the articulatable disposable loading unit.

Figure 37:
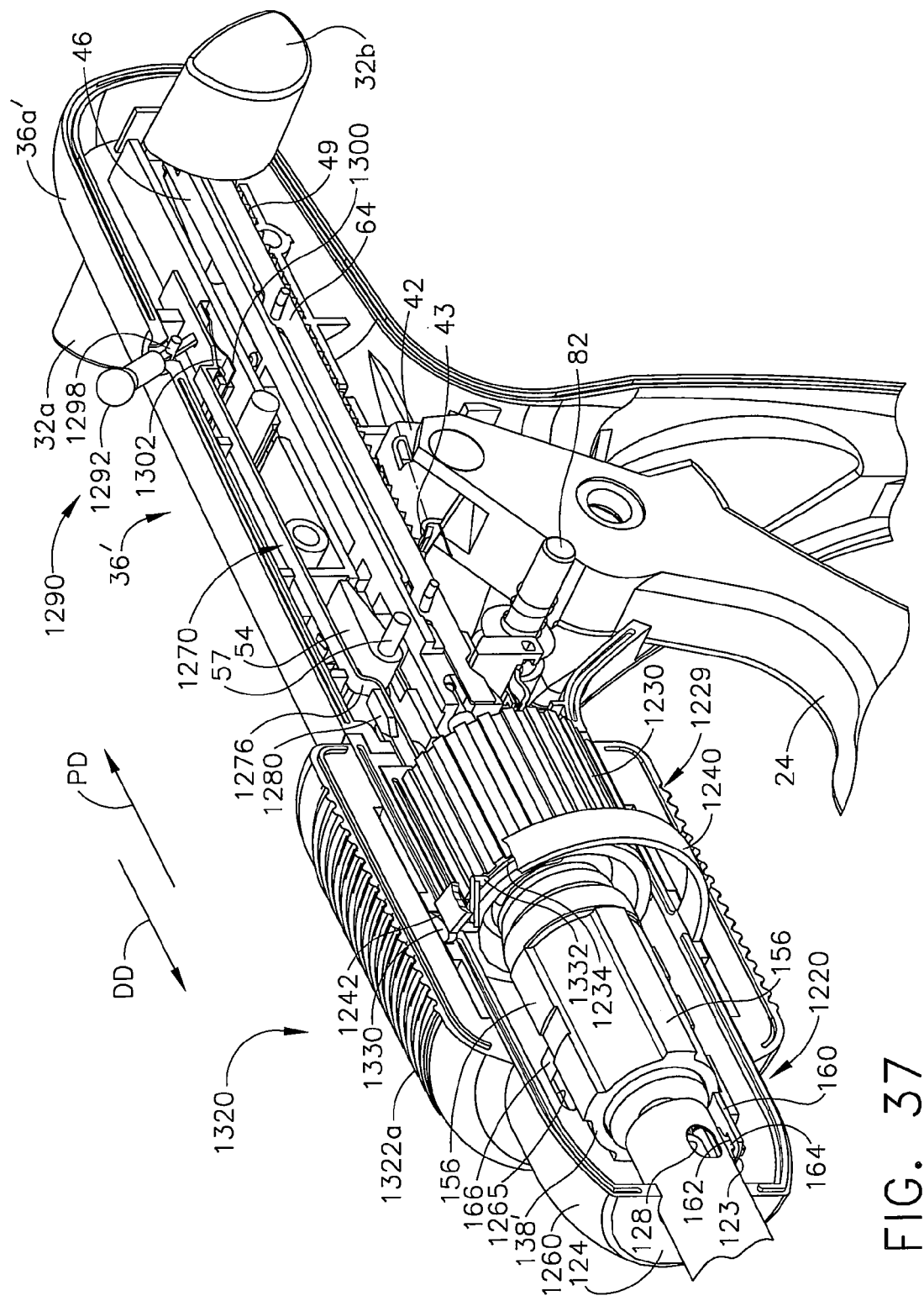
FIG. 37 is a perspective view of a portion of the surgical stapling apparatus embodiment of FIGS. 35 and 36 with a portion of the handle housing removed to show the various components therein in the rotation mode.
Figure 40:
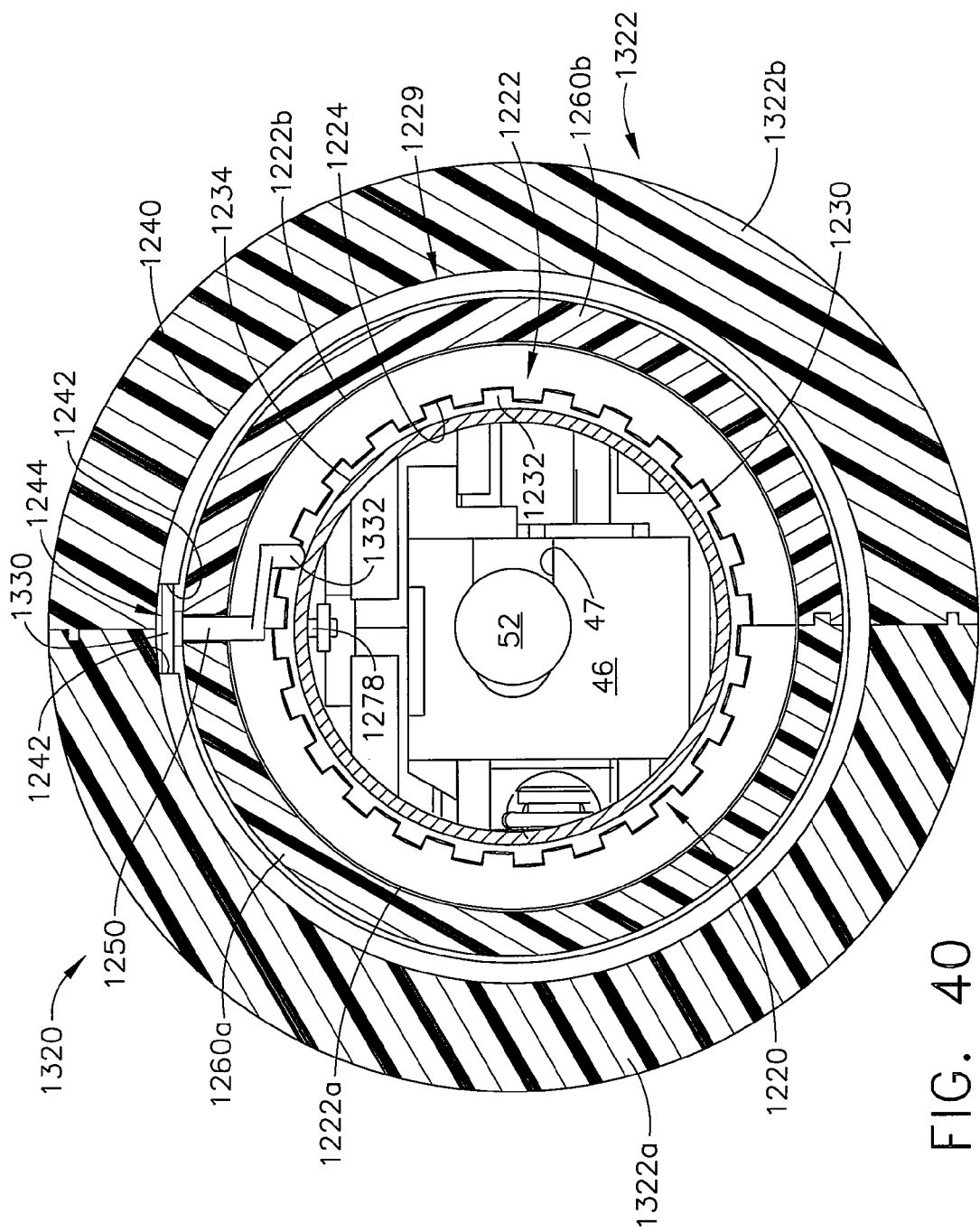
FIG. 40 is a cross-sectional view of the surgical stapling apparatus taken along line 40-40 in FIG. 38.
Figure 41:
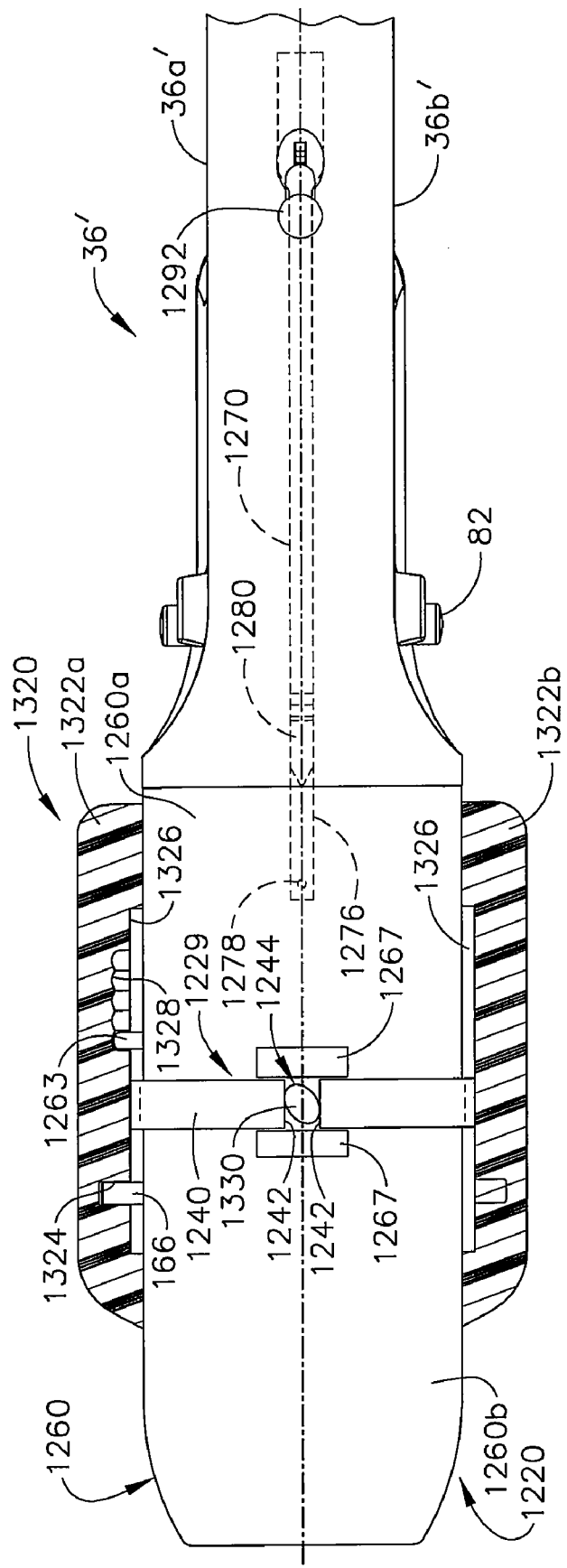
FIG. 41 is a partial top view of the surgical stapling apparatus of FIGS. 35-40 with the grip portion shown in cross-section.

Also in this embodiment, the brake system 1229 may be configured to prevent actuation of the articulation system 1320. For example, referring again to FIG. 36, the band brake 1240 may be configured to be received within spaced shoulder flanges 1267 formed on the exterior of shroud 1260 to form a brake band groove 1269. As can be seen in FIG. 36, the brake band 1240 does not form a complete ring; the ends 1242 of the band brake 1240 are in spaced confronting relationship relative to each other to define a cam-receiving opening 1244 therebetween. The brake band 1240 is installed within the brake band groove 1269 such that the cam opening 1242 is oriented to receive a brake cam 1330 therein. Attached to the brake cam 1330 is a brake arm shift pin 1332 that extends through a brake cam hole 1334 in the shroud 1260. As can be seen in FIG. 37 the brake arm shift pin 1332 is configured to be received within a shifting groove 1234 formed in the distal end of the brake tube 1230. The linear articulation and rotation grip 1322 which comprises a portion of the articulation system 1320 has an undercut area 1326 therein to enable the grip 1320 to move axially relative to the shroud 1260. In various embodiments, the grip segment 1322a may be provided with a series of detents 1328 that is adapted to engage an indicator pin 1263 (FIG. 41) protruding from the shroud 1260 such that as the grip 1320 is axially moved on the shroud 1260, the indicator pin 1263 makes an audible click or sound as it engages the detents 1328. Five detents 1328 are illustrated in that Figure; other numbers of detents 1328 may be used.

The operation of the surgical stapling apparatus 1210 will now be described with reference to FIGS. 37-39, 41, and 42-44. FIGS. 37-39 illustrate the stapling apparatus 1210 in the "rotation" mode wherein the outer casing 124 may be selectively rotated about longitudinal axis "L-L". As can be seen in FIGS. 37 and 38, the selector switch 1292 is pivoted to the distal position wherein the switch bar 1270 is pulled in the proximal direction "PD". When the switch bar 1270 is pulled in the proximal direction, the rotation bolt 1280 is disengaged from the rotation lock ring 1264 (FIG. 39) thereby permitting the shroud 1260 to rotate about longitudinal axis "L-L". As discussed above, the proximal end of casing 124 includes diametrically opposed openings 128, which are dimensioned to receive radial projections 132 formed inside the distal end of shroud 1260. See FIGS. 36 and 38. Projections 132 and openings 128 fixedly secure shroud 1260 and elongated body 14 in relation to each other, both longitudinally and rotatably. Rotation of shroud 1260 with respect to handle assembly 12 thus results in corresponding rotation of elongated body 14 about longitudinal axis L-L with respect to handle assembly 12. Also, because the switch bar 1270 is coupled to the brake tube 1230 by connector pin 1278, as the switch bar 1270 is moved in the proximal direction "PD", the brake tube 1230 also moves in the proximal direction within the cylindrical distal cover 1222. As explained above, the shift pin 1332 of the brake cam 1330 is received in a shifting groove 1234 in the brake tube 1230. When the brake tube 1230 is moved proximally, the shift pin 1332 that is a distal feature of a radius arm that in turn is rigidly affixed to the pin 1250 rotates brake cam 1330 such that it forces the ends 1242 of the brake band 1240 radially outwardly to thereby lock the linear articulation and rotation grip 1322 to the shroud 1260. The brake band 1240 prevents the grip 1322 from moving axially on the shroud 1260; however, rotation of the grip 1322 causes the shroud 1260 to rotate about axis "L-L". Thus, when the selector switch 1292 is pivoted to the distal direction, the elongated body 14 and disposable loading unit attached thereto may be rotated about the longitudinal axis "L-L" by rotating the grip 1320.

Figure 42:
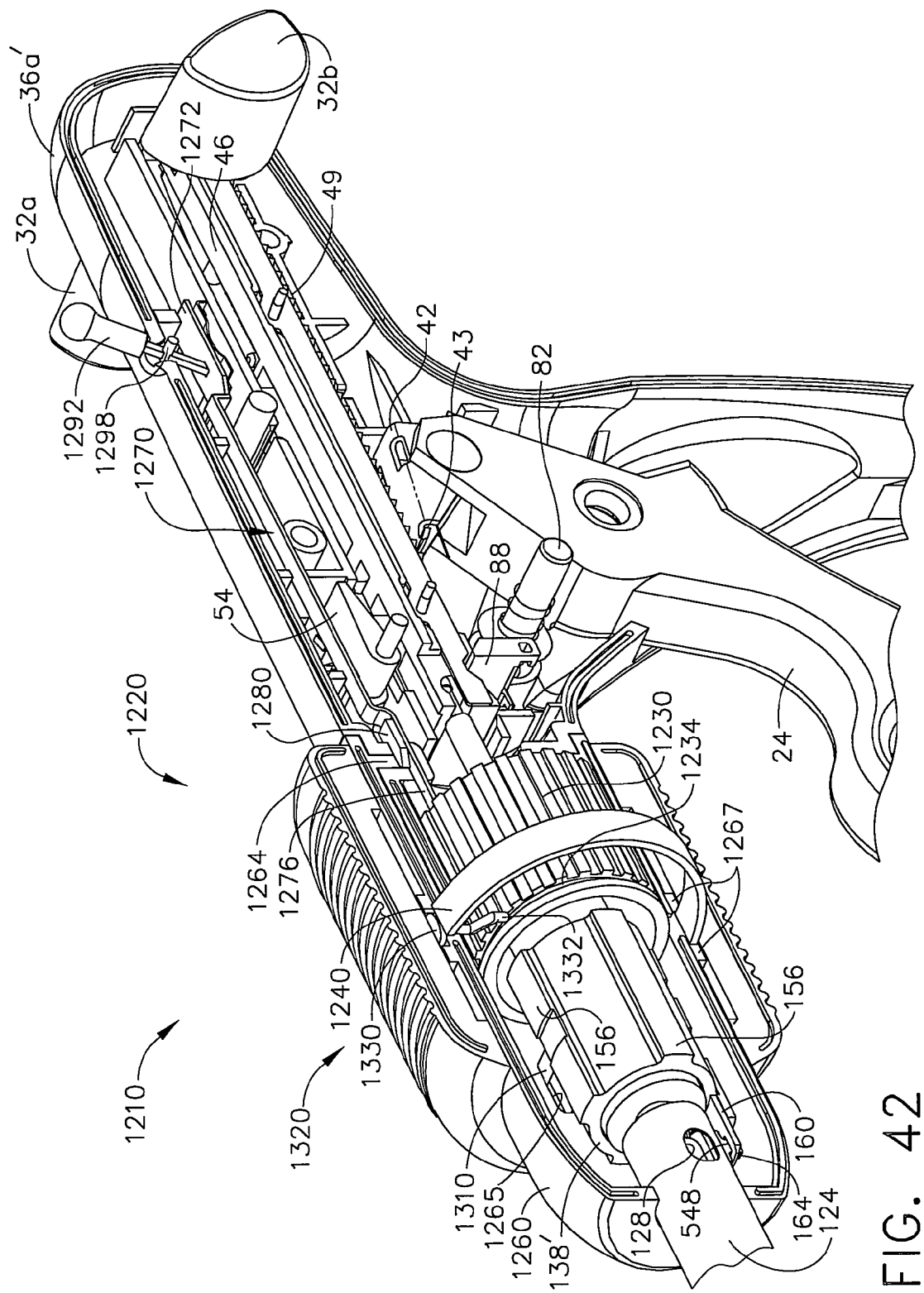
FIG. 42 is a perspective view of a portion of the surgical stapling apparatus embodiment of FIGS. 35-41 with a portion of the handle housing removed to show the various components therein in the articulation mode.
Figure 43:
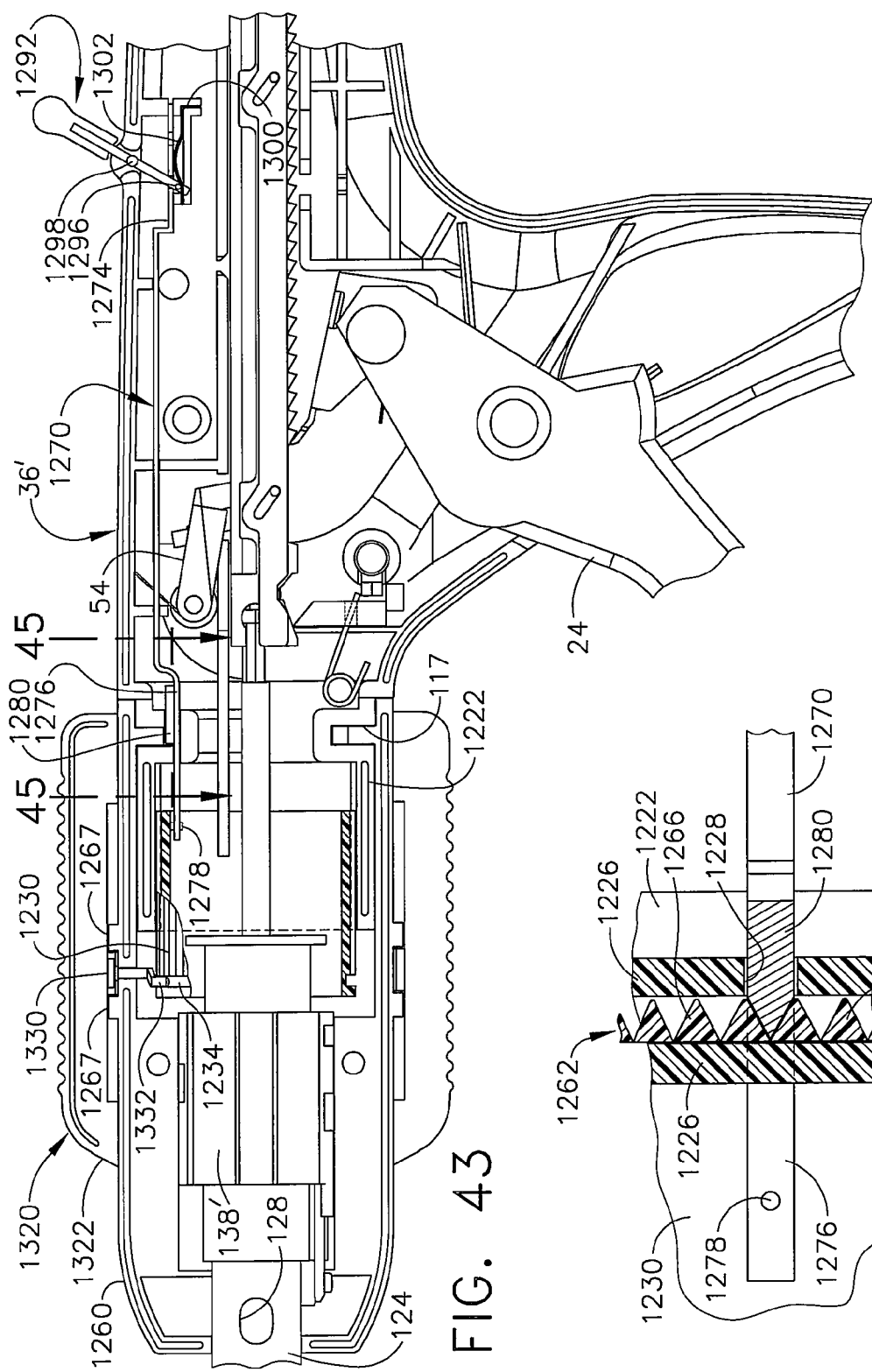
FIG. 43 is a side view of the portion of the surgical stapling apparatus embodiment depicted in FIG. 36 with the selector switch thereof in a proximal locked position.
Figure 46:
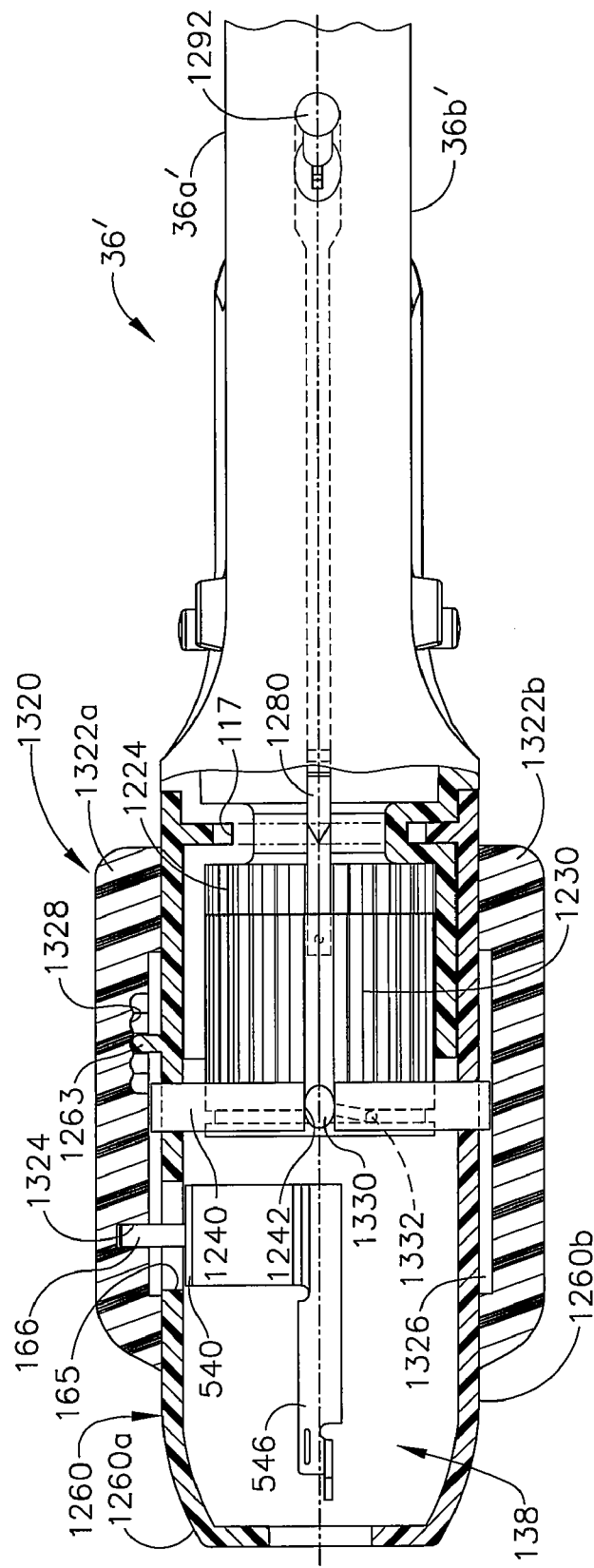
FIG. 46 is a partial cross-sectional view of a handle assembly of a surgical stapling apparatus of the present invention employing an alternate translation member.
Figure 47:
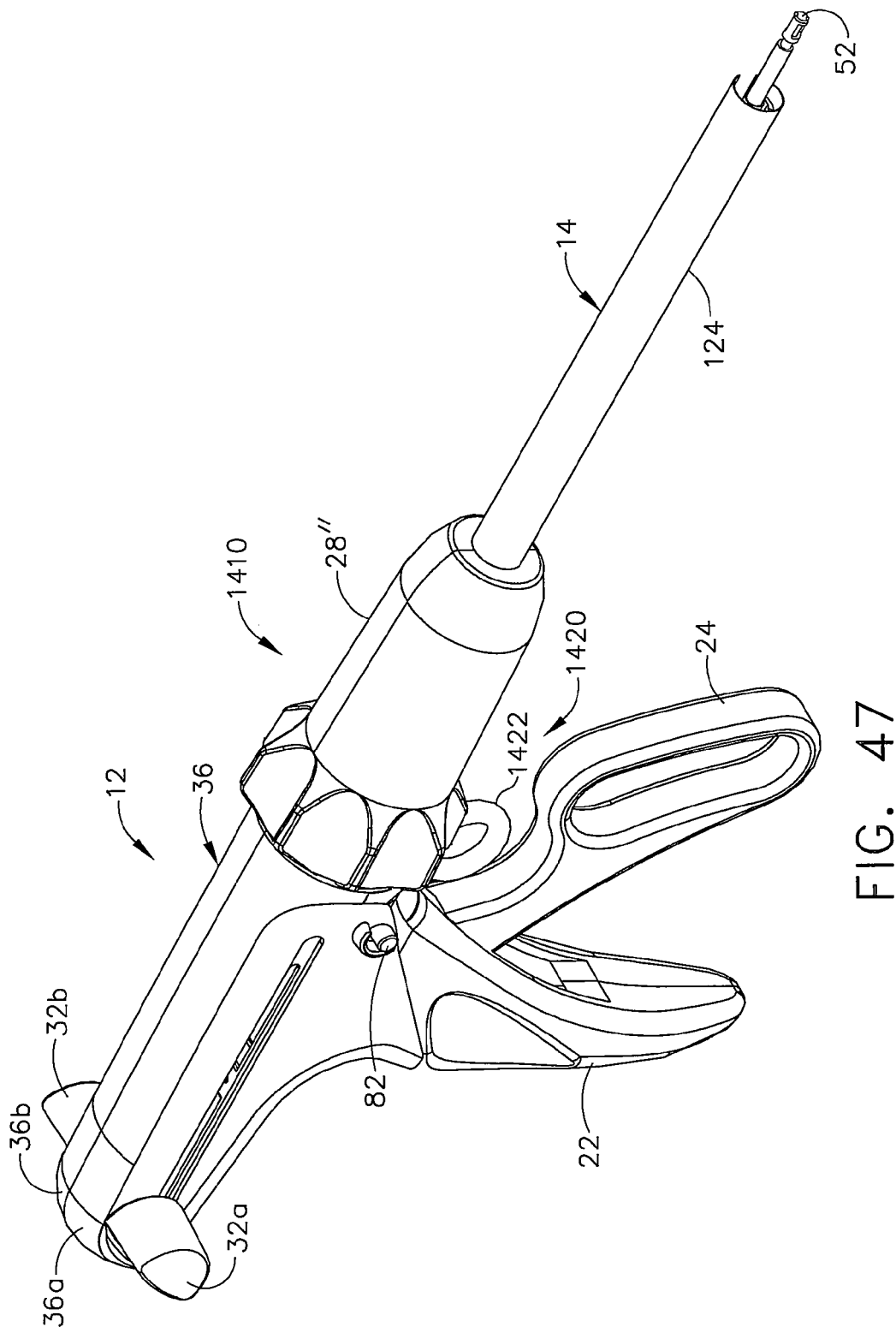
FIG. 47 is a perspective view of another surgical stapling apparatus embodiment of the present invention.
Figure 48:
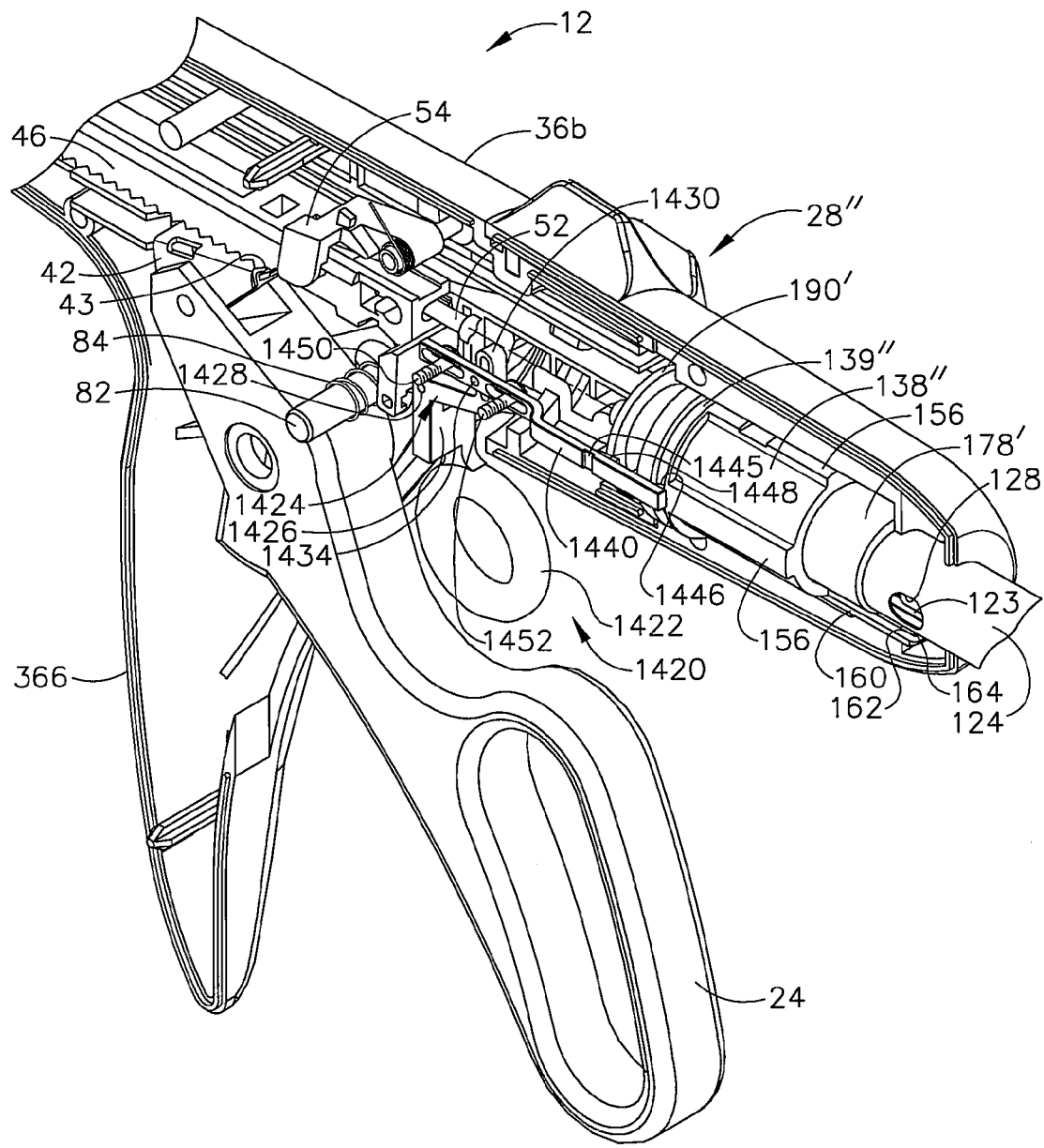
FIG. 48 is an enlarged perspective view of the handle assembly portion of the surgical stapling instrument of FIG. 47 with a portion of the handle housing removed for clarity.

When the clinician desires to articulate the disposable loading unit, the selector switch 1292 is pivoted in the proximal direction "PD" illustrated in FIGS. 42, 43 and 46. As can be seen FIGS. 42, 43 and 46, when the selector switch 1292 is pivoted to the proximal direction, the switch bar 1270 is axially advanced in the distal direction "D-D" bringing the rotation bolt 1280 into locking engagement with the rotation lock ring 1264. When the locking bolt 1280 is engaged with the rotation locking ring 1264, the shroud 1260 (and the elongated body 14 and casing 124) are unable to rotate relative to the handle assembly 12 about the longitudinal axis "L-L". When the switch bar 1270 is moved in the distal direction, the brake tube 1230 is also moved in the distal direction "D-D" because the switch bar 1270 is attached thereto. As the brake tube 1230 moves proximally, the shift pin 1332 is caused to rotate and rotates brake cam 1330 such that it permits the ends 1242 of the brake band 1240 to move inwardly toward each other to thereby permit the grip 1320 to be moved relative to the shroud 1260. See FIG. 46. In various embodiments, an articulation pin 166 extends from translation member 138' through a slot 1265 in the shroud segment 1260a and is received in a hole 1324 in the grip segment 1322a. See FIGS. 36 and 37. Thus, when the clinician moves the rotation grip 1322 axially in the proximal direction "PD" and distal direction "DD", the translation member 138' as well as the articulation link 123 which is attached thereto by an arm 160 also moves. Thus, when the clinician moves the rotation grip 1322 axially in the proximal direction "PD" and distal direction "DD", the translation member 138' as well as the articulation link 123 also moves in those directions to effectuate articulation of the articulatable disposable loading unit. In addition, as the grip 1322 is axially moved on the shroud 1260, the indicator pin 1263 makes an audible click or sound as it engages the detents 1328 to provide the clinician with an audible indication of the progress of the articulation motion.

FIG. 46 depicts use of translation member 138 that has an upstanding arm portion 540 and an arm 546 which includes an opening 548 configured to receive a finger (not shown) extending from the proximal end of articulation link 123 (not shown). See FIGS. 4 and 11. Pin 166 is secured to translation member 138 and dimensioned to extend through the slot 1265 in the shroud and into the hole 1324 in the shroud 1322. This embodiment otherwise works the same as the embodiments depicted in FIGS. 37 and 38. Those of ordinary skill in the art will recognize that the aforementioned embodiment represents a vast improvement over prior instruments adapted for use with disposable loading units such as those disclosed in U.S. Pat. No. 5,865,361. In particular, in the embodiments described above, the clinician may rotate the disposable loading unit to the desired position and then lock the shroud 1260 to prevent further rotation of the shroud 1260. The clinician may then articulate the disposable loading unit while the shroud 1260 remains locked in position. In prior units, the rotation knob was free to rotate while the clinician was trying to articulate the disposable loading unit. Thus, to prevent the disposable loading unit from rotating, the clinician had to manipulate the articulation lever while being careful not to impart a rotation motion to the rotation knob. The above-described embodiments solve that problem.

FIGS. 47-51 illustrate another surgical stapling apparatus 1410 of the present invention constructed for use with a disposable loading unit (not shown) that permits a clinician to articulate and fire the disposable loading unit with one hand. More particularly and with reference to FIG. 47, the surgical instrument 1410 is substantially similar in construction as the various instruments described above, except for the articulation system 1420 as will be described in detail below. Those components that are the same as the components employed in the above-mentioned embodiments will be labeled with the same numbers and those of ordinary skill in the art can refer to the disclosure set forth hereinabove that explains their construction and operation.

In one embodiment, the surgical stapling apparatus 1410 may include a handle assembly 12 that has an elongated body 14 that is operably coupled to the handle assembly 12 and protrudes distally therefrom. A distal end of the elongated body 14 may be coupled to an articulatable disposable loading unit 16. The disposable loading unit may include a tool assembly 17 that is selectively articulatable about an articulation axis "AA-"AA" by articulation motions transferred thereto by the elongated body 14 as is known.

Figure 49:
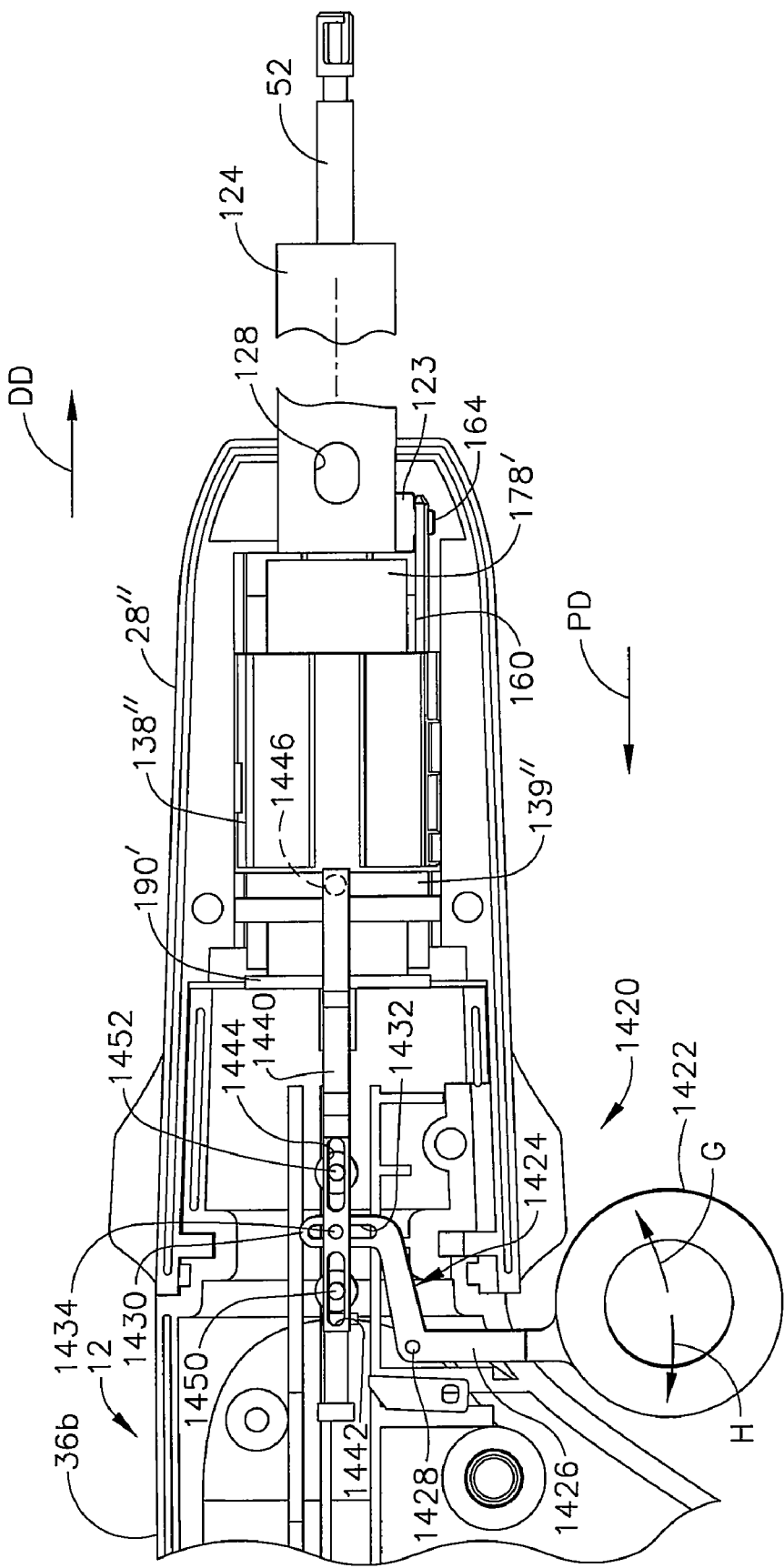
FIG. 49 is partial side view of the handle assembly depicted in FIG. 49 with a portion of the handle housing removed for clarity.

The handle assembly 12 may comprise a handle housing 36 and have a movable handle 24 operably coupled thereto that is movable through actuation strokes relative to the handle housing 36. As in the above-described embodiments, actuation of the movable handle 24 may cause longitudinal actuation motions to be applied to an actuation shaft 46 which is operably coupled to a control rod 52 which comprises a portion of the elongated body 14. As can be seen in FIGS. 48-51, the articulation system 1420 may include an articulation trigger 1422 that may be shaped and oriented relative to the stationary portion 22 of the handle housing 36 and the movable handle 24 to enable the clinician to actuate it with his or her index finger of the hand that is grasping the handle assembly 12 and which actuates the movable handle 24. The trigger 1422 may have a drive bar portion 1424 attached thereto that has a vertical portion 1426 that is pivotally pinned to the handle housing 36 by a pivot pin 1428 such that the articulation trigger 1422 may be selectively pivoted in the "G" and "H" directions about pivot pin 1428. See FIG. 49. The drive bar portion 1424 may further have a drive portion 1430 that has a slot 1432 therein adapted to receive a drive pin 1434 attached to an articulation bar 1440. As can be seen in FIG. 49, the articulation bar 1440 may be provided with a pair of elongated slots 1442, 1444 that are adapted to receive portions of screws 1450, 1452, respectively. Screws 1450, 1452 extend through the elongated slots 1442, 1444, respectively and are attached to the handle housing segment 36a such that the articulation bar 1440 is constrained to move longitudinally within handle housing 36 in the proximal direction "PD" and the distal direction "DD". The distal end of the articulation bar 1440 may have an articulation pin 1446 that is adapted to extend into an annular groove 139" provided in the proximal end of the translation member 138" which may be otherwise identical in construction and operation with respect to translation member 138' described in detail above. That is, the translation member 138" may have a plurality of ridges 156 which are configured to be slidably received within grooves formed along the inner walls of the rotatable knob 28". Engagement between ridges 156 and those grooves prevent relative rotation of the translation member 138" and the rotatable knob 28" while permitting relative linear movement between those components. The distal end of translation member 138" may include an arm 160 which includes an opening 162 configured to receive a finger 164 extending from the proximal end of articulation link 123. See FIGS. 48 and 49. Thus, when the clinician actuates the articulation trigger 1422 in the "G" direction, the drive portion 1430 pulls the articulation bar 1440 in the proximal direction "PD" which also pulls the translation member 138" and the articulation link 123 attached thereto in the proximal direction "PD" which may thereby cause the disposable loading unit coupled thereto to articulate in the right hand direction in the manner described above and hereinbelow. When the clinician pulls the articulation trigger 1422 in the "H" direction, the drive portion 1430 pushes the articulation bar 1440 in the distal direction "DD" which also pushes the translation member 138" and the articulation link 123 attached thereto in the distal direction "DD" which may thereby cause the disposable loading unit coupled thereto to articulate in the left hand direction.

As indicated above, this embodiment may include a sensor cylinder 178' that interfaces with a sensor tube 176 and a sensor link 182 as was described above to detect whether a disposable reload unit has been coupled to the control rod 52 and prevent actuation of the articulation mechanism 1420 when no disposable reload unit has been attached. In this embodiment, however, the flange 190' of the sensor tube 178' is configured to interact with a "no reload" lockout ramp 1448 formed on the articulation bar 1440. See FIGS. 50 and 51. When no disposable loading unit has been coupled to the elongated member 14 and control rod 52, the sensor tube 178' is biased into the position illustrated in FIG. 50. As can be seen in that Figure, the no reload lockout ramp 1448 on the articulation bar 1440 is engaged with the flange 190' on the sensor tub 178' such that the articulation bar 1440 is biased laterally outward in the "I" direction. As can also be seen in that Figure, an inwardly extending locking detent 37 is formed on the handle housing segment 36a and is adapted to be received in a locking notch 1445 in the articulation bar 1440 when the flange 190' engages the no reload lockout ramp 1448 to bias the articulation bar 1440 in the "I" direction. When the detent 37 is received in the locking notch 1445, the articulation bar 1440 cannot be actuated. Thus, when no disposable loading unit is coupled to the instrument 1410, the articulation trigger 1422 cannot be actuated. When a disposable loading unit is coupled to the elongated member 14 and control rod 52 and sensor bar 176, the sensor cylinder 178' is biased in the proximal direction "PD" which causes the flange 190' to disengage the non reload lockout ramp 1448 as shown in FIG. 51 and thereby permit the articulation bar 1440 to move. Thus, the articulation trigger 1422 may be actuated when a disposable loading unit has been coupled to the stapling apparatus 1410.

Those of ordinary skill in the art will appreciate that the articulation mechanism 1420 described above enable the clinician to operate the instrument with one hand. This represents a vast improvement over those articulation mechanisms disclosed in U.S. Pat. No. 5,865,361 and other prior stapling apparatuses configured for use with disposable loading units.

FIGS. 52-64 disclose another surgical stapling apparatus 1510 of the present invention constructed for use with an articulatable disposable loading unit (not shown) that permits a clinician to articulate and fire the disposable loading unit by manipulating the movable handle 24". In one embodiment, the surgical stapling apparatus 1510 may include a handle assembly 12 that has an elongated body 14 that is operably coupled to the handle assembly 12 and protrudes distally therefrom. A distal end of the elongated body 14 may be coupled to an articulatable disposable loading unit 16. The disposable loading unit may include a tool assembly 17 that is selectively articulatable about an articulation axis "A1-A1" by articulation motions transferred thereto by the elongated body 14 as is known. As will be discussed in detail below, the surgical stapling apparatus 1510 may employ a unique and novel selector arrangement 1512 that interfaces with the movable handle 24", the actuation shaft 46 and an articulation system 1520. When the selector arrangement 1512 is in a "firing" orientation, manipulation of the movable handle member 24" through actuation strokes imparts a firing motion to the actuation shaft 46 and when the selector arrangement 1512 is in an "articulation" orientation, manipulation of the movable handle 24" through the actuation strokes actuates the articulation system 1520. Those components that are the same as the components employed in the above-mentioned embodiments will be labeled with the same numbers and those of ordinary skill in the art can refer to the disclosure set forth hereinabove that explains their construction and operation.

Figure 52:
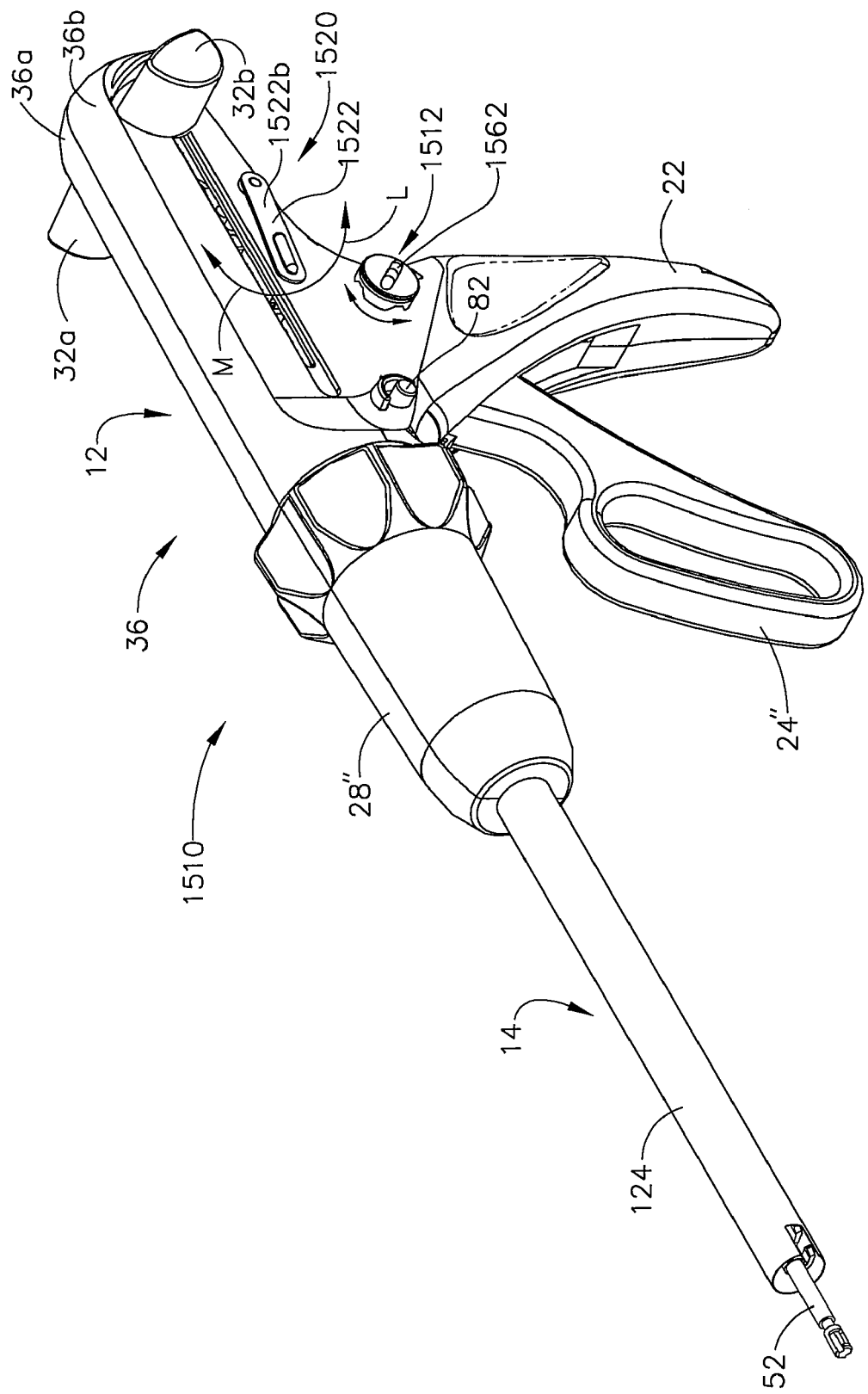
FIG. 52 is a perspective view of another surgical stapling apparatus embodiment of the present invention.
Figure 53:
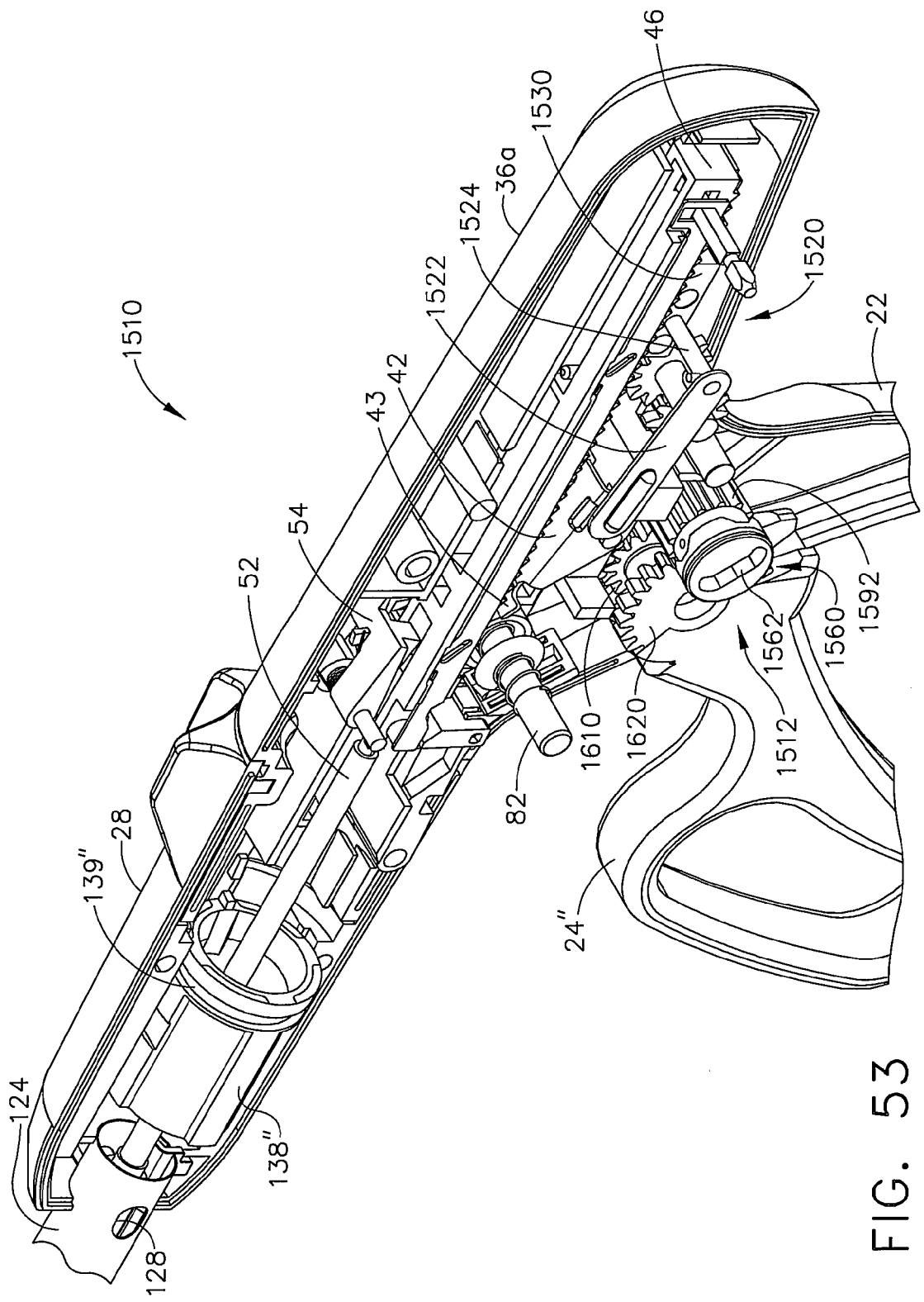
FIG. 53 is a perspective assembly view of the handle assembly portion of the surgical stapling apparatus of FIG. 52 with a portion of the handle housing removed and the sensor cylinder omitted for clarity.
Figure 55:
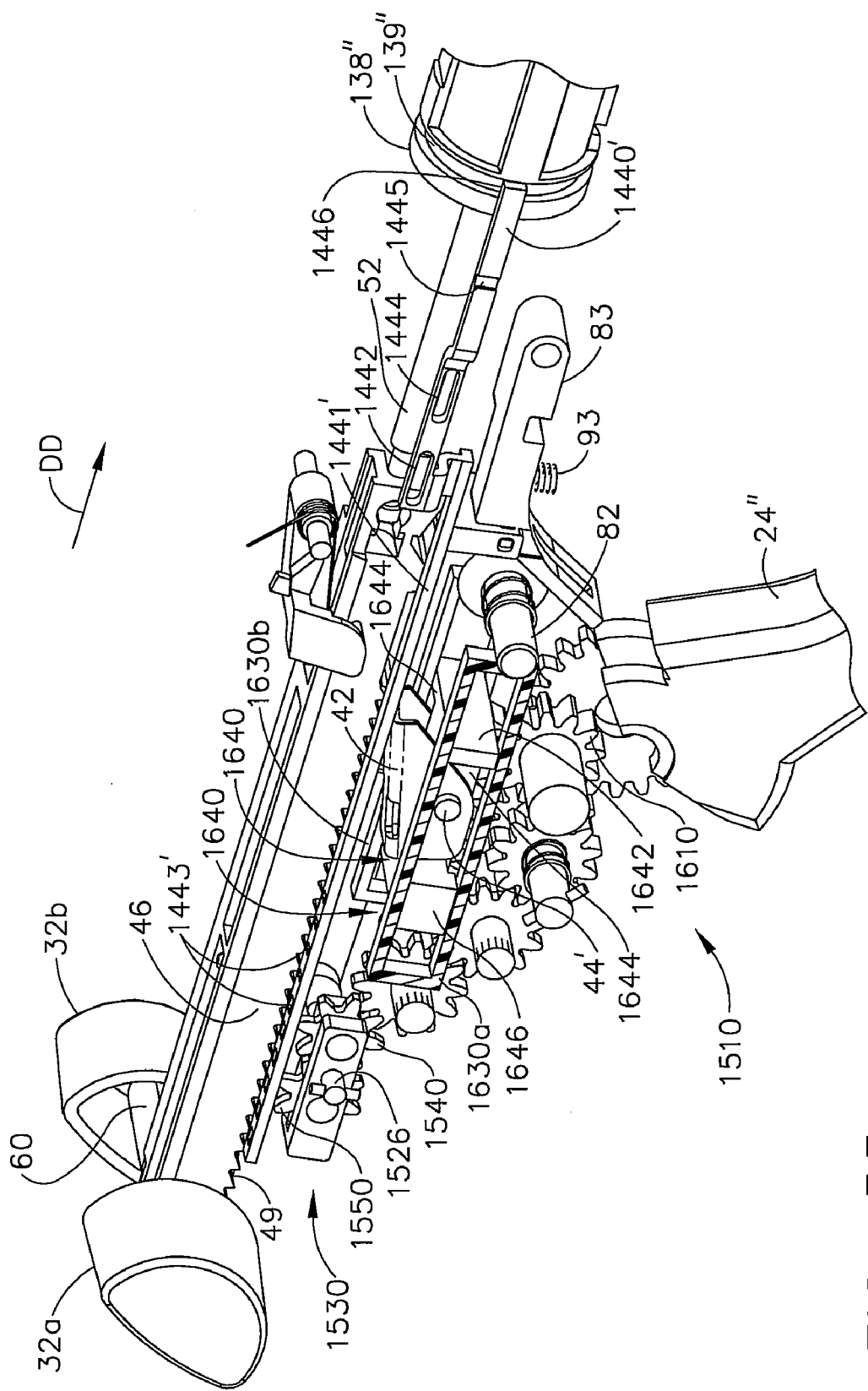
FIG. 55 is a right-side perspective assembly view of a portion of the handle assembly of the surgical stapling apparatus of FIGS. 52-54 with the housing removed for clarity.
Figure 56:
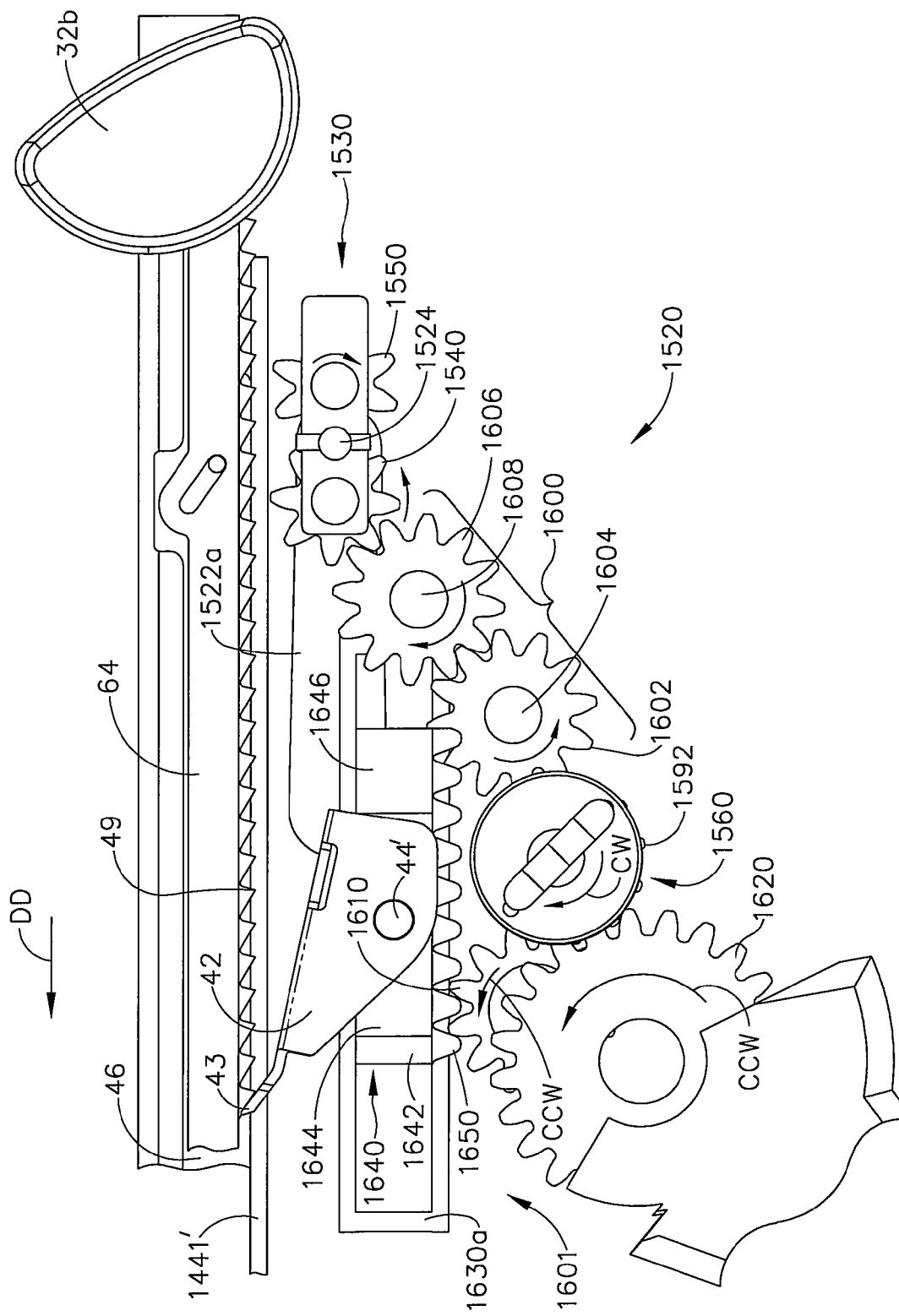
FIG. 56 is a side view of a portion of the articulation system, gear and articulation selector switch embodiments with the articulation switch in a neutral position.
Figure 57:
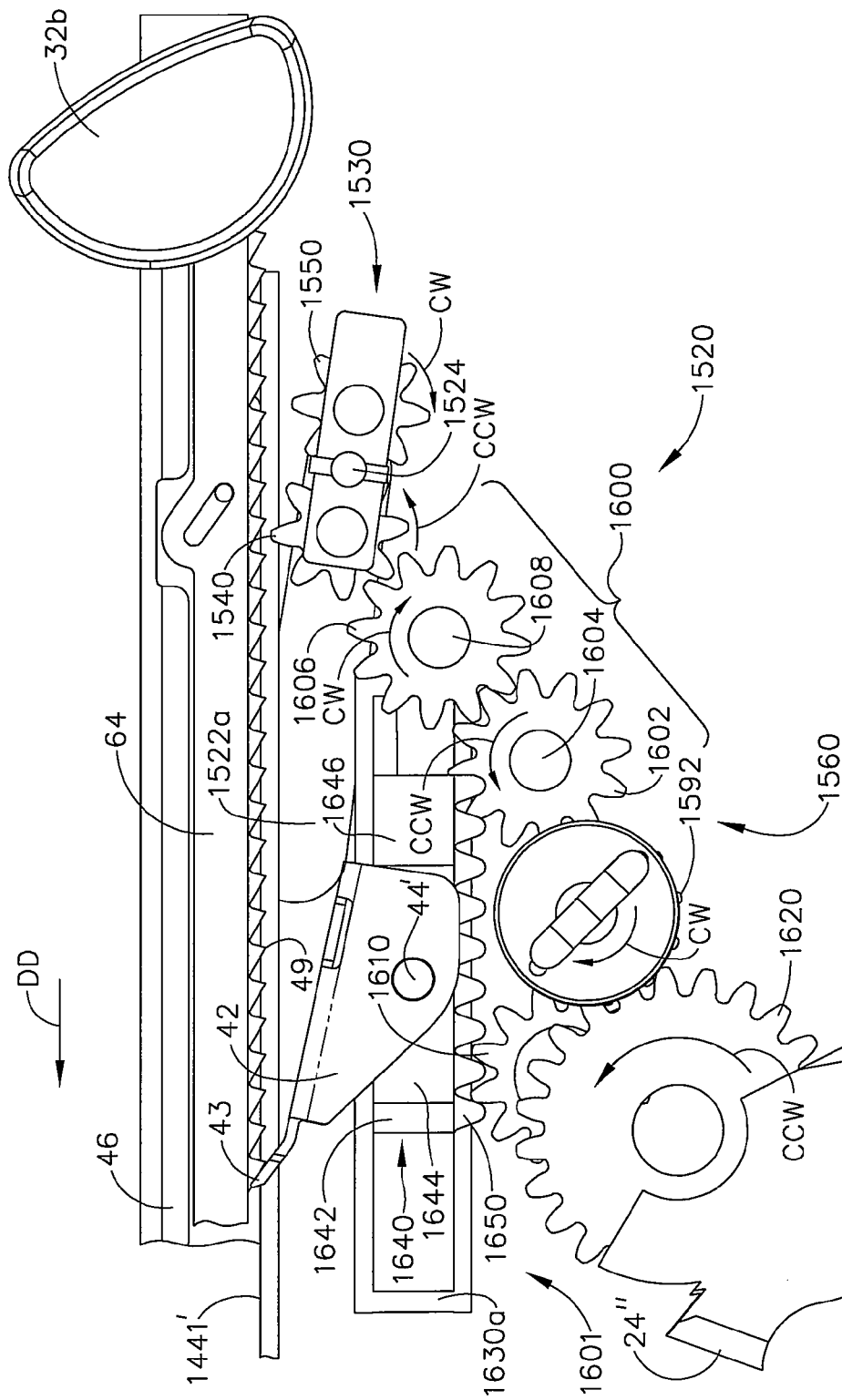
FIG. 57 is another side view of the articulation system, gear and articulation selector switch embodiments with the articulation switch in the left articulation position.
Figure 58:
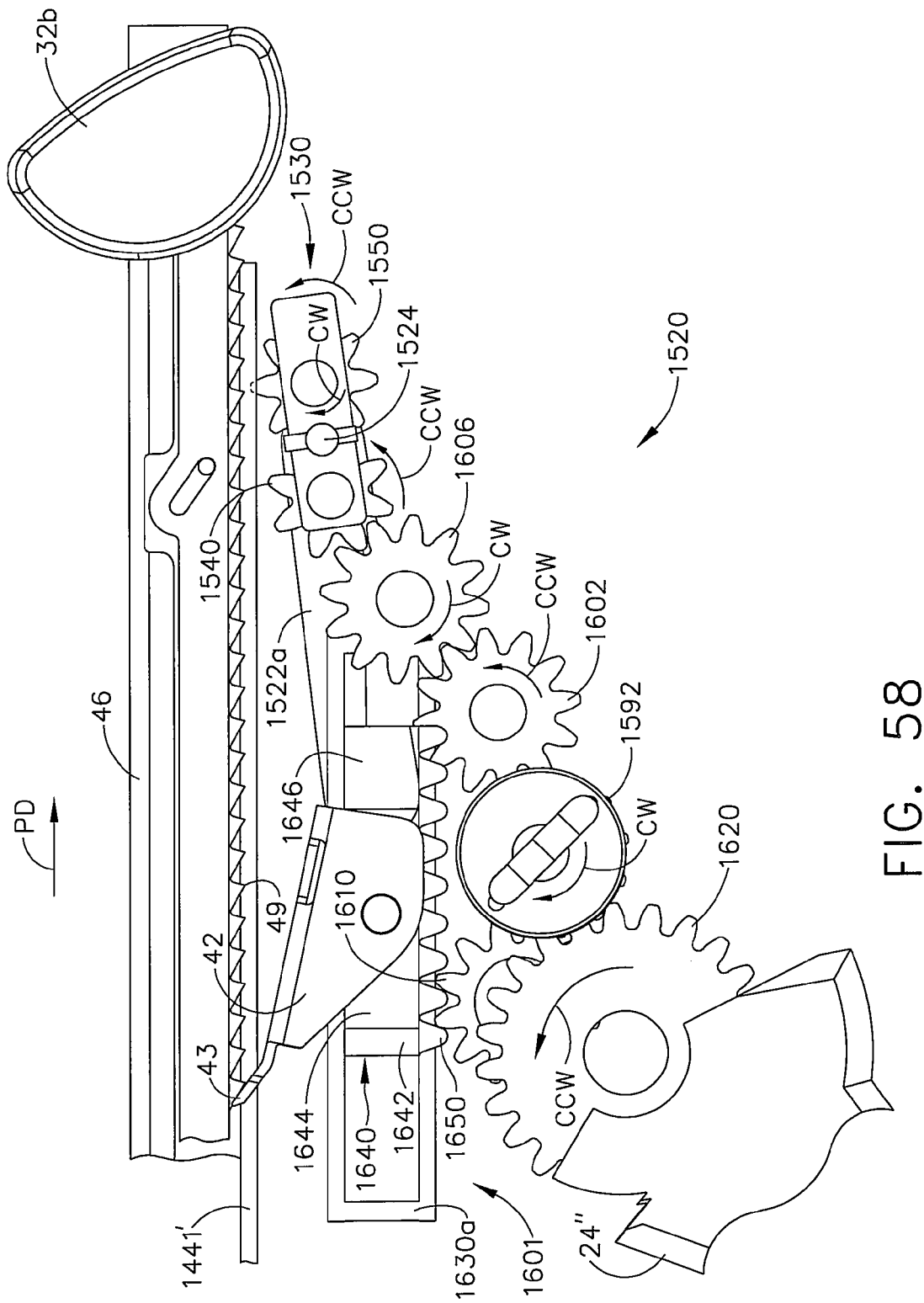
FIG. 58 is another side view of the articulation system and gear and articulation selector switch embodiments with the articulation switch in the right articulation position.

As can be seen in FIGS. 52 and 53, the selector arrangement 1512 may include an articulation selector switch 1522 that is located outside of the handle housing 36 to provide access thereto. The articulation selector switch 1522 may be coupled to an articulation selector switch shaft 1524 that extends through the handle housing segment 36b and is attached to a rocker mount 1530 which comprises a portion of the articulation system 1520. A second articulation selector switch shaft 1526 protrudes outward from the other side of the rocker mount 1530 to extend through the handle housing segment 36a for attachment to a selector switch 1522a such that the rocker mount 1530 is pivotable about rocker axis "RA" defined by the shafts 1524, 1526. See FIG. 60. As can be seen in FIGS. 56-58, the articulation system 1520 further includes a first articulation gear 1540 and a second articulation gear 1550 that are each freely rotatable within the rocker mount 1530. The first and second articulation gears 1540 and 1550 are oriented for selective engagement with an articulation bar extension 1441' that comprises a portion of articulation bar 1440', which is otherwise similar to articulation bar 1440 described above. As can be seen in FIG. 55, the articulation bar extension 1441' has a series of holes 1443' therein adapted to be engaged by the first and second articulation gears 1540, 1550, depending upon the orientation of the rocker mount 1530.

Figure 61:
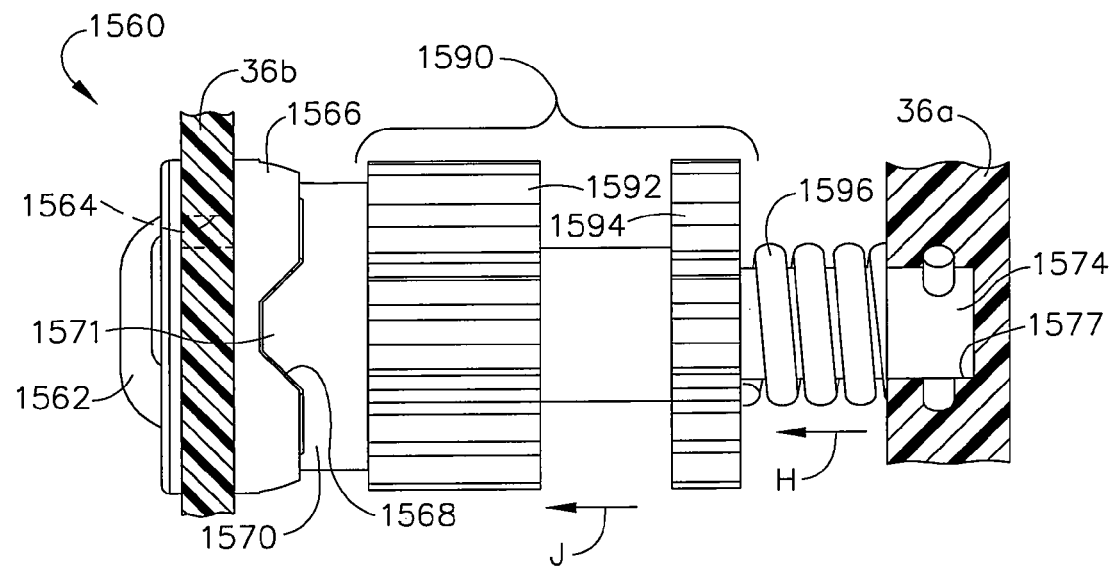
FIG. 61 is an enlarged view of the gear selector switch embodiment in the articulation position.
Figure 62:
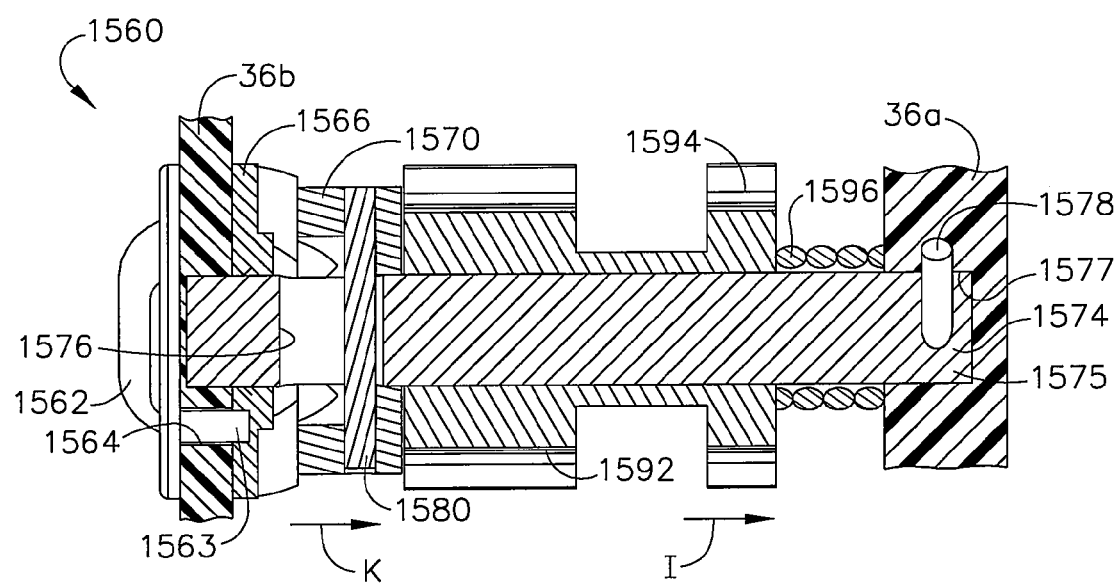
FIG. 62 is a cross-sectional view of the gear selector switch embodiment in the firing position.
Figure 63:
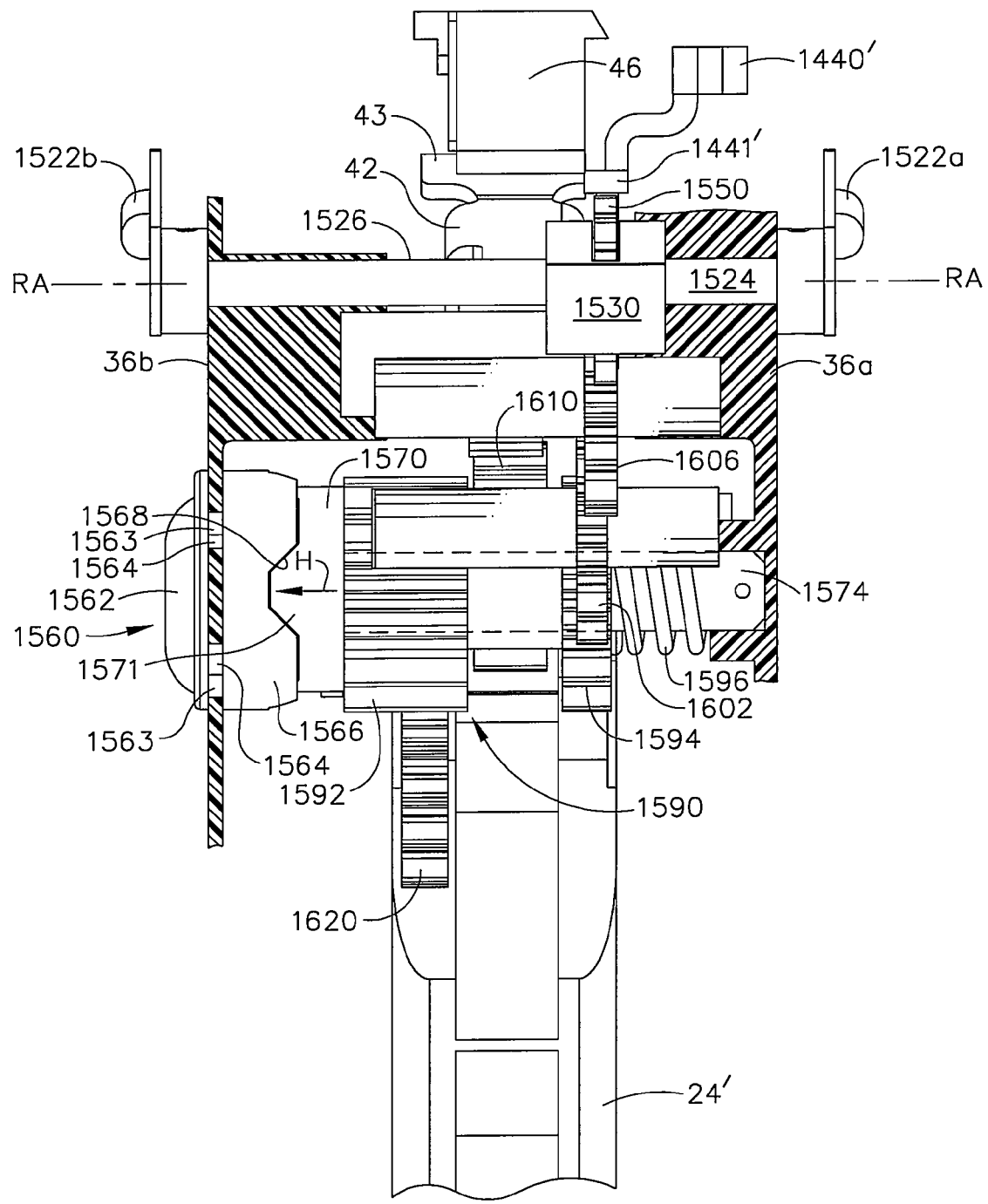
FIG. 63 is an end view of a various components of the surgical stapling apparatus in an articulation mode.

The selector arrangement 1512 may further include a unique and novel gear selector switch assembly 1560 for interfacing between a firing gear 1610 and an articulation transfer gear train 1600 that comprises a portion of the articulation system. In various embodiments, the articulation transfer gear train 1600 may comprise a first transfer gear 1602 that is mounted to a first transfer gear shaft 1604 that is rotatably supported in sockets (not shown) in the handle housing segments 36a, 36b and a second transfer gear 1606 that is mounted on a second transfer gear shaft 1608 that is rotatably supported in sockets (not shown) in the handle housing segments 36a, 36b. In various embodiments, the gear selector switch assembly 1560 may include a function selector switch 1562 that has a pair of pins 1563 protruding therefrom that extend through corresponding arcuate slots 1564 in the handle housing segment 36b and are attached to a drive disc 1566. See FIGS. 61 and 62. As can be seen in those Figures, the drive disc 1566 may have a series of teeth-receiving cavities 1568 therein that are adapted to selectively mesh with corresponding disc teeth 1571 in a shift disc 1570. The shift disc 1570 may be non-rotatably affixed to a stationary shaft 1574. As can be seen in FIGS. 61 and 62, an end 1575 of the stationary shaft 1574 may be received in a cavity 1577 and pinned thereto by a lock pin 1578. In various embodiments for example, the end 1575 may be molded into the handle housing segment 36a such that stationary shaft 1574 is not rotatable relative thereto. As can also be seen in FIG. 62, the shift disc 1570 may be non-rotatably pinned to stationary shaft 1574 by a shift pin 1580 that extends through a transverse slot 1576 in the stationary shaft 1574 to enable the shift disc 1570 to move axially (and non-rotatably) on the stationary shaft 1574.

As can also be seen in FIGS. 61 and 62, the gear selector switch assembly 1560 may further include a drive gear assembly 1590 that comprises a drive gear portion 1592 and an articulation drive gear portion 1594. The drive gear assembly 1590 is configured to move axially on the stationary shaft 1574 and is biased in the "J" direction by a spring 1596 that is journaled on the stationary shaft 1574.

Figure 59:
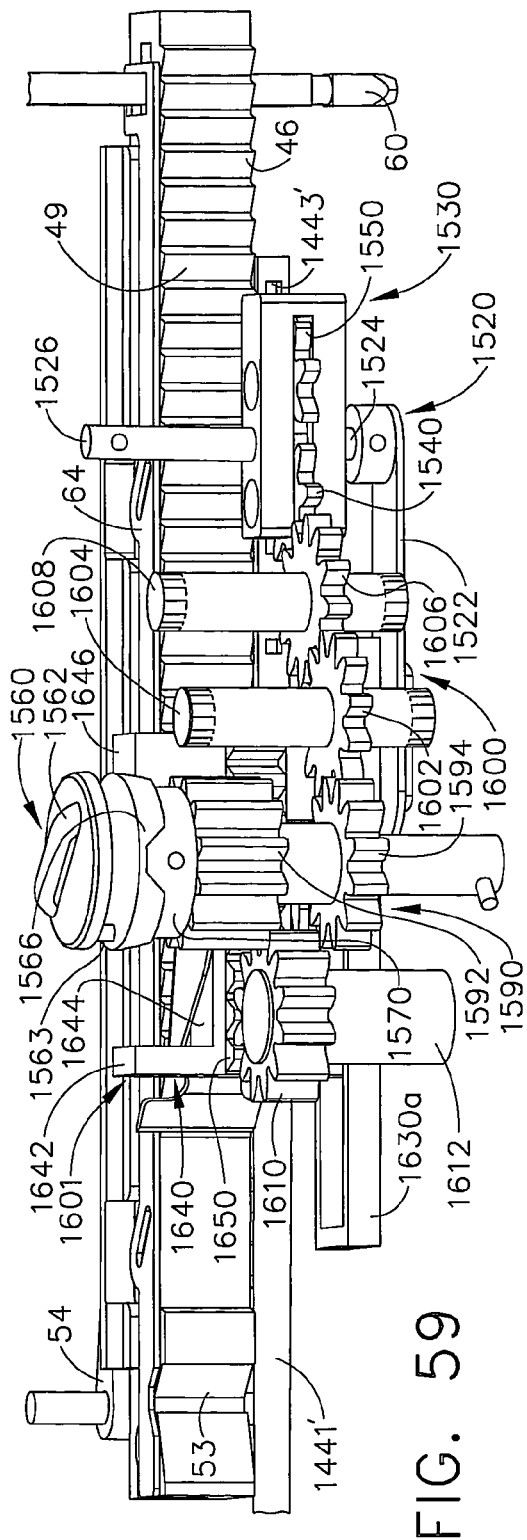
FIG. 59 is a bottom view of the gear selector switch, drive gear assembly, articulation transfer gear train and actuation bar of an embodiment of the present invention with the selector gear selector switch in the articulation position.

The operation of the articulation system 1520 will now be described with reference to FIGS. 57 and 58. To commence the articulation process, the clinician actuates one of the articulation selector switches 1522a, 1522b. In one embodiment, for example, if the clinician desires to articulate the disposable loading unit to the right, the clinician pivots the articulation selector switches 1522a, 1522b downward (arrow "'L" in FIG. 52). By pivoting the selector switches 1522 downward, the rocker mount 1530 is pivoted in the counterclockwise direction "CCW" in FIG. 58 to bring the second articulation gear 1550 into meshing engagement with the holes 1443' in the articulation bar extension 1441'. In the articulation mode, the gear selector switch assembly 1560 is permitted to remain in the unactuated position illustrated in FIGS. 59 and 63. When in that position, the drive gear assembly 1590 is positioned such that a handle gear 1620 attached to or otherwise molded to the movable handle 24 is in meshing engagement with the drive gear portion 1592 of the drive gear assembly 1590. In addition, the articulation drive gear portion 1594 of the drive gear assembly 1590 is in meshing engagement with the first transfer gear 1602. As can be seen in FIG. 59, when the drive gear assembly 1590 is positioned in that manner, the firing gear 1610, which is rotatably supported on a firing gear shaft 1612, is not engaged with the drive gear assembly 1590. Thus, actuation of the movable handle 24 will not affect the firing gear 1610.

When the selector switches 1522a, 1522b, 1562 are positioned in the manner described immediately above, the clinician may articulate the disposable loading unit attached to the stapling apparatus 1510 by actuating (ratcheting or pivoting) the movable handle 24. As the movable handle 24 is actuated, the handle gear 1620 rotates in the counterclockwise direction "CCW" which, in turn, causes the drive gear 1592 to rotate in the clockwise direction "CW" which, in turn, causes the first transfer gear 1602 to rotate in the counterclockwise direction "CCW" which, in turn, causes the second transfer gear 1606 to rotate in the clockwise direction "CW" which, in turn, causes the first articulation gear 1540 to rotate in the counterclockwise direction "CCW" which, in turn, causes the second articulation gear 1550 to rotate in the clockwise direction "CW" which, in turn, drives the articulation bar extension 1441' in the proximal direction "PD". See FIG. 58. As the articulation bar extension 1441' is driven in the proximal direction "PD", the articulation bar 1440' drives the translation member 138" and the articulation link 123 attached thereto is drawn in the proximal direction "PD" which may thereby cause the disposable loading unit coupled thereto to articulate in the right hand direction in the manner described above and hereinbelow. To articulate the disposable loading unit to the left, the clinician pivots the articulation selector switches 1522a, 1522b in the up direction (the "M" direction in FIG. 52). When the selector switches 1522a, 1522b are pivoted in that direction, the articulation rack 1530 is pivoted in the clockwise direction "CW" about the rack axis "RA" to thereby bring the first articulation gear 1540 into meshing engagement with the articulation bar extension 1441'. Because the first articulation gear 1540 is rotating in the clockwise direction "CW", the first articulation gear 1540 drives the articulation bar extension 1441' in the distal direction "DD" as the movable handle is actuated. As the articulation bar extension 1441' is driven in the distal direction "DD", the articulation bar 1440' drives the translation member 138" and the articulation link 123 attached thereto in the distal direction "DD" which may thereby cause the disposable loading unit coupled thereto to articulate in the left hand direction. Also in this embodiment, the articulation bar 1440' may employ the locking arrangement described above with respect to articulation bar 1440 for preventing movement of articulation bar 1440' when no disposable loading unit has been coupled to the stapling apparatus 1510. Thus, in this embodiment, the articulation motions are generated by actuating the movable handle 24.

Figure 54:
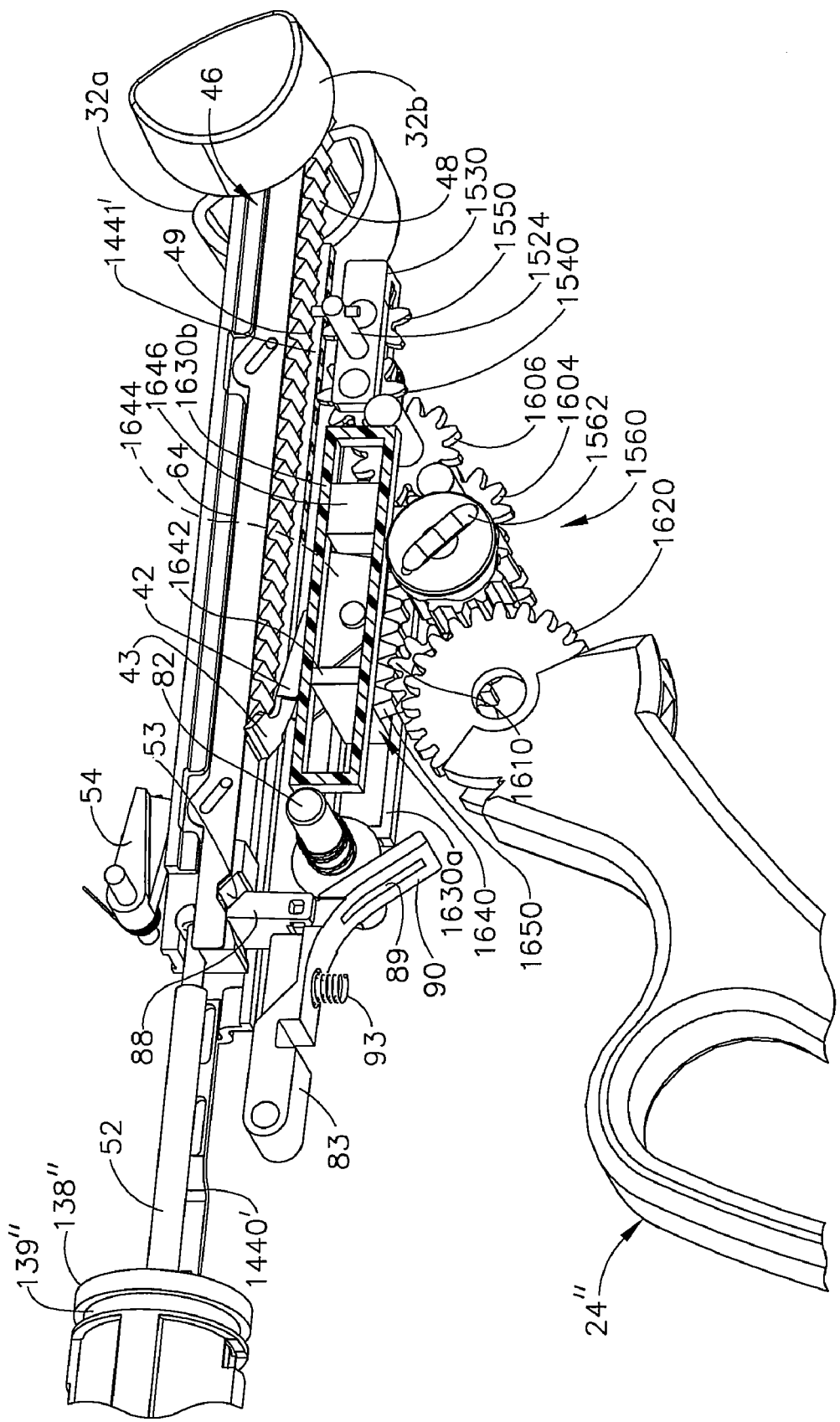
FIG. 54 is a left-side perspective assembly view of a portion of the handle assembly of the surgical stapling apparatus of FIGS. 52 and 53 with the housing removed for clarity.
Figure 64:
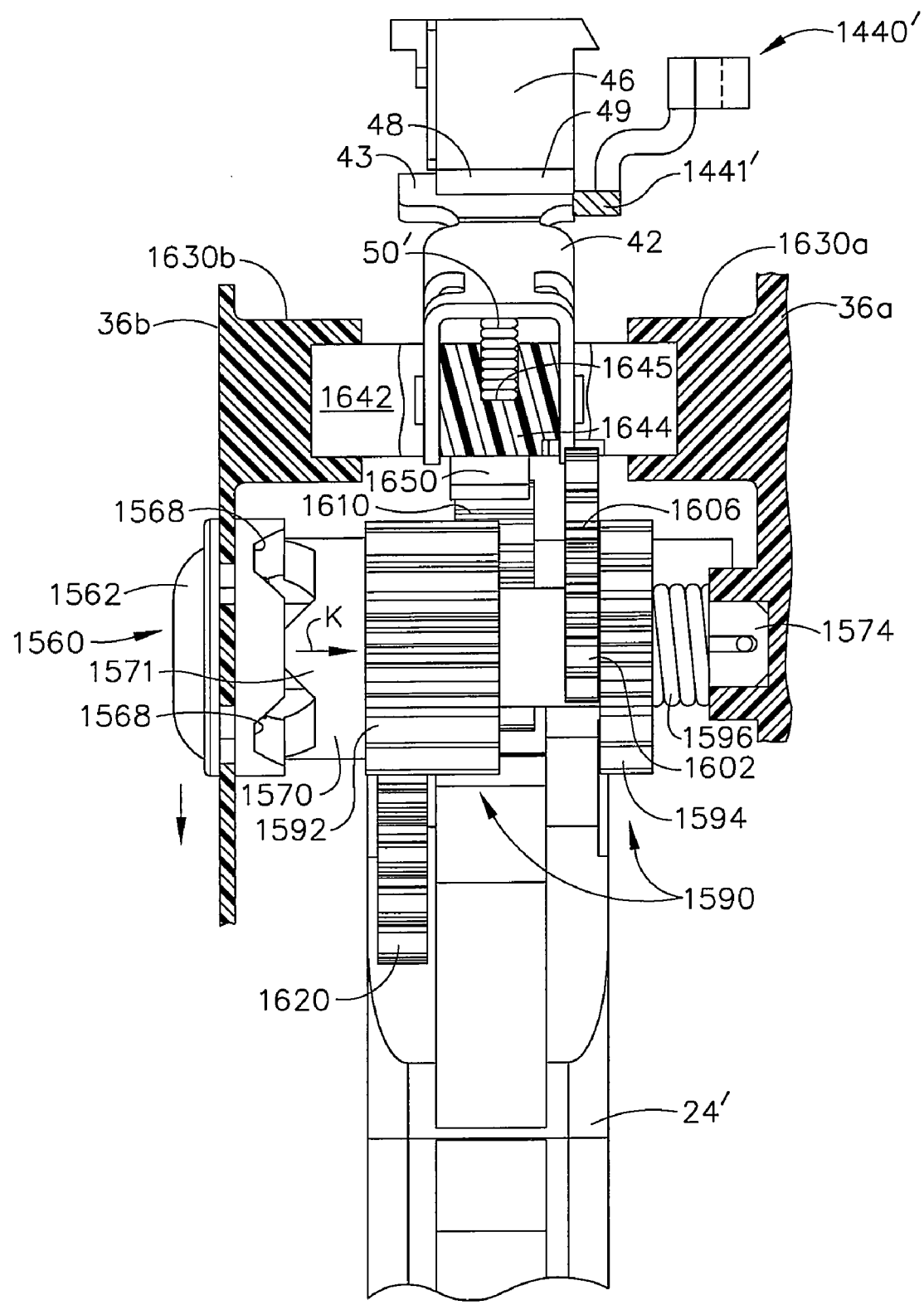
FIG. 64 is another end view of the components depicted in FIG. 63 in a firing mode.

This embodiment may also employ a unique and novel firing system generally designated as 1601, of which firing gear 1610 is a part. More particularly and with reference to FIGS. 55-60, the firing assembly 1601 may also include a pawl slide 1640 that is movably supported in a right hand rack guide 1630a formed in the right hand housing segment 36a and a left hand rack guide 1630b formed in the left hand housing segment 36b as shown in FIG. 54 (the housing segments 36a, 36b have been omitted for clarity in FIG. 54). In various embodiments, the pawl slide 1640 may generally have the shape of a capital "I" with a distal cross bar portion 1642, central bar portion 1644 and a proximal cross bar portion 1646. The cross bar portions 1642, 1646 serve to slidingly support the pawl slide 1640 in the rack guides 1630a, 1630b such that the pawl slide 1640 is able to axially move in the proximal direction "PD" and the distal direction "DD". Also in this embodiment, a drive rack 1650 may be formed on the bottom of, or otherwise attached to, the bottom of the central bar portion 1644 of the pawl slide 1640. The firing rack 1650 is oriented in meshing engagement with the firing gear 1610 as will be discussed in further detail below. Also attached to the central bar portion 1644 is a pawl 42 that has a rack engagement portion 43 for driving engagement of the rack 48 on the actuation shaft 46. As shown in FIGS. 55 and 64, the pawl 42 in various embodiments may be stamped out of metal and formed in a substantially U-shape such that the pawl 42 may be pivotally pinned to the central bar portion 1644 by a pivot pin 44'. A pawl spring 50' may be supported in a hole 1645 in the central bar portion 1644 to bias the pawl 42 into meshing engagement with the rack 48 on the actuation shaft 46. See FIG. 64.

Figure 60:
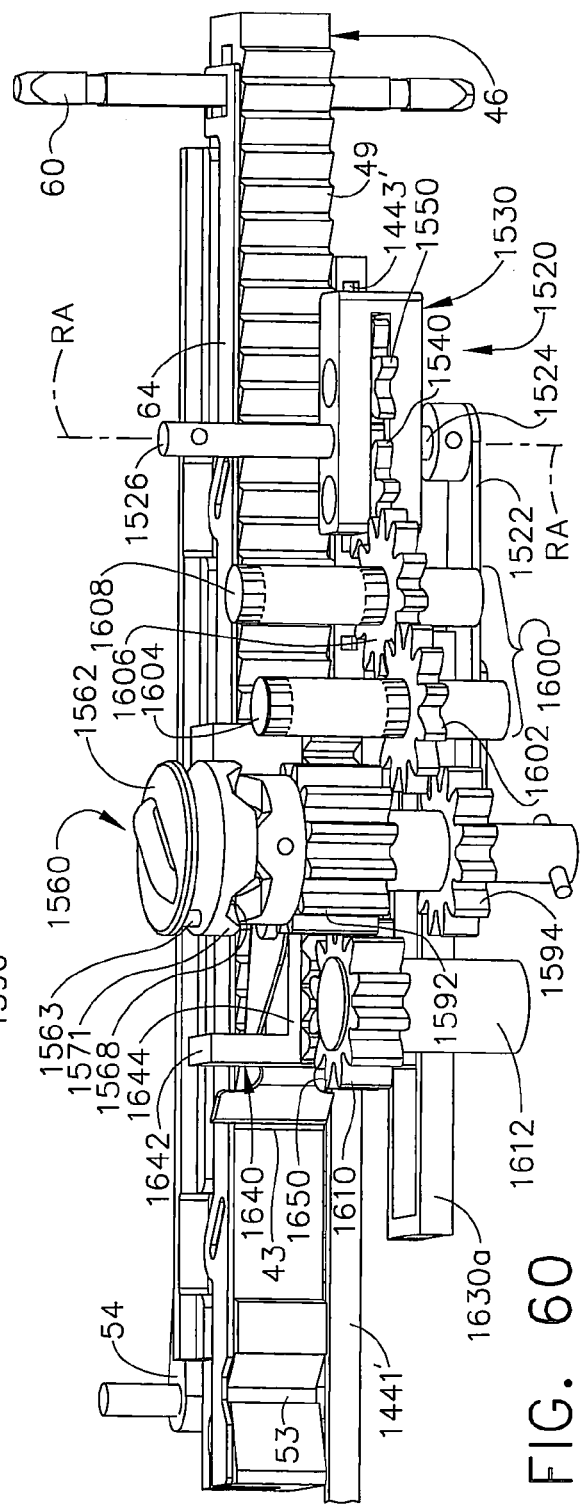
FIG. 60 is a bottom view of the gear selector switch, drive gear assembly, articulation transfer gear train and actuation bar of an embodiment of the present invention with the selector gear selector switch in the firing position.

The operation of the firing system 1601 will now be described with reference to FIGS. 60 and 64. To commence the firing process, the clinician turns the gear selector switch assembly 1560 to the position depicted in FIG. 64, such that the drive gear assembly 1590 is biased in the "K" direction such that the handle gear 1620 remains in meshing engagement with the drive gear 1592 and the articulation gear 1594 of the drive gear assembly 1590 does not mesh with the first articulation transfer gear 1602. In addition, the drive gear 1592 is in meshing engagement with the firing gear 1610 which, as described above, is in meshing engagement with the firing rack 1650. Because the articulation drive gear 1594 does not mesh with the first articulation transfer gear 1602, actuation of the movable handle 24" will not result in the generation of any articulation motions.

When selector switch 1562 is positioned in the manner described immediately above, the clinician may fire the actuation shaft 46 which, in turn, transfers firing motions to the control rod 52 coupled to the actuation shaft 46 which, in turn, transfers firing motions to the disposable loading unit coupled thereto in the manner described in U.S. Pat. No. 5,865,361. As illustrated in FIG. 56, the actuation shaft 46 of this unique and novel embodiment is fired (or moved in the distal direction "DD") by actuating (ratcheting or pivoting) the movable handle 24". As the movable handle 24" is actuated, the handle gear 1620 rotates in the counterclockwise direction "CCW" which, in turn, causes the drive gear 1592 to rotate in the clockwise direction "CW" which, in turn, causes the firing gear 1610 to rotate in the counterclockwise direction "CCW" and drive the firing rack 1650 and pawl 42 attached thereto in the distal direction "DD". The rack engagement portion 43 of the pawl 42 is in engagement with the teeth 49 of the rack 48 on the actuation shaft 46 and thereby drives the actuation shaft 46 in the distal direction "DD". This embodiment otherwise operates as described above. In particular, the clinician continues to ratchet the movable handle 24" until the firing sequence has been completed. When the movable handle 24" is pivoted to a position adjacent the stationary handle portion 22, the clinician releases the movable handle 24" and the movable handle 24" is pivoted to the starting position by the spring 40 (described above) and then the movable handle 24" can be pivoted again for another stroke to advance the pawl 42 and the actuation shaft 46. When the movable handle 24" is released, the rack engagement tooth 43 of the pawl 42 slides over the teeth 49 on the actuation shaft rack 48 as the pawl moves in the proximal direction "PD" and then reengages the teeth 49 when the movable handle 12 is pivoted to drive the actuation shaft in the distal direction "DD".

Those of ordinary skill in the art will understand that the stapling apparatus 1510 is equipped with a movable handle 12 that can be used to fire the instrument as well as to articulate the disposable loading unit attached thereto. It will be further appreciated that such embodiments are able to generate higher articulation forces than another prior devices such as those disclosed in U.S. Pat. No. 5,865,361.

Figure 65:
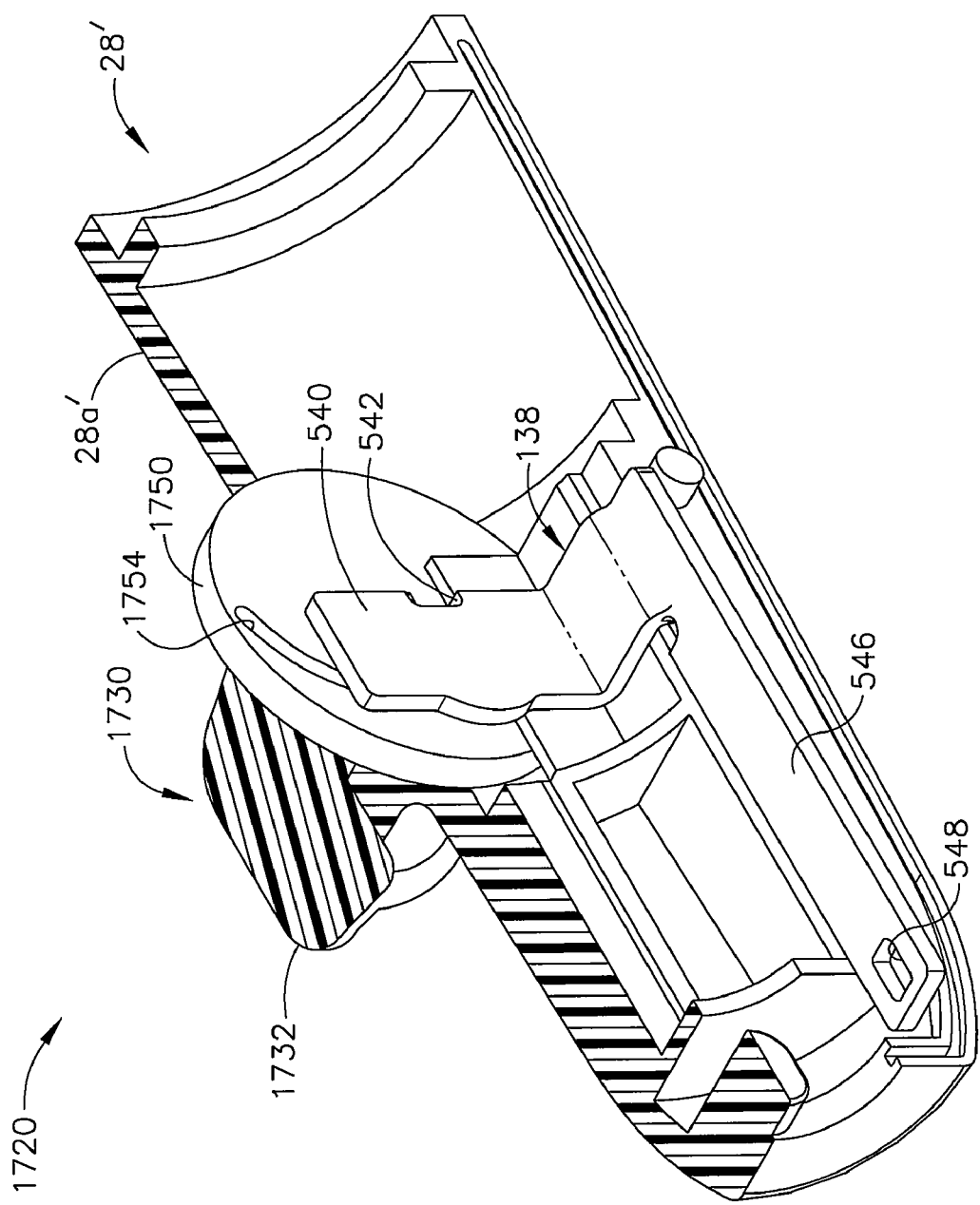
FIG. 65 is a partial cross-sectional perspective view of an alternative articulation mechanism embodiment of the present invention.

FIGS. 65-69 illustrate an alternative articulation mechanism 1720 for axially advancing the translation member 138 to ultimately result in the longitudinal actuation of an articulation link (not shown in FIG. 65). As can be seen in FIGS. 65 and 66, the articulation mechanism 1720 may be used in connection with a rotation knob 28' which may be substantially identical to rotation knob 28 described above, except that rotation knob 28' is configured to support a articulation knob 1730 as shown. As can be seen in FIG. 66, the articulation knob 1730 may include a thumb tab 1732 that is attached to a pivot shaft 1734 that extends through a hole 1736 in the rotation knob segment 28a'. The pivot shaft 1734 may have a squared portion 1735 that is adapted to be non-rotatably received in a corresponding square hole 1752 in a cam disc 1750. The translation member 138 may have an upstanding arm portion 540 that has a notch 542 therein that is sized to receive a tab (not shown) formed on the sensor cylinder (not shown) as was described above. The distal end of translation member 138 may include an arm 546 which includes an opening 548 configured to receive a finger 164 (not shown in FIGS. 65 and 66) extending from the proximal end of articulation link 123 (not shown in FIGS. 65 and 66) as was described above. See FIGS. 4 and 11. A pin 166 that may be constructed from a non-abrasive material, e.g., Teflon® or metal that has been coated with Teflon®, is secured to translation member 138 and dimensioned to be received within an arcuate-shaped cam slot 1754. Thus, as the actuation knob 1730 is rotated, the pin 166 is driven longitudinally either in the proximal direction "PD" or the distal direction "DD", depending upon the direction in which the actuation knob 1730 is rotated. The longitudinal displacement of the pin 166 is illustrated in the series of FIGS. 67-69. For example, FIG. 67 illustrates the position of the cam disc 1750 and pin 166 when the disposable loading unit has been articulated to the left. FIG. 68 illustrates the position of the cam disc 17650 and articulation pin 166 when the disposable loading unit has not been articulated (e.g., is axially aligned with the elongated body) and FIG. 69 illustrates the position of the cam disc 1750 and articulation pin 166 when the disposable loading unit has been articulated to the right. In some embodiments, the arcuate cam slot 1754 may be shaped such that the ramp angle thereof relative to pin 166 throughout the entire actuation sequence is relatively low (under 15 degrees) which may result in an effective articulation lock.

Figure 70:
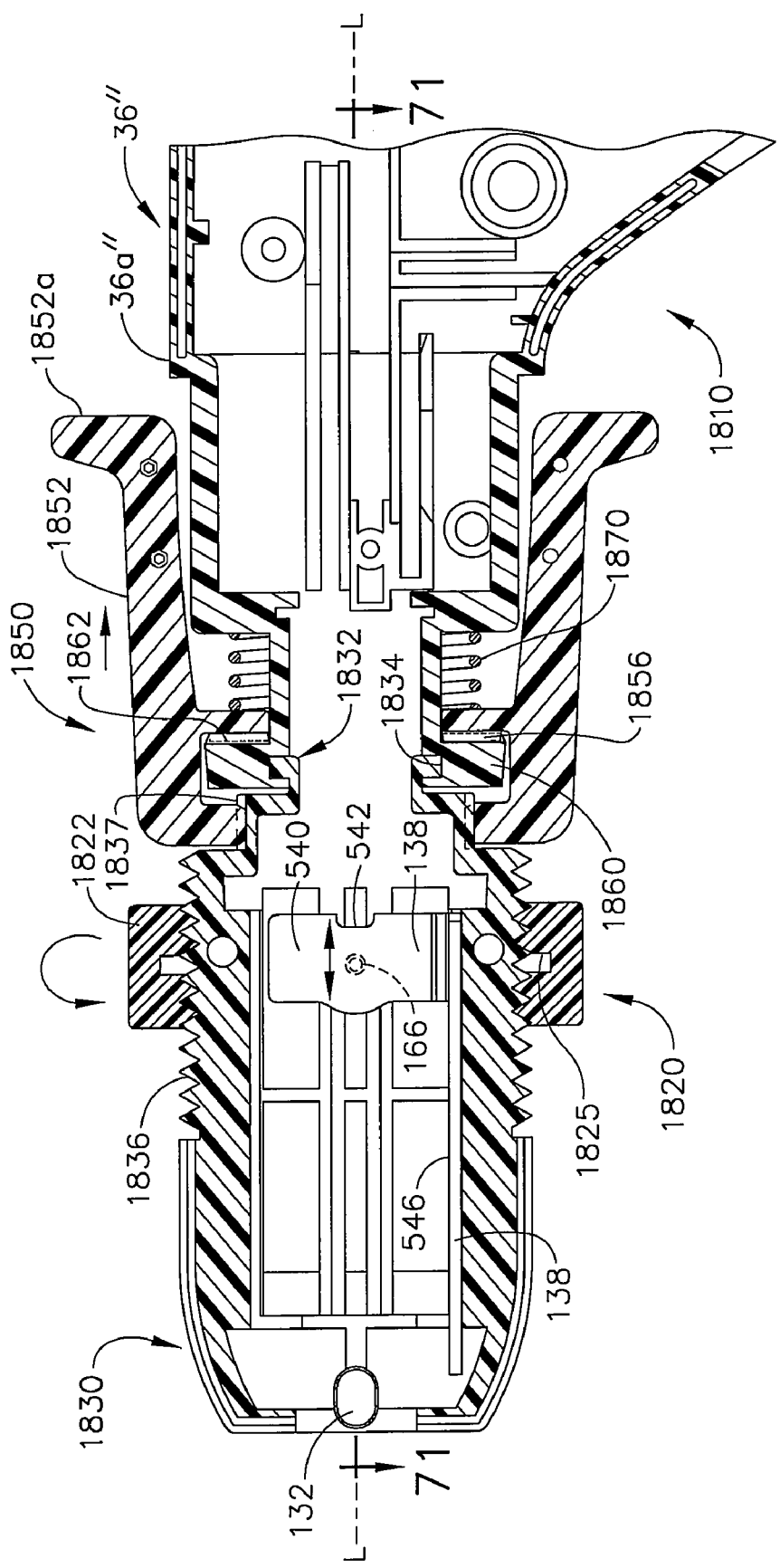
FIG. 70 is a cross-sectional plan view of a portion of another articulation mechanism embodiment of the present invention.
Figure 71:
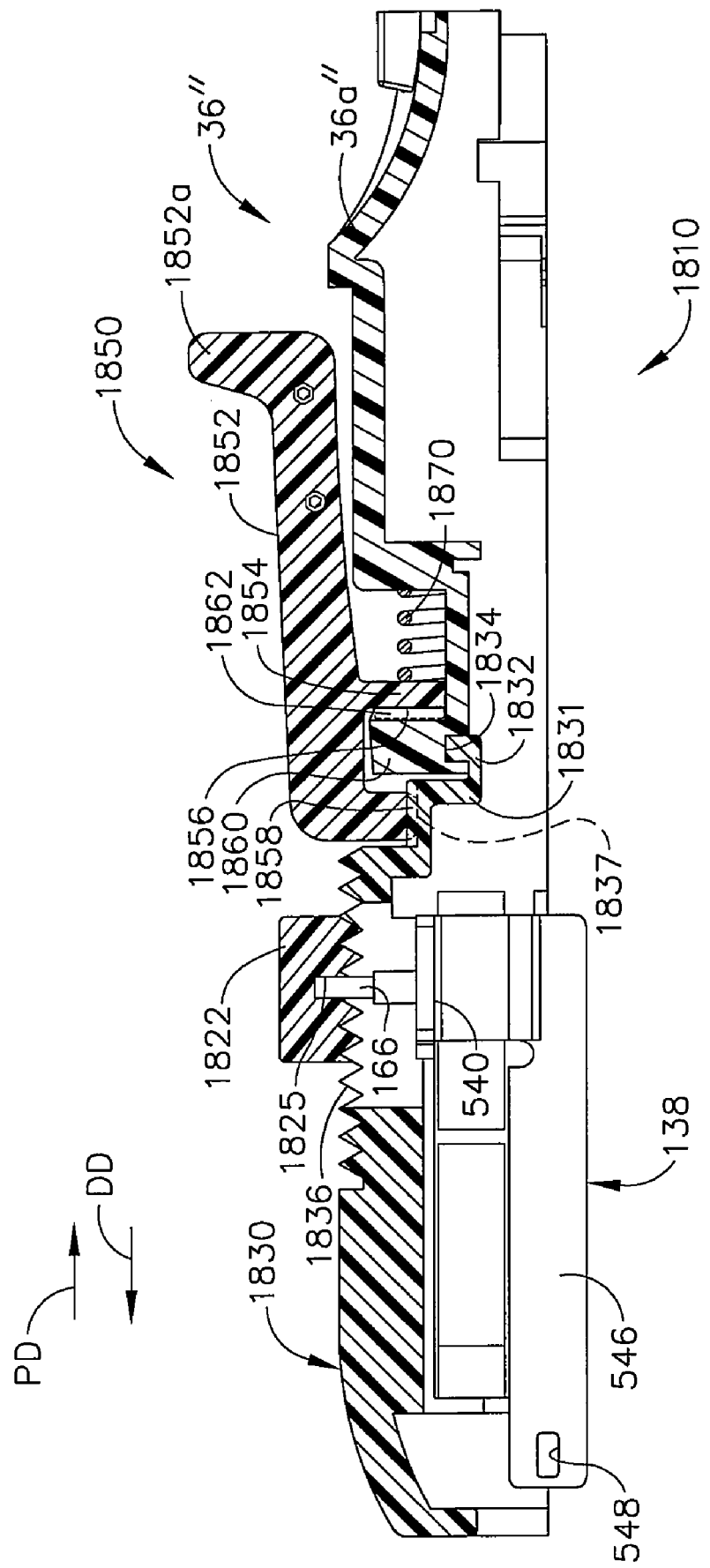
FIG. 71 is a partial cross-sectional view of a portion of the articulation mechanism embodiment of FIG. 70.

FIGS. 70 and 71 illustrate another unique and novel articulation mechanism 1820 and unique and novel lockable rotation system 1850 that may be used in connection with a stapling apparatus 1810 that may employ a disposable loading unit. The articulation mechanism 1820 is constructed to axially advance the translation member 138 to ultimately result in the longitudinal actuation of an articulation link 123 (not shown in FIGS. 70 and 71) that is coupled to the translation member 138. As can be seen in FIGS. 70 and 71, the articulation mechanism 1820 may be used in connection with a handle housing 36" that is formed from handle segments (handle segment 36a" is shown in FIGS. 70 and 71 with it being understood that another handle segment shaped to mate with handle segment 36a" is employed to form handle housing 36"). In various embodiments, the articulation mechanism 1820 is mounted to a rotatable shroud 1830 that has a flanged proximal end 1832 that is adapted to be received in an annular groove 1834 formed in the handle housing 36" such that the rotatable shroud 1830 may be selectively rotated about axis "L-L" relative to handle housing 36" as will be discussed in further detail below. Although not shown in FIGS. 70 and 71, the elongated member 14 and casing 124 described above in connection with other embodiments may be attached to the rotatable shroud 1830 by radial projections 132 formed on the distal end of rotatable shroud 1830. See FIG. 70. Projections 132 and openings 128 in casing 124 fixedly secure rotatable shroud 1830 and elongated body 14 in relation to each other, both longitudinally and rotatably. Rotation of rotatable shroud 1830 with respect to handle housing 36" thus results in corresponding rotation of elongated body 14 with respect to handle housing 36".

As can be seen in FIGS. 70 and 71, the articulation mechanism 1820 may comprise an articulation ring 1822 that is threadedly attached to a series a of threads 1836 provided on the rotatable shroud 1830. The translation member 138 may have an upstanding arm portion 540 that has a notch 542 therein that is sized to receive a tab (not shown) formed on the sensor cylinder (not shown) as was described above. The distal end of translation member 138 may include an arm 546 which includes an opening 548 configured to receive a finger 164 (not shown in FIGS. 70 and 71) extending from the proximal end of articulation link 123 (not shown in FIGS. 70 and 71) as was described above. See FIGS. 4 and 11. A pin 166 that may be constructed from a non-abrasive material, e.g., Teflon® or metal that has been coated with Teflon®, is secured to translation member 138 and dimensioned to be received within an annular slot 1825 formed in the articulation ring 1822. Thus, as the articulation ring 1822 is threadedly advanced on the rotatable shroud 1830 in the proximal direction "PD", the pin 166 also drives the translation member 138 (and the articulation link 123) in the proximal direction "PD" to cause the disposable loading unit to articulate in the right hand direction. Likewise, as the articulation ring 1822 is threadedly advanced on the rotatable shroud 1830 in the distal direction "DD", the pin 166 also drives the translation member 138 (and the articulation link 123) in the distal direction "DD" to cause the disposable loading unit to articulate in the left hand direction.

The embodiment depicted in FIGS. 70 and 71 also has a unique and novel lockable rotation system 1850 which may include a lockable knob 1852 that consists of two knob segments 1852a that are coupled together by screws, glue, snap features, posts, etc. over the distal end of the handle housing 36" such that the lockable knob 1852 is rotatably and axially supported on the distal end of the handle assembly 36". As can also be seen in FIGS. 70 and 71, the distal end of the handle housing 36" has a first lock flange 1860 with a first set of radial gear teeth 1862 formed thereon. The lockable knob 1852 may also have an inwardly extending second lock flange 1854 that has a second set of radial gear teeth 1856 formed thereon. The second set of radial gear teeth 1856 are located in confronting relationship with the first set of radial gear teeth 1862 on the first lock flange 1860 such that the second radial gear teeth 1856 may selectively mesh with the first radial gear teeth 1862. A lock spring 1870 may be used to bias the lock knob 1852 in the distal direction "DD" to bring the second set of radial gear teeth 1856 into meshing engagement with the first set of radial gear teeth 1862. As can also be seen in FIGS. 70 and 71, the proximal end 1831 of the rotatable shroud 1830 has a rotation spline 1837 formed thereon configured to mesh with an inwardly extending toothed flange 1858 formed on the distal end of the lockable knob 1852. Those of ordinary skill in the art will understand that the rotation spline 1837 and toothed flange 1858 serve to rotatably affix the lockable knob 1852 to the rotatable shroud 1830 while enabling the lockable knob 1852 to move axially relative to the rotatable shroud 1830. Thus, to rotate the rotatable shroud 1830 (and the elongate body 14 and disposable loading unit affixed thereto), the clinician biases the lockable knob 1852 in the proximal direction "PD" to disengage the second set of radial gear teeth 1856 from the first set of radial gear teeth 1862 which thereby permits the lockable knob 1852 to rotate about longitudinal axis "L-L" relative to handle housing 36". As the lockable knob 1852 is rotated, the rotatable shroud 1830 also rotates with the lockable knob 1852 by virtue of the engagement between the toothed flange 1858 and the rotation spline 1837. After the clinician has rotated the rotatable shroud 1830 to the desired position, he or she then releases the lockable knob 1852. When the lockable knob 1852 is released, the spring 1870 biases the second set of radial gear teeth 1856 into meshing engagement with the first set of radial gear teeth 1862 to retain the rotatable shroud 1830 in that position. Thus, such unique and novel arrangements solve the problems associated with rotatable knobs and articulation mechanisms employed in prior surgical instruments that are used in connection with disposable loading units. In particular, after the disposable loading unit and elongated body has been inserted into the patient, the clinician may rotate the disposable loading unit about the longitudinal axis "L-L" relative to the handle assembly 12" to a desired orientation and then lock it in that position. Thereafter, the clinician may then articulate the disposable loading unit to the left side or right side of the longitudinal axis. In the embodiments described immediately above, the threaded engagement between the articulation ring and the rotatable knob serves to lock the disposable loading unit in the desired articulated position. As in indicated above, in prior surgical instruments that employ a rotatable knob that has an articulation knob affixed thereto, the rotation knob may move as the clinician actuates the articulation lever making it difficult to accurately position the disposable loading unit.

Figure 72:
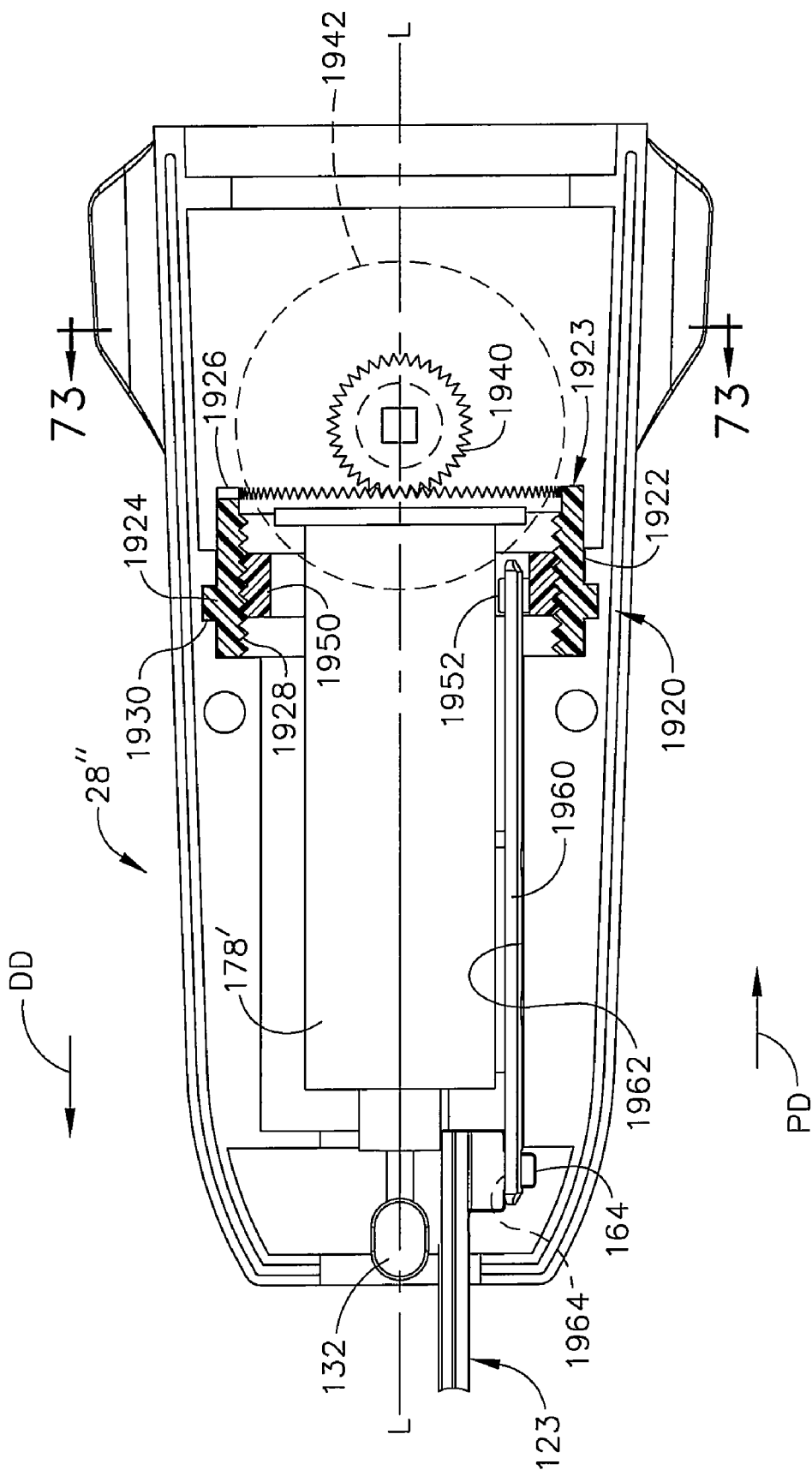
FIG. 72 is a side view of another articulation mechanism embodiment of the present invention with some of the components thereof shown in cross-section.
Figure 73:
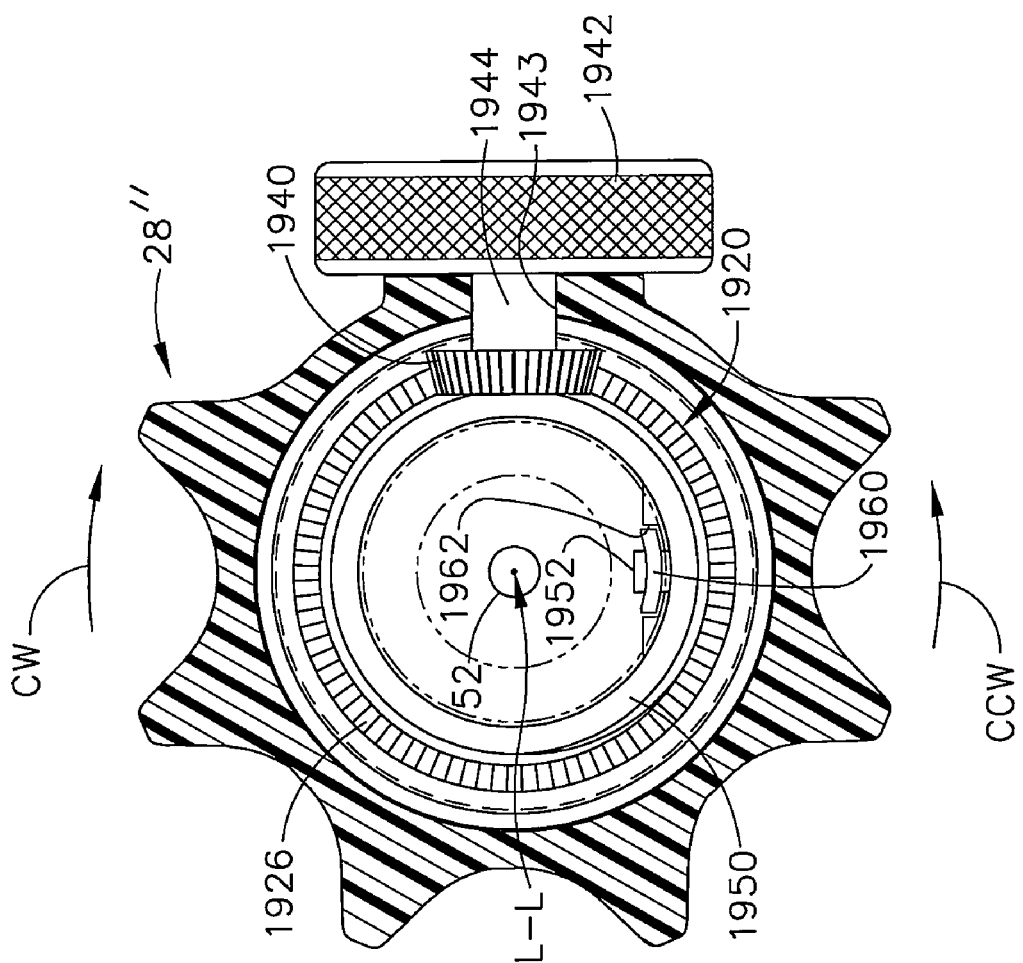
FIG. 73 is a cross-sectional view of the articulation mechanism embodiment of FIG. 72 taken along line 73-73 in FIG. 72.

FIGS. 72 and 73 illustrate another unique and novel articulation mechanism 1920 mounted within a rotatable knob 28" of the type of construction and operation described hereinabove. In this embodiment, the articulation mechanism 1920 may comprise an outer articulation ring 1922 that has a thrust flange 1924 formed thereon configured to be received in an annular groove 1930 formed in the rotatable knob 28" for rotatably supporting the outer articulation ring 1922 in the rotatable knob 28" such that the outer articulation ring 1922 is free to rotate relative to the rotatable knob 28", but it cannot move axially relative thereto. In various embodiments, the proximal end 1923 of the outer articulation ring 1922 may have radial gear teeth 1926 formed thereon for meshing engagement with a spur gear 1940 that is attached to an articulation knob 1942. As can be seen in FIG. 73, the articulation knob 1942 has a shaft 1944 attached thereto that is rotatably received in a through hole 1943 in the rotatable knob 28" and is non-rotatably attached to the spur gear 1940 such that rotation of the articulation knob 1942 causes the spur gear 1940 to rotate. As the spur gear 1940 is rotated, the outer articulation ring 1922 is also rotated about the longitudinal axis "L-L". Those of ordinary skill in the art will understand that the outer articulation ring 1922 may be selectively rotated in the clockwise "CCW" or counterclockwise "CCW" directions about the longitudinal axis L-L, depending upon the direction of rotation of the articulation knob 1942.

As can also be seen in FIG. 72, the outer articulation ring 1922 has an internal thread 1928 formed therein for threaded engagement with an inner articulation ring 1950. In this embodiment, the translation member comprises a metal link 1960 that is attached or pinned to the inner articulation ring 1950 by a pin 1952 or other fastener arrangements. The metal link 1960 is constrained to only move axially in the proximal direction "PD" and "distal direction "DD" because it is received within an axial groove 1962 formed in the rotatable knob 28". The distal end of the metal link 1960 includes an opening 1964 configured to receive a finger 164 extending from the proximal end of articulation link 123. Thus, rotation of articulation knob 1942 will result in the axial movement of the articulation link 123 in the proximal direction "PD" or distal direction "DD" depending upon the direction of rotation of the articulation knob 1942. When the articulation link 123 is advanced in the distal direction "DD", it will result in the disposable loading unit being articulated to left and when the articulation link is pulled in the proximal direction "PD", it will result in the disposable loading unit being articulated to the right as was discussed above. Those of ordinary skill in the art will appreciate that the threaded engagement between the inner articulation ring 1950 and the outer articulation ring 1922 will serve to retain the articulation link (and, ultimately the disposable loading unit) in the desired articulated position until the articulation knob is again rotated. It will be further appreciated that the desired knob rotation can be set by the gear ratio and thread pitch.

Figure 74:
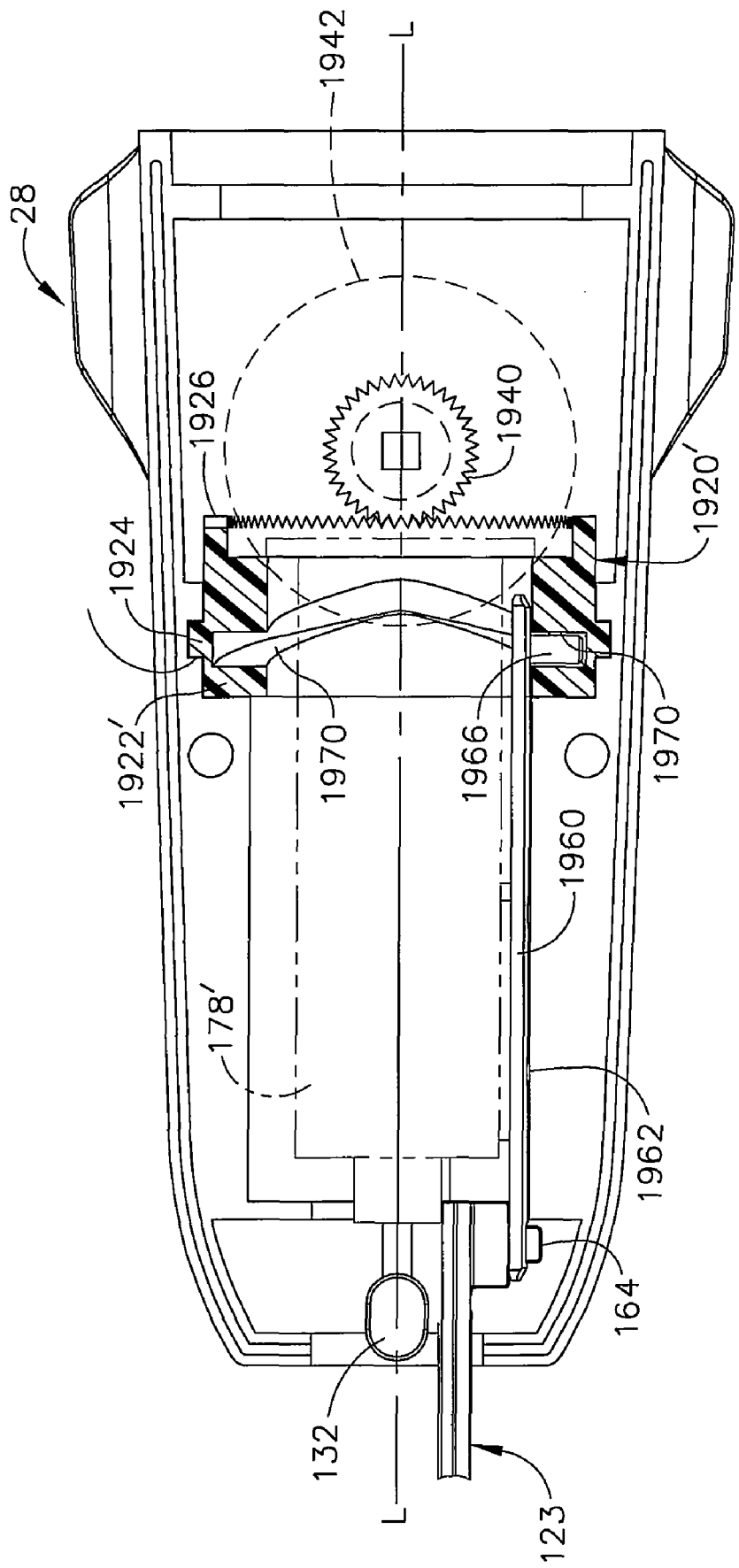
FIG. 74 is a side view of another articulation mechanism embodiment of the present invention with some of the components thereof shown in cross-section.
Figure 75:
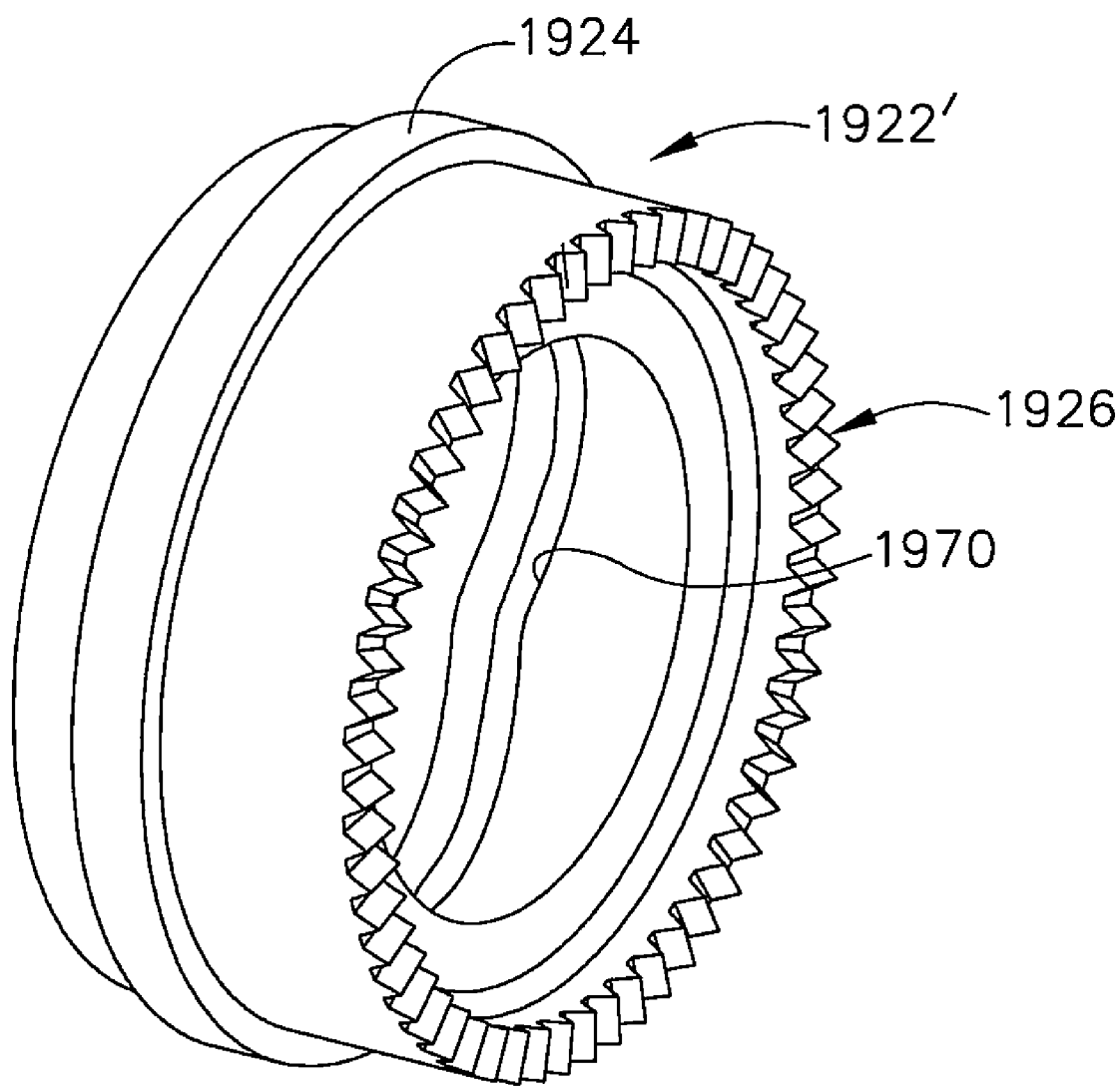
FIG. 75 is a perspective view of an outer articulation ring embodiment of the articulation mechanism of FIG. 74.

FIGS. 74 and 75 depict an another alternative articulation mechanism 1920' that employs an inner articulation ring 1922' that is identical to articulation ring 1922 described above, except that articulation ring 1922' has a cam slot 1970 therein instead of the inner threads 1928. As can be seen in FIGS. 74 and 75, the metal link 1960 has an articulation pin 1966 attached thereto that rides in the cam slot 1970 in the inner articulation ring 1922'. Thus, as the inner articulation ring 1922' is rotated by means of the articulation knob 1942 as was described above, the cam slot 1970 and articulation pin 1966 received therein drives the metal link 1960 in the proximal direction "PD" and the distal direction "DD" which results in the axial movement of the articulation link 123 in those directions as was described above.

When using prior surgical stapling devices that are adapted for use with disposable loading units, often times the control rod gets inadvertently advanced out of the end of the casing of the elongated body prior to attachment of the disposable reload unit. When that happens, and the disposable reload unit is attached to the apparatus, the reload unit cannot be fired. Instead, the clinician must first retract the control rod before attaching the reload unit. This occurrence can engender confusion and results in unnecessary downtime during the operation. In addition, during the firing sequence, the firing bar may become jammed requiring the clinician to retract the firing bar which can be difficult at times depending upon the nature of the jam. The embodiment of the surgical stapling apparatus 2010 of the present invention addresses such problems.

More particularly and with reference to FIG. 76, the surgical stapling apparatus 2010 may be substantially similar in construction as the various instruments described above, except for the unique and novel retraction system 2020 as will be described in detail below. Those components that are the same as the components employed in the above-mentioned embodiments will be labeled with the same element numbers and those of ordinary skill in the art can refer to the disclosure set forth hereinabove that explains their construction and operation.

In one embodiment, the surgical stapling apparatus 2010 may include a handle assembly 2012 that has an elongated body 14 that is operably coupled to the handle assembly 2012 and protrudes distally therefrom. A distal end of the elongated body 14 may be coupled to an articulatable disposable loading unit 16 (or a non-articulatable disposable loading unit). The disposable loading unit 16 may include a tool assembly 17 that is selectively articulatable about an articulation axis "A1-"A1" by articulation motions transferred thereto by the elongated body 14 as is known. See FIG. 76. In various embodiments, the proximal end of the elongated body 14 is coupled to a rotatable knob 28 that is coupled to handle housing 2036. As can be seen in FIGS. 76 and 77, the handle housing 2036 may be formed from a right housing segment 2036a and a left housing segment 2036b that are attached together.

Figure 76:
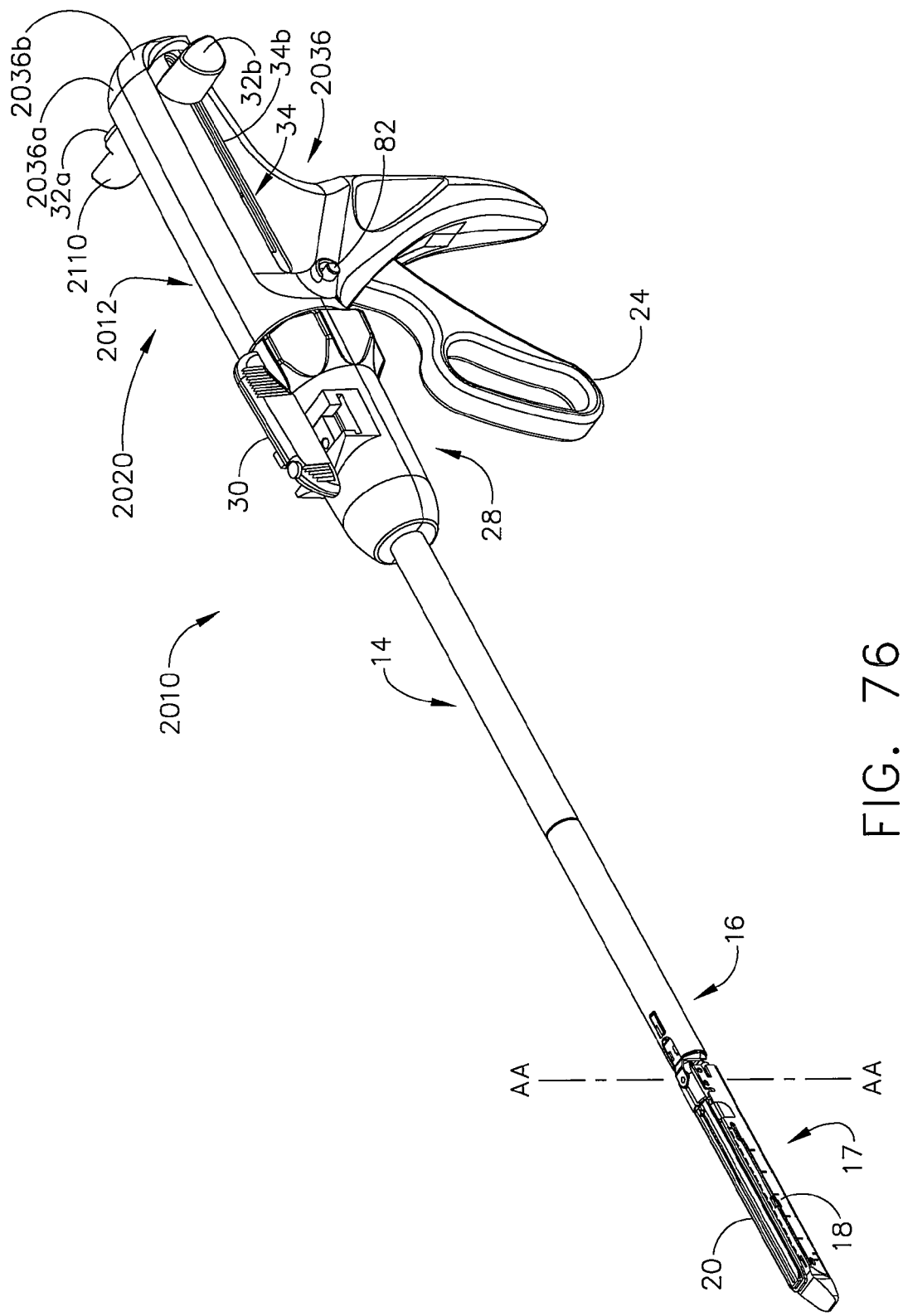
FIG. 76 is a left side perspective view of another surgical stapling apparatus embodiment of the present invention.
Figure 77:
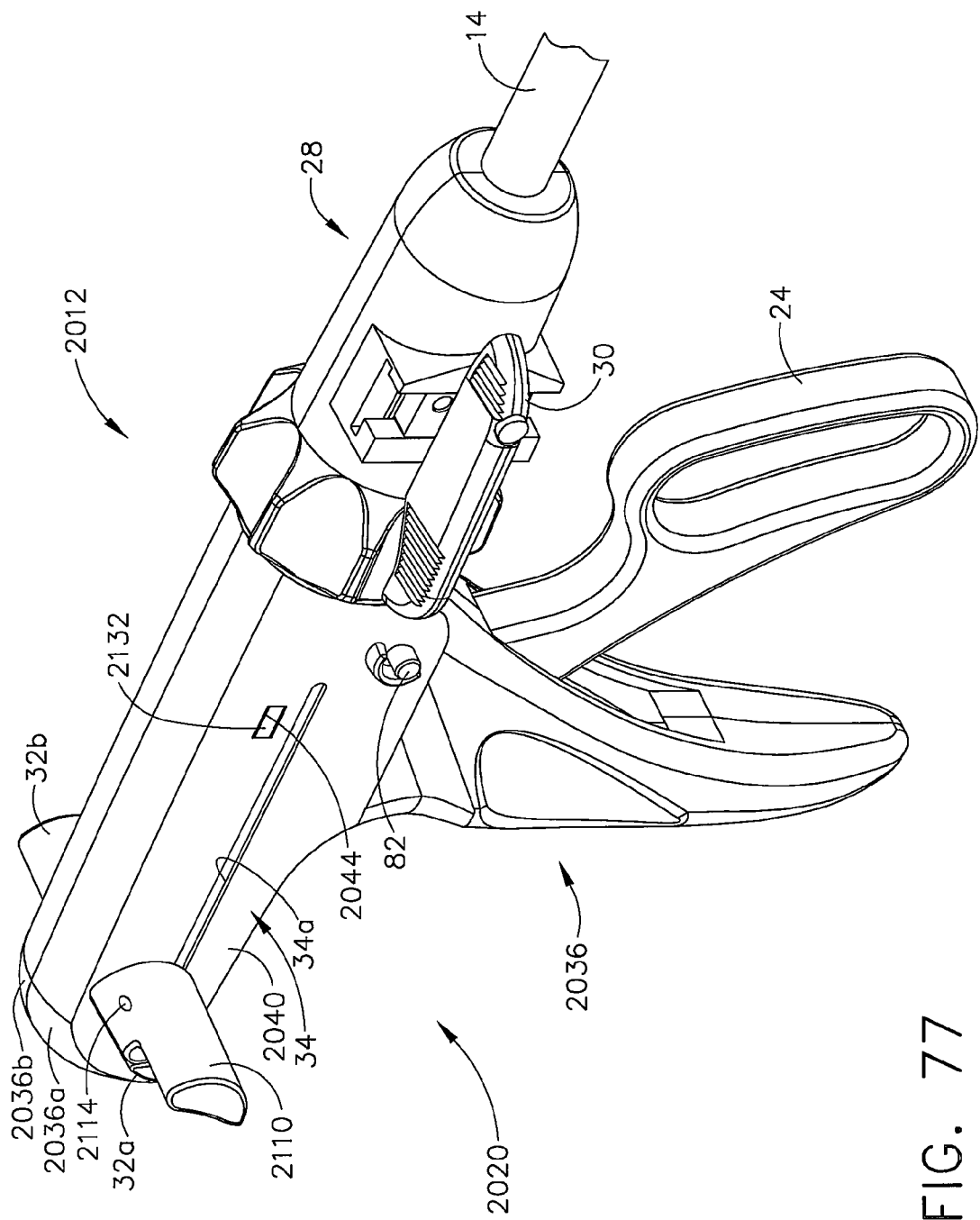
FIG. 77 is a right side perspective view of the surgical stapling apparatus embodiment depicted in FIG. 76.
Figure 78:
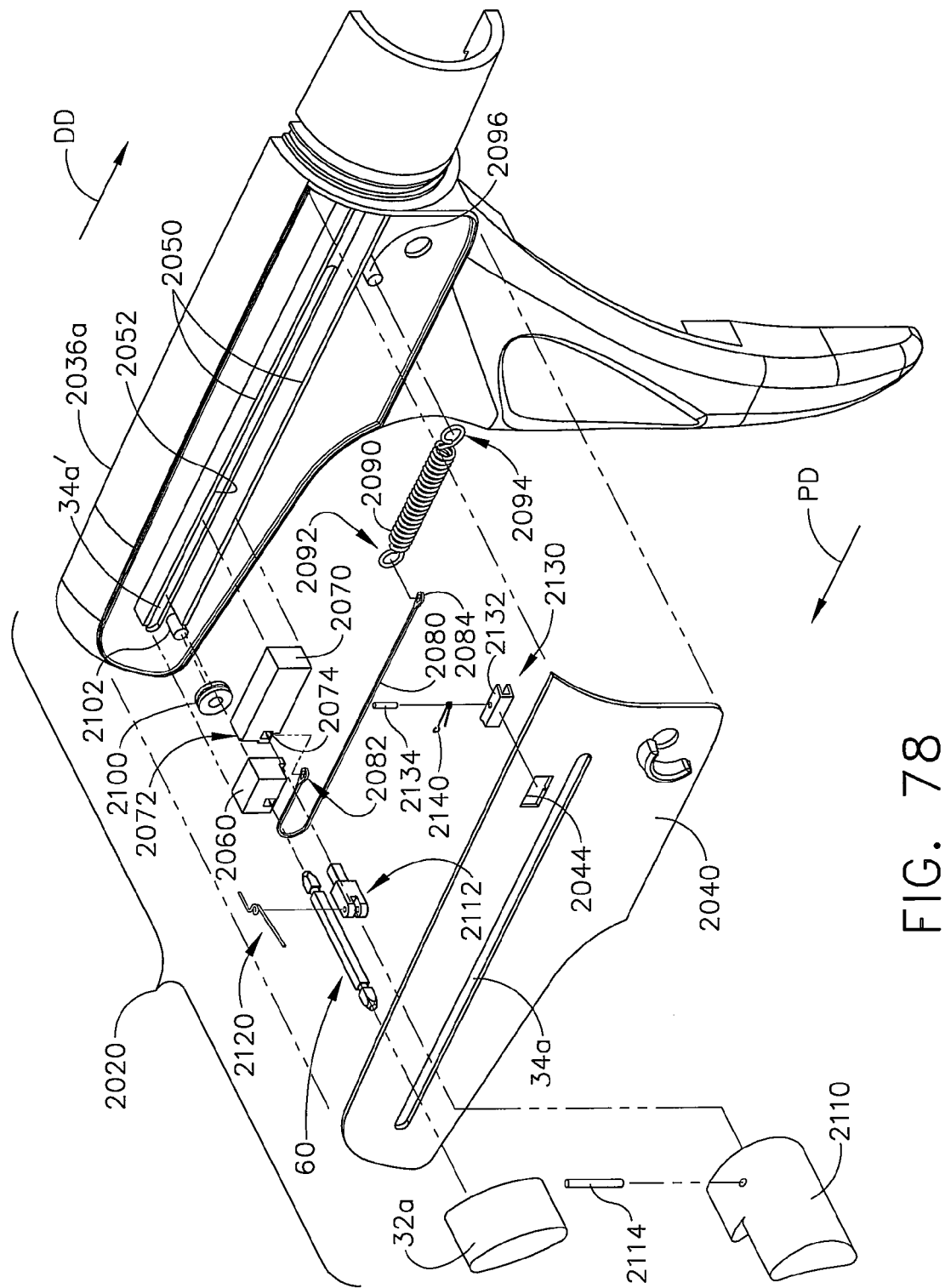
FIG. 78 is an exploded assembly view of the right housing segment of the handle assembly with the removable cover detached from the housing segment.
Figure 79:
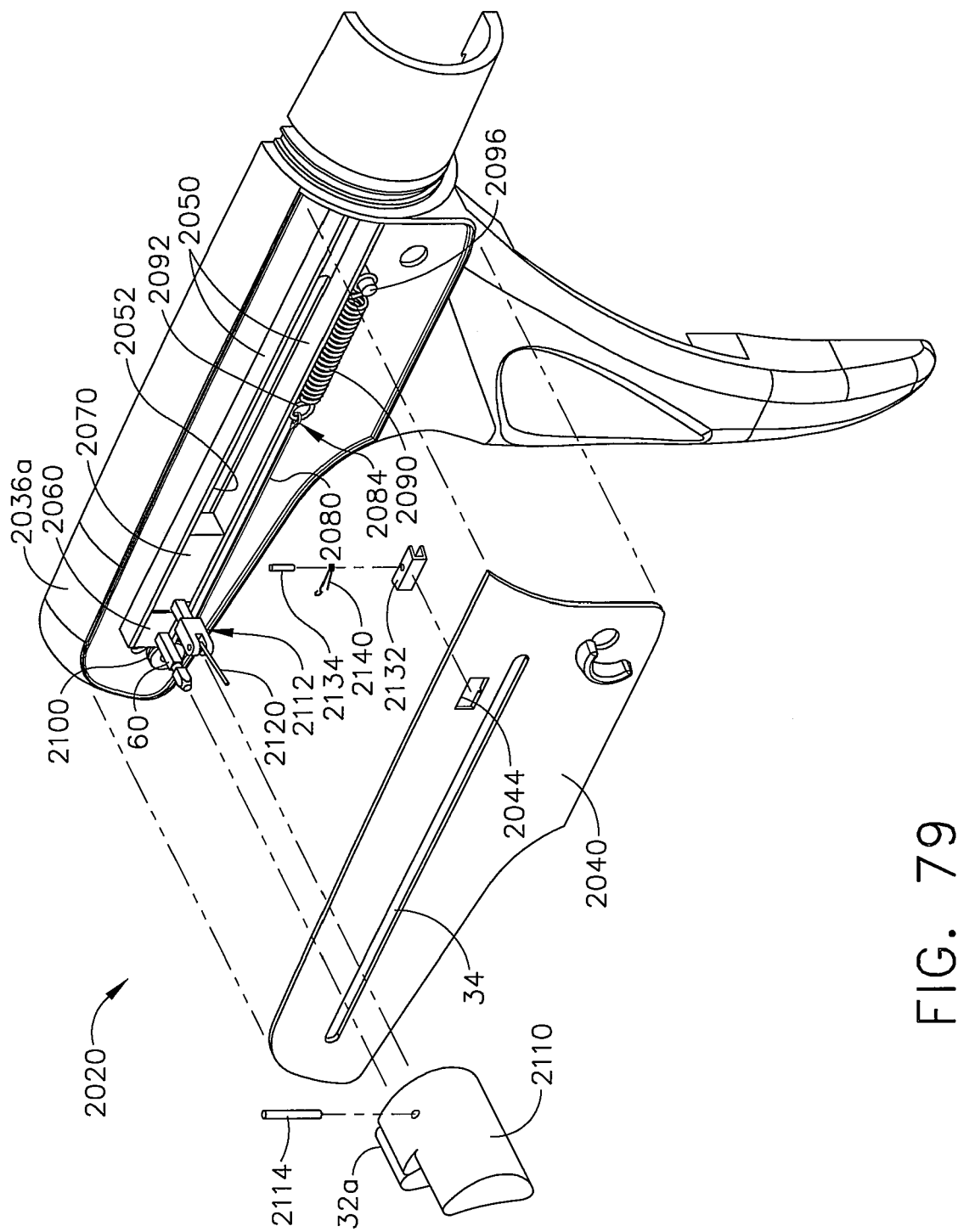
FIG. 79 is another view of the right housing segment of the handle assembly with the removable cover detached from the housing segment.
Figure 81:
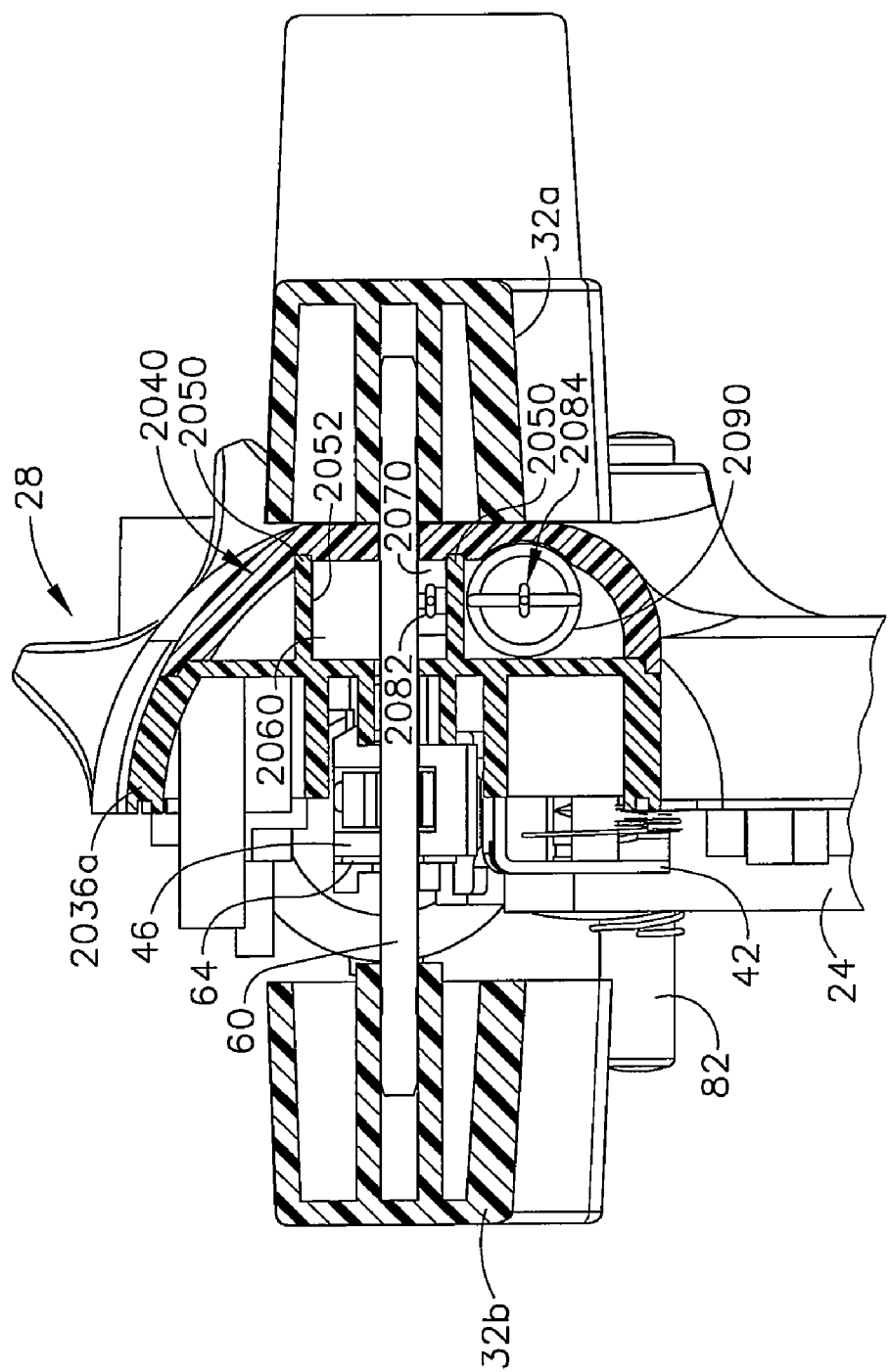
FIG. 81 is a cross-sectional view of the housing assembly taken along line 81-81 in FIG. 80.

As shown in FIGS. 76-78, the right hand housing segment 2036a may have a removable cover 2040 that is coupled to the right housing segment 2036a by snaps, screws, pin inserts or a releasable detent post inserted into a boss. As will be discussed in further detail below, this embodiment also employs a release plate 64 (FIG. 81) of the type and construction described above which has a coupling rod 60 attached thereto. The coupling rod 60 extends through an elongated retract slot 34b in the left housing segment 2036b (FIG. 76) as well as through an elongated retract slot 34a in the removable cover 2040 (FIG. 77) to have retractor knobs 32a, 32b attached thereto as was described above. The right housing segment 2036a further has a retract slot 34a' formed therein that corresponds with the retract slot 34a in the removable cover 2040 when the removable cover 2040 is attached thereto by snap features, adhesive, screws, etc. In this embodiment, the right housing segment 2036a may have a pair of spaced elongated guide ribs 2050 formed therein that serve to define an elongated retract passage 2052 therebetween. Also in various embodiments, a retract slide member 2060 may be received on the coupling rod 60 and be constrained to axially move in the distal direction "DD" and proximal direction "PD" within the elongated retract passage 2052. The retraction system 2020 may further include a cable slide 2070 that is also constrained to move longitudinally within the retract passage 2052 as can be seen in FIGS. 79 and 84-86. The proximal end 2072 of the cable slide 2070 may have a notch 2074 therein to enable a proximal end 2082 of a retract cable 2080 to be pinned or otherwise attached thereto. A distal end 2084 of the retract cable 2080 may be attached to a proximal end 2092 of a retraction spring 2090. The distal end 2094 of the retraction spring 2090 may be attached to a retraction spring post 2096 formed on the right housing segment 2036a. See FIGS. 78 and 83-85. The retraction cable 2080 may be journaled on a retract pulley 2100 that is rotatably supported on a pulley post 2102 formed on the right housing segment 2036a.

Figure 83:
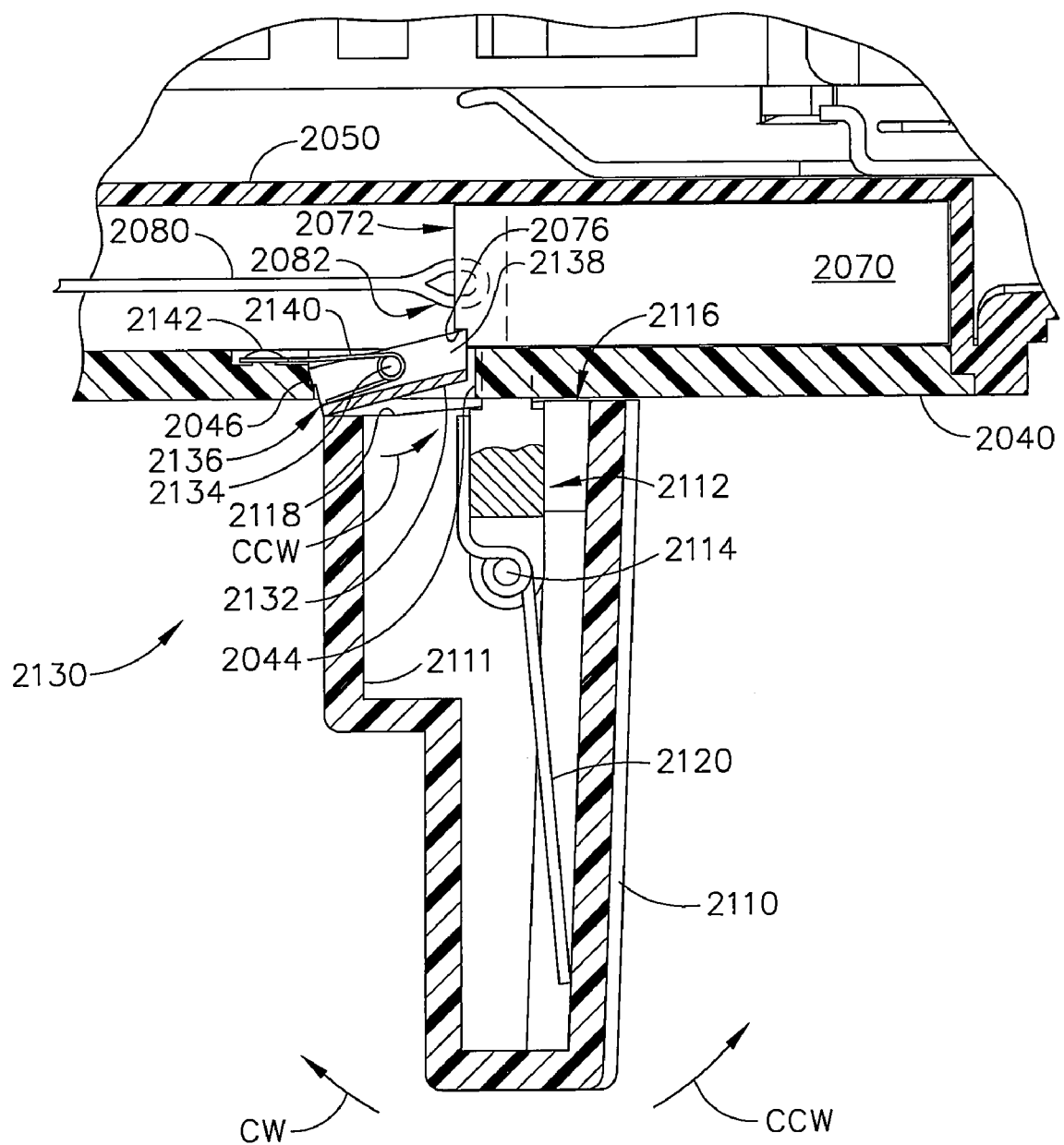
FIG. 83 is a cross-sectional view of a portion of the housing assembly and cocking knob taken along line 83-83 in FIG. 80.

In various embodiments, the retraction system 2020 may be configured to enable the control rod 52 to be automatically retracted at the end of the firing sequence or, if desired, manually retracted. For example, as can be seen in FIG. 83, a cocking lug 2110 may have a hollow cavity 2111 therein and be attached to the cable slide 2070 by a clevis-like lug mount 2112 and pin 2114 that is received within the hollow cavity 2111. As can be seen in FIG. 83, the cocking lug 2110 may further have an inner end portion 2116 that is arranged to be adjacent to the removable cover 2040 and also have a relieved area or notch 2118 formed therein. A lug spring 2120 configured as shown in FIGS. 78 and 83, may be journaled on the pin 2114 to bias the cocking lug 2110 about the pin 2114 in the counterclockwise "CCW" direction as shown in FIG. 83. The retraction system 2020 may further include a retraction lock assembly 2130.

Figure 82:
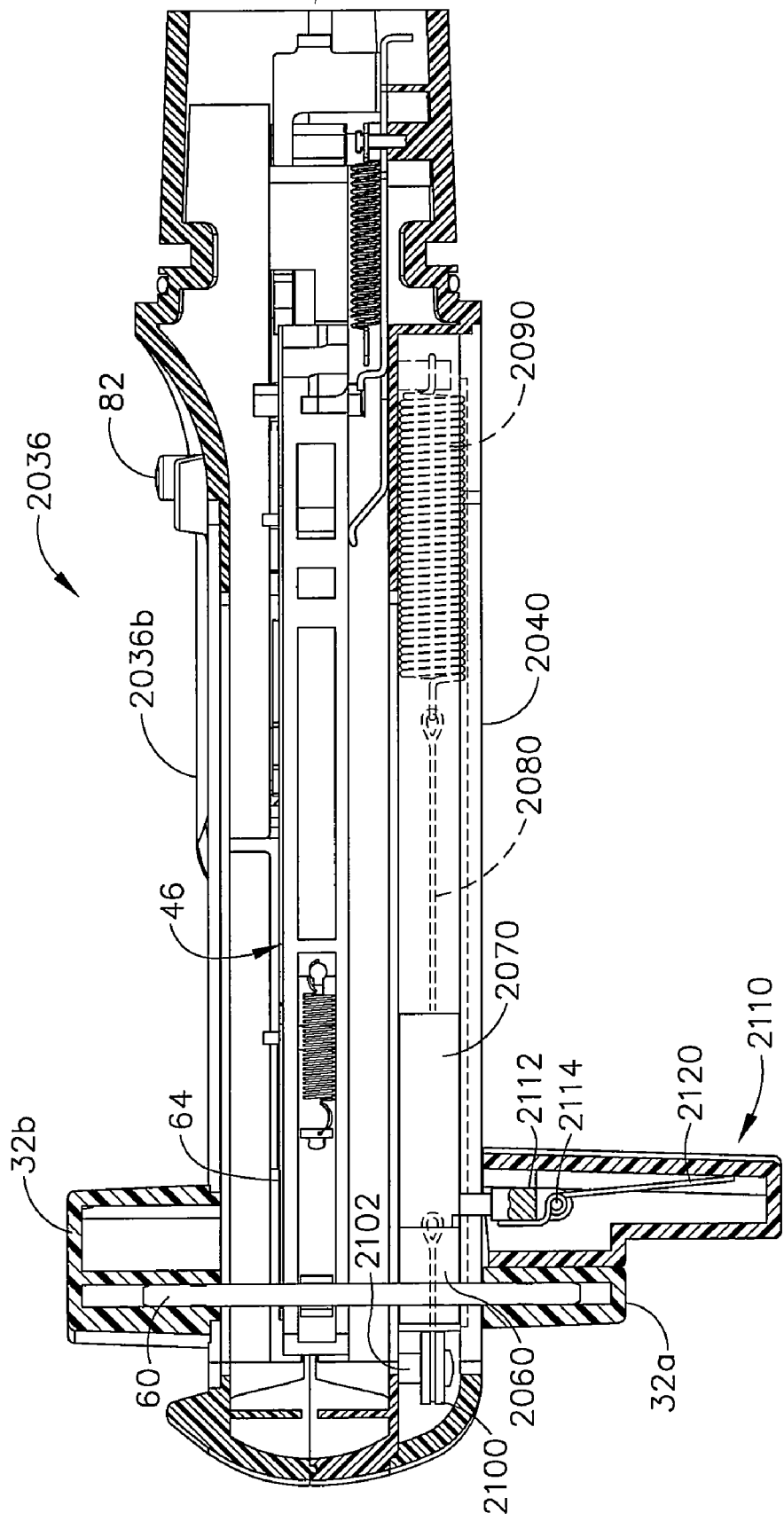
FIG. 82 is a cross-sectional view of the housing assembly taken along line 82-82 in FIG. 80.

The retraction lock assembly 2130 may include a lock member 2132 that is pivotally pinned to the removable cover 2040 by a lock pin 2134. A lock spring 2140 configured as shown in FIGS. 82 and 83, may be journaled on the lock pin 2134 and attached to the cover 2040 by a screw 2142 or other suitable fastener such that the lock spring 2140 is biased in the counterclockwise "CCW" direction in FIG. 83. As can further be seen in FIG. 83, the lock member 2132 is configured to protrude through a window 2044 in the cover 2040 and has a notched proximal end 2136 adapted to engage a notch 2046 in the cover 2040. See FIG. 83. The lock member 2132 may have a distal end 2138 that is adapted to retainingly engage a notch 2076 in the proximal end 2072 of the cable slide 2070.

Figure 80:
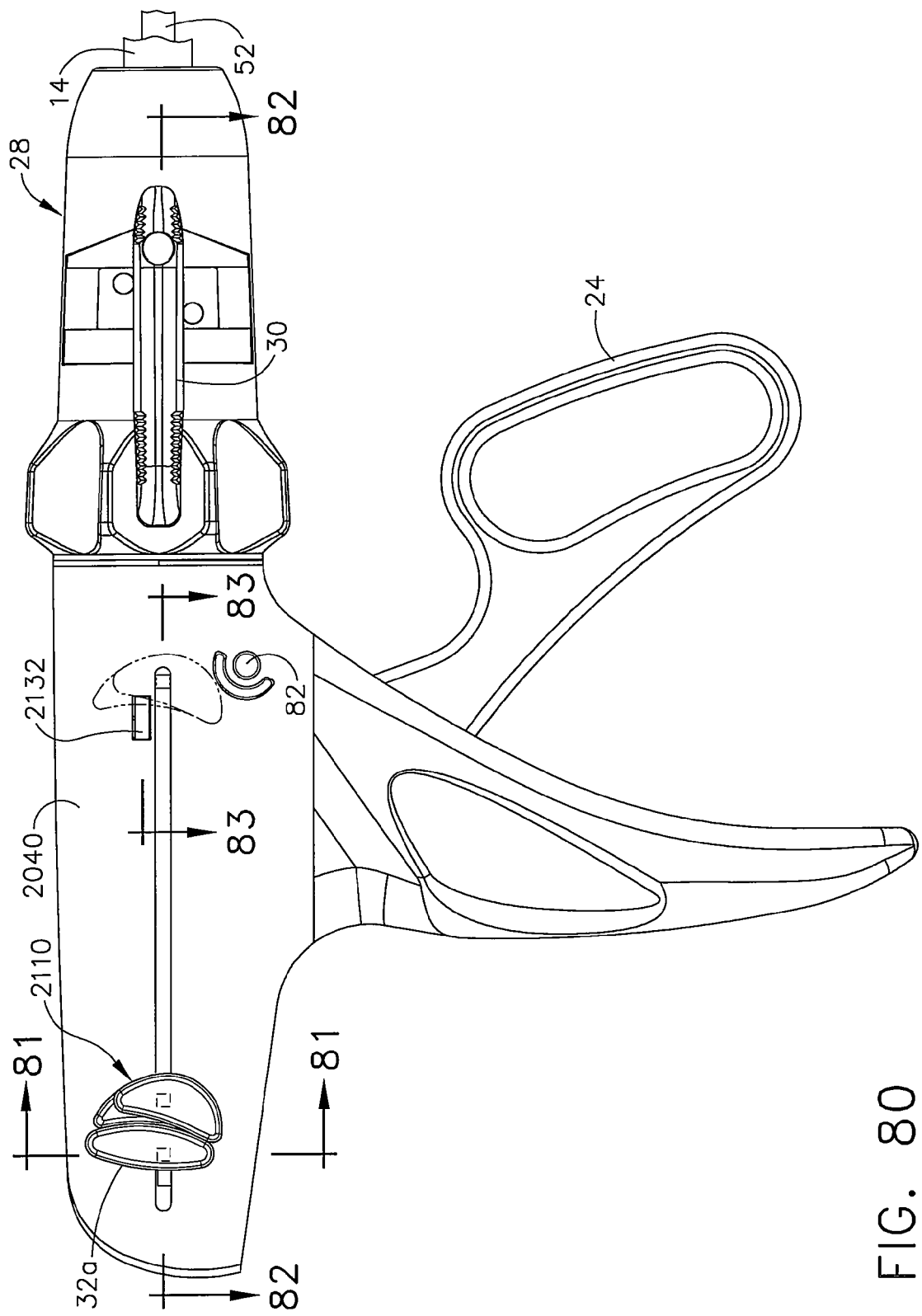
FIG. 80 is a right side view of the handle assembly of the surgical stapling apparatus depicted in FIGS. 76-78.
Figure 84:
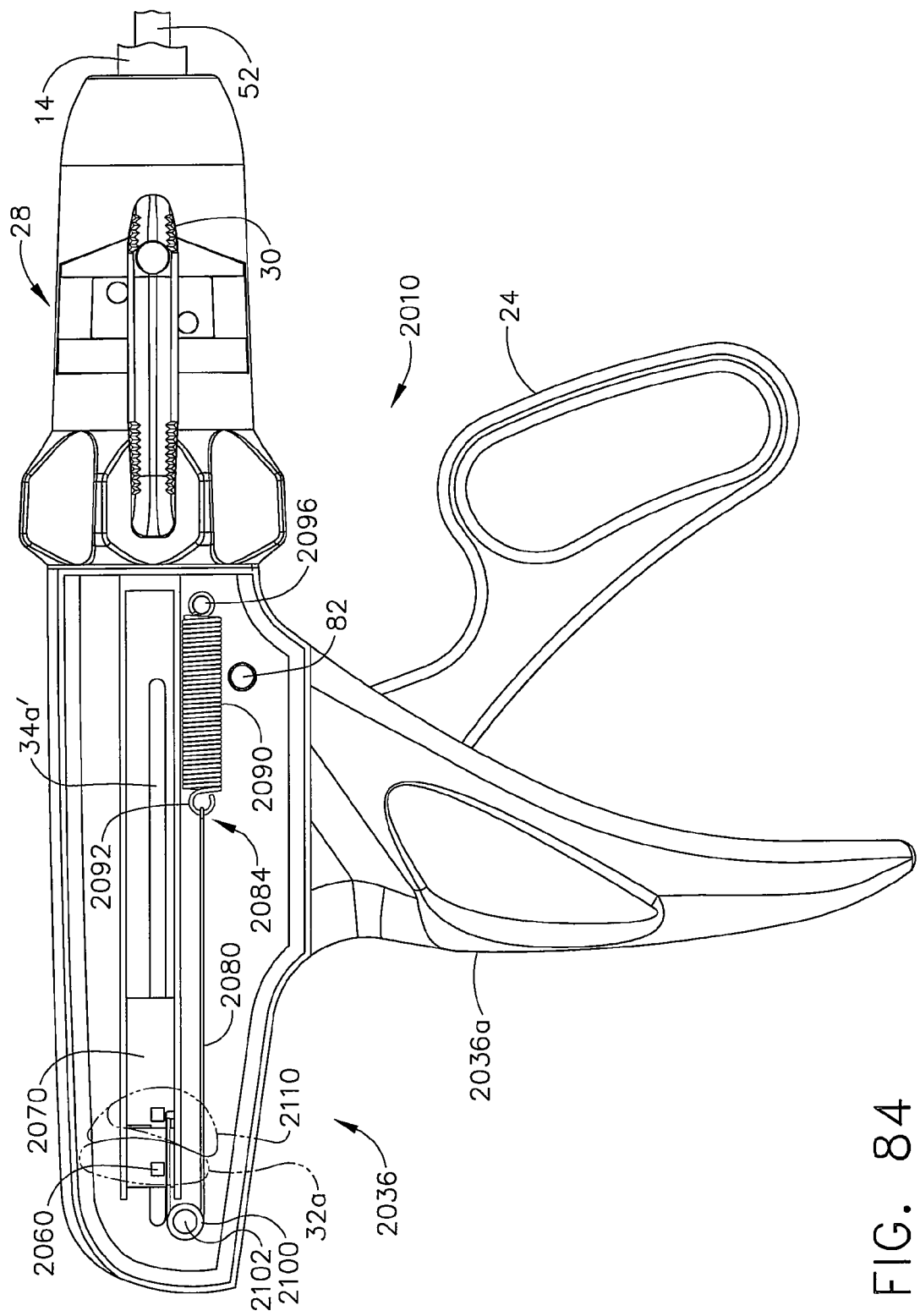
FIG. 84 is a right side view of the handle assembly of the surgical stapling apparatus depicted in FIGS. 76-83 with the removable cover removed to show the retract knob and the cocking knob in the "pre-fired" position.
Figure 85:
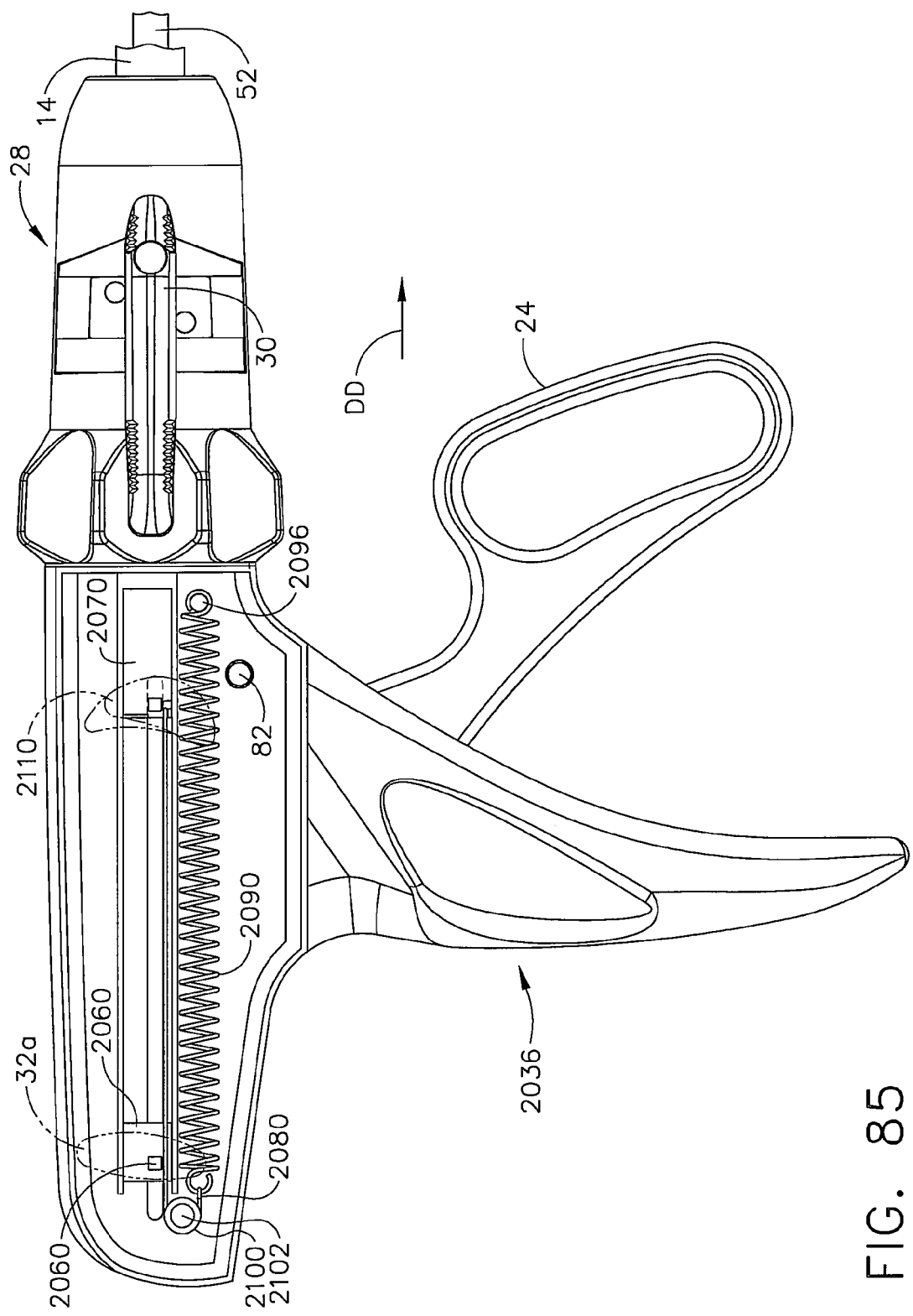
FIG. 85 is another right side view of the handle assembly of FIG. 84 with the cocking knob in a cocked position.
Figure 86:
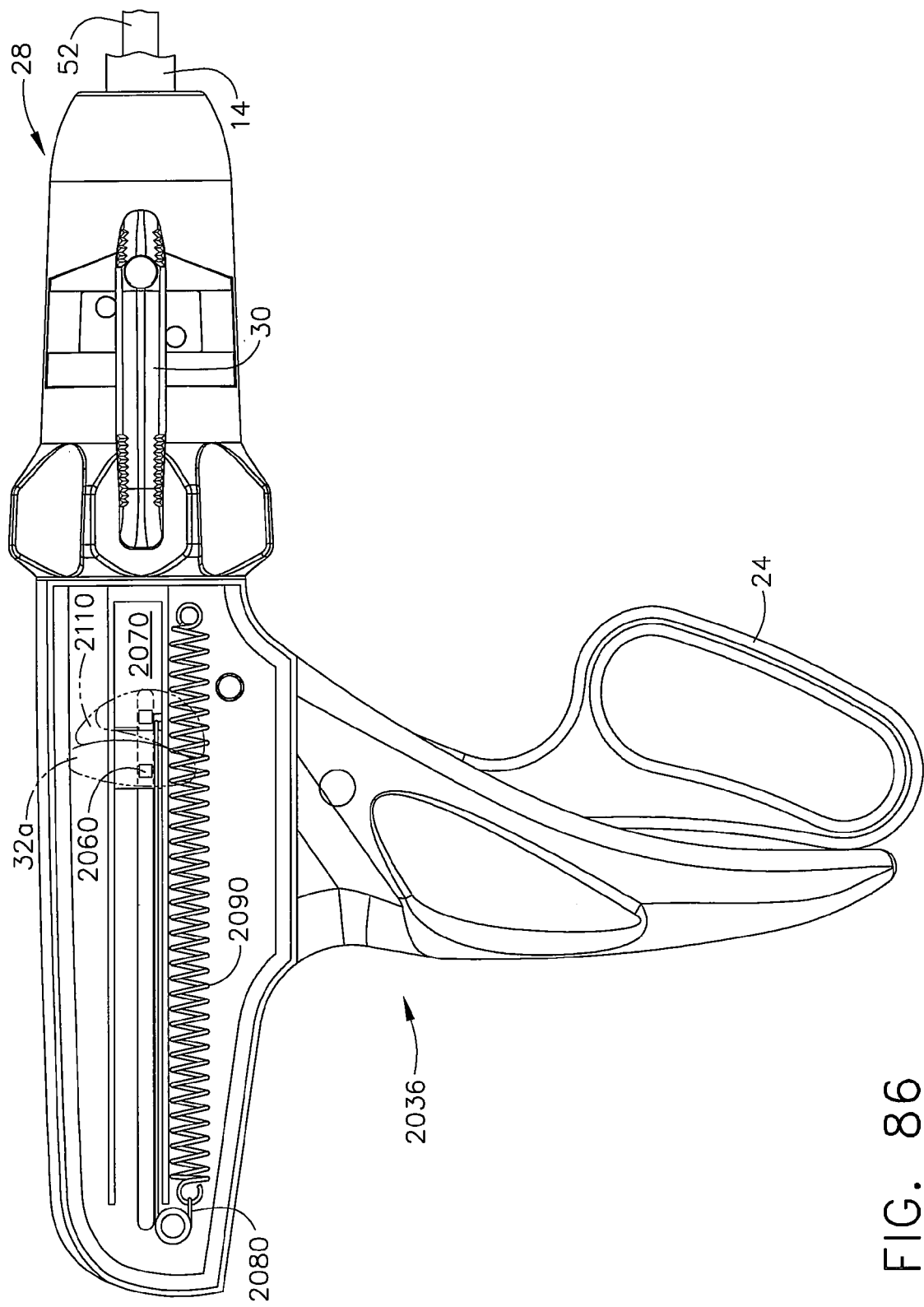
FIG. 86 is another right side view of the handle assembly of FIGS. 84 and 85 showing the position of the retract knob and the cocking knob prior to reaching the fully fired position.
Figure 87:
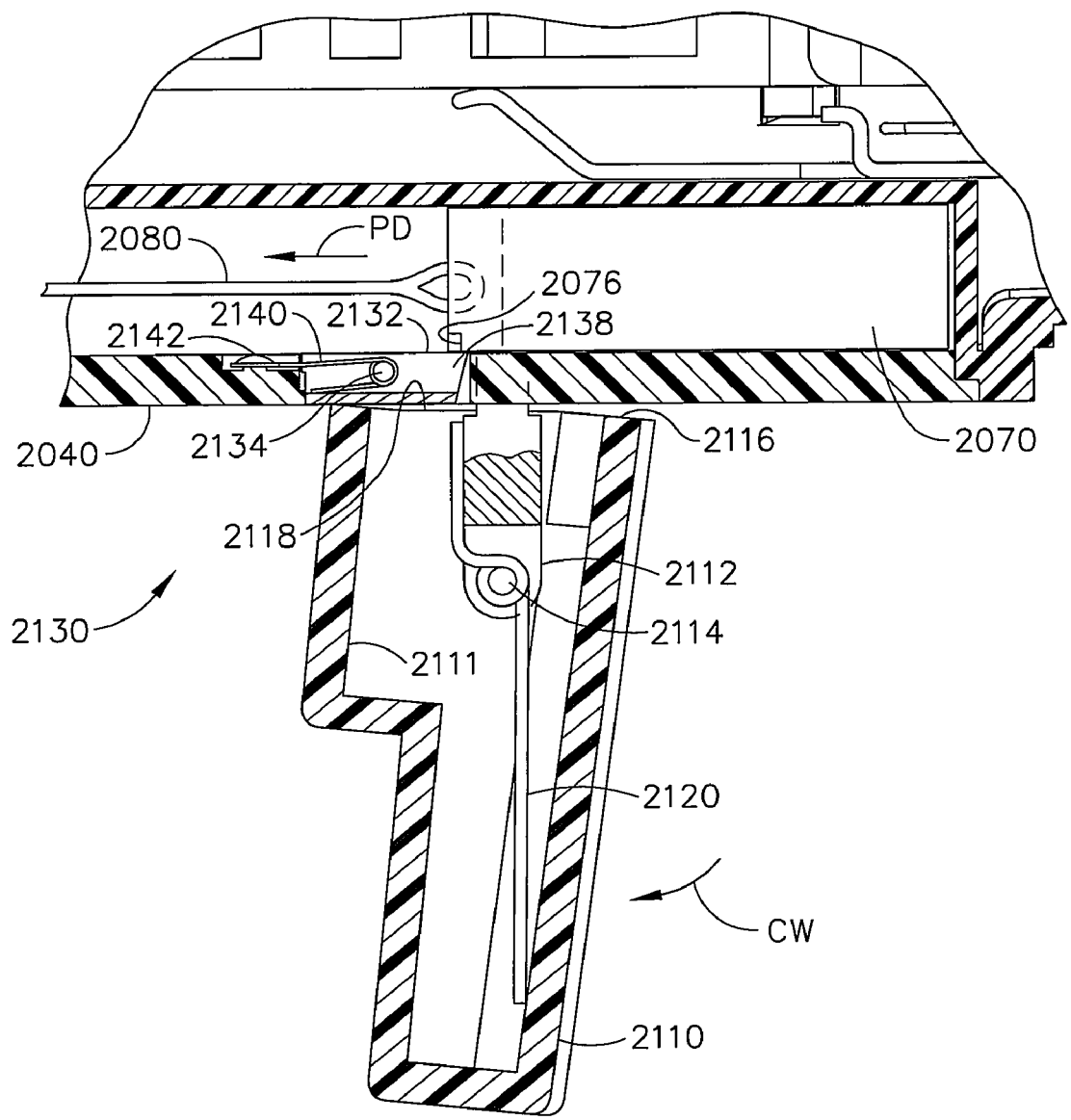
FIG. 87 is a partial cross-sectional view of the handle assembly and cocking knob with the cocking knob biased in a clockwise direction to release the lock member.
Figure 88:
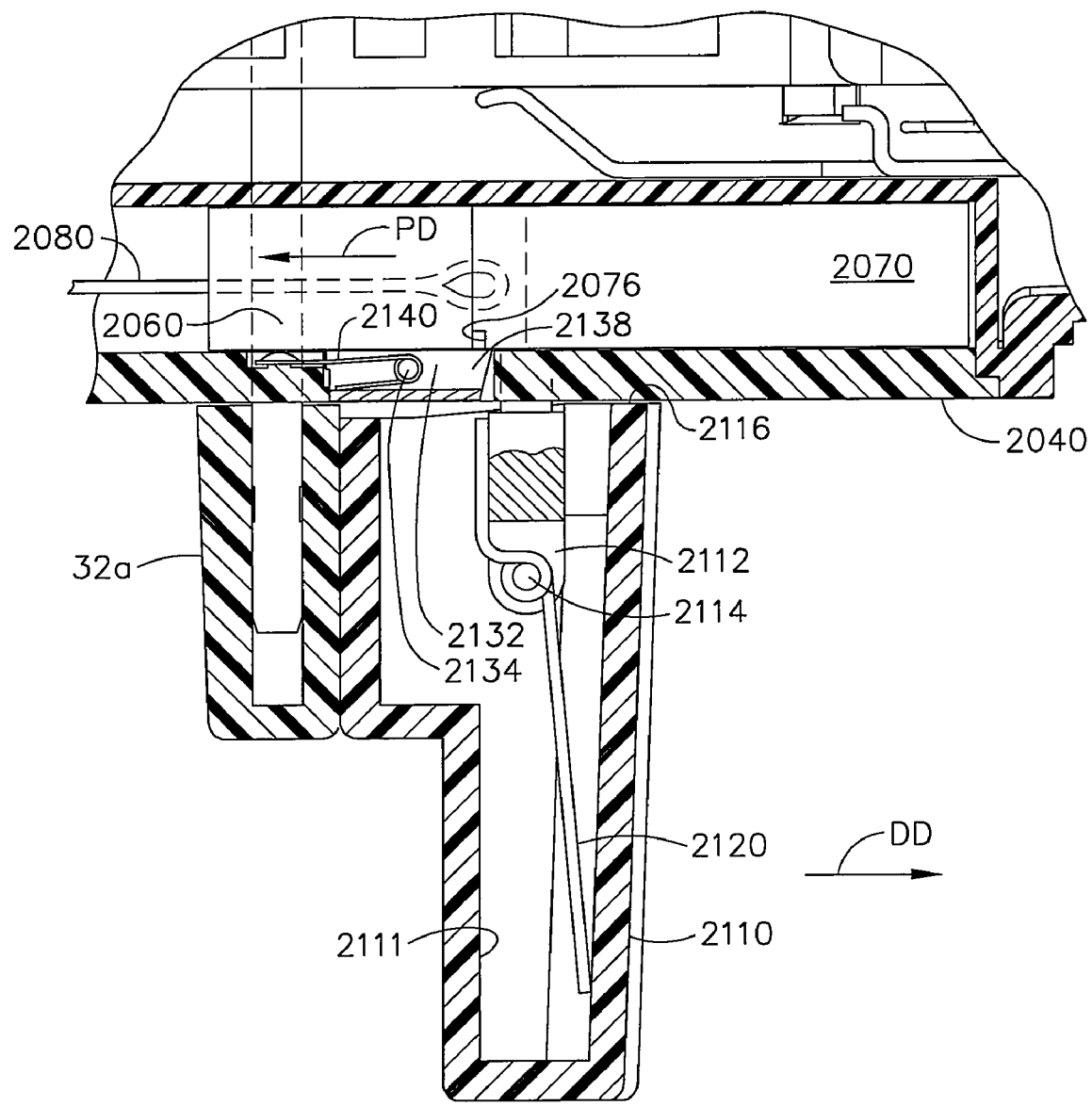
FIG. 88 is another partial cross-sectional view of the handle assembly, cocking knob and retract knob wherein the retract knob has released the lock member to permit the actuation shaft to be automatically retracted.

Operation of the surgical stapling apparatus 2010 will now be described with reference to FIGS. 84-88. FIG. 84 illustrates the surgical stapling apparatus 2010 in an initial "pre-fired" position wherein the retract knob 32a and the cocking knob 2110 (FIG. 80) are in the "pre-fired" position located at the proximal end of the handle housing 2036. Prior to commencing the firing sequence, the clinician may push the cocking lug 2110 in the distal direction "DD" to the cocked position shown in FIG. 85. As can be seen in that Figure, when the cocking lug 2110 is in the cocked position, the retraction spring 2090 is stretched and serves to store retraction energy therein. After the cocking lug 2110 has been moved to the cocked position, the clinician may press the firing button 82 (as was discussed above) and then commence the firing sequence by ratcheting the movable handle 24. As the clinician advances the actuation shaft 46 in the distal direction "DD" by ratcheting the movable handle 24, the retract knobs 32a, 32b move distally with the actuation shaft 46 until they reach the position shown in FIG. 86 which is prior to the end of the firing stroke (i.e., the control rod 52 has been advanced as far as it can go in the distal direction to cause the disposable reload unit to be completed fired). If the clinician wishes to manually retract the control rod 52 prior to reaching the final firing stroke (at any time during the firing sequence), the clinician simply biases the cocking lug 2110 in the clockwise "CW" direction shown in FIG. 87 which causes the cocking lug 2110 to bias the lock member 2132 in the clockwise direction "CW" to thereby cause the distal end 2138 to move out of the locking notch 2076 in the cable slide 2070 to thereby permit the cable slide 2070 to move in the proximal direction "PD" under the force of the retraction spring 2090 and thereby force the retract slide 2060 in the proximal direction "PD". Because the retract bar 60 extend through the retract slide 2060 and is attached to the retraction plate 64, the retract bar 60 causes the retract plate 64 to retract the actuation shaft 46 (and the control rod 52) by virtue of its attachment to the actuation shaft 46.

If the clinician does not wish to manually actuate the retraction system 2020, the clinician may keep ratcheting the movable handle 24 until the firing sequence is completed. When the actuation shaft 46 has been distally advanced to its distal most position at the completion of the firing sequence, (FIG. 88) the retract slide 2060 biases the lock member 2132 to the position shown in FIG. 88 such that the distal end 2138 is moved out of retaining engagement with the notch 2076 in the cable slide 2070 which permits the cable slide 2070 to move to the proximal most retracted position under the force of the retraction spring 2090. Thus, when the retract knob 32a reaches the fully fired position, it causes the retract system 2020 to automatically retract the actuation shaft 46 and control rod 52.

Those of ordinary skill in the art will readily appreciate that these embodiments serve to avoid the problem of the control rod 52 not being fully retracted to a position wherein another disposable reload unit may be attached to the stapling apparatus. In addition, the retraction spring serves to assist the clinician in retracting the control rod, should it be necessary to do so during the firing sequence.

Figure 89:
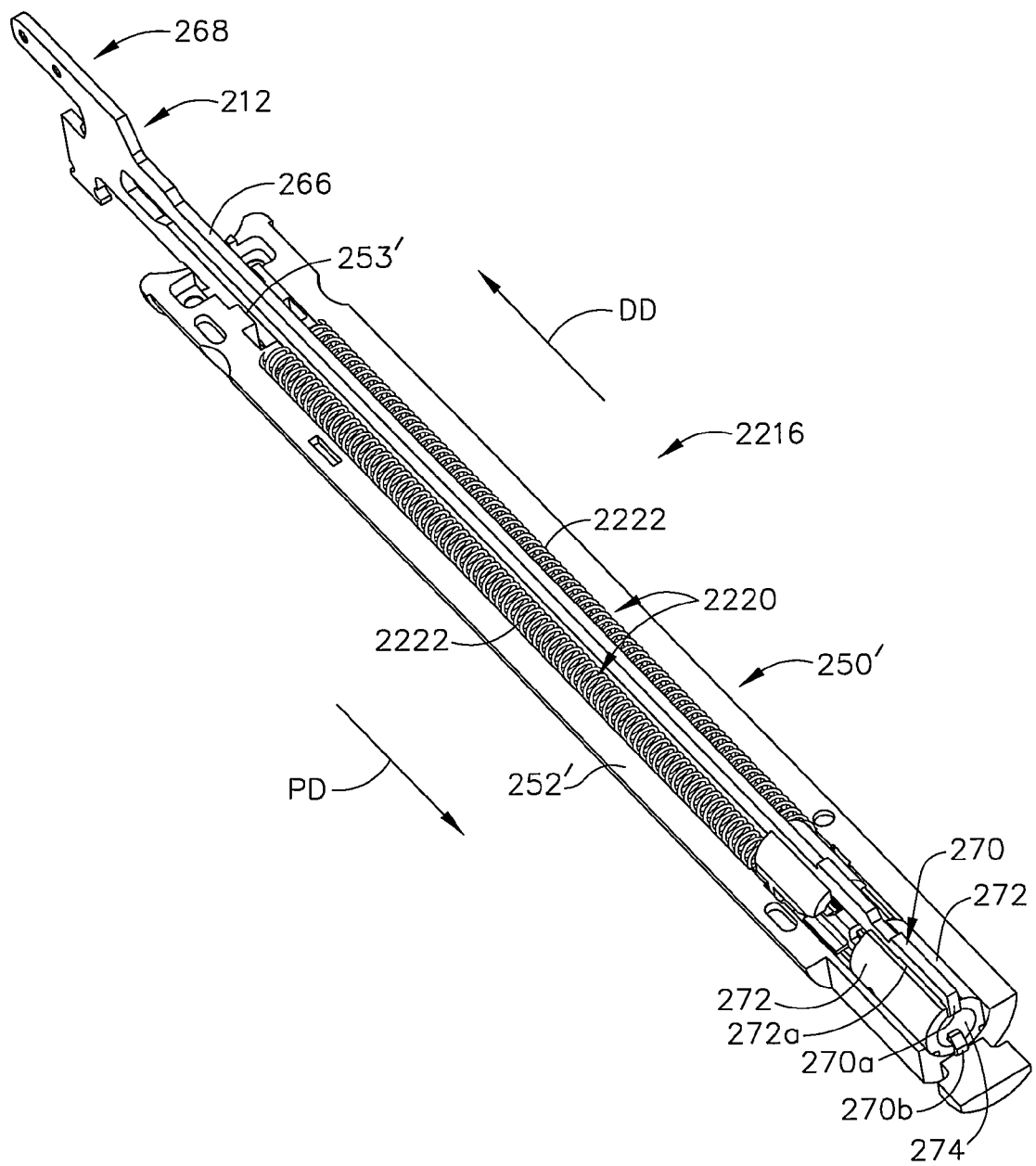
FIG. 89 is a partial perspective view of a portion of a disposable loading unit of various embodiments of the present invention.

FIG. 89 illustrates an alternative disposable loading unit 2216 that has an elongated housing portion 250' that may include an upper housing half (not shown) and a lower housing half 252'. The distal end of the housing 250' is attached to a tool assembly 17 (FIG. 76) and removably attachable to the elongated body 14. Housing halves define a channel 253' for slidably receiving axial drive assembly 212 therein. As will be discussed further below, the drive assembly 212 includes an elongated drive beam 266 including a distal working head 268 and a proximal engagement section 270. Drive beam 266 may be constructed from a single sheet of material or, preferably, from multiple stacked sheets. Engagement section 270 may include a pair of engagement fingers 270a and 270b which may be dimensioned and configured to mountingly engage a pair of corresponding retention slots 272a formed in drive member 272. Drive member 272 may include a proximal porthole 274 configured to receive the distal end of control rod 52 when the proximal end of disposable loading unit 2216 is engaged with elongated body 14 of surgical stapling apparatus 10. In this embodiment, at least one, and preferably a pair of, energy storing members 2220 are also supported in the housing 250' as shown. Energy storing members 2220 may comprise compression springs 2222. As control rod 52 is axially advanced in the distal direction "DD", the drive member 272 and drive beam 266 are driven in that direction compressing the springs 2222 (i.e., storing retraction energy therein). After the firing sequence has been completed or, if during the firing sequence it becomes necessary to retract the drive beam 266, the compressed springs 2222 will release the stored retraction energy and serve to assist in the retraction processes by releasing their stored energy to bias the drive beam 266 and drive member 272 in the proximal direction "PD".

Prior instruments, such as those disclosed in U.S. Pat. No. 5,865,361 suffer from the inability to be fired in thicker tissues (e.g., tissues with thicknesses greater than 3.5 mm) due to the increased loads applied to the firing system. Such increased loads can, for example, increase the likelihood that the firing system will fail when the knife is still in the anvil and may therefore require that the end effector be cut off of the tissue. Such failure mode can have serious patient injury consequences. Various embodiments of the present invention are directed to improved actuation transfer mechanisms or assemblies that are constructed to act as a fail safe "fuse" or device that would prevent advancement of the actuation shaft 46 (e.g., prevent transfer of actuation motions to the disposable loading unit) when the firing load resulting from thick tissue exceeds a predetermined magnitude.

Figure 90:
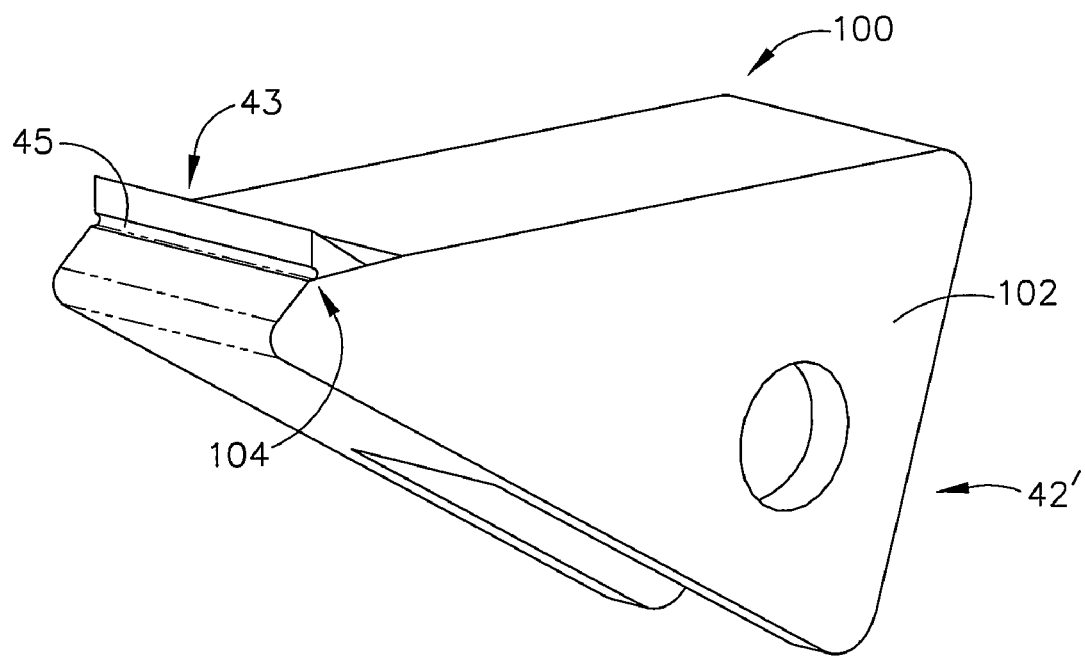
FIG. 90 is a perspective view of a pawl embodiment of various embodiments of the present invention.

FIG. 90 illustrates one actuation transfer assembly 100 that includes a driving pawl 42' that has a pawl body portion 102 that has rack engagement member or tooth 43 that is attached to or formed on the pawl body portion 102 at an attachment area generally designated as 104. In the embodiment depicted in FIG. 90, an undercut or weakened area 45 is formed along at least a portion of the attachment area 104. The characteristics of the undercut or weakened area 45 may be sized such that the tooth 43 will shear off of the driving pawl 42' or otherwise assume a non-driving position when the firing load attains a predetermined maximum value to thereby prevent advancement of the actuation shaft 46—even though the manually actuatable handle member 24 continues to be actuated. In various embodiments, the predetermined maximum value may be selected so that the tooth 43 shears off or otherwise assumes a non-driving position before any other components would fail or otherwise become inoperable due to the resistance experienced by the drive beam due to jamming or other restriction.

Figure 91:
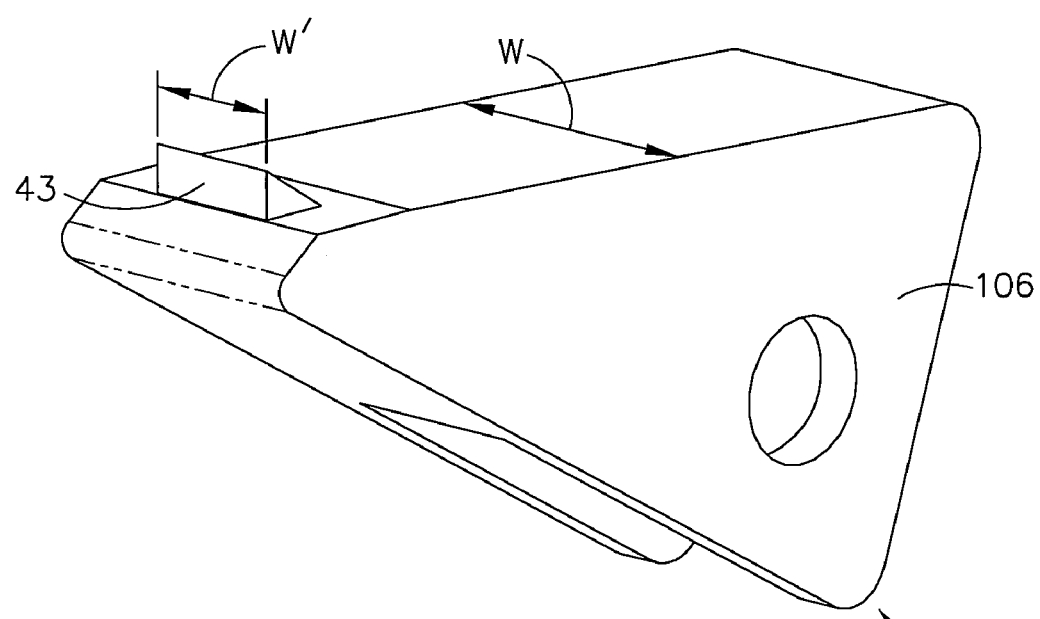
FIG. 91 is a perspective view of another pawl embodiment of various embodiments of the present invention.

Another pawl arrangement is depicted in FIG. 91. As can be seen in that Figure, the pawl 42" has a pawl body 106 a width "W" and the engagement tooth 43 has a width "W"' that is less than "W", such that the engagement tooth 43 will shear or otherwise fail when the firing load exceeds a predetermined magnitude to prevent the actuation shaft 46 from being further advanced—even though the manually actuatable handle member 24 continues to be actuated. In various embodiments, the pawls 42', 42" may be fabricated (molded, machined, etc.) from a single material. In other embodiments, the engagement tooth 43 may be formed separately from the pawl body 106 and may be attached thereto by a shear pin (not shown) or other means such as adhesive to support the engagement tooth 43 in a position for driving engagement with the actuation shaft 46 under normal loads, yet shear off to permit the tooth 43 to pivot to a non-engaged position when the firing load exceeds a predetermined magnitude.

Figure 92:
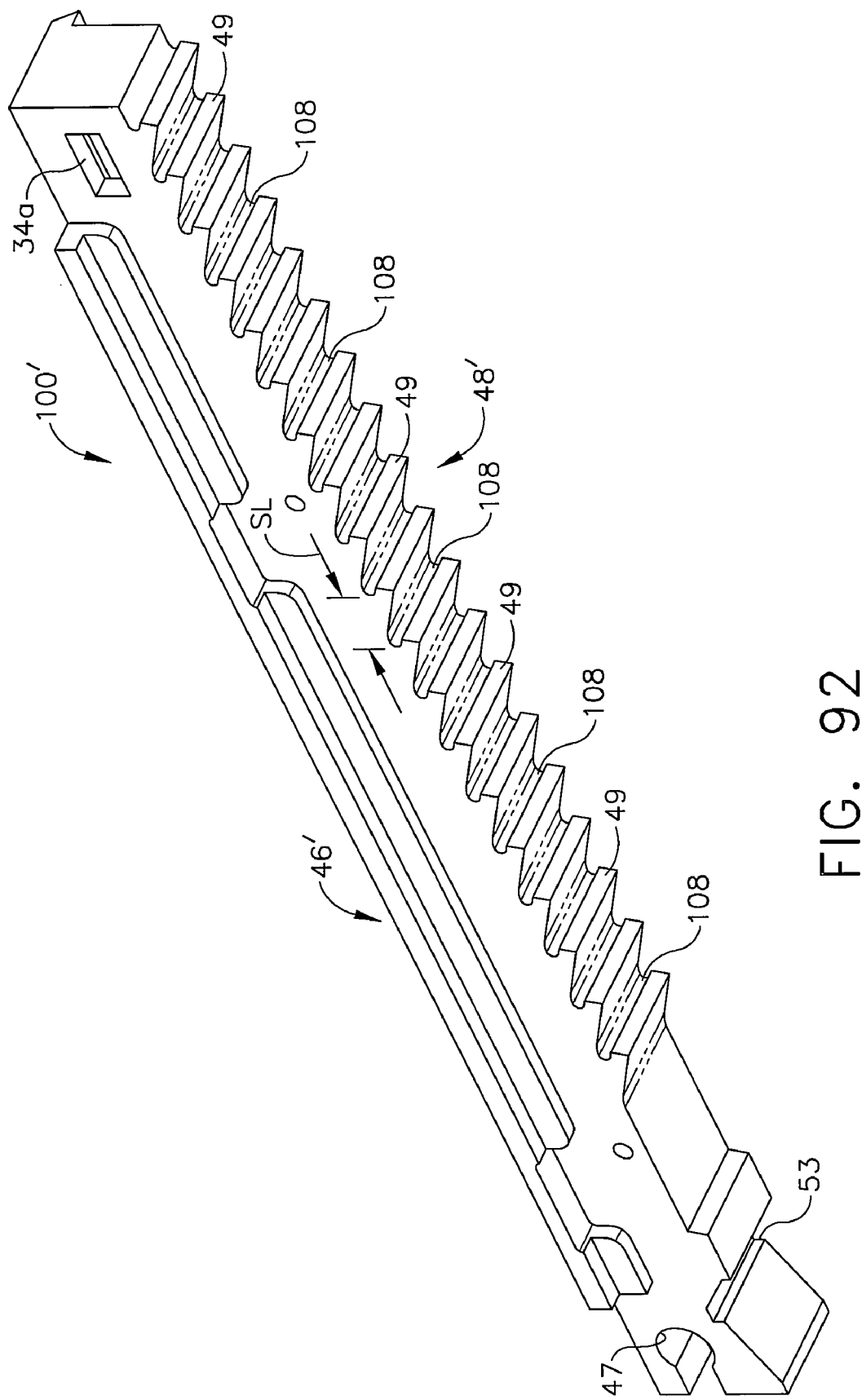
FIG. 92 is a bottom perspective view of an actuation shaft embodiment of various embodiments of the present invention.
Figure 93:
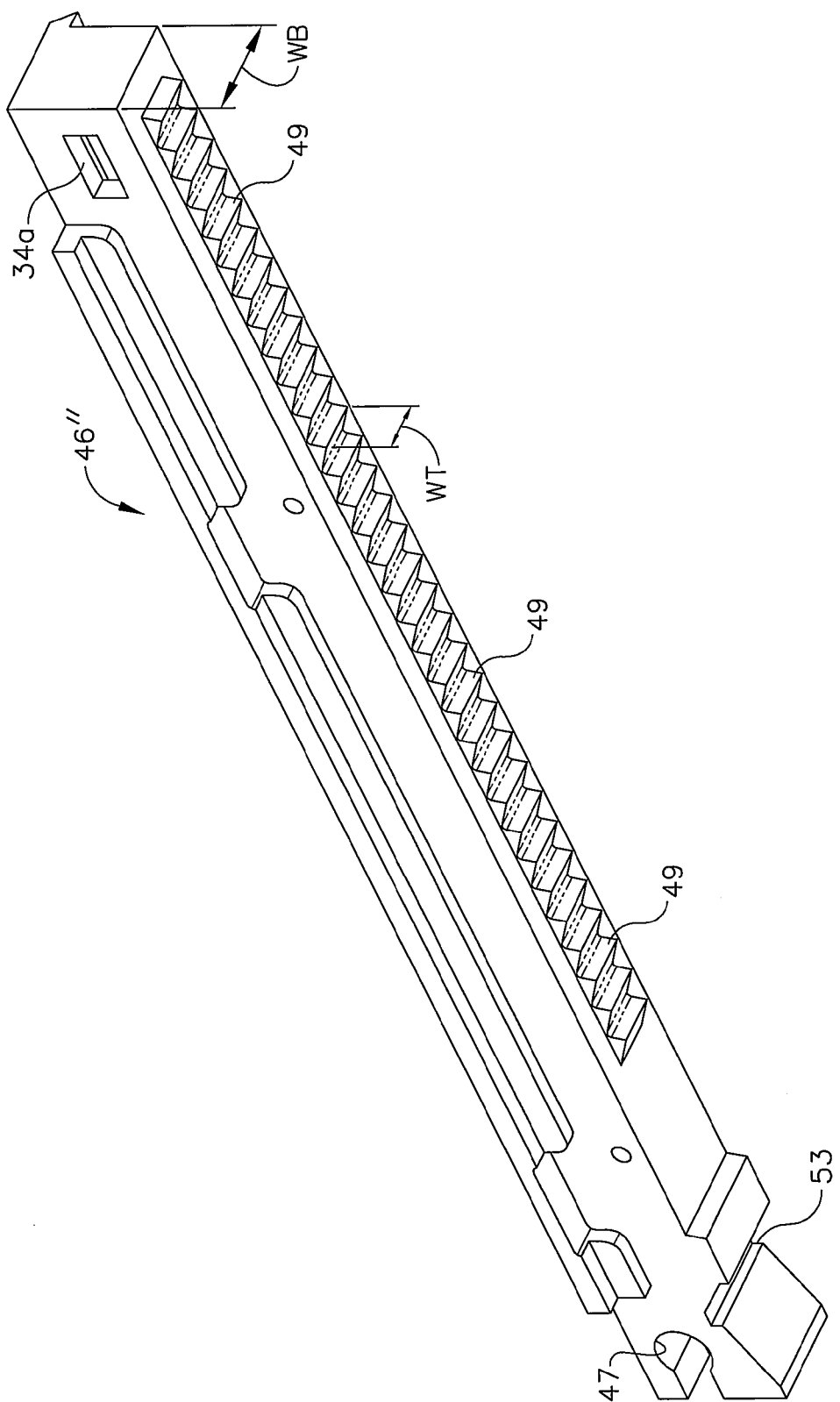
FIG. 93 is a bottom perspective view of another actuation shaft embodiment of various embodiments of the present invention.

FIG. 92 illustrates another actuation transfer assembly 100' that includes an actuation shaft 46' that is designed to fail when the firing load exceeds a predetermined magnitude. In this embodiment, an undercut area 108 is provided between adjacent teeth 49 and is sized to form a shear area length "SL" that will facilitate in the shearing of the tooth 49 or otherwise permit the tooth 49 to drivingly disengage from the tooth 43 or permit the tooth 43 on the pawl 42 to slip over the tooth 49 on the rack 48' when the firing load attains or exceeds the predetermined magnitude described above. In an alternative embodiment illustrated in FIG. 93, the actuation bar 46" has a width "WB" and each tooth 49 has a width "WT" that may be less than the width "WB". The width "WT" may be sized to enable the teeth 49 to shear off of the actuation shaft 46" or otherwise fail or drivingly disengage from the tooth 43 on the pawl 42 when the firing load attains or exceeds a predetermined magnitude as was discussed above. Further, the transfer assembly may be sized to buckle or flex under appropriate load so as to disengage the teeth from the pawl at a predetermined load. The teeth on the pawl and the rack in various embodiments may be designed at a very wide range of minimum failure loads depending upon the degree of safety desired. Such minimum failure loads may be attained by altering the geometry, design and/or materials from which the teeth, adhesive, shear pins, etc. are made.

Those of ordinary skill in the art will appreciate that the foregoing described actuation transfer assembly arrangements of the present invention represent vast improvements over prior surgical instruments that are adapted to actuate disposable reload units. In particular, such actuation transfer assemblies of the present invention will prevent the clinician from advancing the cutting and stapling components in the reload unit when the reload unit has encountered firing forces that might lead to the jamming and/or failure of the cutting and stapling components to advance completely through the tissue clamped in the unit. In prior units, the clinician might be unaware that the thickness of the tissue clamped in the unit was too great to complete the procedure and unwittingly continue to advance the cutting and stapling components in the unit by actuating the handle until the handle assembly exploded or otherwise failed destroying the ability to retract the knife. If the components become jammed, the clinician may be unable to retract the components and therefor have to cut the unit from the tissue. The various arrangements of the present invention described above, address such problems.

Figure 93A:
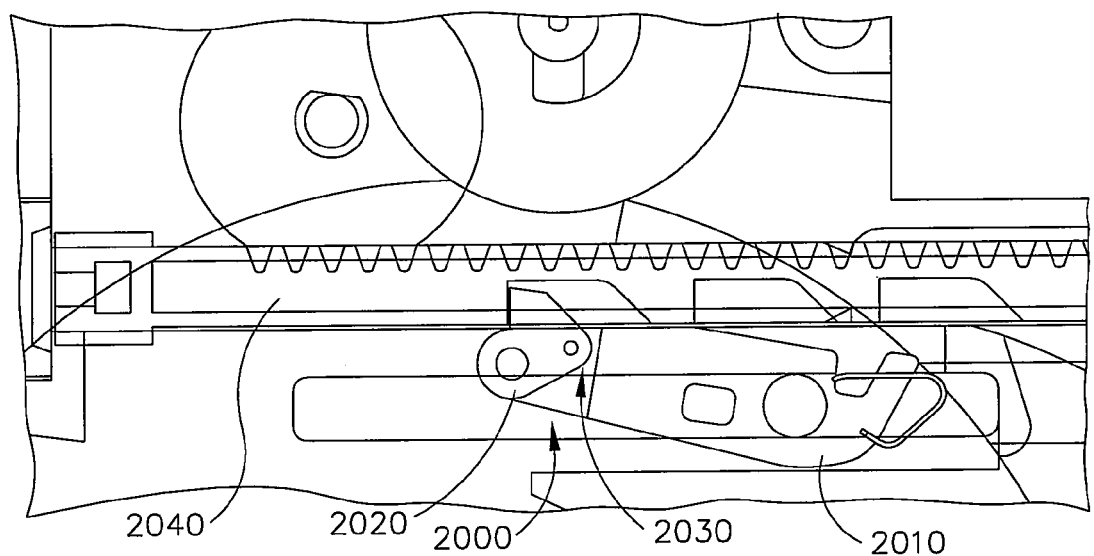
FIG. 93A is a side view of a portion of a firing system embodiment of the present invention used in connection with a surgical stapling instrument of the type disclosed in U.S. patent application Ser. No. 11/821,277 with the tooth in driving engagement with the firing member.
Figure 93B:
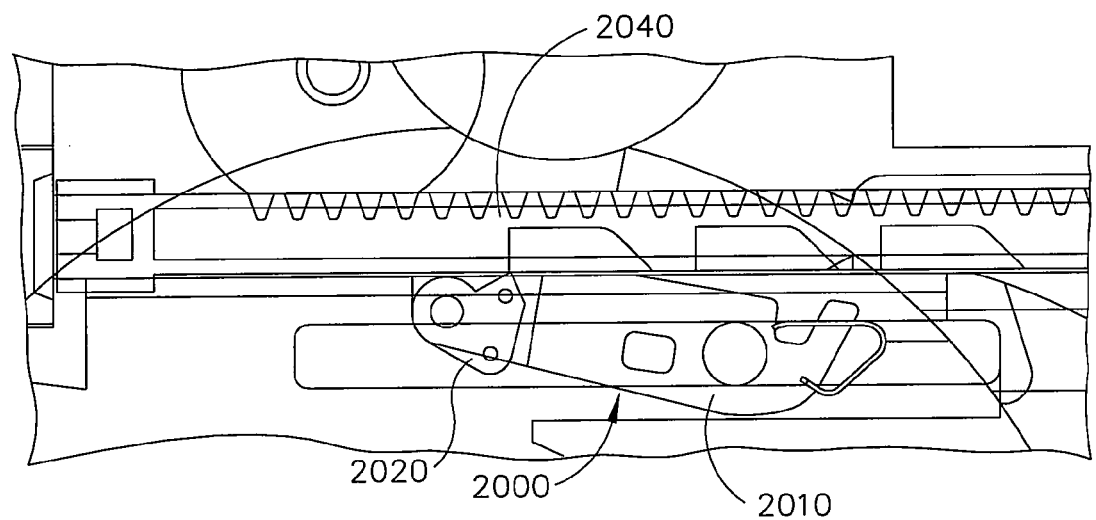
FIG. 93B is another side view of the firing system embodiment of FIG. 93A with the tooth in the disengaged position.

These unique and novel features may also be effectively employed with other surgical cutting and stapling apparatuses that use a driving pawl arrangement. For example, FIGS. 93A and 93B illustrate the use of a two part pawl arrangement 2000 that can be effectively employed with the surgical instruments disclosed in U.S. patent application Ser. No. 11/821,277, to Chad P. Boudreaux and Jeffrey S. Swayze, filed Jun. 22, 2007, entitled Surgical Stapling Instruments, the disclosure of which is herein incorporated by reference in its entirety. In particular, the two part pawl assembly 2000 may comprise a pawl body 2010 that may be configured and otherwise operated as described in the aforementioned patent application except that, in this embodiment, the tooth portion 2020 is pivotally or otherwise movably coupled to the pawl body 2010. The tooth portion 2020 may be normally supported in a driving orientation (FIG. 93A) by a shear pin 2030 or other suitable arrangement such as adhesive, etc. that is selected to shear or otherwise fail when the firing member 2040 thereof encounters a predetermined amount of firing load or resistance during firing. FIG. 93A illustrates the tooth 2020 in driving engagement with the firing member 2040. FIG. 93B illustrates the position after the firing member 2040 has encountered a resistance that exceeds the predetermined firing load which thereby caused the shear pin 2030 to shear off permitting the tooth 2020 to pivot to a non-engaged position. Thus, when in the non-engaged position, the firing member 2040 cannot be advanced distally even though the firing trigger continues to be actuated.

Figure 94:
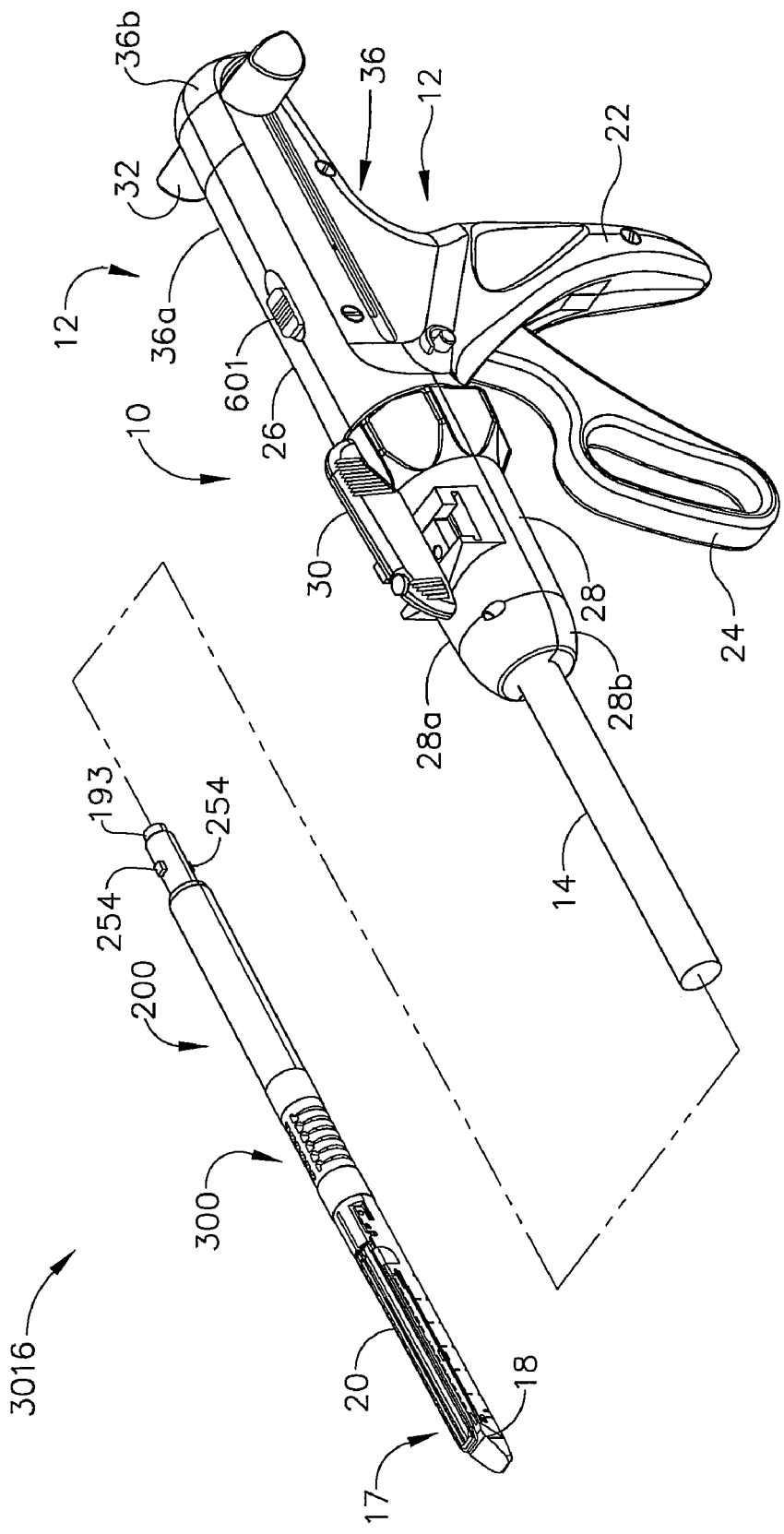
FIG. 94 is a perspective view of a surgical stapling apparatus and a disposable loading unit embodiment of the present invention.
Figure 95:
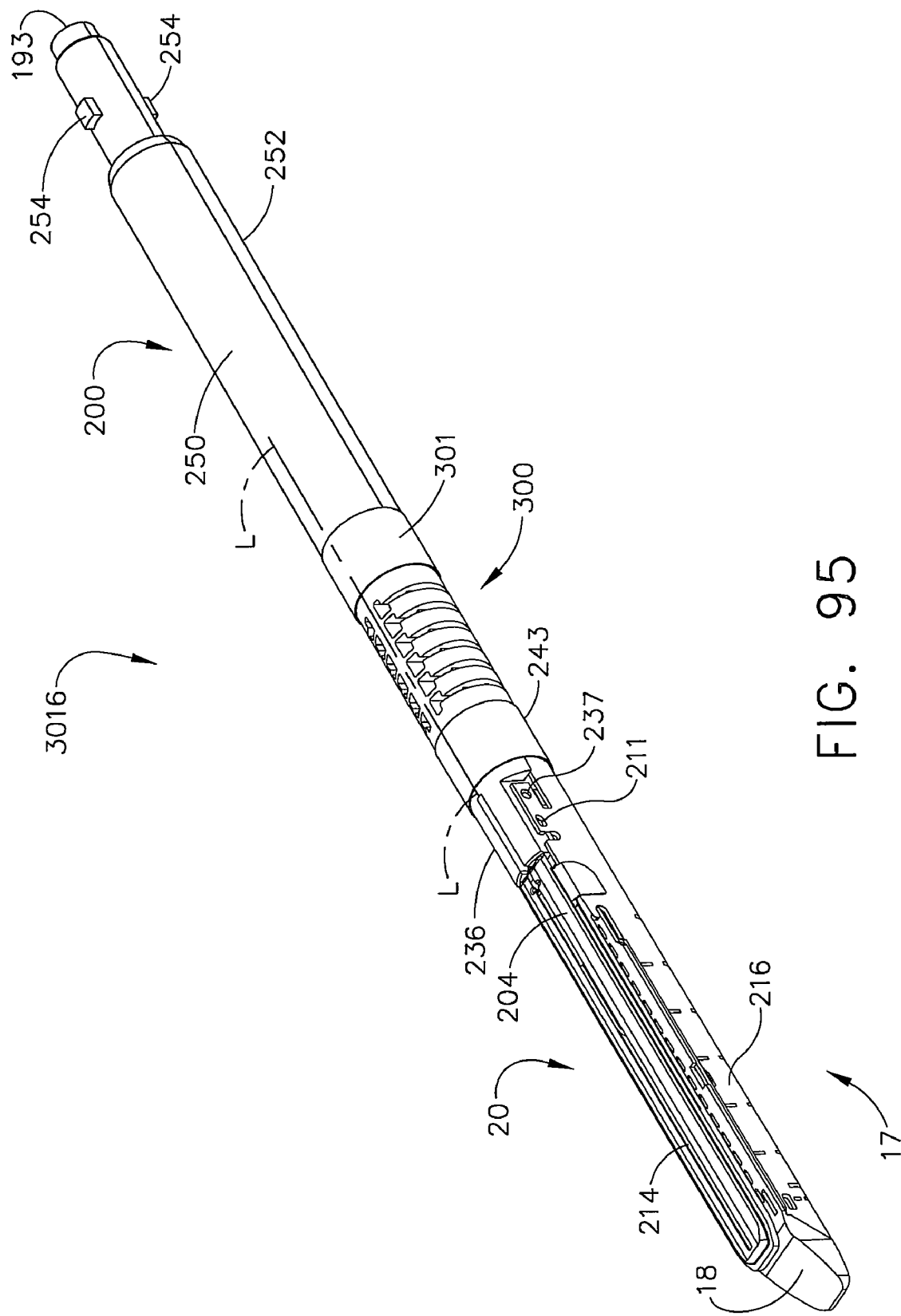
FIG. 95 is a perspective view of the disposable loading unit embodiment depicted in FIG. 94.
Figure 96:
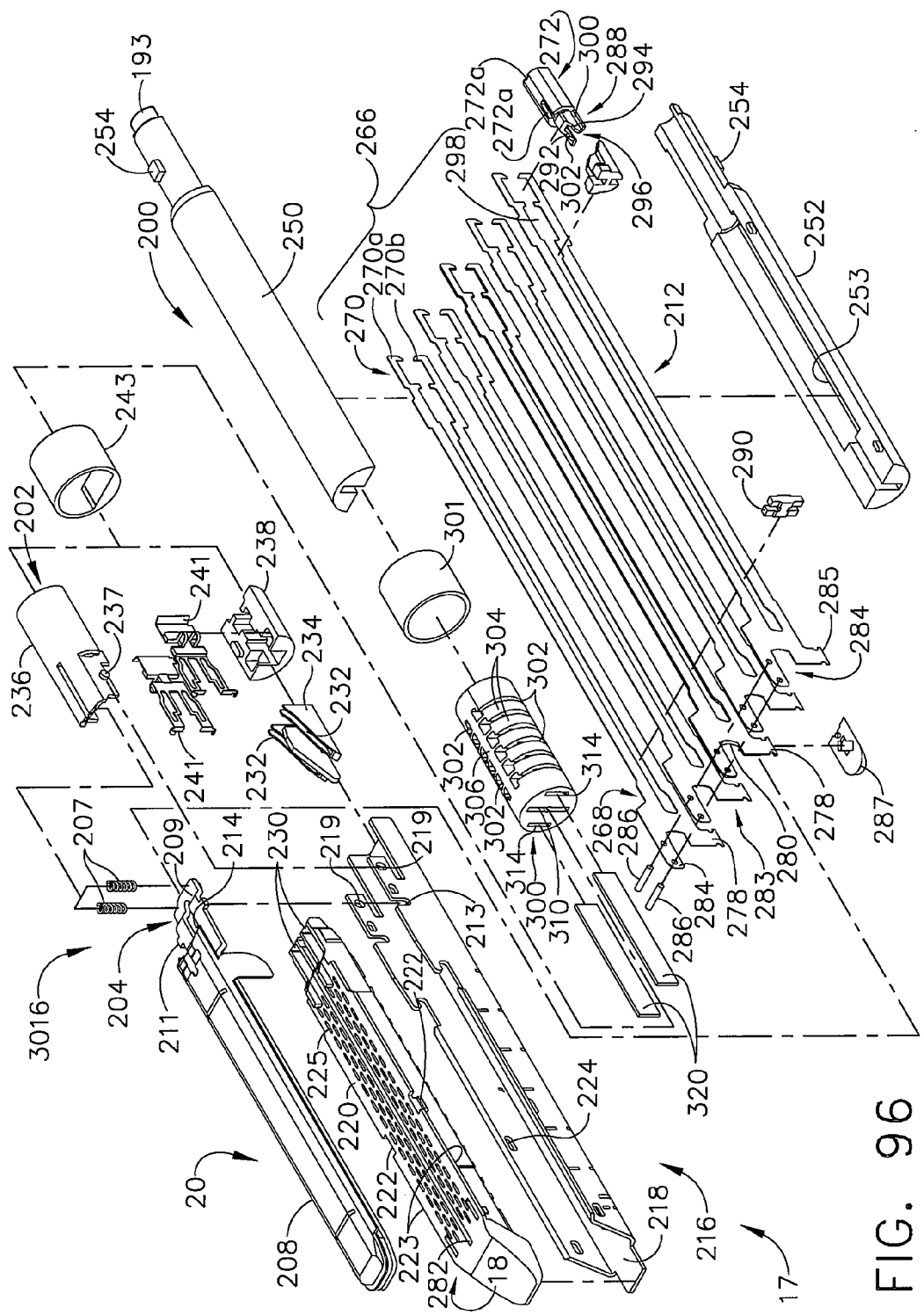
FIG. 96 is an exploded assembly view of the disposable loading unit embodiment of FIG. 95.

FIGS. 94-97 illustrate a unique and novel articulatable disposable reload unit 3016 that may be employed with the surgical stapling apparatus 10 or any of the other various surgical stapling apparatuses described herein above. Referring to FIG. 96, the disposable loading unit 3016 may include a tool assembly 17 that has an anvil assembly 20 and cartridge assembly 18. Anvil assembly 20 may include anvil portion 204 that may have a plurality of staple deforming concavities (not shown) formed in the undersurface thereof. A cover plate 208 may be secured to a top surface of anvil portion 204 to define a cavity therebetween. The cavity may be dimensioned to receive a distal end of an axial drive assembly 212. A longitudinal slot 214 extends through anvil portion 204 to facilitate passage of retention flange 284 of axial drive assembly 212 into the anvil cavity. A camming surface 209 formed on anvil portion 204 may be positioned to engage axial drive assembly 212 to facilitate clamping of tissue between the anvil assembly 20 and the cartridge 18. A pair of pivot members 211 formed on anvil portion 204 may be positioned within slots 213 formed in carrier 216 to guide the anvil portion 204 between the open and clamped positions.

In various embodiments, cartridge assembly 18 may include a carrier 216 which defines an elongated support channel 218. See FIG. 96. Elongated support channel 218 may be dimensioned and configured to receive a staple cartridge 220. Corresponding tabs 222 and slots 224 formed along staple cartridge 220 and elongated support channel 218 may function to retain staple cartridge 220 within support channel 218. A pair of support struts 223 may be formed on staple cartridge 220 such that they are positioned to rest on side walls of carrier 216 to further stabilize staple cartridge 220 within support channel 218.

Staple cartridge 220 may include retention slots 225 for receiving a plurality of fasteners and pushers as is known. A plurality of spaced apart longitudinal slots 230 extend through staple cartridge 220 to accommodate upstanding cam wedges 232 of an actuation sled 234. A central longitudinal slot 282 extends along the length of staple cartridge 220 to facilitate passage of a knife blade 280. During operation of surgical stapler 10, actuation sled 234 translates through longitudinal slots 230 of staple cartridge 220 to advance cam wedges 232 into sequential contact with pushers operably supported in the slots 225, to cause pushers (not shown) to translate vertically within slots 225 and urge the fasteners associated with the pushers (not shown) from slots 225 into the staple deforming cavities of the anvil assembly 20.

Various embodiments may include a mounting assembly 202 that may comprise upper and lower mounting portions 236 and 238. In one embodiment, the upper mounting portion 236 may be provided with a pair of trunnions 237 that are adapted to be pivotally received within holes 219 in the side walls of the carrier 216. A pair of anti-buckling springs 241 may be supported in corresponding cavities formed in the mounting assembly 202 to provide support to the laminated knife assembly within the mounting assembly 202. A proximal portion of mounting assembly 202 may be non-rotatably mounted in a distal body adapter 243 as shown in FIG. 96.

Housing portion 200 of disposable loading unit 3016 may include an upper housing half 250 and a lower housing half 252. The proximal end of housing half 250 may include engagement nubs 254 for releasably engaging elongated body 14 (FIG. 94) and an insertion tip 193. Nubs 254 form a bayonet type coupling with the distal end of body 14 as described in U.S. Pat. No. 5,865,361.

As can also be seen in FIG. 96, axial drive assembly 212 may include an elongated drive beam 266 including a distal working head 268 and a proximal engagement section 270. Drive beam 266 may be constructed from a single sheet of material or, preferably, from multiple stacked sheets. Engagement section 270 may include a pair of engagement fingers 270a and 270b which may be dimensioned and configured to mountingly engage a pair of corresponding retention slots 272a formed in drive member 272. Drive member 272 may include a proximal porthole (not shown) configured to receive the distal end 276 of control rod 52 (described above) when the proximal end of disposable loading unit 3016 is engaged with elongated body 14 of surgical stapling apparatus 10.

The distal end of drive beam 266 may be defined by a vertical support strut 278 which supports a knife blade 280, and an abutment surface 283 which engages the central portion of actuation sled 234 during a stapling procedure. Surface 285 at the base of surface 283 may be configured to receive a support member 287 slidably positioned along the bottom of the carrier 216. Knife blade 280 may be positioned to translate slightly behind actuation sled 234 through a central longitudinal slot 282 in staple cartridge 220 to form an incision between rows of stapled body tissue. To provide support to the drive beam 266 within the housing 200 as the drive beam 266 is advanced axially, a blade stabilizing member 290 may be mounted within the housing 200.

A retention flange 284 may project distally from vertical strut 278 and may support a pair of cylindrical cam rollers 286 at its distal end. Cam rollers 286 may comprise pressed in or welded in pins and be dimensioned and configured to engage camming surface 209 on anvil body 204 to clamp anvil portion 204 against body tissue. A pair of springs 207 may be provided between the proximal end of the anvil portion 204 and the upper mounting portion 236 to bias the anvil assembly 20 to a normally open position.

The reload unit 3016 depicted in FIGS. 94-97 employs a "passive" articulation arrangement. As can be seen in those FIGS., the reload unit 3016 includes a flexible articulation member 300 that is coupled to a housing assembly 200 by, for example, a proximal body collar 301. The flexible articulation member 300 has a body portion 301 that may be fabricated from polyethylene, poly propylene or other suitable materials, for example, and include a plurality of kerfs 302 separated by ribs 304. In various embodiments, the kerfs 302 and ribs 304 may be equally spaced along the flexible articulation member 300 thereby promoting a continuous bend radius when the flexible articulation member is articulated. A flexible articulation member 300 having multiple bend radii may be achieved by providing unequal spacing between the kerfs 302 and the ribs 304. For example, such arrangement may be achieved by spacing the ribs 304 more closely at one end and farther apart at the other end. As will be appreciated by those of ordinary skill in the art, increasing the spacing of the kerfs 302 and/or the ribs 304 reduces the bend radius of the section having increased spacing, more closely approximating a pivot point bend connection. Conversely spacing the kerfs 3402 and/or ribs 304 more closely results in a more gradual bend, having a larger bend radius. Alternatively, the flexible articulation member 300 may be fabricated from a combination of materials, the exterior of which may be slotted stainless steel, which will function in a similar manner to the above-mentioned plastics and polymeric materials.

In the embodiment illustrated in FIGS. 94-97, the kerfs 302 comprise annular grooves that extend at least partially around the perimeter of the flexible articulation member 300. The kerfs 302 preferably, however, comprise semi-annular grooves which are separated by a central longitudinal spine 306 passing down the longitudinal axis L-L of the flexible articulation member 300 such that a first plurality of ribs are formed on one lateral side of the spine 306 and a second plurality of ribs are formed on another lateral side of the spine 306. This spine 306 assists in providing stiffening to the flexible articulation member 300 and accommodates a slot 310 therethrough for receiving the surgical tools, such as the drive assembly 212. The longitudinal spine 306 may run the entire longitudinal length of the flexible articulation member 300. The flexible articulation member 300 may also include a pair of side slots 314 passing through each rib 304 on each lateral side for receiving a corresponding articulation plate 320. See FIG. 96. Such articulation plates 320 may be fabricated from a material that is relatively inelastic. That is, the plates 320 may be fabricated from a material that retains its position after bending. Articulation plates 320 may be fabricated from materials such as, for example, lead, copper, stainless steel, titanium, etc.

Figure 97:
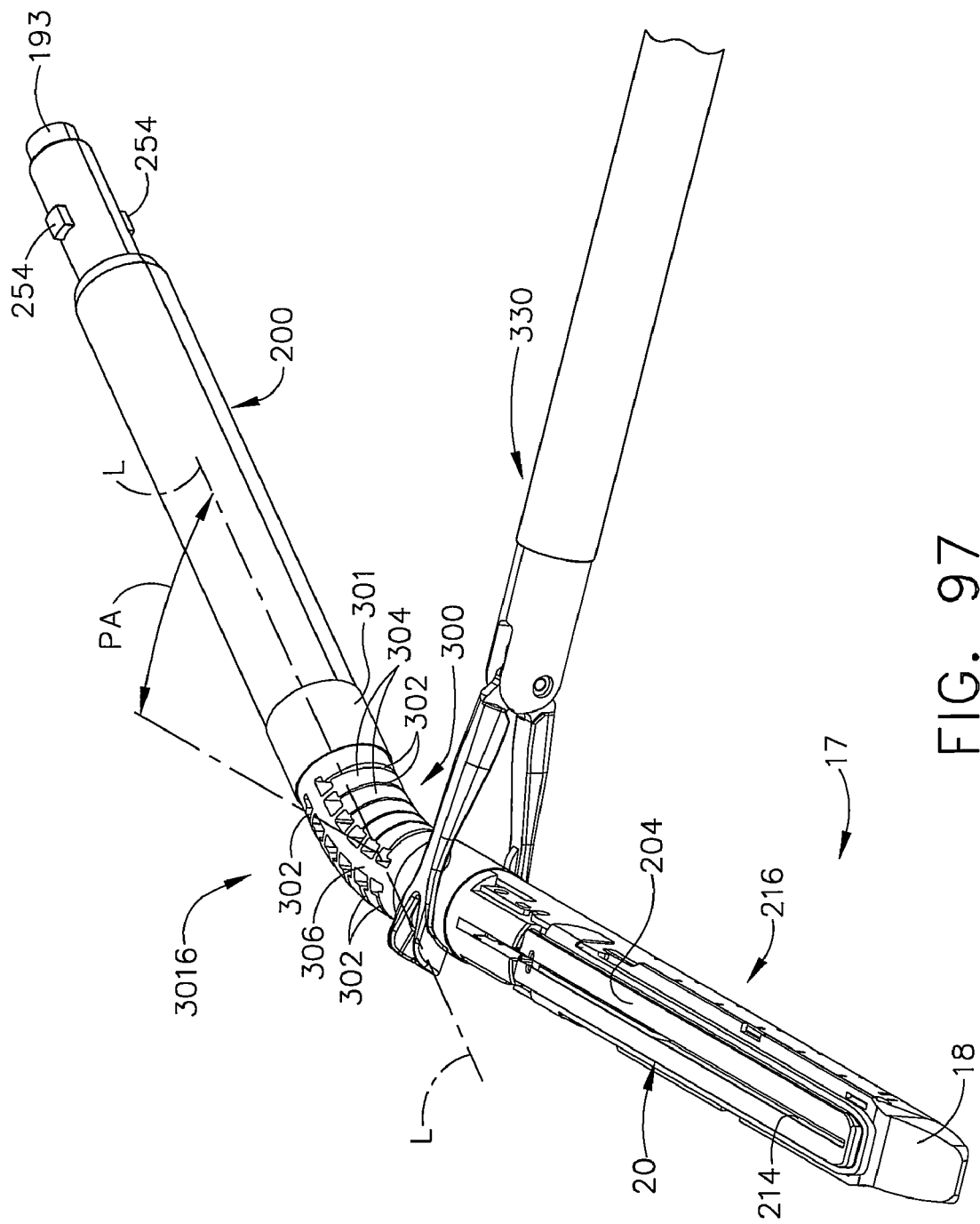
FIG. 97 is a perspective view of the disposable loading unit of FIGS. 95 and 96 being articulated with a pair of surgical graspers.

The disposable loading unit 3016 is sized for insertion, in a non-articulated state as depicted in FIGS. 94 and 95, through a trocar cannula passageway to a surgical site in a patient (not shown) for performing a surgical procedure. For example, the disposable loading unit 3016 may be sized to be inserted through a gastroscope or colonoscope. After the tool assembly 17 portion of the disposable loading unit 3016 has been inserted through the trocar cannula passageway, the clinician can move the tool assembly 17 to a desired articulated orientation by "passively" bringing the tool assembly 17 into contact with the organ or other portion of the body or another medical instrument 330 (e.g., graspers—FIG. 97) to apply an external force to the tool assembly 17 to cause it to articulate within a plane relative to the housing portion 200 of the disposable loading unit 3016. The person of ordinary skill in the art will appreciate once the tool assembly 17 is articulated to the desired position, the articulation plates 320 serve to retain the tool assembly 17 in that configuration. The tool assembly 17 can be articulated through an angle "PA" as illustrated in FIG. 97.

Figure 98:
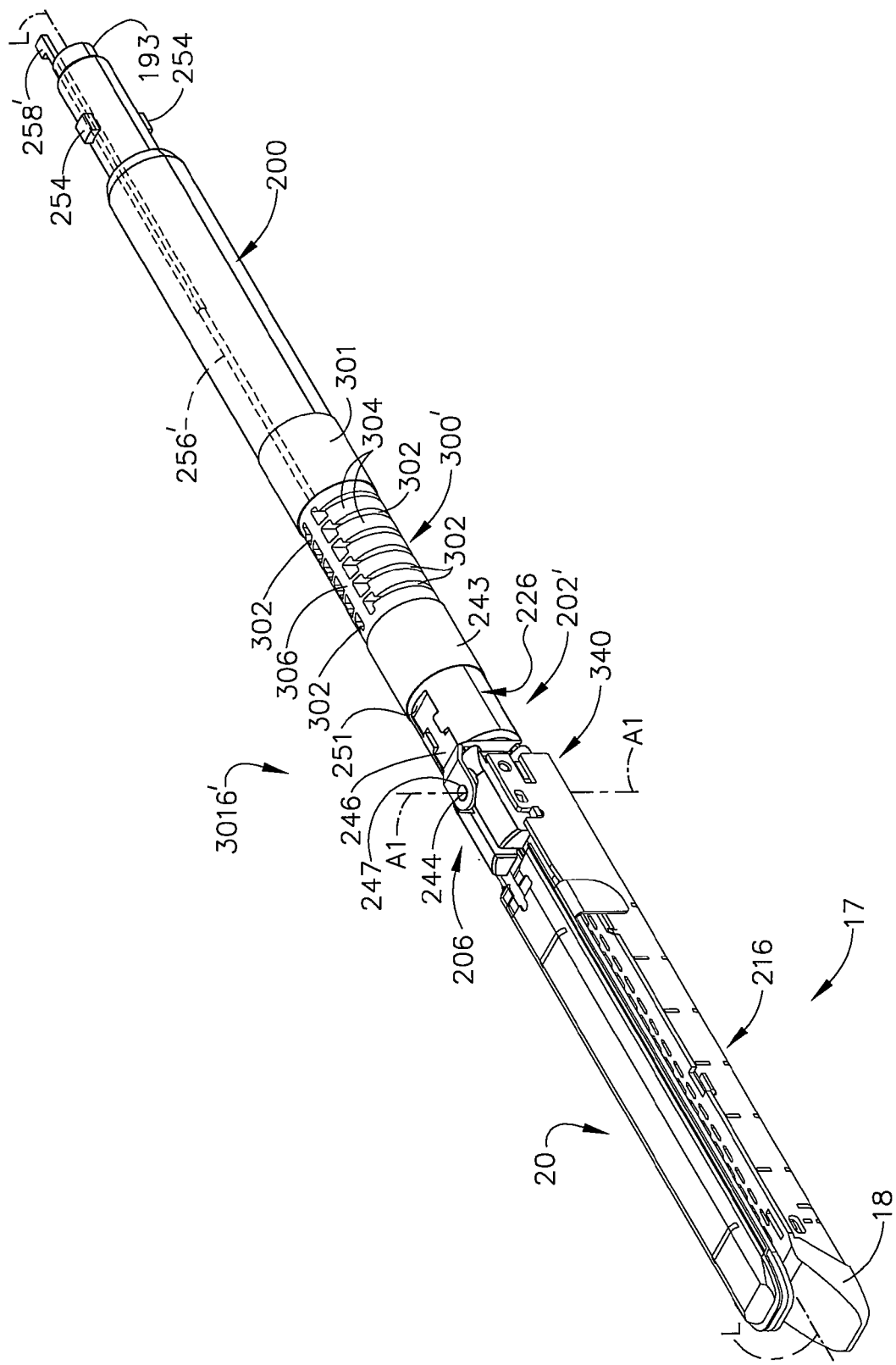
FIG. 98 is a perspective view of another disposable loading unit embodiment of the present invention.
Figure 99:
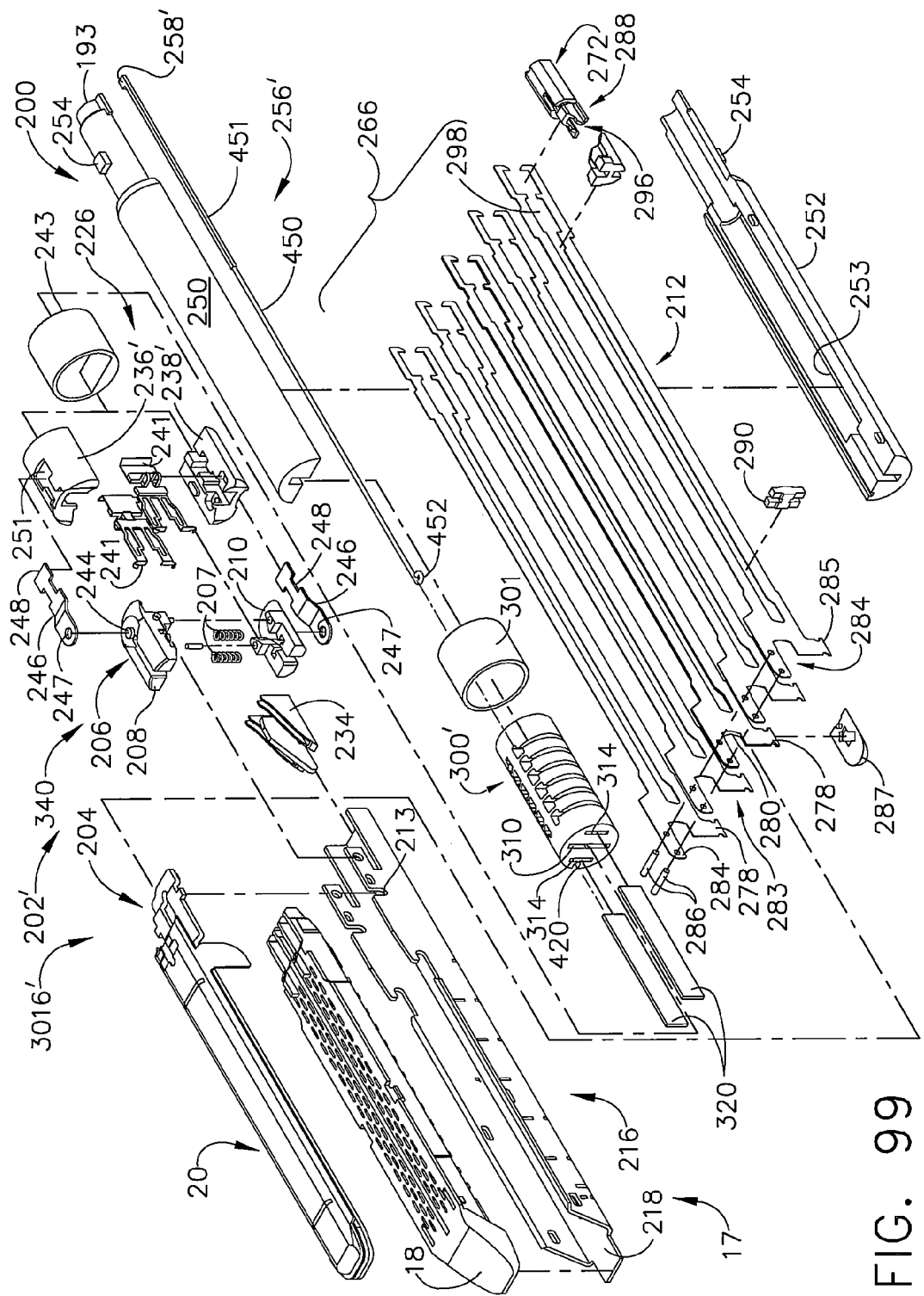
FIG. 99 is an exploded assembly view of the disposable loading unit embodiment of FIG. 98.
Figure 100:
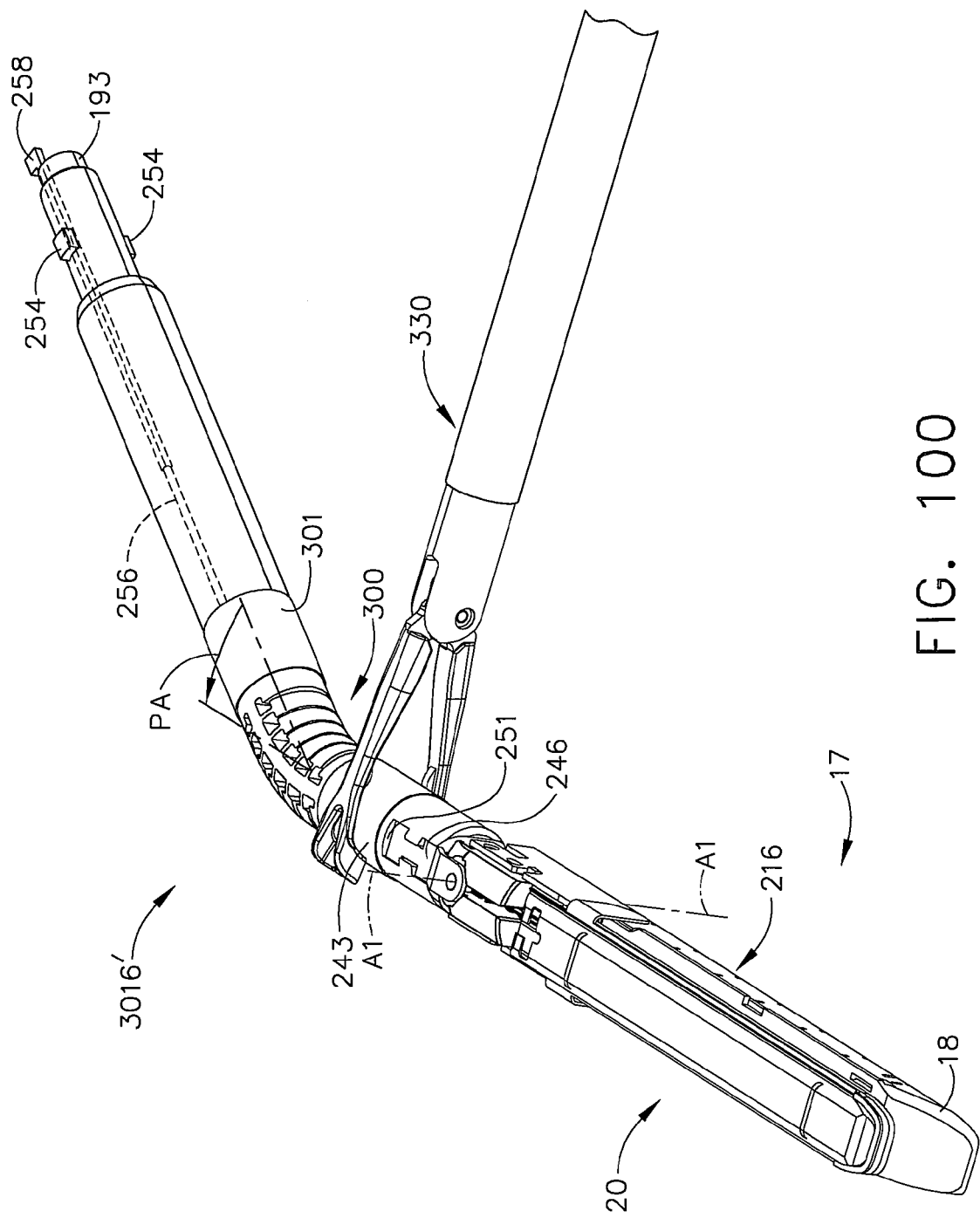
FIG. 100 is a perspective view of the disposable loading unit of FIGS. 98 and 99 being articulated with a pair of surgical graspers.

FIGS. 98-101 illustrate another reload unit 3016' embodiment of the present invention. Reload unit 3016' is substantially identical to reload unit 16, except that reload unit 3016' is constructed to be passively articulated as well as actively articulated. As can be seen in FIGS. 98 and 99, the reload unit 3016' includes a first articulation joint 340 that is formed from a mounting assembly 202' that includes a distal portion 206 and a proximal portion 226 that is pivotally coupled thereto. In various embodiments, the distal portion 206 includes an upper mounting portion 208 and a lower mounting portion 210. A pivot pin 244 may be formed on each of the mounting portions 206', 208' to define a pivot axis "A1" which may be substantially perpendicular to the longitudinal axis "L'L' of the disposable reload unit 3016'. The proximal portion 226 of the mounting assembly 202' may comprise an upper mounting portion 236' and a lower mounting portion 238'. The distal portion 206 of the mounting member 202' and the proximal portion 226 of the mounting member 202' may be pivotally coupled together by a pair of coupling members 246. Coupling members 246 each have a hole 247 therethrough for receiving a corresponding pin 244 therethrough. The proximal end 248 of each coupling member 246 is configured to be interlockingly received in a corresponding groove 251 formed in the upper mounting portion 236' and lower mounting portion 238'. The proximal portion 226 of mounting assembly 202' may be non-rotatably mounted in a distal body adapter 243 as shown in FIG. 99. Housing portion 200 of disposable loading unit 3016' may include an upper housing half 250 and a lower housing half 252. The proximal end of housing half 250 may include engagement nubs 254 for releasably engaging elongated body 14 (not shown in FIG. 99) and an insertion tip 193. Nubs 254 form a bayonet type coupling with the distal end of body 14 which will be discussed in further detail below. Housing halves 250 and 252 define a channel 253 for slidably receiving axial drive assembly 212 therein. A pair of springs 207 may be provided between the proximal end of the anvil portion 204 and the upper mounting portion to bias the anvil assembly 20 to a normally open position.

This embodiment may also employ a flexible articulation member 300' that may be substantially similar to the flexible articulation member 300 described above, except for the differences noted below. The distal end of the flexible articulation member 300' may be non-rotatably affixed to the distal body adapter 243 and the proximal end of the flexible articulation member 300' may be non-rotatably affixed to the proximal body collar 301 that is attached to the housing portion 200. In this embodiment, an articulation link 256' may be employed to also enable the user to actively articulate the tool assembly 17. Articulation link 256' may have an elongated flexible wire portion 450 that terminates in a distal hook portion 452. The wire portion 450 may be received in a lumen 420 in the flexible articulation member 300'. The hooked end 452 may be pinned between distal portion 206 and lower mounting portion 210 by a pin affixed therebetween. See FIG. 99. The flexible wire portion 450 may be attached to a rod portion 451 that has a tab or other hook portion 258' that is configured for hooking engagement with a distal hook 165 formed on the distal end of the first articulation link 123 in a known manner as described in U.S. Pat. No. 5,865,361. See FIG. 10. Such reload unit 3016' arrangement may be passively articulated using flexible articulation member 300' about angle "PA" in the manner described above through a range of travel "PA" or, if desired, the clinician may actively articulate the tool assembly 17 thereof about the first articulation axis "A1-A1" through a range of travel "AA" by activating the articulation lever 30 in the manner described in U.S. Pat. No. 5,865,361. See FIG. 101.

Figure 102:
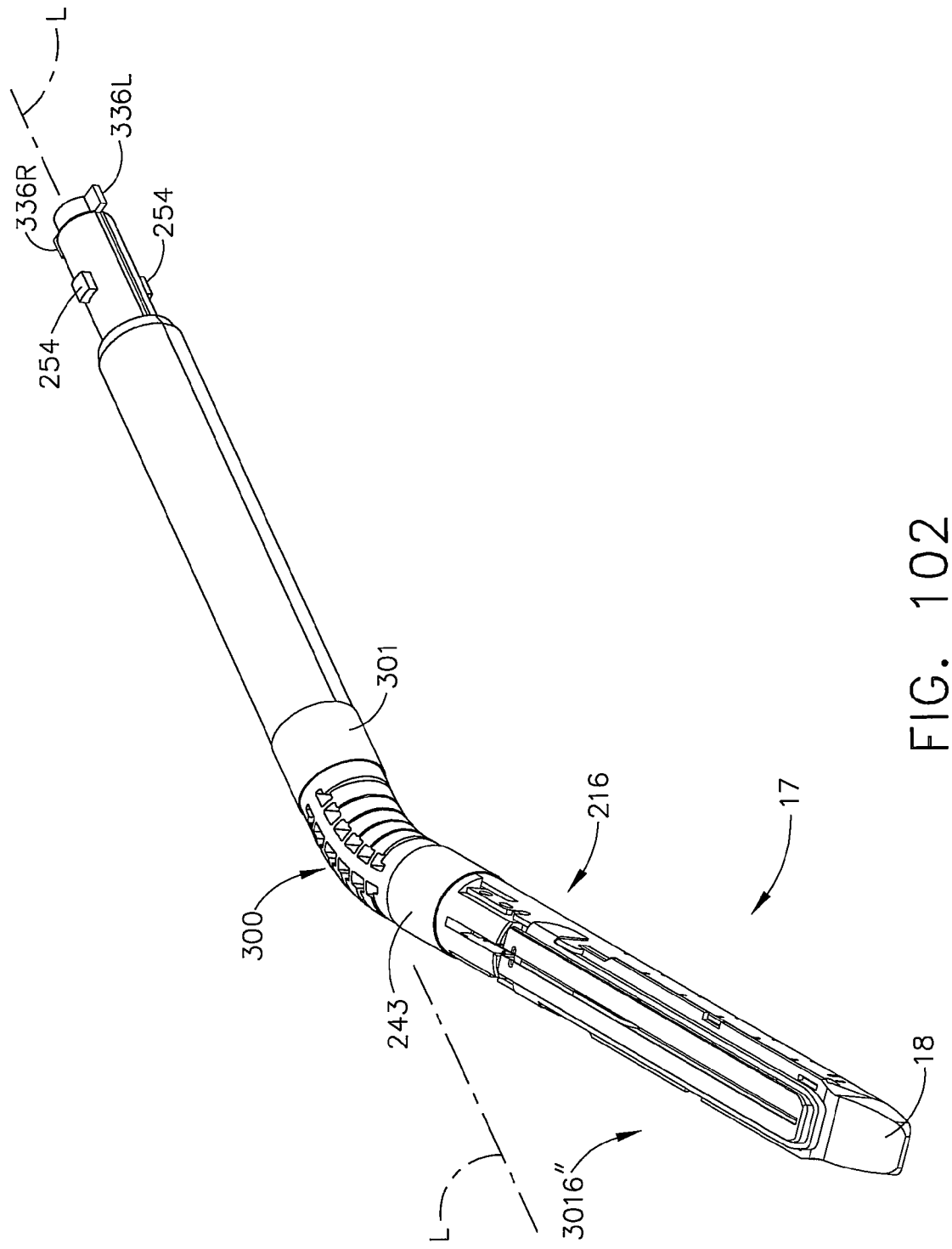
FIG. 102 is a perspective view of another disposable loading unit embodiment of the present invention.
Figure 103:
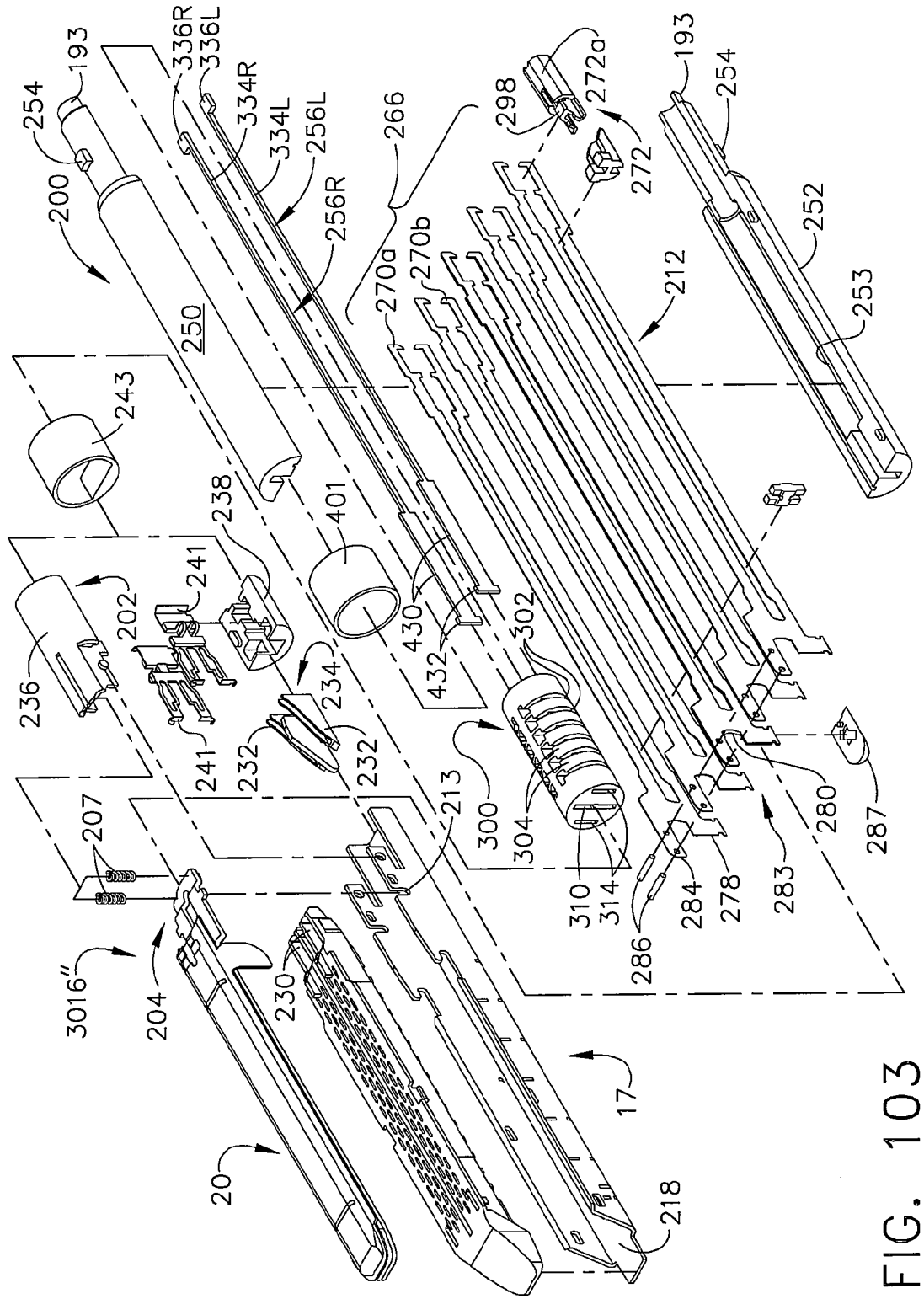
FIG. 103 is an exploded assembly view of the disposable loading unit embodiment of FIG. 102.
Figure 104:
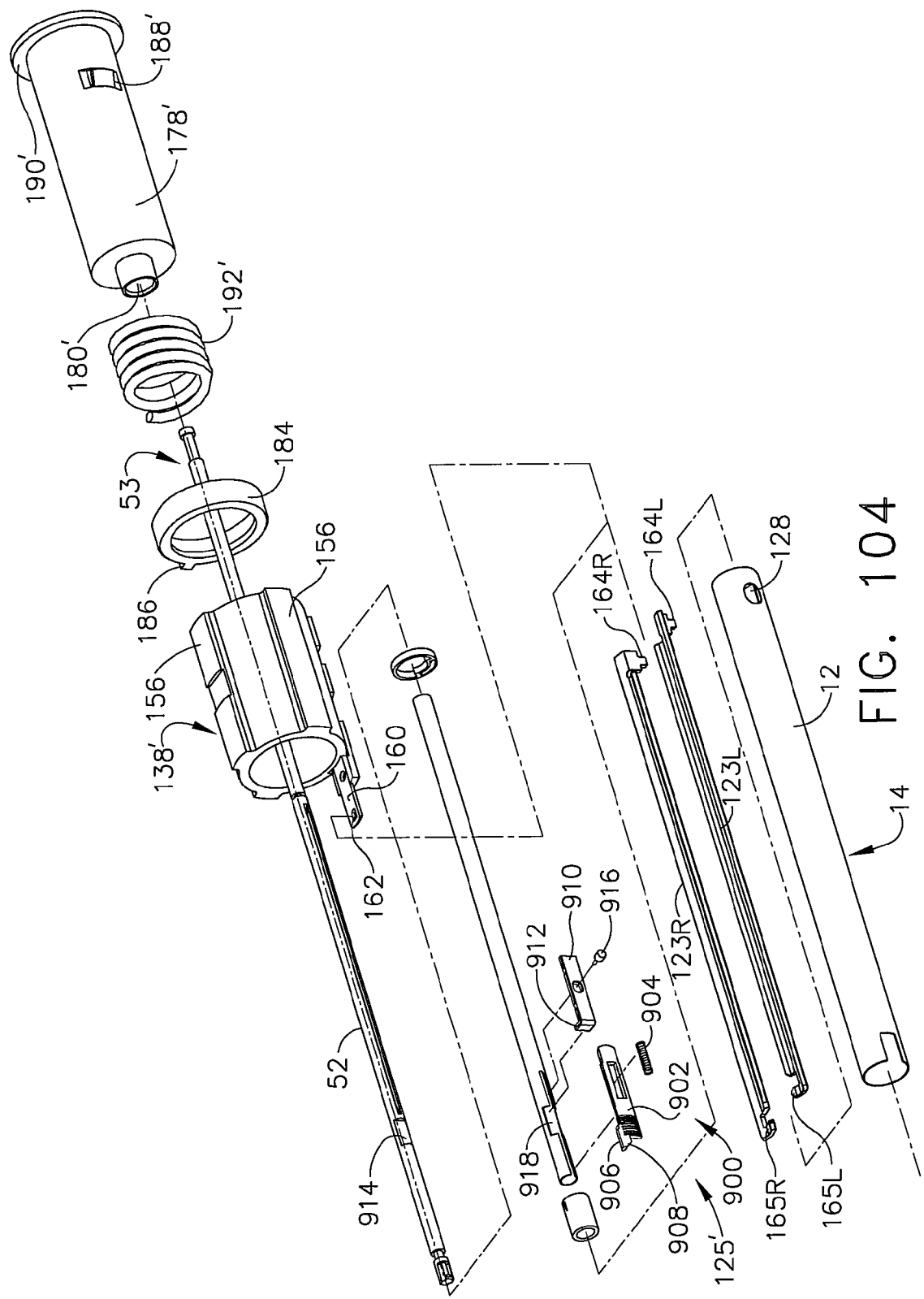
FIG. 104 is an exploded assembly view of another disposable loading unit sensing mechanism and control rod assembly embodiment of various embodiments of the present invention.

FIGS. 102-104 illustrate another reload unit 3016" embodiment of the present invention. Reload unit 3016" may be substantially identical to reload unit 3016', except that reload unit 3016" is constructed with two active articulation links 256R, 256L that enables the articulation link 300 to be actively pulled on one side while being actively pushed on the opposite side. As can be seen in FIG. 103 articulation links 256R and 256L may have a distal plate portion 430 that is sized to extend through a corresponding side slot 314 in the articulation member 300. A thrust attachment feature 432 may be formed on the distal end of each distal plate portion 430 to retain the distal plate portion 430 within its respective side slot 314. In alternative embodiments, the thrust feature may be molded into the articulation member 300 or other attachment arrangements may be used. Articulation link 256R, 256L may further have an elongated extension portion 334R, 334L that terminates in a hook portion 336R, 336L, respectively. In various embodiments, the articulation links 256R, 256L may be fabricated from metal or a series of laminated or stacked plates.

Figure 101:
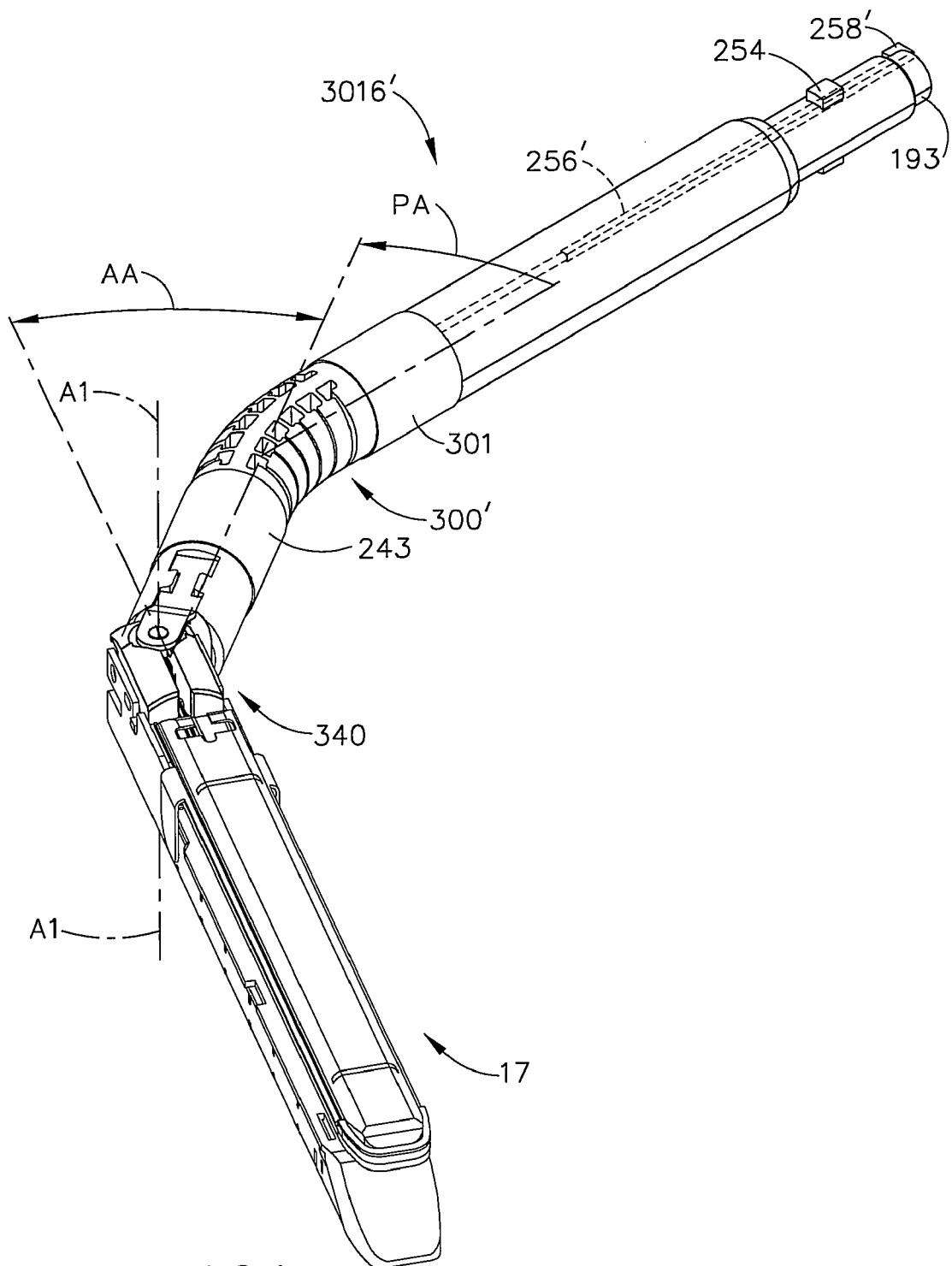

Referring to FIG. 104, there is shown a control rod assembly 125' that may be substantially similar to control rod assembly 125 described above, except that control rod assembly 125' includes a right articulation link 123R and a left articulation link 123L. The right articulation link 123R may have a distal hook 165R formed thereon for detachable engagement with the hook portion 336R of the articulation link 256R in the disposable loading unit 3016". See FIG. 103. Likewise, the left articulation link 123L may have a distal hook portion 165L formed thereon for detachable engagement with the hook portion 336L of the articulation link 256L in the disposable loading unit 3016". The right articulation link 123R may further have a finger 164R protruding from its proximal end, and the left articulation link 123L may have a finger 164L protruding from its proximal end. Although not specifically illustrated in FIG. 103, a linkage bar, gear train, etc. may be employed to movably couple the fingers 164R, 164L to the arm 160 attached to the translation member 138' such that as the translation member 138' is axially advanced in the distal "DD" direction as described in detail above, the right articulation links 123R and 256R are advanced in the distal direction "DD" and the left articulation links 123L and 256L are pulled in the proximal direction "PD" to thereby cause the tool assembly 17 to pivot about the first articulation axis "A1-A1" to the right of the longitudinal axis L-L as illustrated in FIG. 101 or visa-versa. Likewise, in various embodiments, when the translation member 138' is advanced in the proximal direction "PD", the right articulation links 123R and 256R are pulled in the proximal direction "PD" and the left articulation links 123L and 256L are advanced in the distal direction "DD" to thereby cause the tool assembly 17 to pivot to the left of the longitudinal axis L-L or visa-versa. Those of ordinary skill in the art will understand that such "pushing" and "pulling" action results in less stresses being applied to a single articulation link than those prior articulation arrangements that only employ a single articulation link. The flexible articulation member 300' may require more force to bend or flex as opposed to the pivot pin arrangement like in 206.

Figure 105:
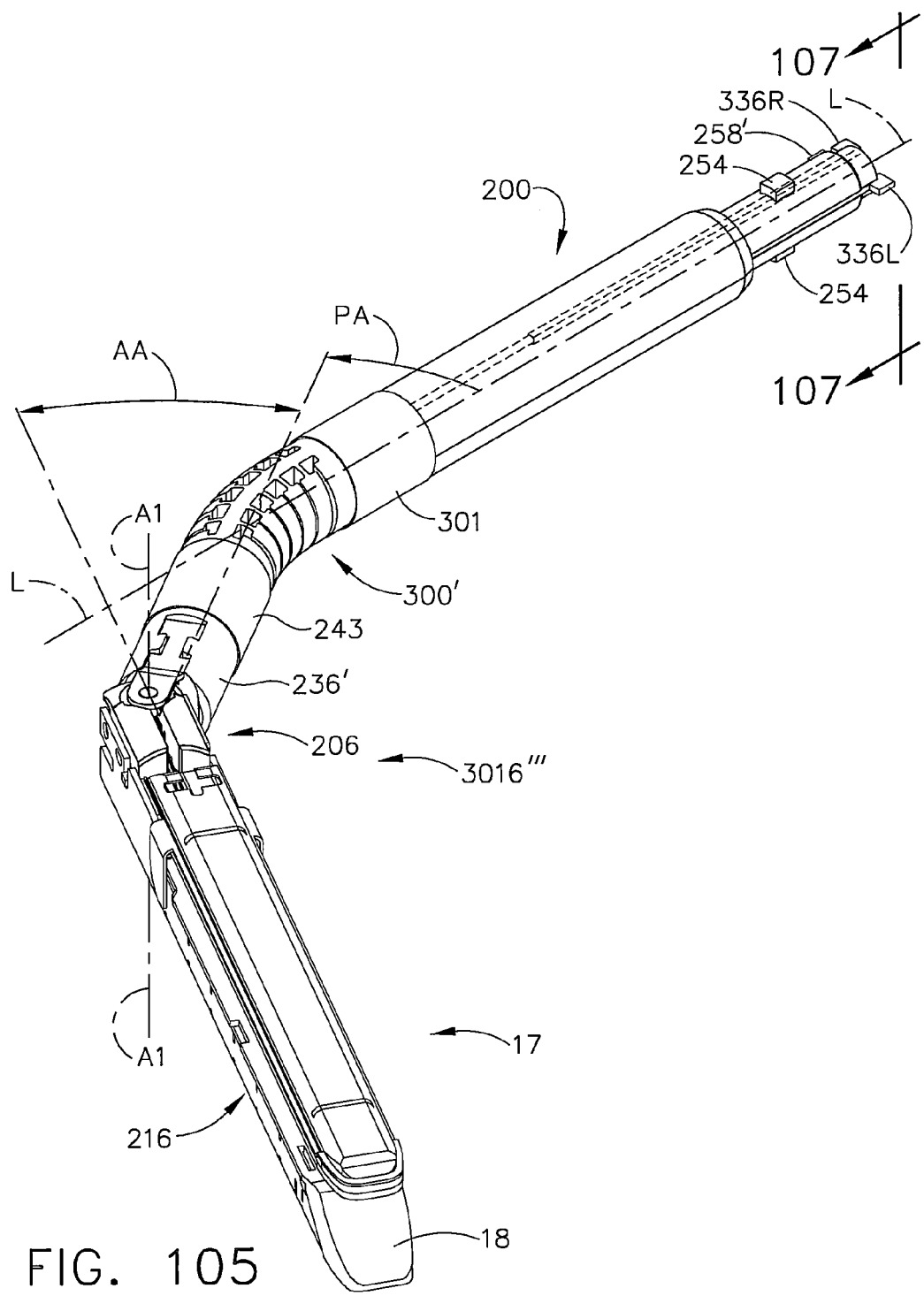
FIG. 105 is a perspective view of another disposable loading unit embodiment of the present invention illustrating passive articulation travel and active articulation travel thereof.
Figure 106:
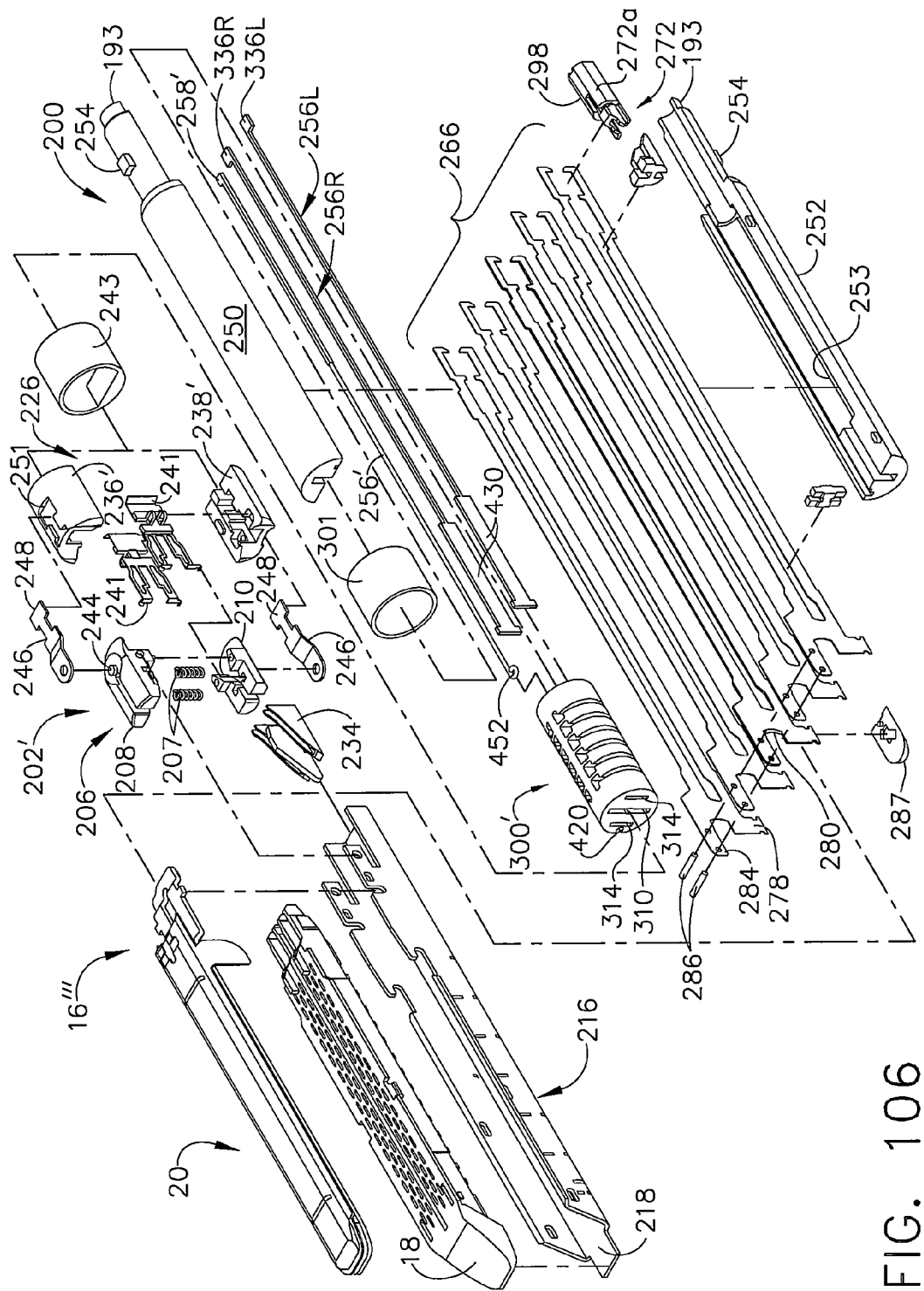
FIG. 106 is an exploded assembly view of the disposable loading unit of FIG. 105.
Figure 107:
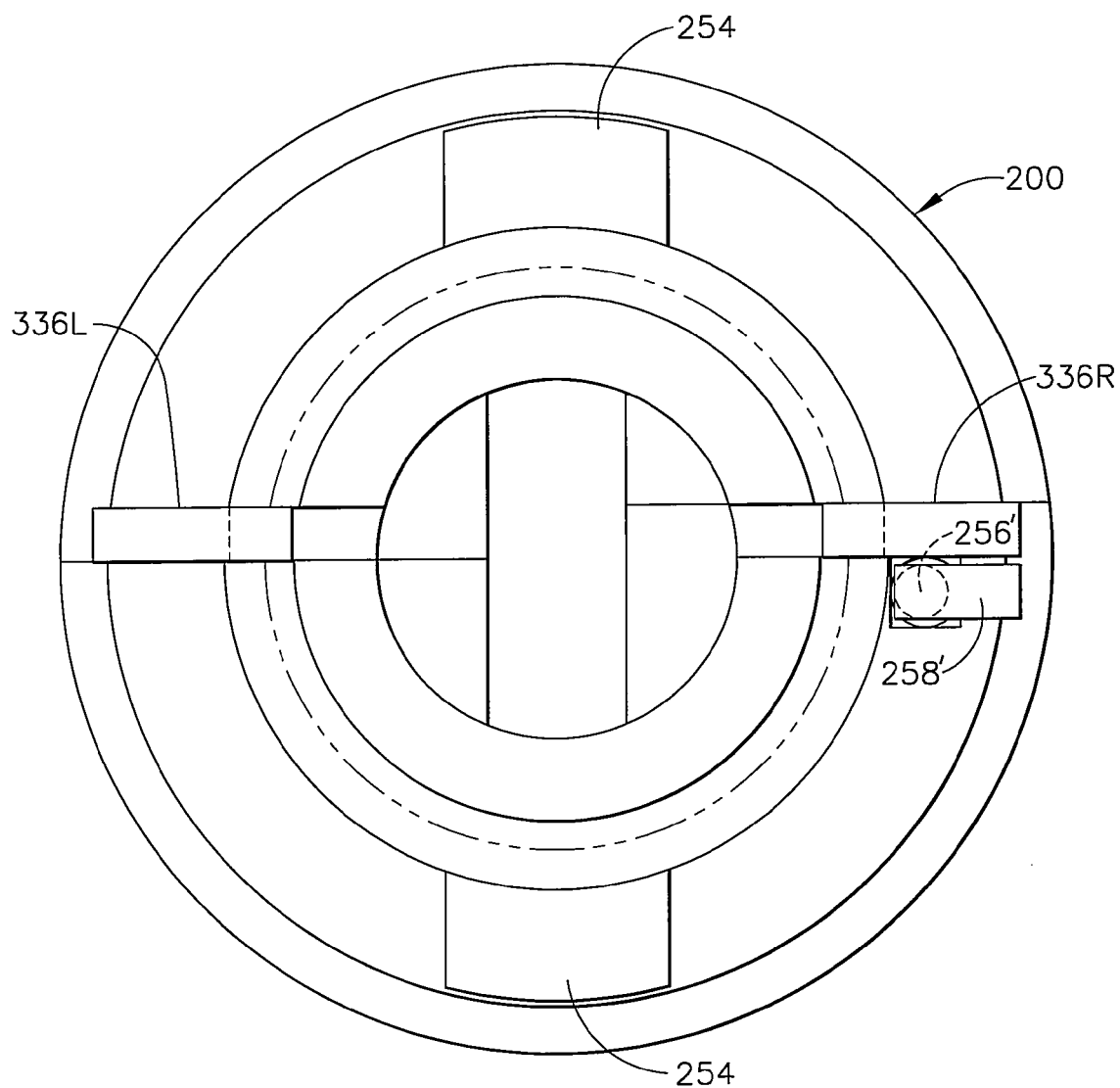
FIG. 107 is a proximal end view of the disposable loading unit of FIGS. 105 and 106 taken in the direction represented by arrows 107-107 in FIG. 105.

FIGS. 105-107 illustrate another reload unit 3016'" embodiment of the present invention. Reload unit 3016'" is essentially a combination of reload units 3016 and 3016' in that reload unit 3016'" employs the articulation link 256' and the articulation links 256R and 256L that enables the articulation link 300' to be passively articulated through a range of travel "PA" and actively articulated through an additional range of travel "AA".

Figure 108:
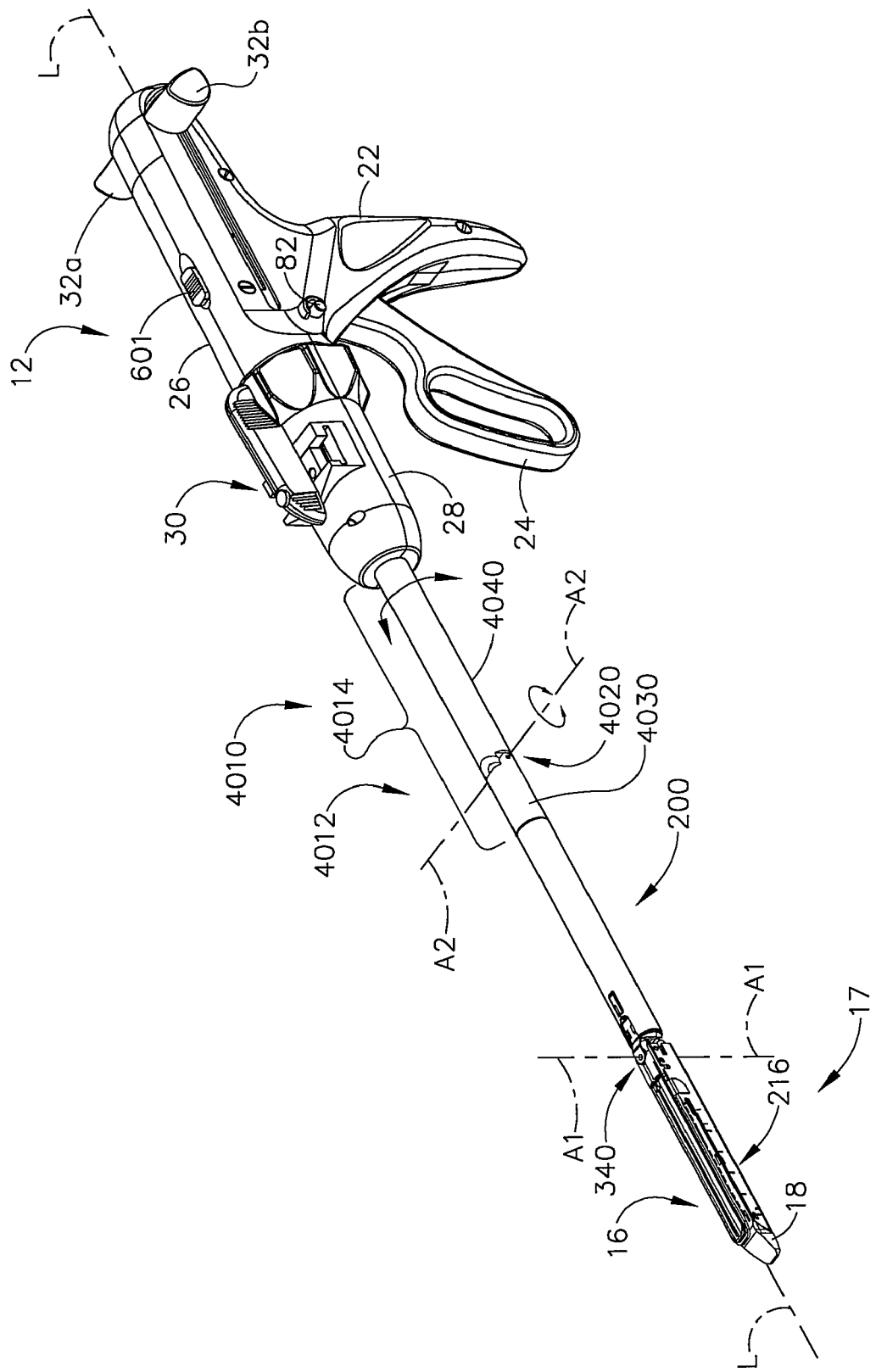
FIG. 108 is a perspective view of another surgical stapling apparatus embodiment of the present invention.

FIGS. 108-111 illustrate another surgical stapling apparatus 4010 of the present invention that is constructed for use with a disposable loading unit. FIG. 108 depicts a disposable loading unit 16 that has a first articulation joint 340 of the type and construction described above that enables the tool assembly 17 to pivot about a first pivot axis A1-A1 relative to the disposable loading unit housing 200 that is attached to the surgical stapling apparatus 4010. The surgical stapling apparatus 4010 may have aspects and components that are substantially similar to the aspects and components of the various stapling apparatus embodiments described above, except for the unique and novel articulation system 4012, various configurations of which, will be described in detail below. Those components that are the same as the components employed in the above-mentioned surgical stapling apparatus embodiments will be labeled with the same element numbers and those of ordinary skill in the art can refer to the disclosure set forth hereinabove that explains their construction and operation. As can be seen in FIG. 108, the articulation system 4012 may include an intermediate articulation joint 4020 that is situated in the elongated body assembly 4014 between the disposable loading unit 16 and the handle assembly 12 such that the disposable loading unit 16 may be selectively pivoted relative to the handle assembly 12 about a second articulation axis A2-A2. As illustrated in FIG. 108, the second articulation axis A2-A2 is substantially transverse to the longitudinal axis L-L and the first articulation axis A1-A1.

Figure 109:
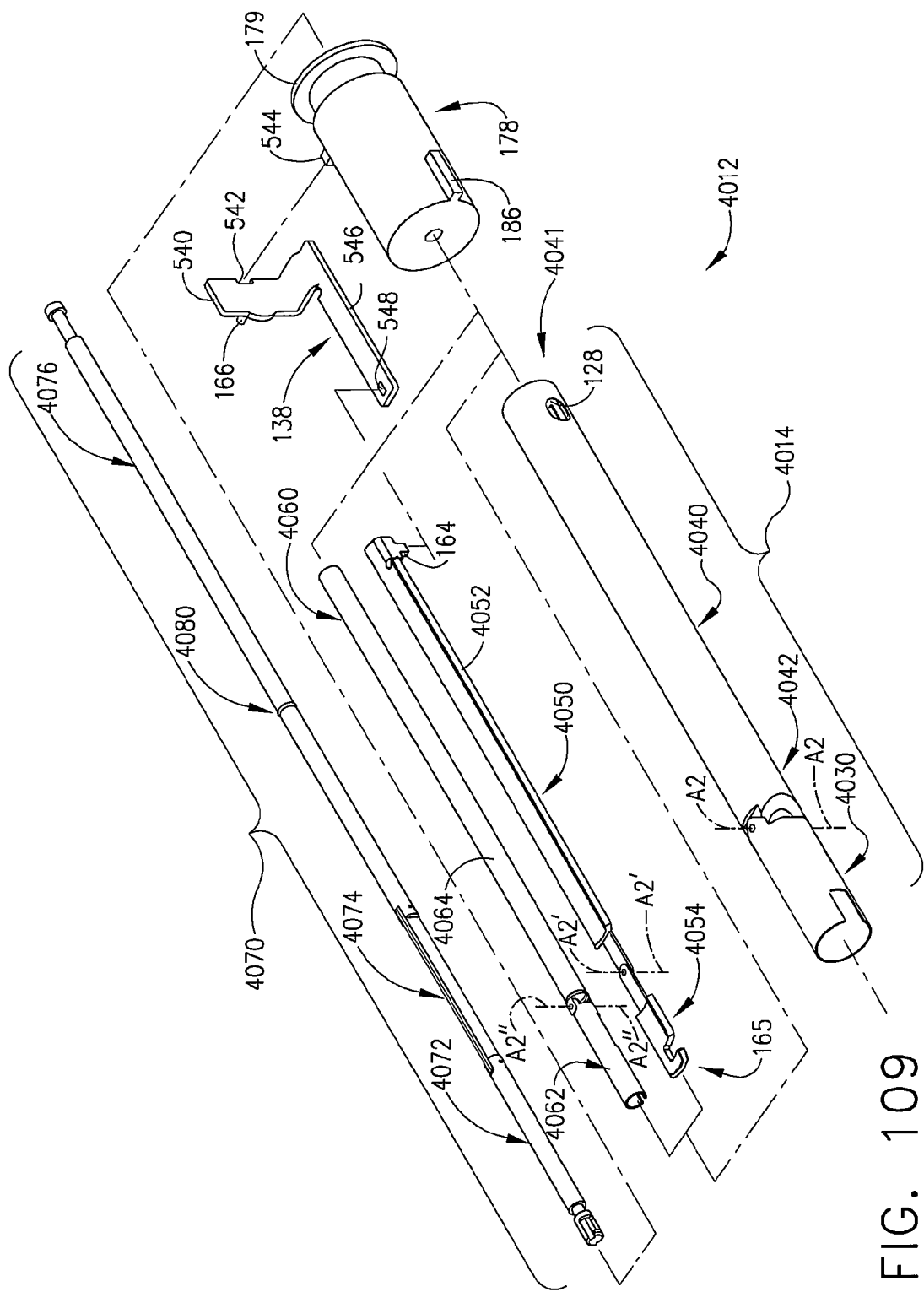
FIG. 109 is an exploded assembly view of an articulation system embodiment of the present invention employed in the surgical stapling apparatus of FIG. 108.

As can be seen in FIGS. 108 and 109, the elongated body assembly 4014 may comprise a distal body segment 4030 and a proximal body segment 4040 that are coupled together at the intermediate articulation joint 4020. The articulation system 4012 may further include a translation member 138 that has an upstanding arm portion 540 that has a notch 542 therein that is sized to receive a tab 544 formed on the sensor cylinder 178. The distal end of translation member 138 may include an arm 546 which includes an opening 548 configured to receive a finger 164 extending from the proximal end of articulation link 4050. A pin 166 that may be constructed from a non-abrasive material, e.g., Teflon® or metal coated with Teflon®, is secured to translation member 138 and dimensioned to be received within stepped camming surface 148 (shown in FIG. 11). The operation of those components was described above.

Figure 110:
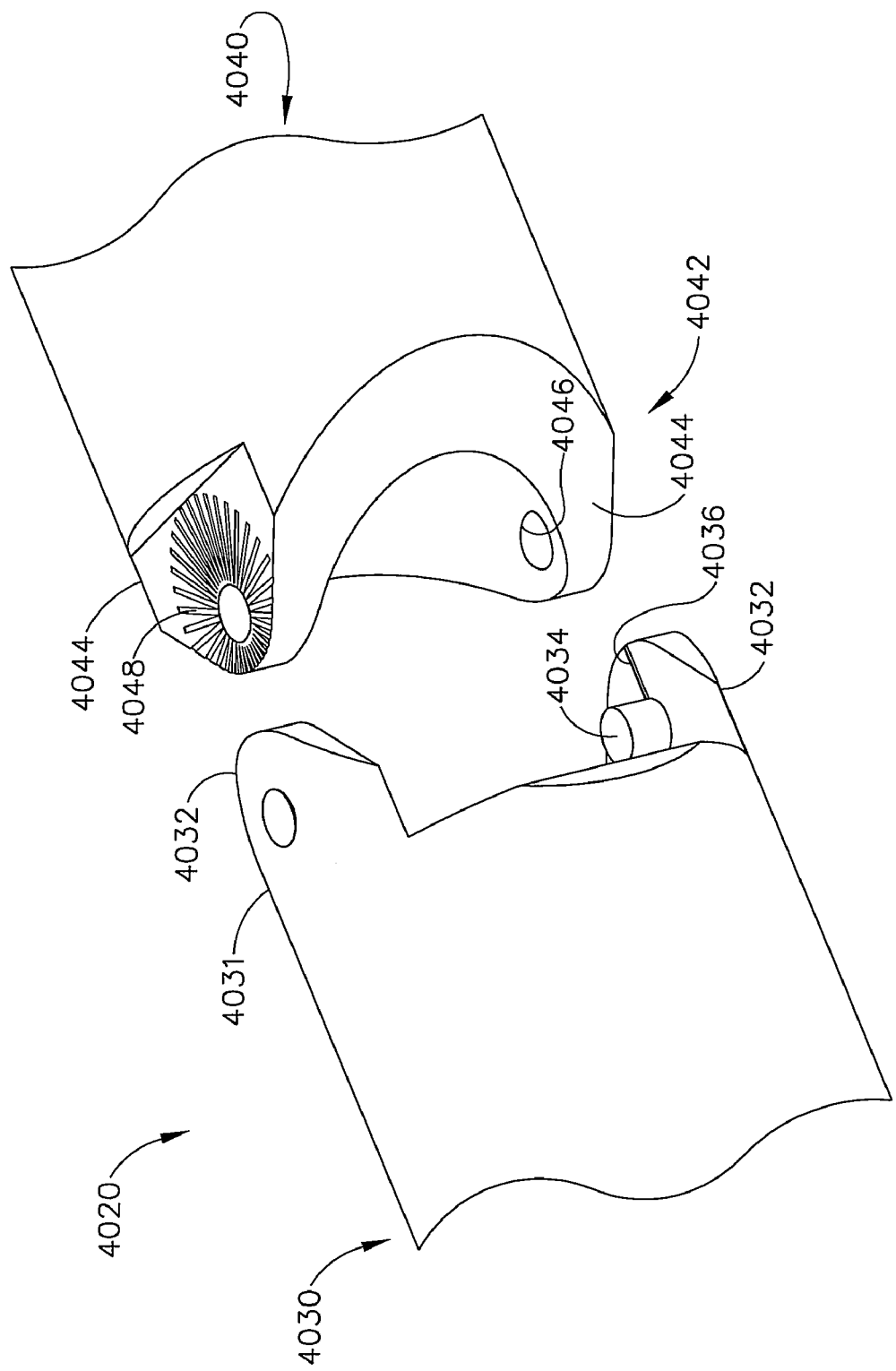
FIG. 110 is an exploded assembly view of portions of the intermediate articulation joint of the articulation system of FIG. 109.

FIG. 110 illustrates an intermediate articulation joint embodiment 4020 of the present invention. As can be seen in that Figure, the distal body segment 4030 is hollow and has a proximal end 4031 that has two proximally protruding lugs 4032 formed thereon. Each lug 4032 may have a pin 4034 protruding therefrom and at least one locking rib 4036 formed thereon. The proximal body segment 4040 is hollow and, as can be seen in FIG. 109, has a proximal end 4041 that has openings 128 for receiving a corresponding radial projection 132 (shown in FIG. 10) formed on the rotatable knob 28 as was described above. As can be seen in FIG. 110, the distal end 4042 of the proximal body segment 4040, may have a pair of distally protruding lugs 4044 that each have a pin receiving hole 4046 therethrough for receiving a corresponding pin 4034 on the distal body segment 4030 to enable the distal body segment 4030 to pivot relative to the proximal body segment 4040. Each lug 4044 may have a series of radial grooves 4048 formed thereon to mesh in confronting engagement with the corresponding locking ribs 4036 on the lugs 4032. Thus, when assembled together, the pins 4034 and holes 4046 serve to define the second articulation axis A2-A2 and are loosely fitted to enable the distal body segment 4030 to be pivoted to a desired position relative to the proximal body segment 4040 by applying a force to the distal body segment 4030 while keeping the proximal body segment 4040 stationary or visa-versa. The interaction between the locking ribs 4036 and the grooves 4048 serve to retain the distal body segment 4030 in the desired position relative to the proximal body segment 4040 after the articulation force has been discontinued. In alternative embodiments, the locking ribs 4036 may be formed on the distally protruding lugs 4044 and the radial grooves 4048 may be formed on the proximally protruding lugs 4032. In still other embodiments, at least one locking rib 4036 may be formed on one lug 4032 and radial grooves 4048 may be provided on the lug 4044 attached thereto and at least one locking rib 4036 may be provided on the other lug 4044 and the grooves 4048 provided on the lug 4032 attached to that lug 4044. When coupled together by the intermediate articulation joint 4020, the distal body segment 4030 and the proximal body segment 4040 of the elongated body assembly 4014 define the longitudinal axis L-L.

As indicated above, the articulation system 4012 may further comprise an articulation link 4050 that includes a proximal portion 4052 that has a finger 164 protruding therefrom that is configured to be received in the opening 548 in the arm 546 of the translation member 138. See FIG. 109. The articulation link 4050 may further have a distal portion 4054 that is pivotally pinned to the proximal portion 4052 such that the distal portion 4054 can pivot relative to the proximal portion 4052 about an articulation axis A2'-A2'. The distal end of the distal portion 4054 has a distal hook 165 formed thereon for detachable engagement with the hook portion of the articulation link in the disposable loading unit 16 in a known manner. As can also be seen in FIG. 109, this embodiment may employ a hollow sensor tube 4060 that has a distal portion 4062 that is pivotally coupled to a proximal portion 4064 for pivotal travel relative thereto about an articulation axis A2"-A2". The distal portion 4062 and the proximal portion 4064 of the sensor tube 4060 may be loosely coupled together to enable the sensor tube 4060 to accommodate some axial misalignment of components. For example, in various embodiments, the sensor tube portions 4062 and 4064 may be coupled to permit a ±0.125" axial movement of those components relative to each other. The sensor tube 4060 may operate in the same way as was described above with respect to sensor tube 123 and may have a control rod locking mechanism (not shown) of the type described above attached thereto.

As can also be seen in FIG. 109, the articulation system 4012 may include a control rod assembly 4070 that is similar in operation to control rod 52 above, except for the articulation segment 4074 that interconnects a distal portion 4072 and a proximal portion 4076. The articulation segment 4074 may comprise a series of laminated metal strips that will enable the control rod assembly 4070 to bend as the elongated body assembly 4014 is articulated about the intermediate articulation joint 4042, yet be sufficiently stiff to axially transmit the firing forces from the handle assembly 12 to the disposable loading unit 16. Other flexible joint arrangements could also be employed. In addition, an O-ring 4080 may be provided between the proximal portion 4076 of the control rod assembly 4070 and the sensor tube 4060 to provide additional support to the control rod assembly 4070 therein. When assembled together, those of ordinary skill in the art will appreciate that the articulation link 4050 and the sensor tube 4060 are supported within the elongated body assembly 4014 such that the axes A2"-A2" and A2'-A2' substantially coincide with the second articulation axis A2-A2. Likewise, the control rod assembly 4070 is supported within the elongated body assembly 4014 such that the articulation segment 4074 spans the intermediate articulation joint 4020.

Figure 111:
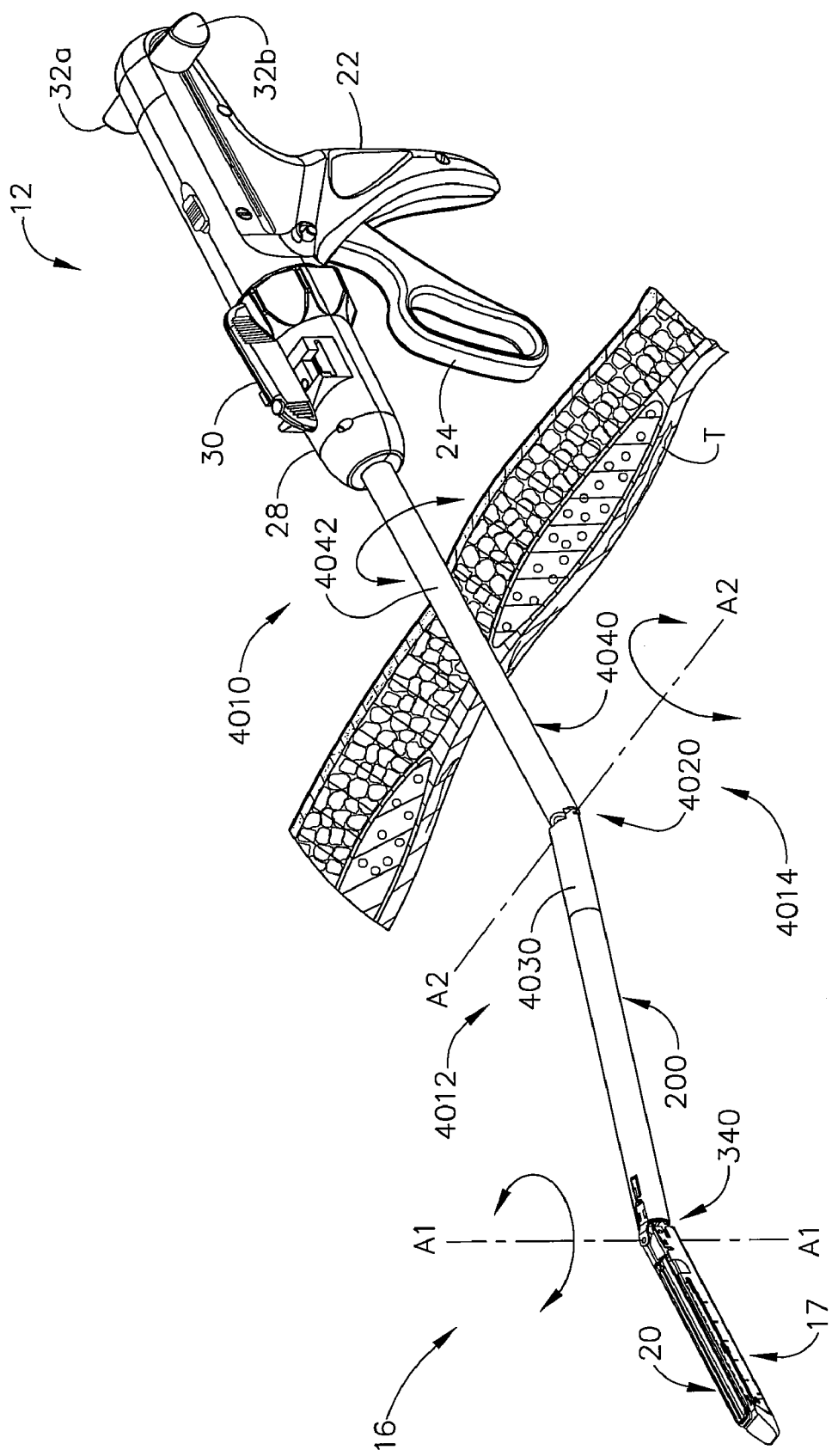
FIG. 111 is a perspective of the surgical stapling apparatus of FIG. 108 employed in an open surgical application.
Figure 112:
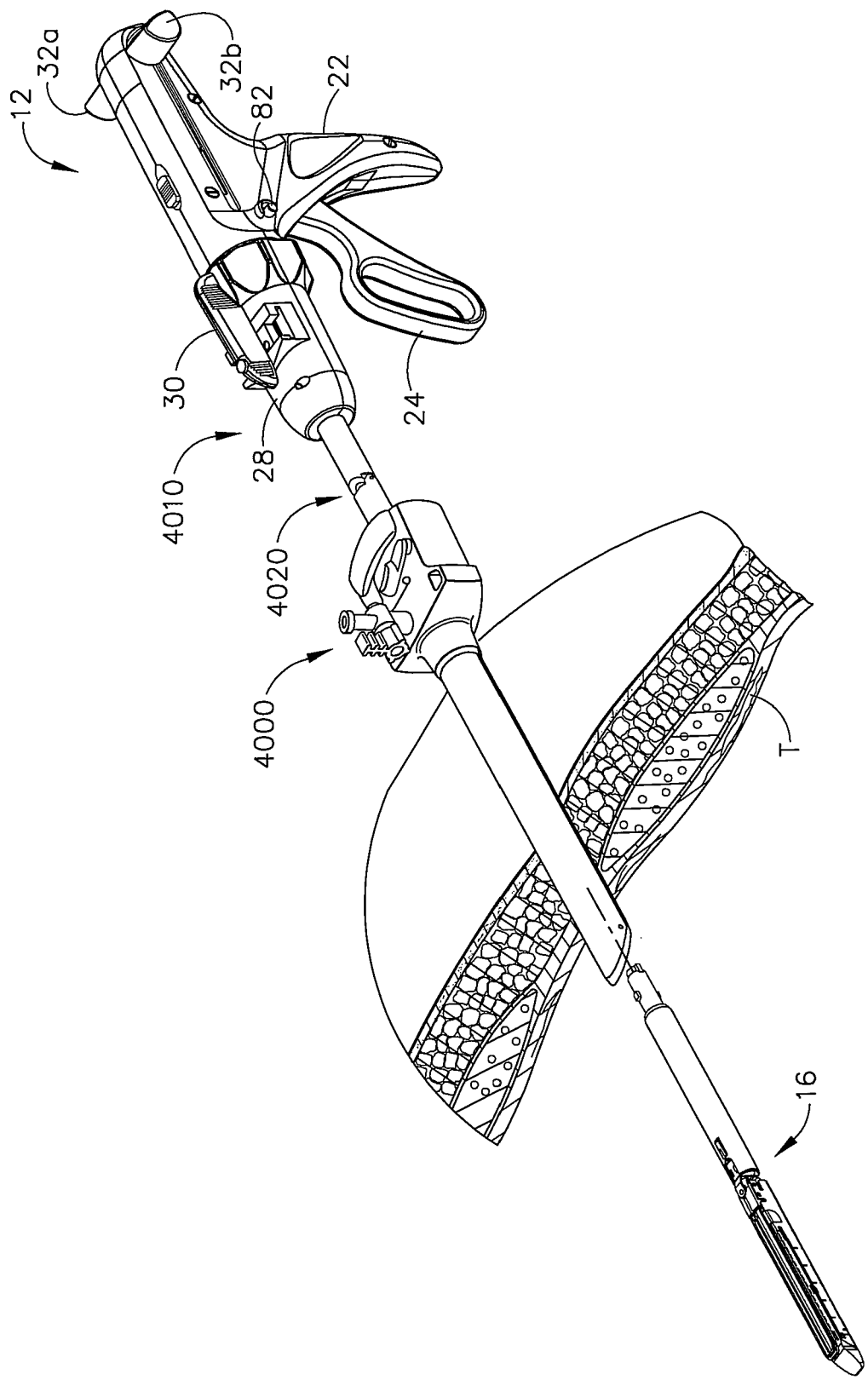
FIG. 112 is a perspective view of another surgical stapling apparatus embodiment of the present invention employed in connection with a conventional trocar to perform an endoscopic surgical procedure.

FIG. 111 depicts use of the surgical stapling apparatus 4010 in an "open" surgery setting wherein the disposable loading unit 16 and elongated body assembly 4014 are inserted into the patient through an open incision in the tissue "T". As can be understood from reference to that Figure, the tool assembly 17 may be selectively articulated about the first articulation axis A1-A1 by manipulating the articulation lever 30 as was described above. The disposable loading unit 16 may also be pivoted about the second articulation axis A2-A2 relative to the proximal body segment 4040 of the elongated body assembly 4014 and handle assembly 12 by "passively" bringing the tool assembly 17 into contact with the organ or other portion of the body or by grasping the disposable reload unit 16 with another surgical instruments such as, for example, graspers (not shown) to apply an external force to the tool assembly 17 to cause it to articulate about the second articulation axis A2-A2. The person of ordinary skill in the art will appreciate that once the tool assembly 17 is articulated to the desired position about the second articulation axis A2-A2, it is retained in that position by virtue of the engagement between the locking ribs 4036 and radial grooves 4048 as described above. To enable the stapling apparatus 4010 to be used endoscopically through a conventional trocar 4000 as shown in FIG. 112, the intermediate articulation joint 4020 may be provided adjacent the rotation knob 28 such that the articulation joint 4020 can remain external to the trocar 4000 to enable the handle assembly 12 to be pivoted about the second articulation axis A2-A2, relative to the portion of the surgical stapling apparatus 4010 protruding into the patient through the trocar 4000.

Figure 113:
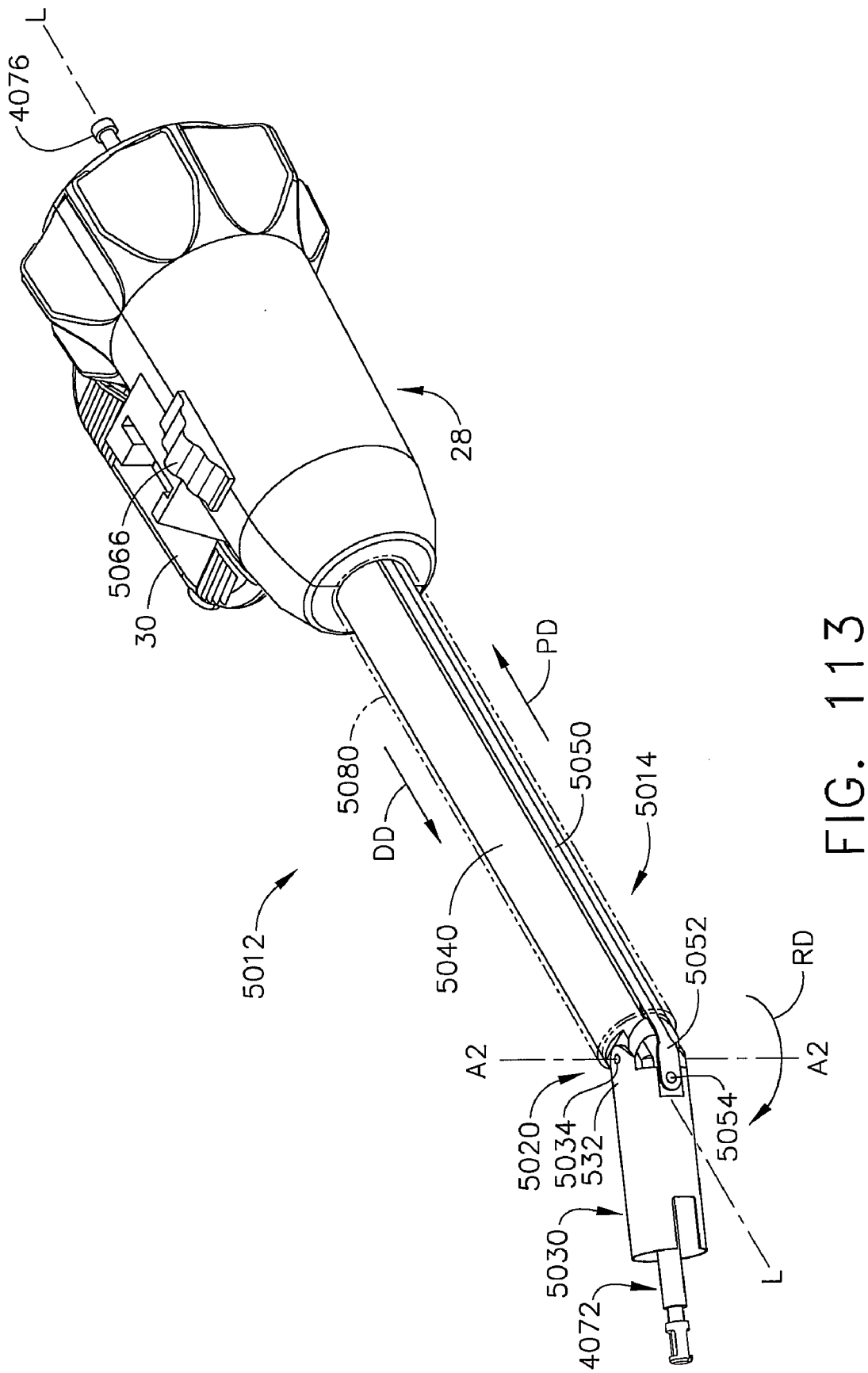
FIG. 113 is a perspective view of another articulation system embodiment of the present invention.
Figure 114:
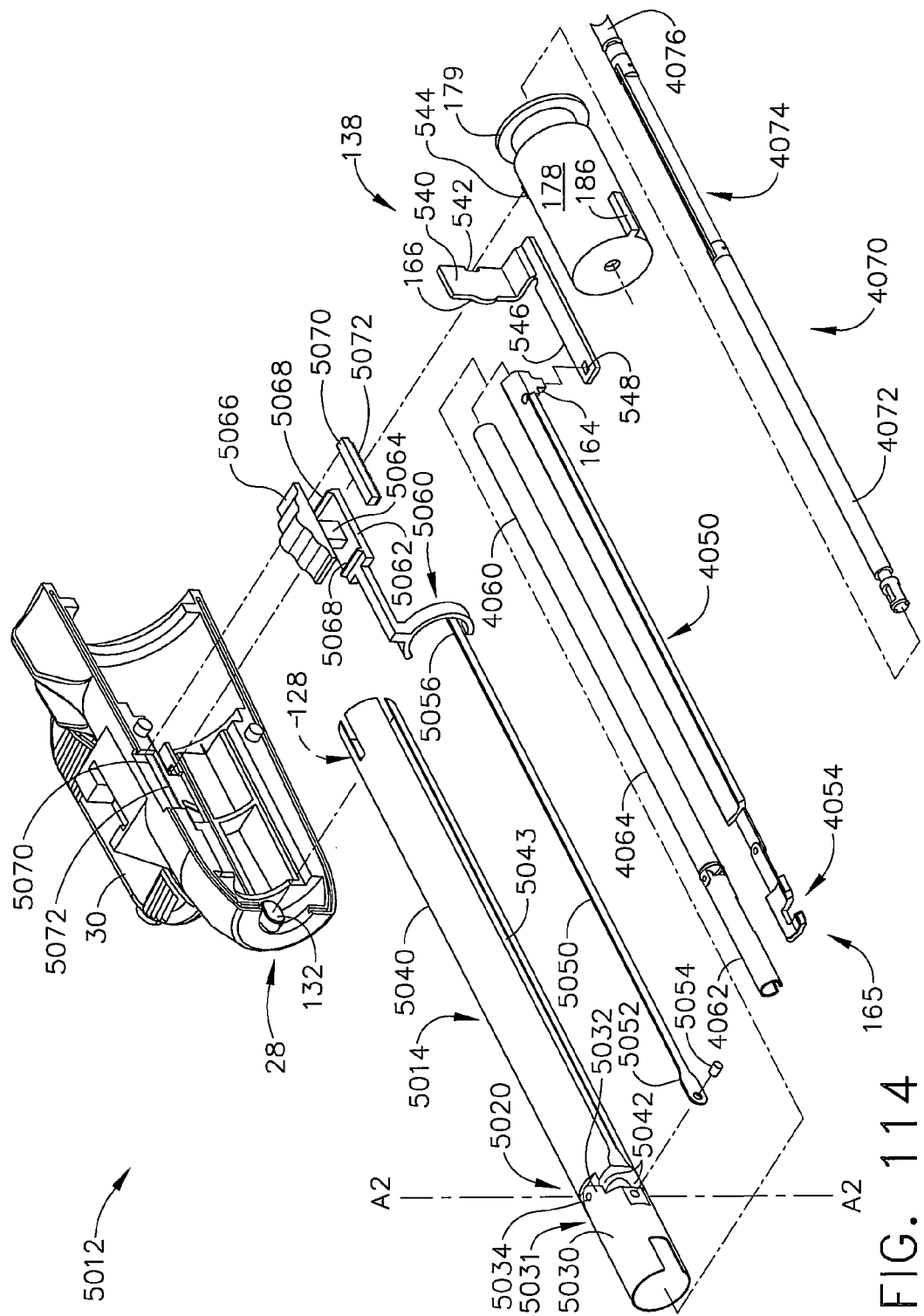
FIG. 114 is a partial exploded assembly view of the articulation system of FIG. 113.
Figure 115:
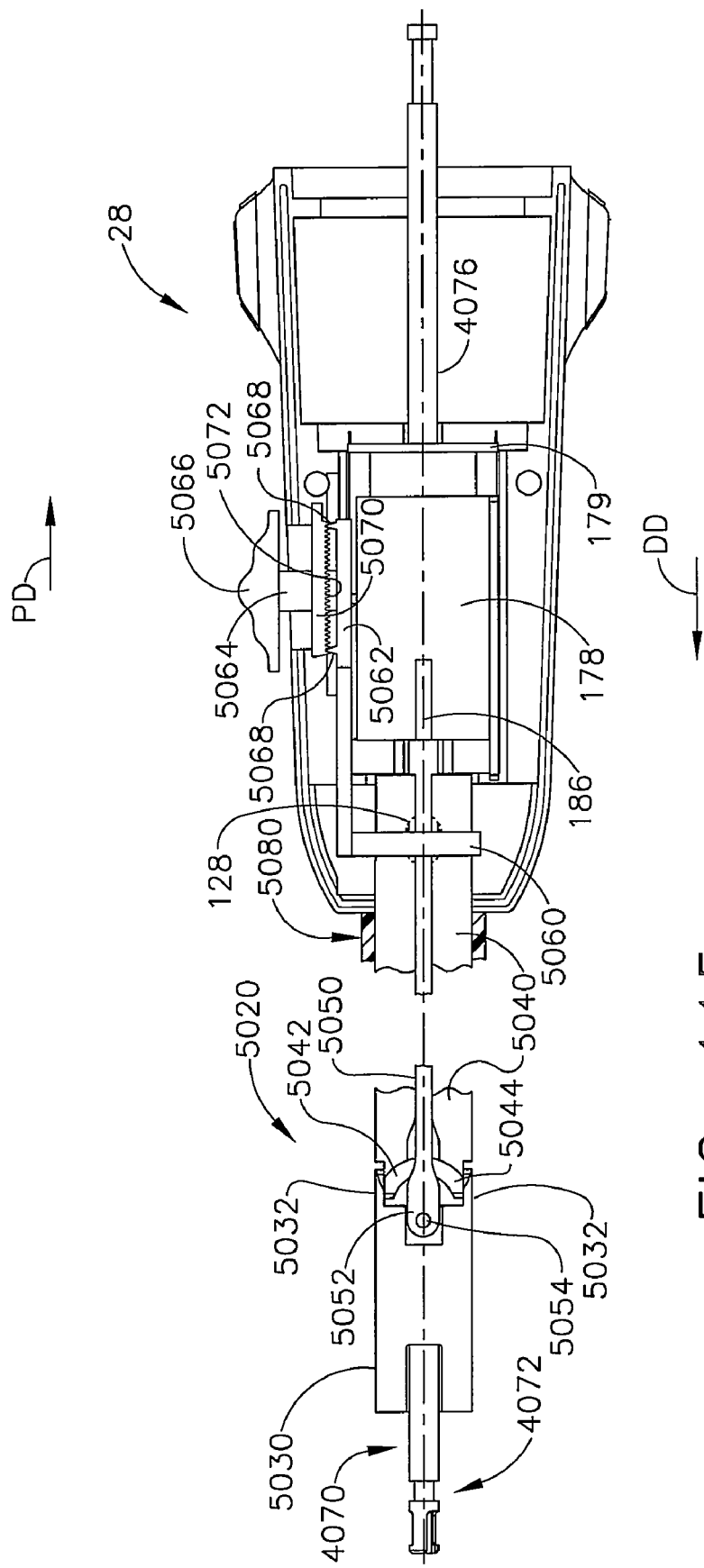
FIG. 115 is a side assembly view of the articulation system of FIGS. 113 and 114.

FIGS. 113-115 illustrate an articulation system 5012 that may be employed with various surgical stapling apparatuses of the present invention. Those components that are the same as the components employed in the above-mentioned embodiments will be labeled with the same element numbers and those of ordinary skill in the art can refer to the disclosure set forth hereinabove that explains their construction and operation. The articulation system 5012 may include an intermediate articulation joint 5020 in the elongated body assembly 5014 that facilitates pivotal travel of the disposable reload unit 16 relative to the handle assembly 12 about a second articulation axis A2-A2 that is substantially transverse to the longitudinal axis L-L and the first articulation axis A1-A1. The elongated body assembly 5014 may comprise a distal body segment 5030 and a proximal body segment 5040 that are coupled together at the intermediate articulation joint 5020. As shown in FIG. 114, the articulation system 5012 may further include a translation member 138 that has an upstanding arm portion 540 that has a notch 542 therein that is sized to receive a tab 544 formed on the sensor cylinder 178. The distal end of translation member 138 may include an arm 546 which includes an opening 548 configured to receive a finger 164 extending from the proximal end of articulation link 4050. A pin 166 that may be constructed from a non-abrasive material, e.g., Teflon® or metal coated with Teflon® is secured to translation member 138 and dimensioned to be received within stepped camming surface 148 (shown in FIG. 11). The operation of these components was described above.

As further shown in FIG. 114, the distal body segment 5030 is hollow and has a proximal end 5031 that has two proximally protruding lugs 5032. Each lug 5032 has a pin 5034 protruding therefrom. The proximal body segment 5040 is hollow and has an opening 128 for receiving a corresponding radial projection 132 formed on the rotatable knob 28 as was described above. See FIGS. 114 and 115. The distal end 5042 of the proximal body segment 5040 may have a pair of distally protruding lugs 5044 that each have a pin receiving hole (not shown) therethrough for receiving a corresponding pin 5034 on the distal body segment 5030, to enable the distal body segment 5030 to pivot relative to the proximal body segment 5040. In various embodiments, the intermediate articulation joint 5020 may be formed with the radial grooves 4048 and locking ribs 4036 as was described above. The intermediate articulation joint 5020 in other embodiments may be made without such radial grooves and locking ribs.

The articulation system 5012 illustrated in FIGS. 113-115 is an "active" articulation system and may include an articulation bar 5050 that has a distal end 5052 that is pinned or otherwise attached to the distal body segment 5030 by a pin 5054. As shown in FIG. 114, the articulation bar 5050 may ride in an elongated bar slot 5043 provided in the proximal body segment 5040 of the elongated body assembly 5014. To provide additional support to the articulation bar 5050, a shroud 5080 may be placed over the proximal body segment 5040. See FIGS. 113 and 115. The articulation bar 5050 may have a proximal end 5056 that is integrally formed with or otherwise non-movably attached to a stabilizing collar 5060. The stabilizing collar 5060 may be sized to fit about the proximal body segment 5040 and have a base portion 5062 attached thereto that is attached to or formed with a button post 5064 that terminates in an articulation button 5066. As can be seen in FIGS. 114 and 115, the base portion 5062 may be formed with two upwardly extending lock detents 5068 that are adapted to retainingly engage locking racks 5072 formed on two locking plates 5070 that are non-movably supported in the rotation knob 28. As shown in FIGS. 114 and 115, two locking plates 5070 may be employed—one on each side of the button post 5064.

Figure 116:
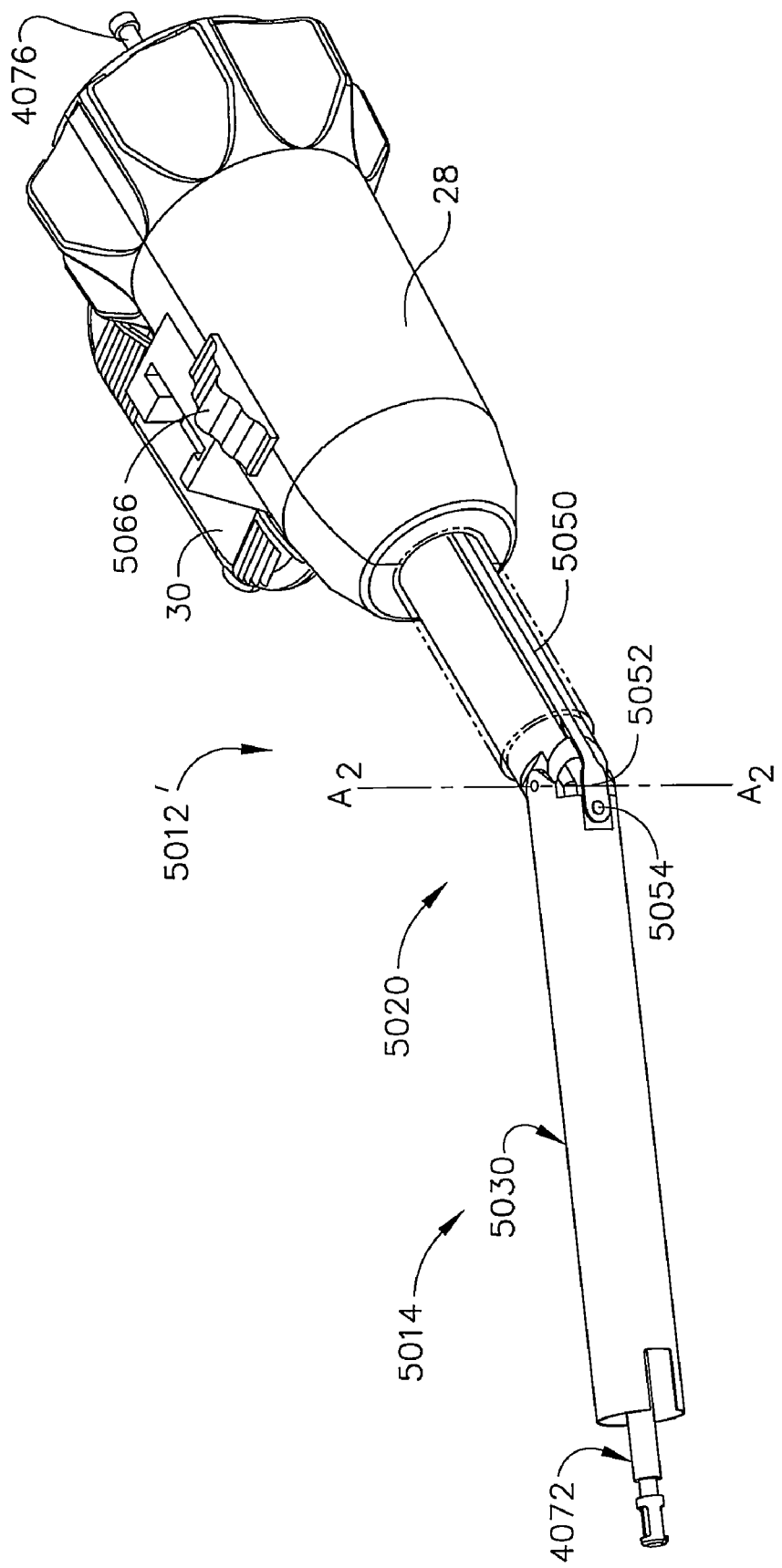
FIG. 116 is a perspective view of another articulation system embodiment of the present invention.

Referring to FIG. 113, to articulate the distal body segment 5030 as well as the distal portion 4072 of the control rod assembly 4070 (and the disposable loading unit attached thereto) in the right direction "RD" about the second articulation axis A2-A2, the clinician simply slides the articulation button 5066 in the distal "D-D" direction. To articulate the distal body segment 5030, distal portion 4072 of the control rod assembly 4070 and the disposable loading unit in the left direction "LD", the clinician slides the articulation button 5066 in the proximal direction "PD". Those of ordinary skill in the art will understand that the articulation system 5020 may be effectively employed with surgical stapling apparatuses that are adapted to receive articulatable and non-articulatable disposable reload units. The articulation system 5012 depicted in FIGS. 113-115 is well adapted for use in open surgical applications. The articulation system 5012' depicted in FIG. 116 may be better suited for endoscopic applications. As can be seen in that Figure, the articulation joint 5020 is closer to the rotation knob 28 such that when in use, the articulation joint 5020 is external to the trocar through which the distal body segment 5030 of the elongated body assembly 5014 extends.

Figure 117:
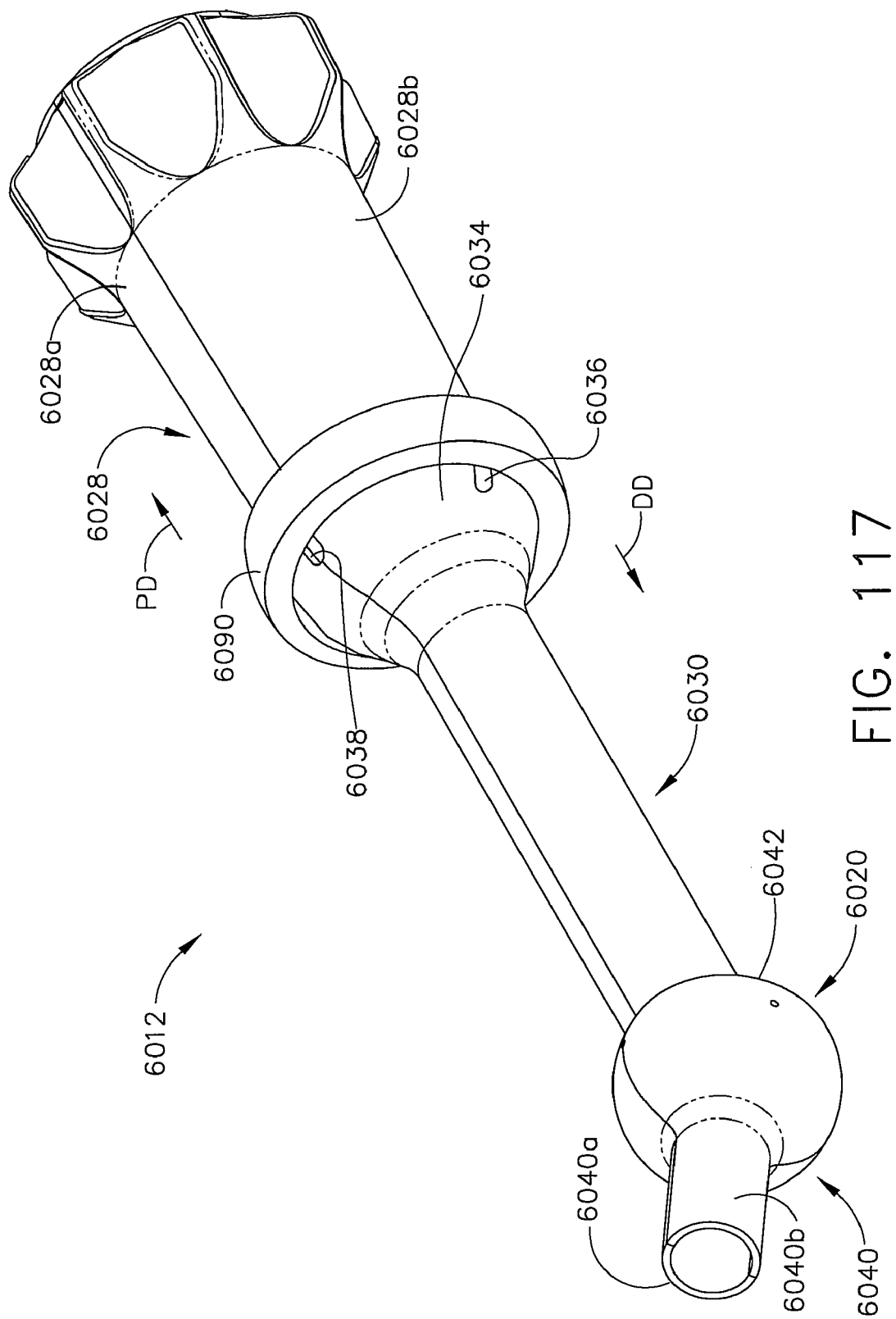
Figure 118:
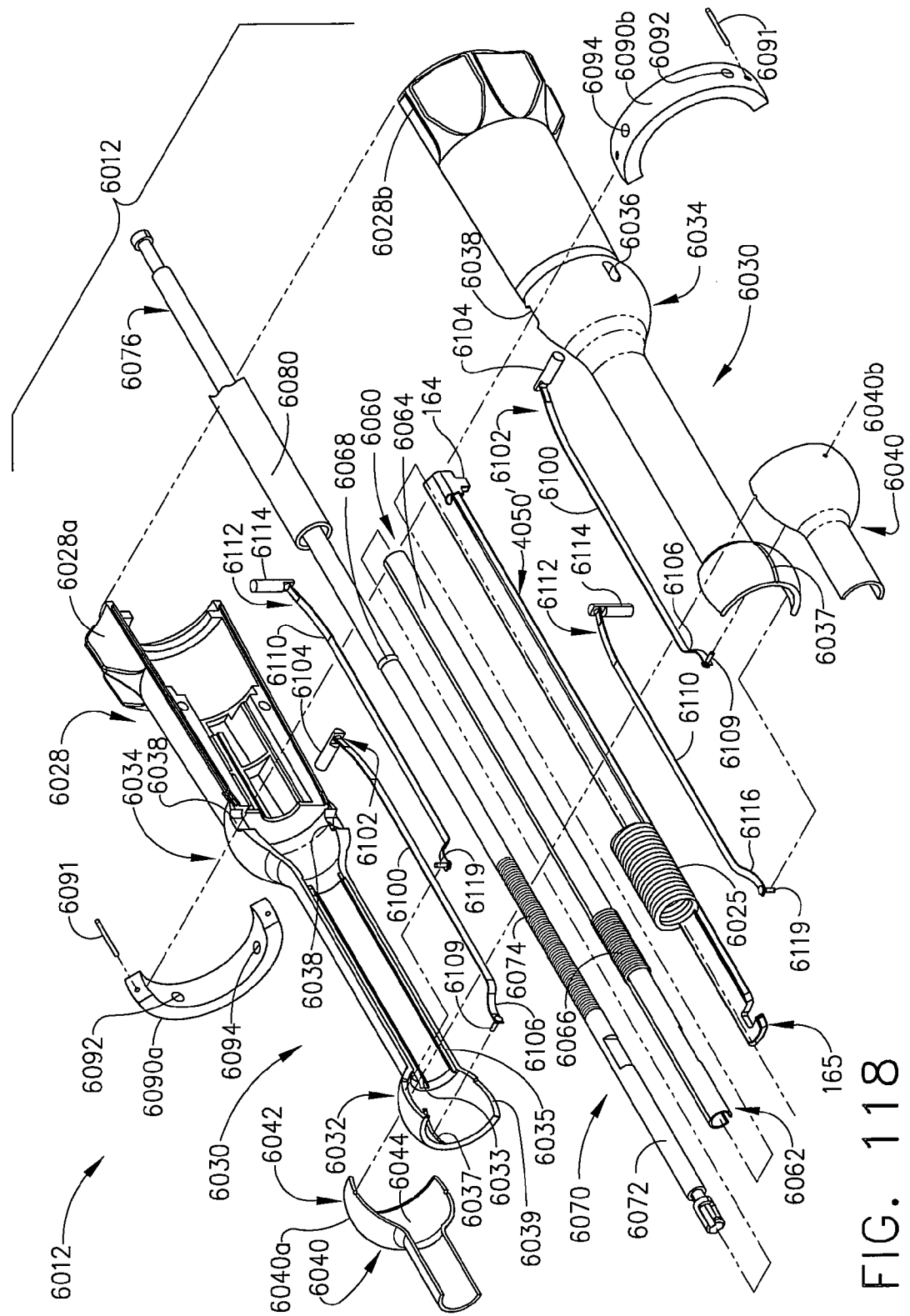

FIGS. 117-121 illustrate a unique and novel "active" articulation system 6012 that may be used in connection with various surgical stapling apparatuses adapted for use with disposable loading units. Those components of the articulation system 6012 that are the same as the components employed in the above-mentioned embodiments will be labeled with the same element numbers and those of ordinary skill in the art can refer to the disclosure set forth hereinabove that explains their construction and operation. In various embodiments, the articulation system 6012 includes a rotation knob assembly 6028 that, except for the differences noted below, is similar to rotation knob 28 described above. As can be seen in FIG. 118, the rotation knob 6028 has an articulation shroud extension 6030 that has a distal articulation ball 6032 formed thereon. In various embodiments, the rotation knob assembly 6028 may be formed from two segments 6028a and 6028b that are molded from plastic or other suitable material and which may be interconnected by, for example, snap features, screws, adhesive, etc. See FIG. 117. Rotatably received on the distal articulation ball 6032 is a distal body segment 6040 whose proximal end 6042 forms an articulation socket 6044 that may be formed from cover segments 6040a and 6040b that may be interconnected by snap features, adhesive, etc. As illustrated in FIG. 118, the articulation system 6012 may also include a translation member of the type and construction described above which is configured to receive a finger 164 extending from the proximal end of articulation link 4050'. Articulation link 4050' is similar to articulation link 4050 described above except that the articulation link 4050' has a flexible connector portion (coil spring, etc.) 6025 formed therein.

Figure 119:
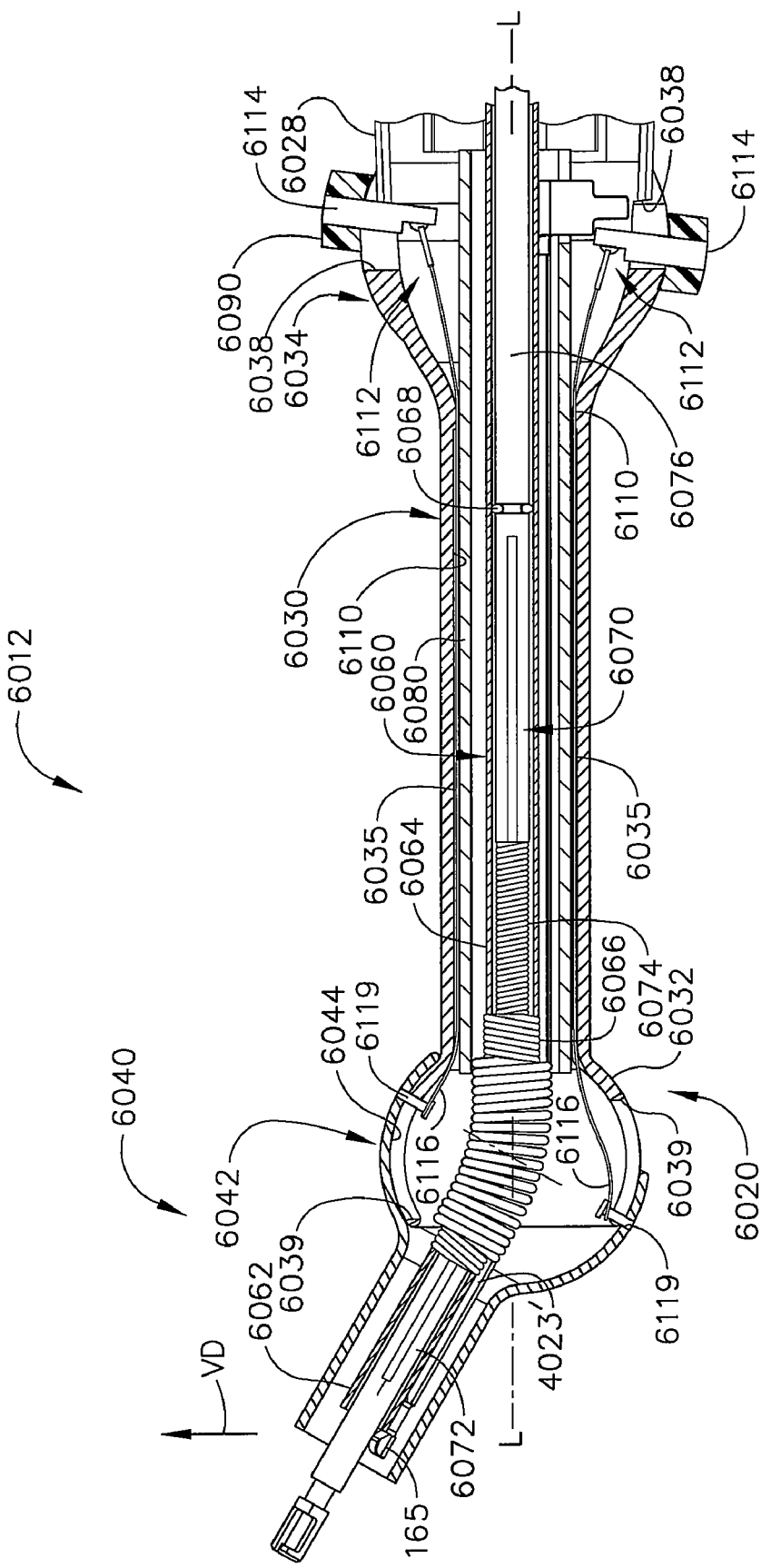

As can be seen in FIG. 118, the articulation system 6012 may further comprise a hollow sensor tube 6060 that has a distal portion end 6062 that is coupled to a proximal portion 6064 by a flexible connector (coil spring, etc.) 6066. The sensor tube 6060 may operate in the same way as was described above with respect to sensor tube 123 and may have a control rod locking mechanism (not shown) of the type described above attached thereto. As can also be seen in FIG. 118, the articulation system 6012 may include a control rod assembly 6070 that is similar in operation to control rod 52 above, except for the flexible connector segment 6074 that interconnects a distal portion 6072 and a proximal portion 6076. The flexible connector segment 6074 may comprise a coil spring, etc. that will enable the control rod assembly 6070 to bend during articulation, yet be sufficiently stiff to axially transmit the firing forces from the handle assembly 12 to the disposable loading unit 16. As can be seen in FIGS. 118 and 119, the control rod assembly 6070 extends through the sensor tube 6060 and the proximal end portion 6076 is supported therein by an O-ring 6068. To provide additional axial support to the proximal portion 6076 of the control rod assembly 6070 and the flexible connector segment 6074, a proximal firing rod tube 6080 may be employed. See FIGS. 118 and 119. When assembled together, those of ordinary skill in the art will appreciate that the flex connector portion 6025 of articulation link 4050', flexible connector portion 6066 of the sensor tube 6060 and the flexible connector segment 6074 are supported within the articulation ball 6032 as shown in FIG. 119.

Figure 120:
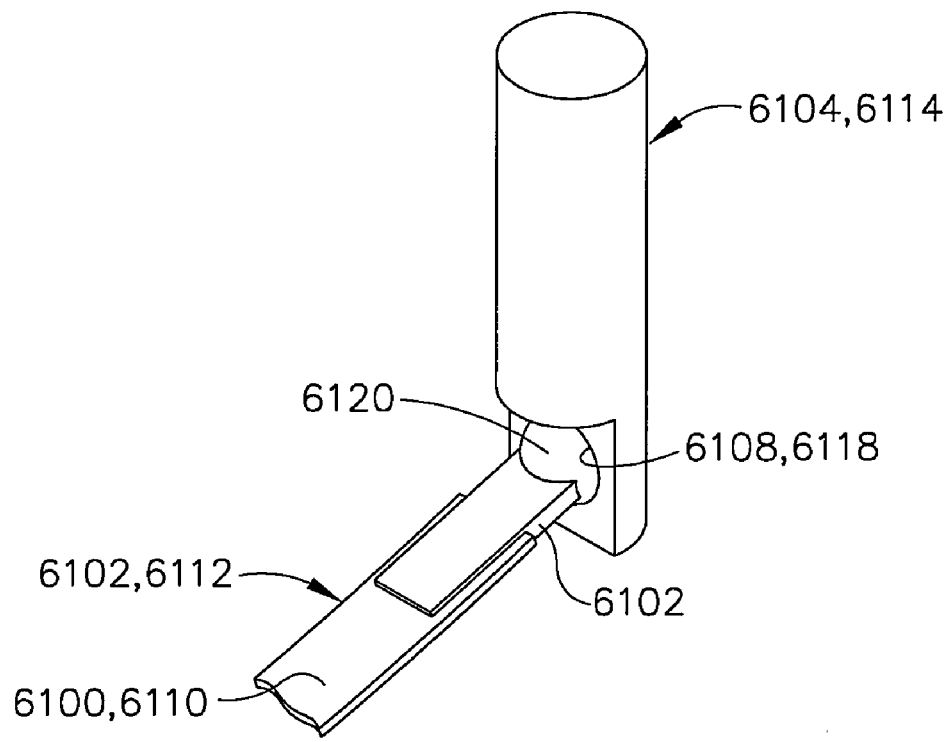
Figure 121:
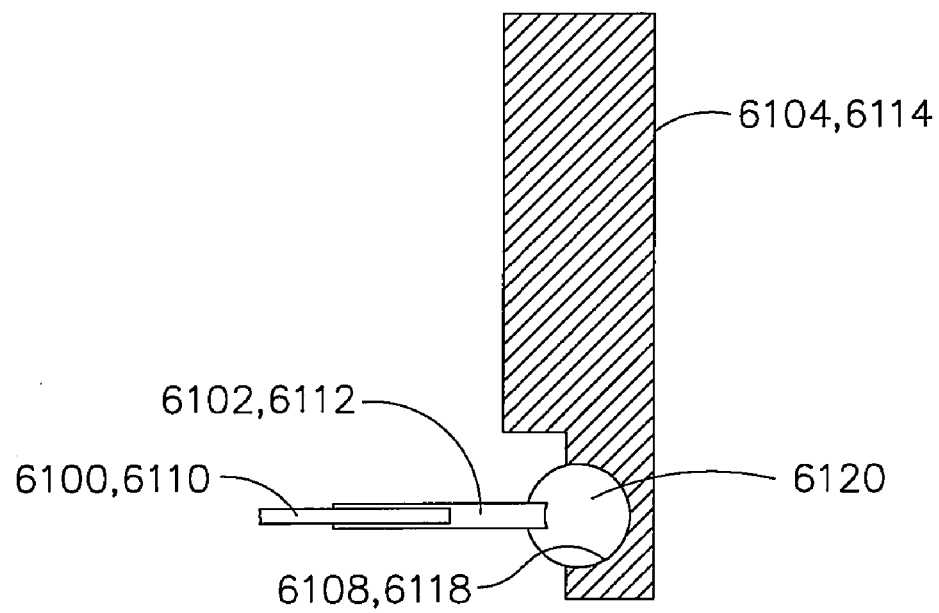

As can be seen in FIGS. 118 and 119, the articulation system 6012 further comprises a articulation handle 6090 that is movably supported on the distal end 6034 of the shroud extension 6030. In various embodiments, the articulation handle 6090 may be formed from two arcuate segments 6090a and 6090b that are coupled together, by, for example, screws 6091 or other suitable fastener arrangements. The articulation handle 6090 is coupled to two diametrically opposed horizontal articulation bands 6100 and two diametrically opposed vertical articulation bands 6110. See FIG. 118. referring now to FIGS. 120 and 121, in various embodiments, the proximal end 6102 of each horizontal articulation band 6100 may be pivotally coupled to a horizontal articulation pin 6104. Likewise the proximal end 6112 of each vertical articulation band 6110 may be pivotally coupled to a vertical articulation pin 6114. FIGS. 120 and 121, illustrate one form of attaching the proximal end 6102 of a horizontal articulation band 6100 to a horizontal articulation pin 6104 as well as of attaching the proximal end 6112 of a vertical articulation band 6110 to a vertical articulation pin 6114. As can be seen in those Figures, a ball connector 6120 may be coupled to the distal ends 6102, 6112 and be rotatably received in a corresponding socket 6108, 6118 in the horizontal and vertical articulation pins 6104, 6114, respectively. The horizontal articulation pins 6104 may extend through diametrically opposed horizontal slots 6036 (FIG. 118) in the proximal end portion 6034 of the shroud extension 6030 to be received in holes 6092 in the articulation handle 6090. Similarly, the vertical articulation pins 6114 extend through vertical slots 6038 formed in the proximal end portion 6034 of the shroud extension 6030 to be received in holes 6094 in the articulation ring 6090.

In various embodiments, the horizontal articulation bands 6100 and the vertical articulation bands 6110 may comprise metal bands that will bend or flex about their weak axis (i.e., the axis that extends transversely to their length), but will not bend or flex in their strong axis (i.e., their elongated axis extending along their length). To provide support to the articulation bands 6100, 6110 along their respective lengths, the horizontal articulation bands 6100 may be movably supported in elongated horizontal slots 6033 formed in the elongated shroud 6030. The distal end 6106 of each horizontal articulation band 6100 may have a distal articulation pin 6109 protruding therefrom that extends through a corresponding horizontal slot 6037 in the ball portion 6032 of the elongated shroud 6030 to be coupled to the distal body segment 6040. In various embodiments, the distal articulation pin 6109 extends through a hole in the corresponding distal end 6106 of the horizontal articulation band 6100 to enable the distal end 6106 thereof to rotate there around. Similarly, the distal end 6116 of each vertical articulation band 6110 may have a distal articulation pin 6119 protruding therefrom that extends through a corresponding vertical slot 6039 in the ball portion 6032 of the elongated shroud 6030 to be coupled to the distal body segment 6040. See FIG. 119. The distal articulation pins 6119 may extend through a hole in the distal end 6116 of a corresponding vertical articulation band 6110 to enable the distal end 6116 to rotate therearound.

Although not specifically illustrated in FIGS. 117-118, those of ordinary skill in the art will understand that the distal body segment 6040 may be configured for operable attachment to an articulatable disposable loading unit or a non-articulatable disposable loading unit in the manner described above or in the manner that is known in the art. However, in this embodiment, the clinician can selectively articulate the distal body segment 6040 and the disposable loading unit attached thereto by selectively pivoting the articulation handle 6090 on the proximal end 6034 of the shroud extension 6030. For example, FIG. 119 illustrates the articulation handle 6090 pivoted to a position wherein the distal body segment 6040 is pivoted in the vertical direction "VD". To pivot the distal body segment 6040 in a horizontal direction (the direction perpendicular to the direction VD depicted in FIG. 119), the clinician first brings the articulation handle back to a vertical neutral position (wherein the distal body segment 6040 is coaxial with the shroud extension 6030 and then the clinician pivots the articulation handle such that one side portion of the handle 6090 moves in the distal direction, while the other side moves in the proximal direction (represented by arrows "DD" and "PD" in FIG. 117). Such active articulation comprises substantially bi-planar articulation. That is, the distal body segment 6040 and the disposable loading unit coupled thereto can only be selectively articulated through a vertically extending plane or through a horizontally extending plane that is substantially orthogonal to the vertically extending plane. The distal body segment 6040 and the disposable loading unit cannot be articulated in the vertical and horizontal directions at the same time. However, those of ordinary skill in the art will appreciate that the rotation knob 6028 by virtue of its rotatable attachment to the handle assembly facilitates selective rotation of the distal body segment 6040 and the disposable loading unit coupled thereto about the longitudinal axis L-L.

Figure 122:
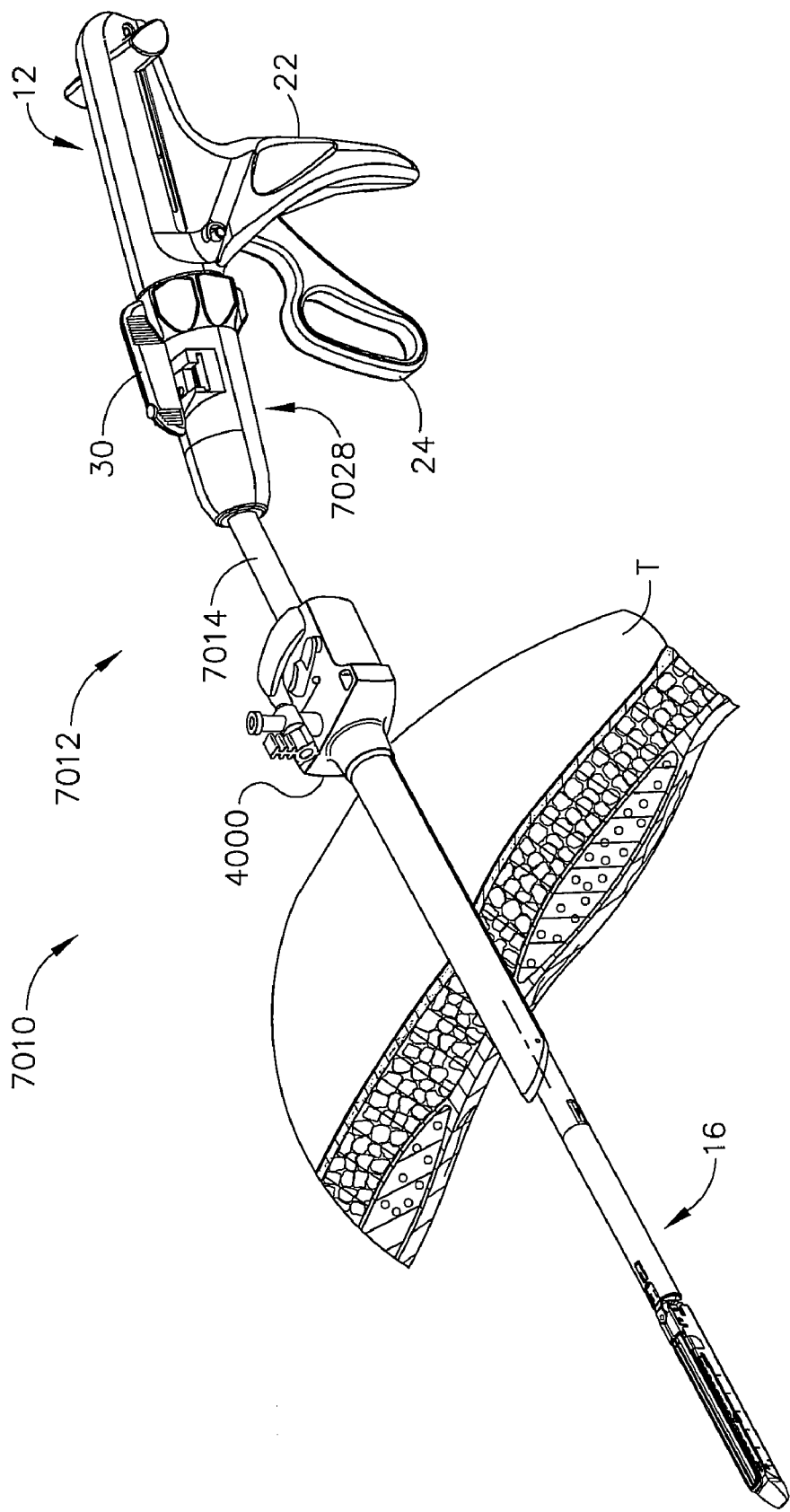
Figure 123:
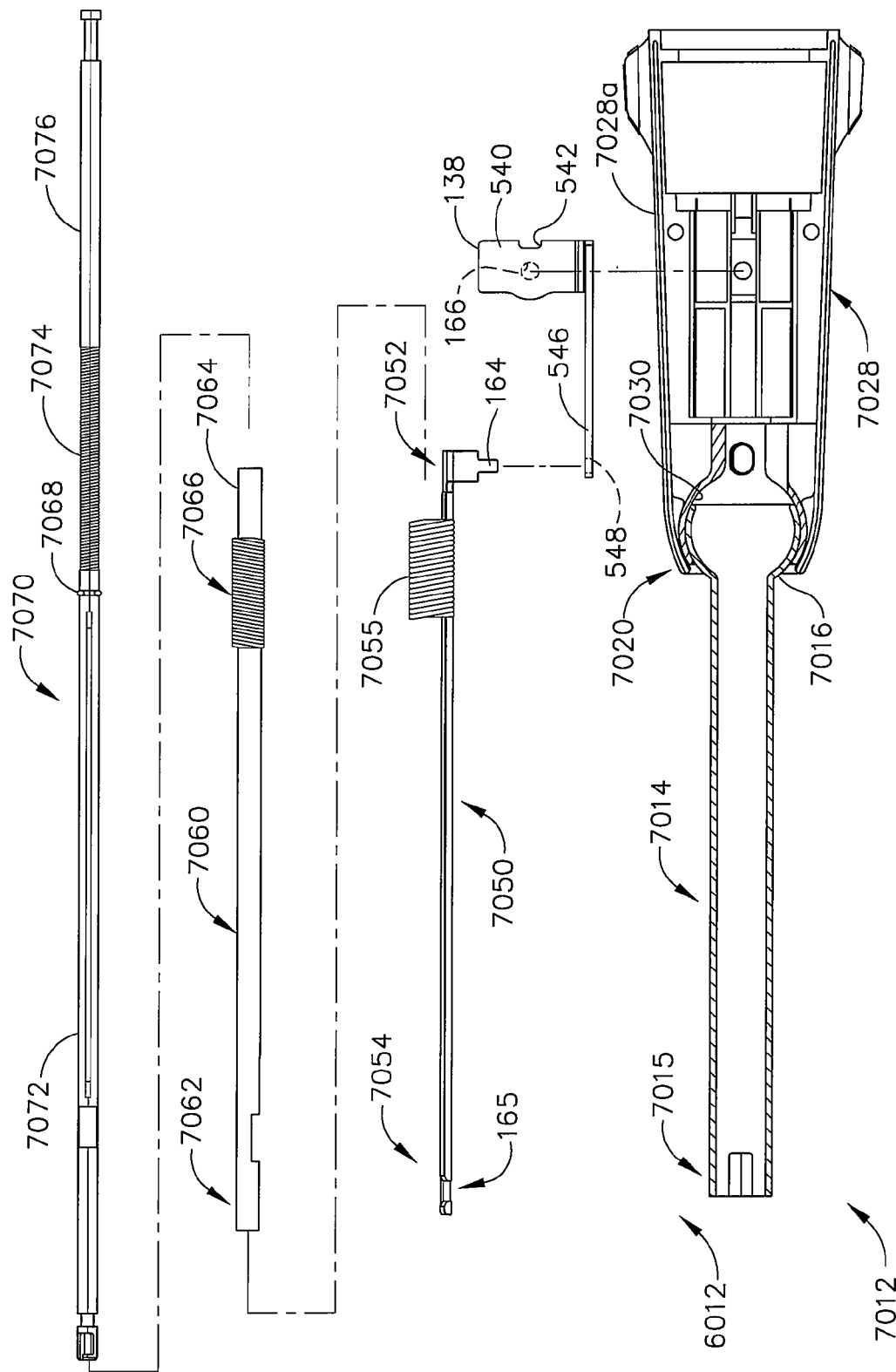

FIGS. 122 and 123 illustrate another surgical stapling apparatus embodiment 7010 of the present invention that employs a passive articulation system 7012. As can be seen in those Figures, the passive articulation system 7012 may comprise a rotation knob 7028 that is somewhat similar to rotation knob 28 described above, except for the differences discussed below. Those components of the surgical stapling apparatus 7010 that are the same as the components employed in the above-mentioned embodiments will be labeled with the same element numbers and those of ordinary skill in the art can refer to the disclosure set forth hereinabove that explains their construction and operation. As can be seen in FIG. 123, the rotation knob 7028 has an articulation socket 7030 formed therein that is sized to rotatably receive a ball 7016 formed on an elongated body assembly 7014. In alternative embodiments, the socket 7030 may be formed in a casing segment that is non-rotatably supported within the rotatable knob 7028. The distal end 7015 of the elongated body assembly 7014 is configured for operable attachment to an articulatable or non-articulatable disposable loading unit in a known manner. As can also be seen in FIG. 123, the articulation system 7012 may further include a translation member 138 that has an upstanding arm portion 540 that has a notch 542 therein that is sized to receive a tab (not shown) formed on the sensor cylinder (not shown) in the manner described above. The distal end of translation member 138 may include an arm 546 which includes an opening 548 configured to receive a finger 164 extending from the proximal end 7052 of articulation link 7050. The distal end 7054 of the articulation link 7050 has a distal hook 165 formed thereon which can hookingly engage an articulation tab or hook formed on an articulation link supported in the disposable reload unit. A pin 166 that may be constructed from a non-abrasive material, e.g., Teflon® or metal coated with Teflon®, is secured to translation member 138 and dimensioned to be received within stepped camming surface 148 (shown in FIG. 11). As can be seen in FIG. 123, a flexible member 7055 in the form of a coil spring or the like may be provided in the articulation link 7050 adjacent the proximal end 7052 thereof.

The passive articulation system 7012 may further comprise a hollow sensor tube 7060 that has a distal portion end 7062 that is coupled to a proximal portion 7064 by a flexible connector (coil spring, etc.) 7066. The sensor tube 7060 may operate in the same way as was described above with respect to sensor tube 123 and may have a control rod locking mechanism (not shown) of the type described above attached thereto. As can also be seen in FIG. 123, the articulation system 7012 may include a control rod assembly 7070 that is similar in operation to control rod 52 above, except for the flexible connector segment 7074 that interconnects a distal portion 7072 and a proximal portion 7076. The flexible connector segment 7074 may comprise a coil spring, etc. that will enable the control rod assembly 7070 to bend during articulation, yet be sufficiently stiff to axially transmit the firing forces from the handle assembly 12 to the disposable reload unit 16. The firing rod assembly 7070 extends through the sensor tube 7060 and the distal portion 7072 is supported therein by an O-ring 7068. When assembled together, those of ordinary skill in the art will appreciate that the flex connector portion 7055 of articulation link 7050, flexible connector portion 7066 of the sensor tube 7060 and the flexible connector segment 7074 of the control rod assembly 7070 are at least partially supported within the articulation ball 7016 and socket 7030.

FIG. 122 illustrates use of the surgical stapling apparatus 7010 of the present invention with a conventional trocar 4000. As can be seen in that Figure, a disposable loading unit 16 is coupled to the elongated body assembly 7014. Although an articulatable disposable loading unit 16 is illustrated, the person of ordinary skill in the art will understand that the apparatus 7012 may be effectively employed with non-articulating disposable loading units. After the trocar 4000 has been installed through the tissue "T" utilizing known techniques, the clinician can insert the disposable loading unit 16 through the trocar into the patient. If an articulatable disposable loading unit 16 is employed, the clinician must orient the disposable loading unit in a non-articulated state to insert it through the trocar. After the disposable loading unit 16 has been inserted into the patient and actuated to clamp onto the target tissue in the manners described above, the clinician may articulate the handle simply by pivoting the handle assembly 12 about the ball and socket articulation joint 7020. The ball portion 7016 may be sized relative to the socket 7030 such that a sufficient amount of friction is established between the components at rest to retain them in position, yet not be so great as to prevent manipulation of those components relative to each other. In other embodiments, detents may be provided in the ball and socket joint components to retain the joint in various positions. The clinician may also manipulate the handle assembly 12 relative to the elongated body assembly 7014 prior to clamping onto the target tissue by grasping the proximal end of the elongated body assembly protruding from the trocar 4000 and then manipulating the handle assembly 12 relative thereto.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device may be reconditioned for reuse after at least one use. Reconditioning may include any combination of the steps of disassembly of the device, followed by cleaning or replacement of particular pieces, and subsequent reassembly. In particular, the device may be disassembled, and any number of particular pieces or parts of the device can be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical stapling apparatus, comprising:
   a handle assembly including handle housing and a movable handle, the movable handle being movable relative to the handle housing through an actuation stroke;
   an actuation shaft supported at least in part within said handle housing and mounted to generate actuation motions in response to manipulation of said movable handle;
   a rotatable shroud movably coupled to said handle housing;
   an elongated body coupled to said rotatable shroud for rotational travel therewith about a longitudinal axis defined by said elongated body, said elongated body having a distal end configured to be operably attached to a disposable loading unit and a proximal end interfacing with said actuation shaft to transfer said actuation motions from said actuation shaft to said disposable loading unit; and
   a lockable rotation system for selectively locking said rotatable shroud to prevent rotation thereof about said longitudinal axis.

2. The surgical stapling apparatus of claim 1 further comprising an articulation system operably supported by said handle housing and interfacing with said elongated body to selectively apply articulation motions thereto.

3. The surgical stapling apparatus of claim 2 wherein said lockable rotation system comprises a brake system configured to prevent movement of said articulation system during rotation of said rotatable shroud.

4. The surgical stapling apparatus of claim 3 wherein said brake system comprises:
   a rotation lock ring on a portion of said rotatable shroud; and
   a locking bolt movably supported in said handle housing for selective meshing engagement with said rotation lock ring such that when said locking bolt is engaged with said rotation lock ring, said rotatable shroud is prevented from rotating about said longitudinal axis.

5. The surgical stapling apparatus of claim 3 further comprising a grip movably supported on said rotatable shroud and being operably coupled to said articulation system, said grip interfacing with said brake system such that said brake system may selectively lock said grip to said rotatable shroud to prevent axial movement of said grip on said rotatable shroud.

6. The surgical stapling apparatus of claim 5 wherein said brake system comprises:
   a rotation lock ring on a portion of said rotatable shroud;
   a brake tube movably supported within said handle housing for selective axial travel therein;
   a switch bar coupled to said brake tube and a selector switch such that actuation of said selector switch moves said brake tube axially within said handle housing;
   a locking bolt associated with said switch bar for selective meshing engagement with said rotation lock ring on said rotatable shroud such that when said locking bolt is engaged therewith, said rotatable shroud is prevented from rotating about said longitudinal axis and when said locking bolt is disengaged from said rotation lock ring, said rotatable shroud can rotate relative to said handle housing;
   a selectively expandable brake band supported on said rotatable shroud between said rotatable shroud and said grip, said expandable brake band being selectively movable between an expanded position and an unexpanded position such that when said expandable brake band is in said expanded position, said grip is prevented from moving axially on said rotatable shroud and when said expandable brake band is in said unexpanded position, said grip can move axially on said rotatable shroud; and
   a brake arm pin interfacing with said expandable brake band and said brake tube such that axial movement of said brake tube in one axial direction causes said expandable brake band to move to said expanded position and movement said brake tube in an opposite axial direction causes said expandable brake band to move to said unexpanded position.

7. The surgical stapling apparatus of claim 5 wherein said articulation system is actuated by moving said grip axially on said rotatable shroud.

8. The surgical stapling apparatus of claim 7 wherein when said grip is axially moved on said rotatable shroud in a distal direction, said articulation system imparts an articulation motion in a first direction and when said grip is axially moved on said rotatable shroud in a proximal direction, said articulation system imparts articulation motion in a second direction.

9. The surgical stapling apparatus of claim 2 further comprising means for providing an audible indication of a position of said articulation system.

10. The surgical stapling apparatus of claim 2 wherein said articulation system comprises:
    a translation member movably supported within said rotatable shroud for selective longitudinal movement therein, said translation member interfacing with the elongated body; and
    an articulation member movably supported on said rotatable shroud and operably interfacing with said translation member.

11. The surgical stapling apparatus of claim 10 wherein said articulation member comprises:
    an articulation ring threadably attached to an exterior of said rotatable shroud; and
    an articulation pin engaging said articulation ring and said translation member such that as said articulation ring is threadedly advanced on said rotatable shroud, said translation member is caused to move axially therein.

12. The surgical stapling apparatus of claim 1 wherein said lockable rotation system comprises a lockable knob movably supported on said handle housing for selective movement between a first locked position wherein said lockable knob engages said rotatable shroud to prevent rotation thereof relative to said handle assembly and a second unlocked position wherein said rotatable shroud may be rotated relative to said handle assembly by rotating said is lockable knob.

13. The surgical stapling apparatus of claim 12 further comprising a biasing member between said handle housing and said lockable knob assembly to bias said lockable knob assembly into the first locked position.

* * * * *